United States Patent
Thielemans et al.

(10) Patent No.: US 9,408,909 B2
(45) Date of Patent: *Aug. 9, 2016

(54) ENHANCING THE T-CELL STIMULATORY CAPACITY OF HUMAN ANTIGEN PRESENTING CELLS IN VITRO AND IN VIVO AND ITS USE IN VACCINATION

(71) Applicant: Vrije Universiteit Brussel, Brussels (BE)

(72) Inventors: Kris Maria Magdalena Thielemans, Wilrijk (BE); Aude Bonehill, Essene (BE)

(73) Assignee: Vrije Universiteit Brussel, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/974,563

(22) Filed: Aug. 23, 2013

(65) Prior Publication Data
US 2014/0056939 A1   Feb. 27, 2014

Related U.S. Application Data

(63) Continuation-in-part of application No. 13/593,393, filed on Aug. 23, 2012, which is a continuation-in-part of application No. 12/677,476, filed as application No. PCT/EP2008/062174 on Sep. 12, 2008, now Pat. No. 8,476,419.

(30) Foreign Application Priority Data

Sep. 14, 2007   (WO) .................. PCT/EP2007/059732

(51) Int. Cl.
| | |
|---|---|
| A61K 48/00 | (2006.01) |
| A61K 39/39 | (2006.01) |
| A61K 39/00 | (2006.01) |
| C12N 5/0784 | (2010.01) |

(52) U.S. Cl.
CPC .............. *A61K 39/39* (2013.01); *A61K 39/0011* (2013.01); *C12N 5/0639* (2013.01); *A61K 2039/5154* (2013.01); *A61K 2039/5156* (2013.01); *A61K 2039/5158* (2013.01); *A61K 2039/53* (2013.01); *A61K 2039/54* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 6,969,609 B1 | 11/2005 | Schlom et al. | |
| 7,378,277 B2 | 5/2008 | Hwu et al. | |
| 7,754,482 B2 | 7/2010 | Riley et al. | |
| 2003/0202963 A1* | 10/2003 | Crystal et al. | ............... 424/93.2 |
| 2005/0059624 A1* | 3/2005 | Hoerr et al. | ................... 514/44 |
| 2006/0188490 A1* | 8/2006 | Hoerr et al. | ............. 424/93.21 |
| 2011/0027310 A1* | 2/2011 | Medin et al. | ............. 424/204.1 |

FOREIGN PATENT DOCUMENTS

| | | |
|---|---|---|
| WO | WO 2005/012509 | 2/2005 |
| WO | WO 2006/042177 | 4/2006 |
| WO | WO 2007/078196 | 7/2007 |

OTHER PUBLICATIONS

Thornburg et al., 2000, J. Immunother. vol. 23: 412-418.*
Mor et al., 2005, J. Immunol. vol. 175: 3439-45.*
Curran et al., 2010, PNAS, vol. 107: 4275-80.*
Gavrilov et al., 2012, Jayle J. Biol. Med. vol. 85: 187-200.*
Kreiter et al., 2010, Canc. Res. vol. 70:9031-40.*
Weide et al., 2009, J. Immunother. vol. 32: 498-507.*
Huang et al.,2005, Canc. Res. vol. 65: 5009-14.*
International Search Report for International Application No. PCT/EP2008/062174, mailed on Dec. 30, 2008.
Abdel-Wahab, et al., "Cotransfection of DC with TLR4 and MART-1 RNA Induces MART-1 Specific Responses," Journal of Surgical Research, vol. 124, No. 2, pp. 264-273, Apr. 2005.
Bonehill, et al. "Enhancing the T-cell Stimulatory Capacity of Human Dendritic Cells by Co-electroporation with CD40L, CD70 and Constitutively active TLR4 Encoding mRNA," Molecular Therapy, vol. 16, No. 6, pp. 1170-1180, Jun. 2008.
Croft, "Control of Immunity by the TNFR-related Molecule OX40 (CD134)," The Annual Review of Immunology, vol. 28, pp. 57-78, 2010.
Hori, "Developmental Plasticity of Foxp3+ regulatory T Cells," Current Opinion in Immunology, vol. 22, pp. 575-582, 2010.
Hori, "Regulatory T Cell Plasticity: Beyond the Controversies," Trends in Immunology vol. 32, No. 7, pp. 295-300, Jul. 2011.
Jonuleit, et al. "Pro-inflammatory Cytokines and Prostaglandins Induce Maturation of Potent Immunostimulatory Dendritic Cells under Fetal Calf Serum-free Conditions," European Journal of Immunology, vol. 27, No. 12, pp. 3135-3142, Dec. 1997.
Koch, et al. "T-bet Controls Regulatory T Cell Homeostasis and Function During Type-1 Inflammation," Nature Immunology, vol. 10, No. 6, pp. 595-602, Jun. 2009.
Kubo, et al. "Regulatory T Cell Suppression and Anergy are Differentially Regulated by Proinflammatory Cytokines Produced by TLR-activated Dendritic Cells," The Journal of Immunology, vol. 173, pp. 7249-7258, 2004.

(Continued)

*Primary Examiner* — Amy Juedes
(74) *Attorney, Agent, or Firm* — Dinsmore & Shohl LLP

(57) ABSTRACT

We provide new methods of in vitro or in vivo enhancing the T-cell stimulatory capacity of human DCs and the use thereof in cancer vaccination. The method includes the introduction of different molecular adjuvants to human DCs by contacting or modifying them with mRNA or DNA molecule(s) encoding CD40L, and CD70 or constitutively active TLR4 (caTLR4).

11 Claims, 93 Drawing Sheets

(56) References Cited

OTHER PUBLICATIONS

Liu, et al. "Adenovirus-mediated CD40 Ligand Gene-engineered Dendritic Cells Elicit Enhanced CD8+ Cytotoxic T-cell Activation and Antitumor Immunity," Cancer Gene Therapy, vol. 9, pp. 202-208, 2002.

McClymont, et al. "Plasticity of Human Regulatory T Cells in Healthy Subjects and Patients with Type 1 Diabetes," The Journal of Immunology, vol. 186, pp. 3918-3926, Mar. 2011.

Oldenhove, et al. "Decrease of Foxp3+ Treg Cell Number and Acquisition of Effector Cell Phenotype During Lethal Infection," Immunity, vol. 31, No. 5, 29 pages, Nov. 20, 2009, Author Manuscript.

Pasare, et al. "Toll Pathway-dependent Blockade of CD4+CD25+ T Cell-mediated Suppression by Dendritic Cells," Science, vol. 299, pp. 1033-1036, Feb. 14, 2003.

Ramirez-Montagut, et al. "Glucocorticoid-induced TMF Receptor Family Related Gene Activation Overcomes Tolerance/Ignorance to Melanoma Differentiation Antigens and Enhances Antitumor Immunity," The Journal of Immunology, vol. 176, pp. 6434-6442, 2006.

Stephens, et al. "Engagement of Glucocorticoid-induced TNFR Family-related Receptor on Effector T Cells by its Ligand Mediates Resistance to Suppression by CD4+CD25+ T Cells," The Journal of Immunology, vol. 173, pp. 5008-5020, 2004.

Tuyaerts, et al. "Current Approaches in Dendritic Cell Generation and Future Implications for Cancer Immunotherapy," Cancer Immunology Immunotherapy, vol. 56, No. 10, pp. 1513-1537, May 15, 2007.

Warger, et al. "Synergistic Activation of Dendritic Cells by Combined Toll-like Receptor Ligation Induces Superior CTL Responses in vivo," Blood, vol. 108, No. 2, pp. 544-550, Jul. 15, 2006.

Wei, et al. "Global Mapping of H3K4me3 and H3K27me3 Reveals Specificity and Plasticity in Lineage Fate Determination of Differentiating CD4+ T Cells," Immunity 30, pp. 155-167, Jan. 16, 2009.

Wilgenhof S, Van Nuffel Am, Corthals J, Heirman C, Tuyaerts S, Benteyn D, De Coninck A, Van Riet I, Verfaillie G, Vandeloo J, Bonehill A, Thielemans K, Neyns B. J. Therapeutic vaccination with an autologous mRNA electroporated dendritic cell vaccine in patients with advanced melanoma. Immunother. Jun. 2011; 34(5):448-56.

Zhou, et al. "TGF-β-induced Foxp3 Inhibits TH17 Cell Differentiation by Antagonizing RORγt Function," Nature, vol. 453, pp. 236-241, May 8, 2008.

Final Office Action dated Feb. 8, 2016 which pertains to U.S. Appl. No. 13/593,393, filed Aug. 23, 2012.

Ahonen et al., "Combined TLR and CD40 Triggering induces Potent CD8+ T Cell Expansion with Variable Dependence on Type I IFN", J. Exp. Med., 2004, vol. 199, pp. 775-784.

\* cited by examiner

Figure 4B-1    CD107a assay
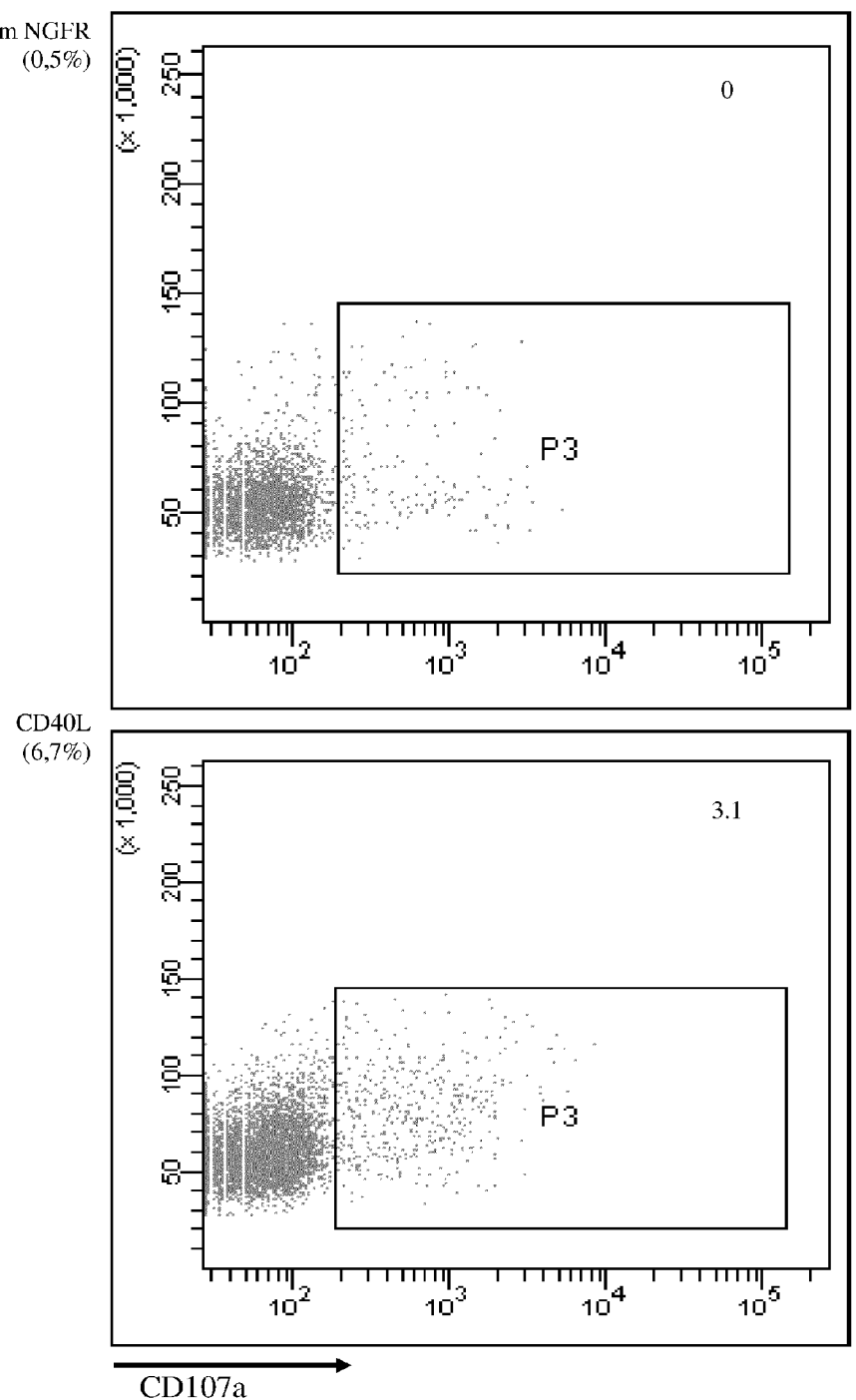

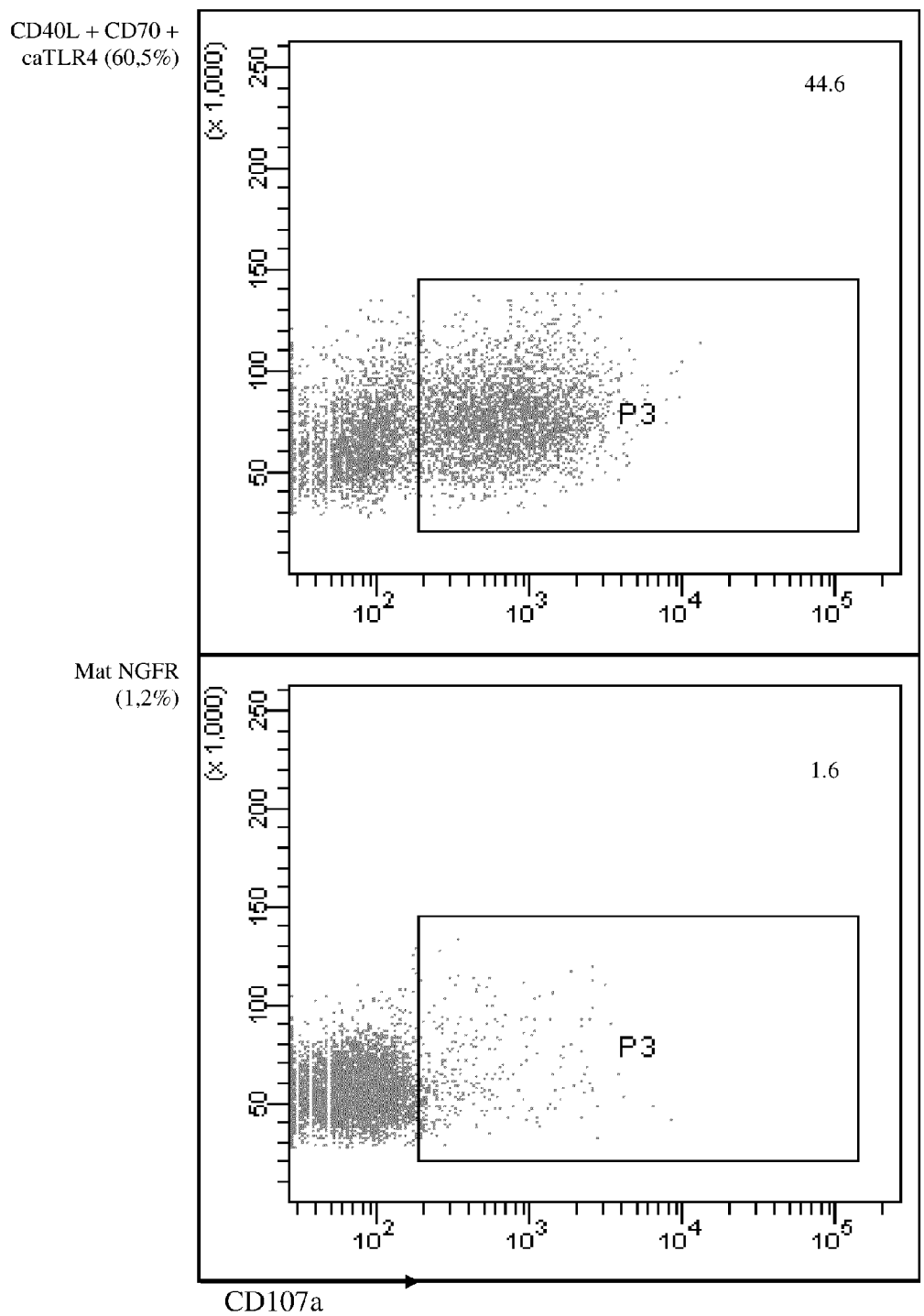

Figure 5B-6
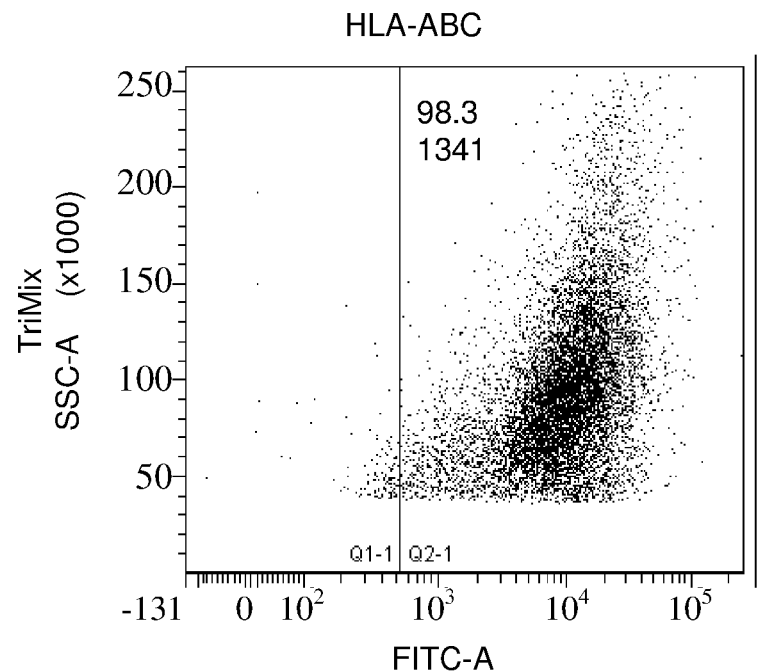
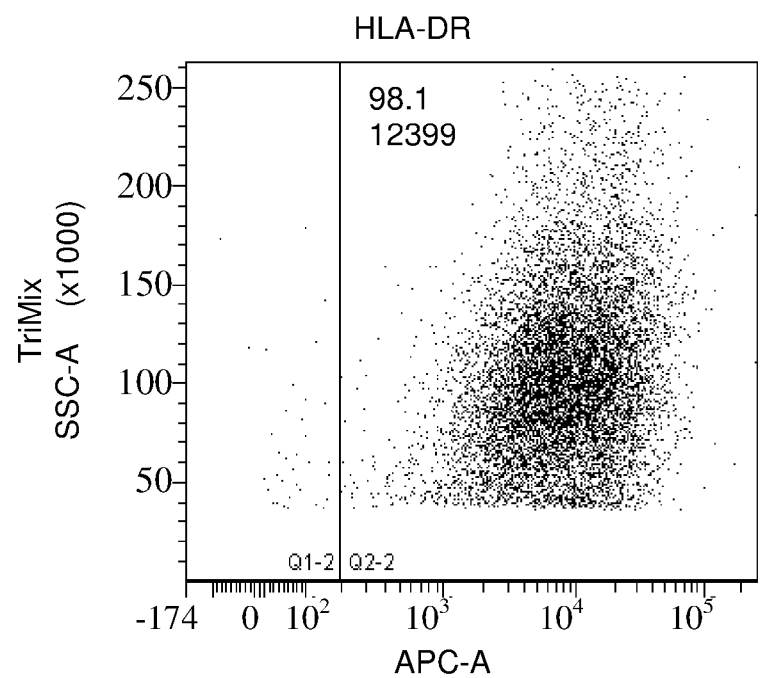

Figure 5B-8
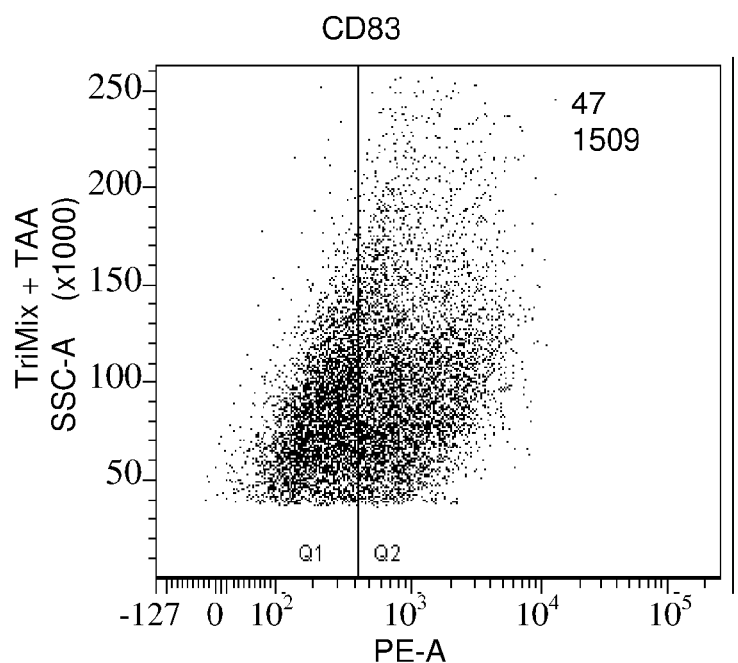
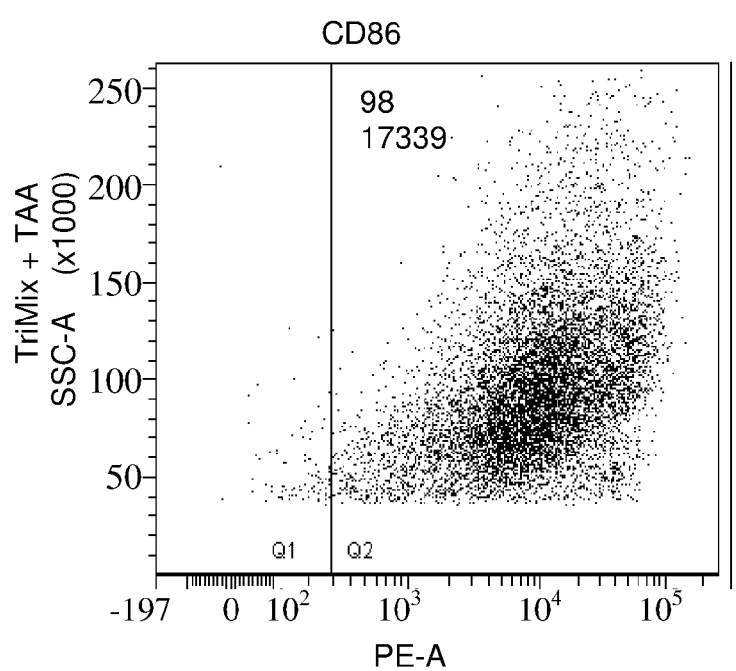

Figure 5B-9
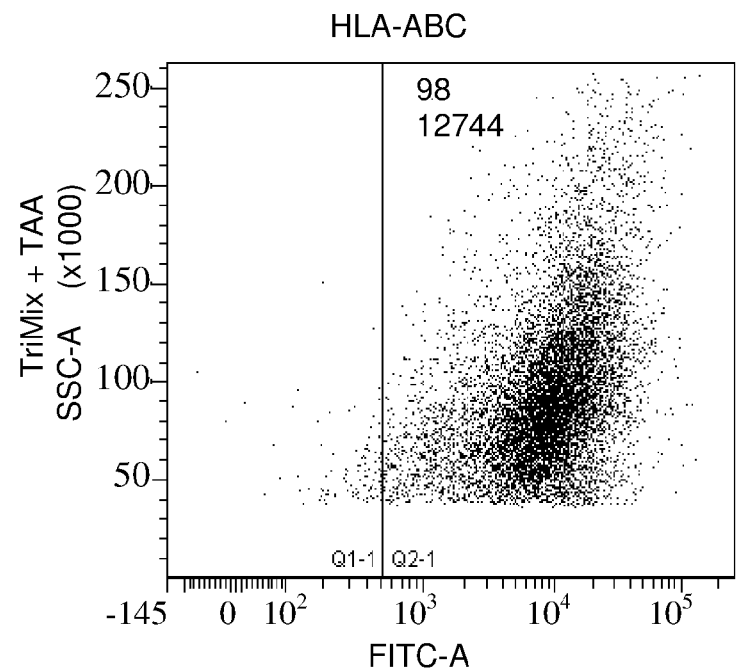
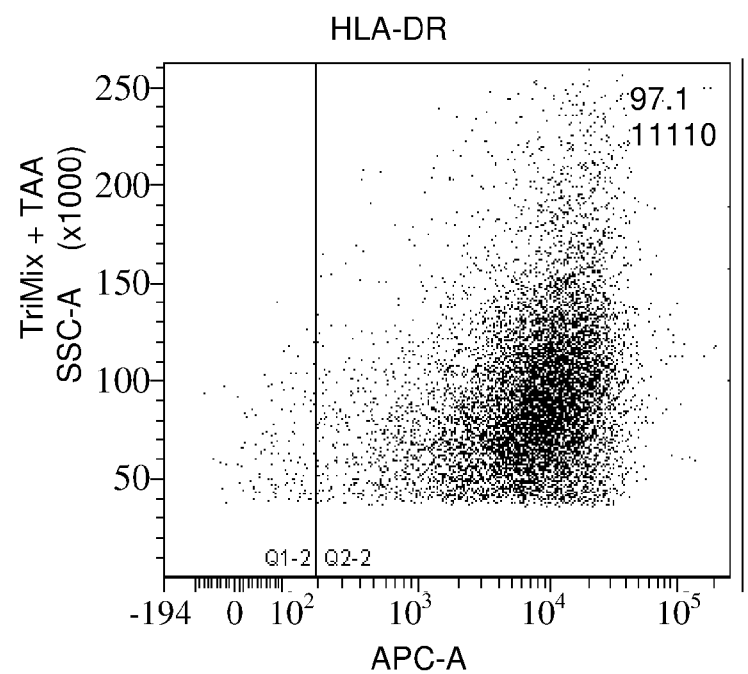

Figure 5B-10
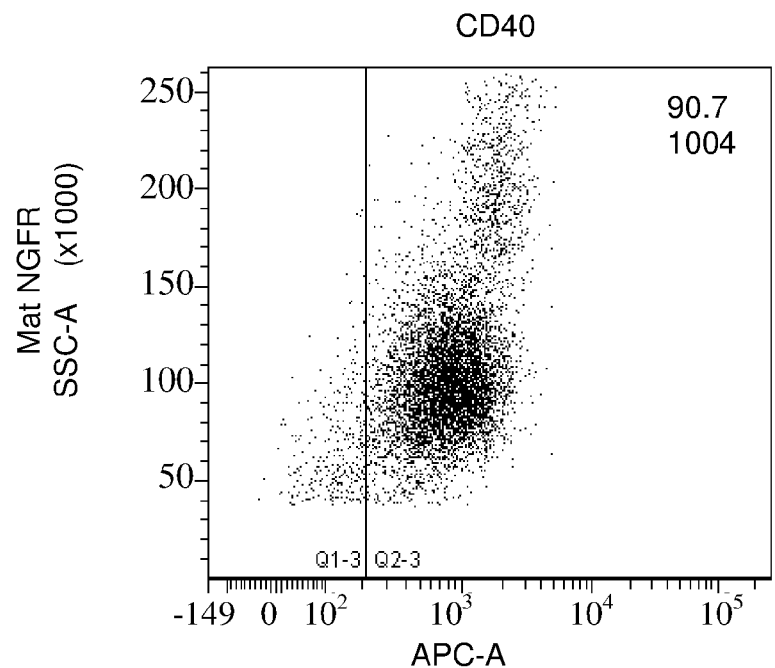
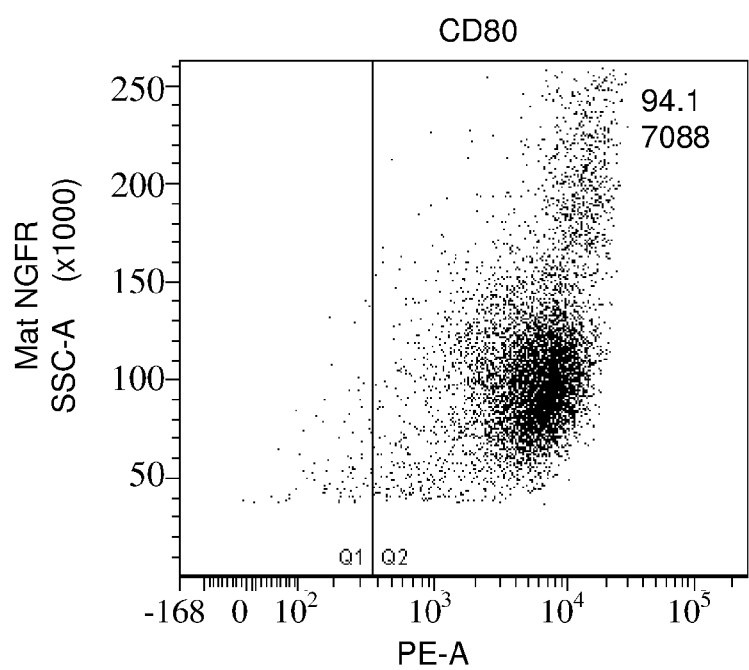

Figure 5B-11
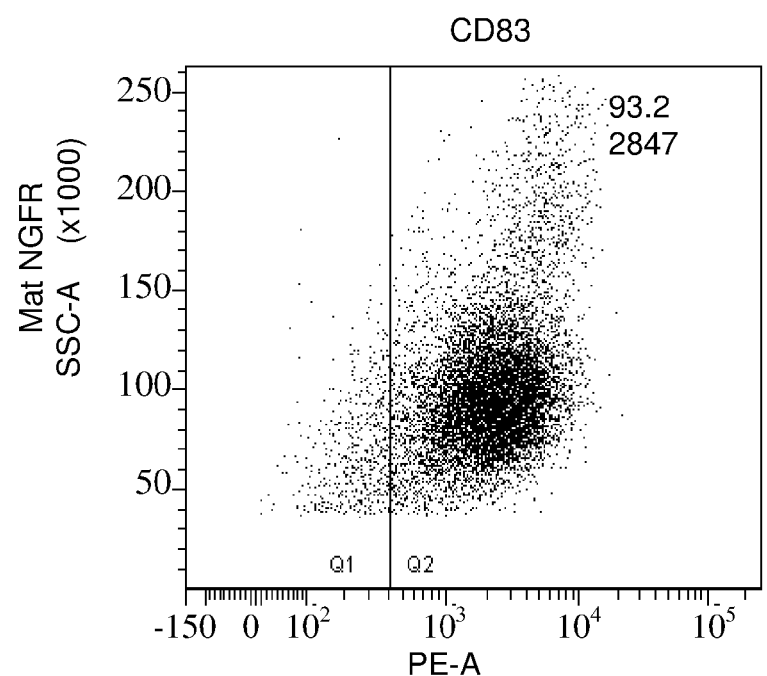
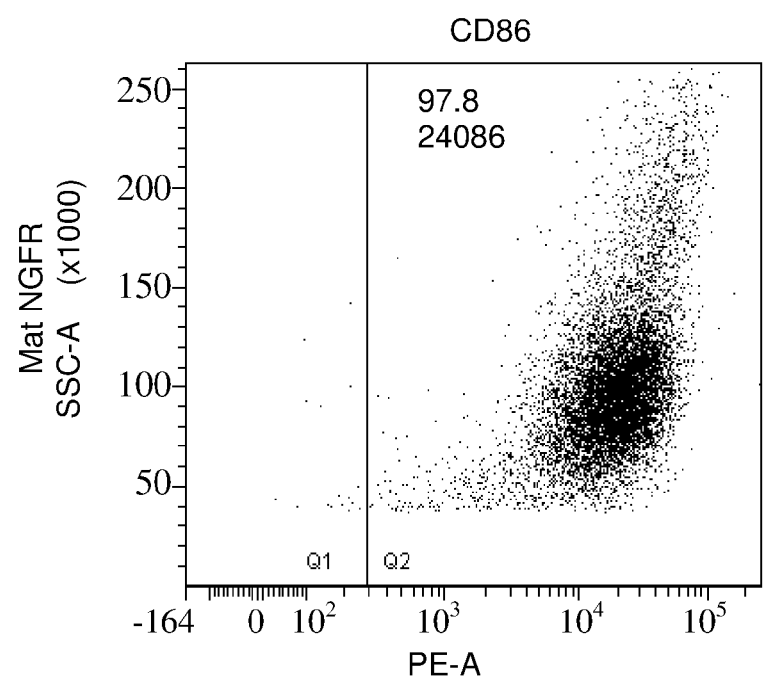

Figure 5B-12
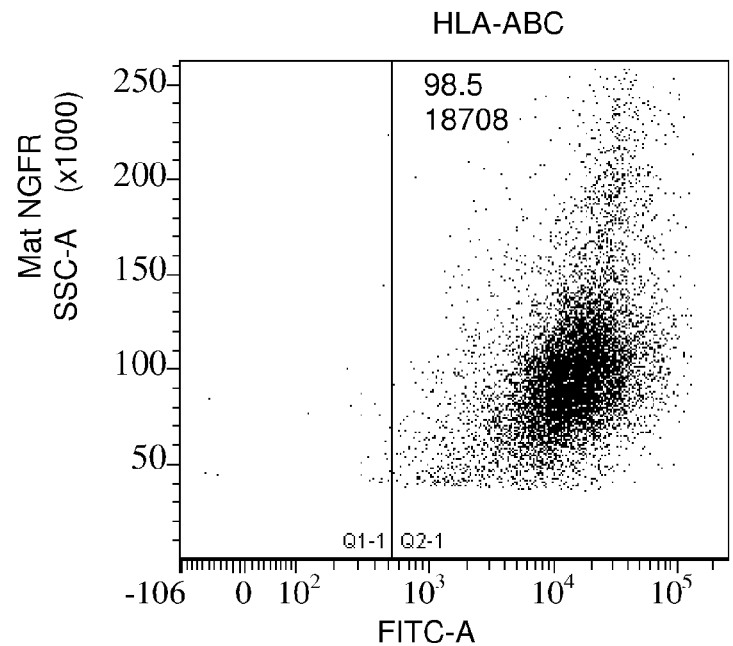
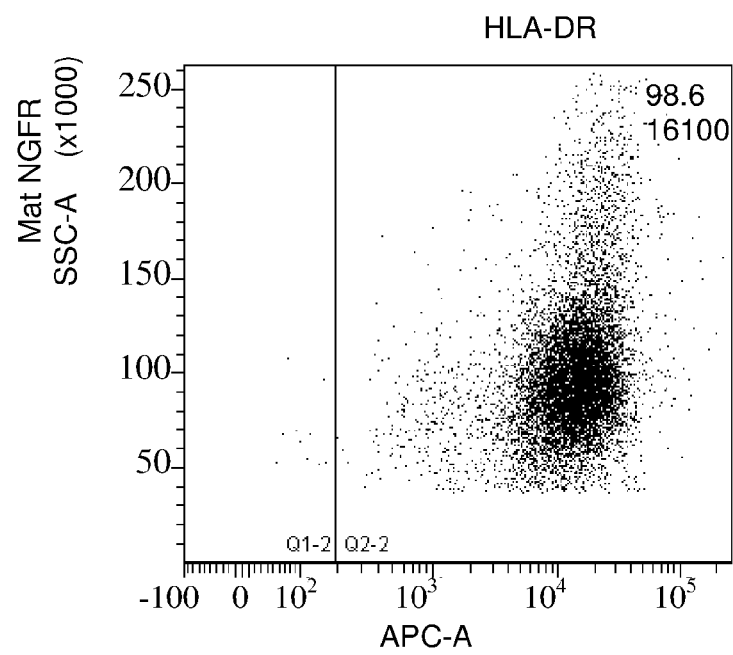

Figure 6B and C
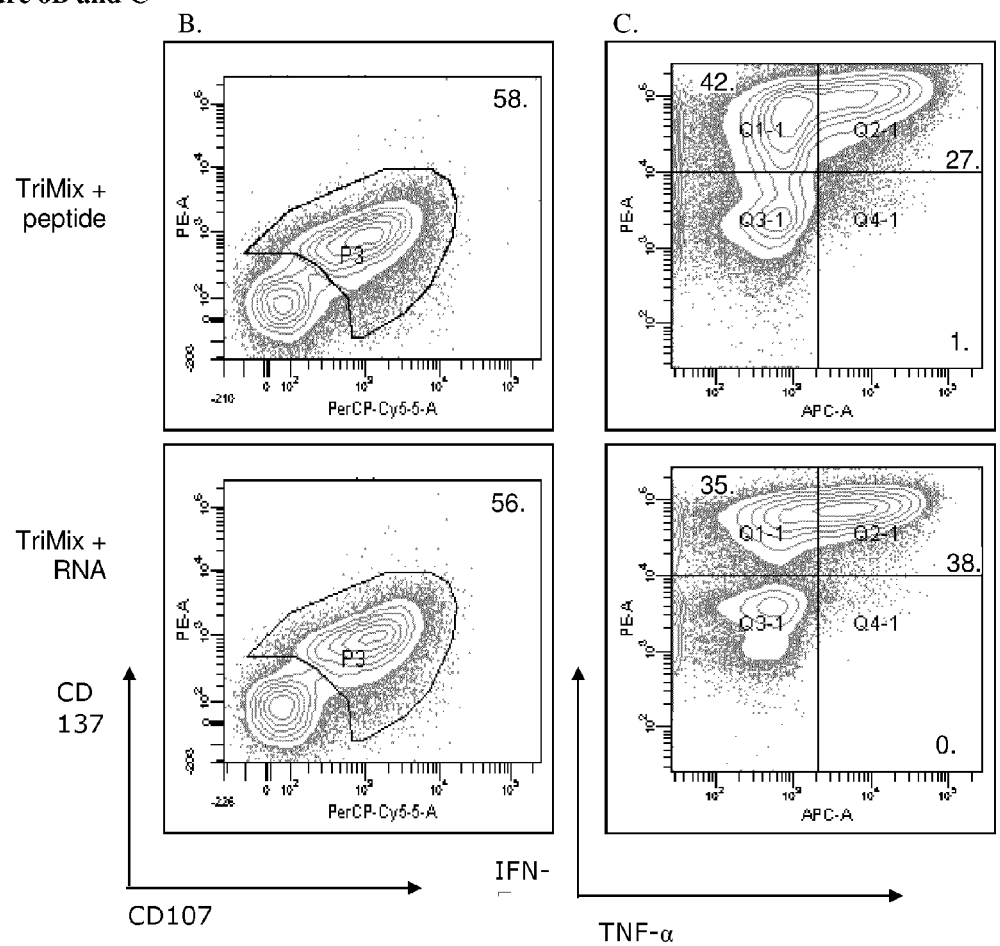

Patient 2 before vaccination: NGFR

Patient 2 before vaccination: MageA3

Figure 8B-2   Patient 2 before vaccination: MageC2
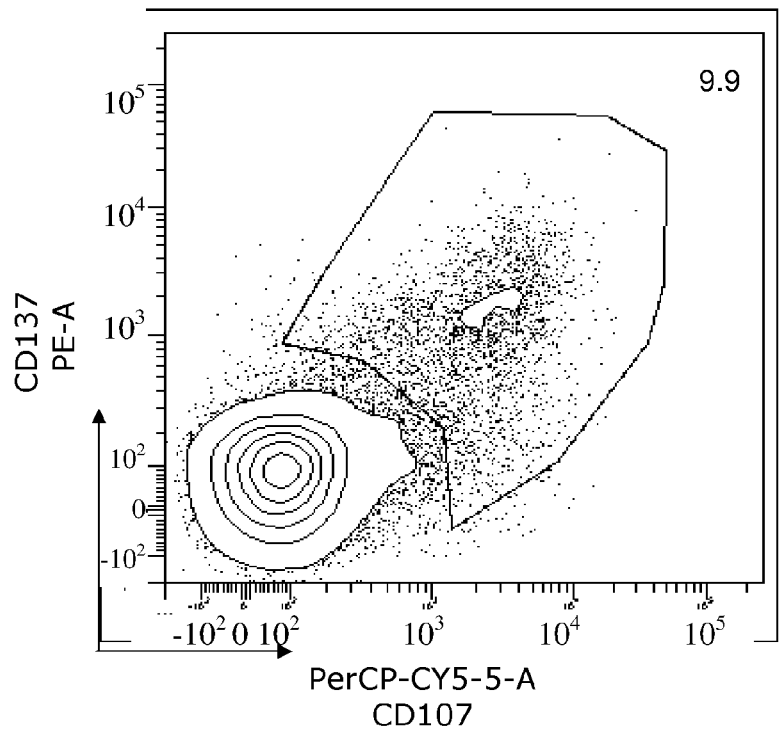
Patient 2 before vaccination: Tyrosinase
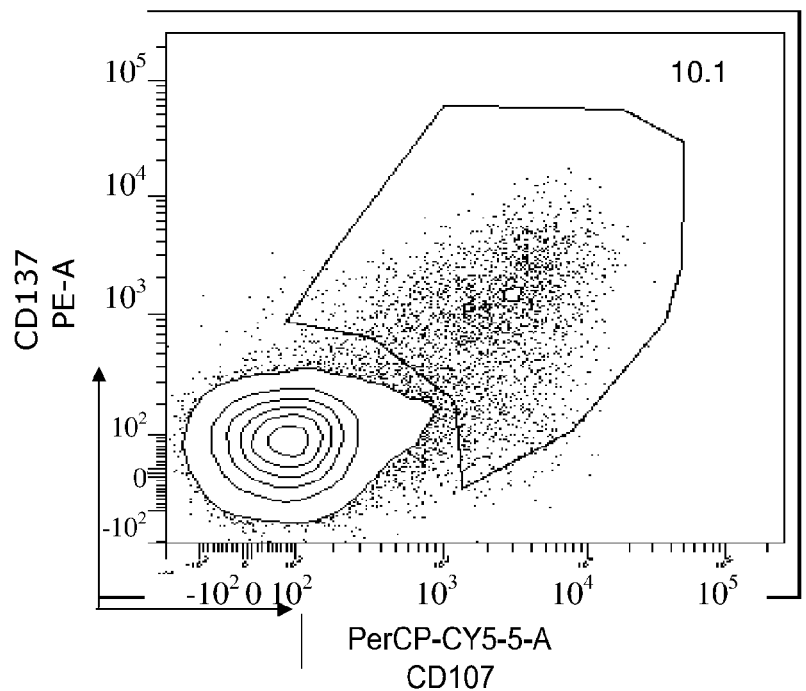

Figure 8B-11
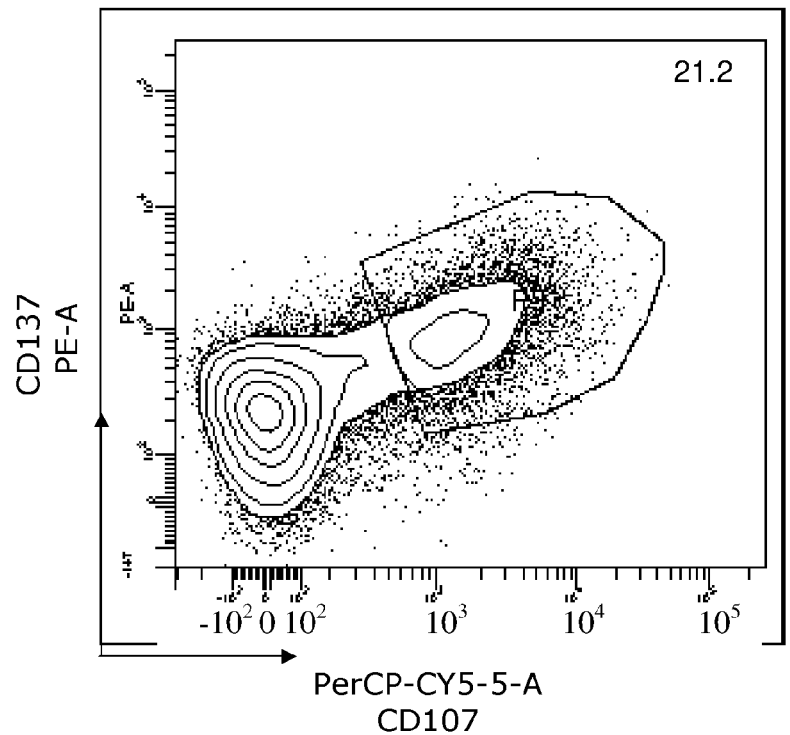
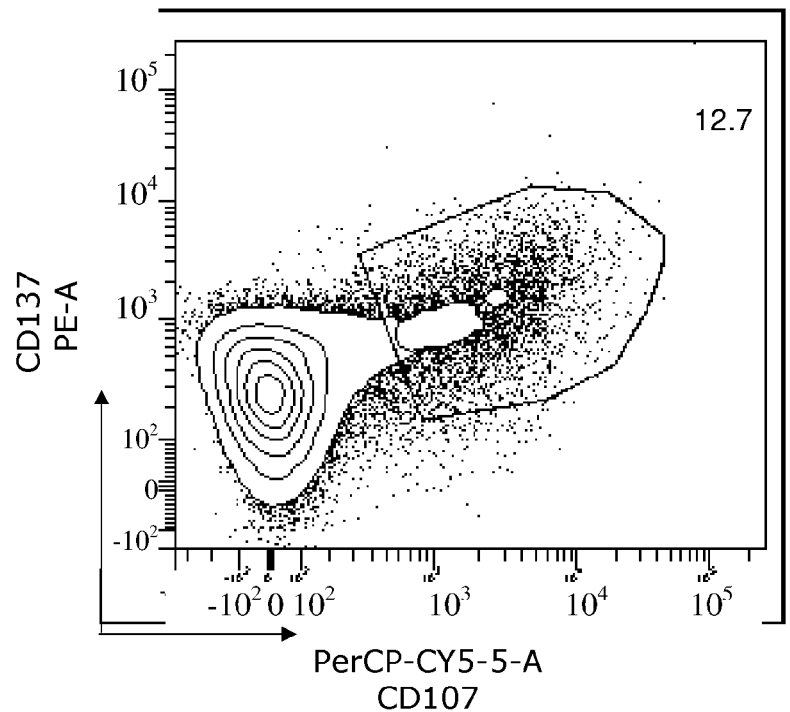

Patient 2 before vaccination: MageC2

Patient 2 before vaccination: Tyrosinase

Figure 8C-11
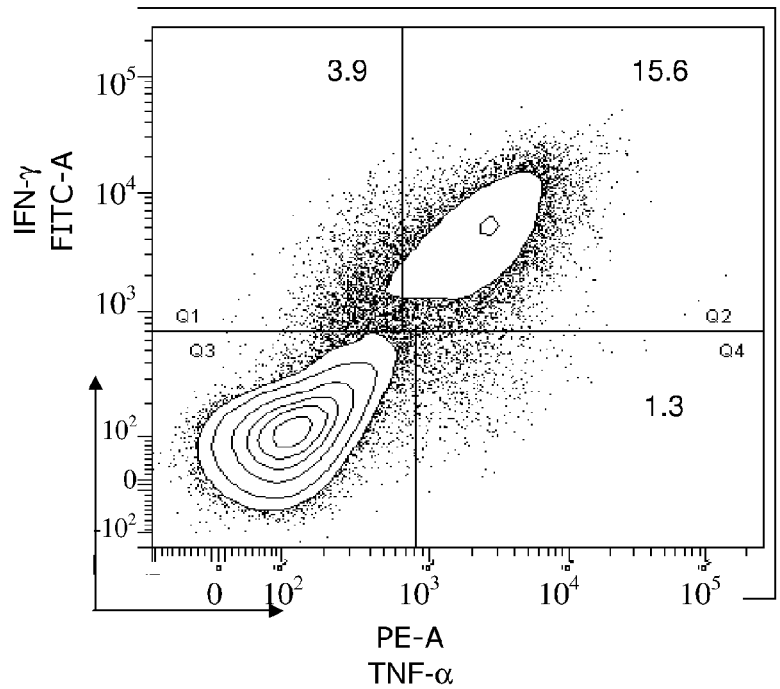
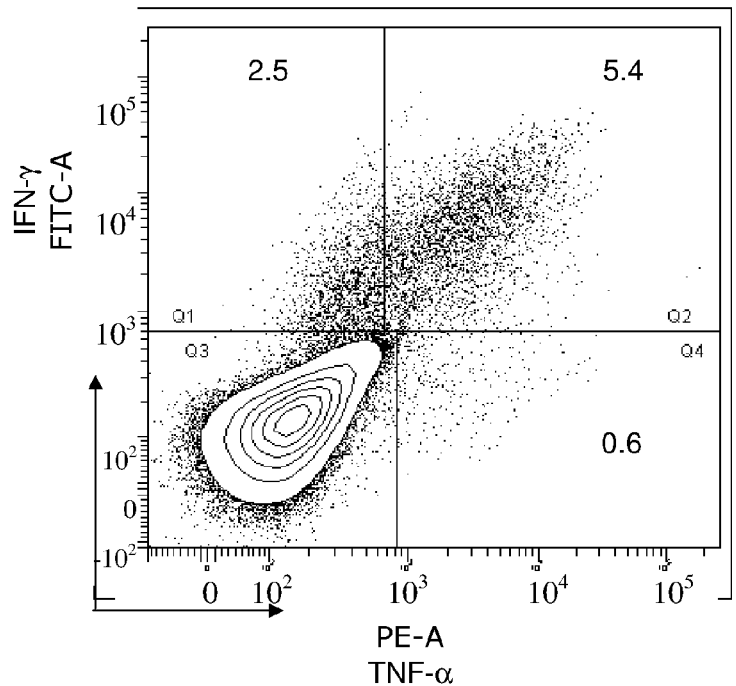

C

F

D

E

PBS              +              −
Diphteria toxin  −              +
FLuc mRNA        +              +

CD11c

High FLuc
mRNA
expression

High FLuc
mRNA
expression

TriMix          pp65 CMV-TriMix

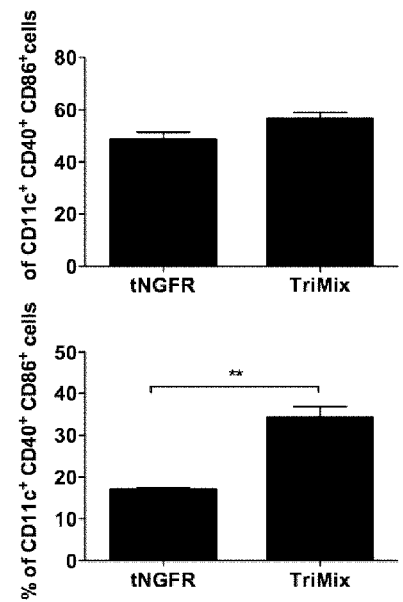
Figure 20
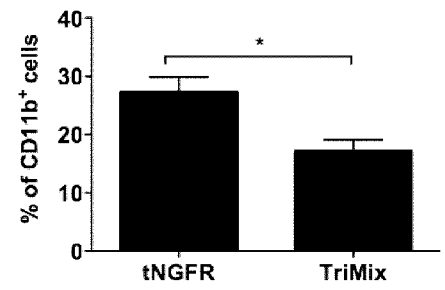 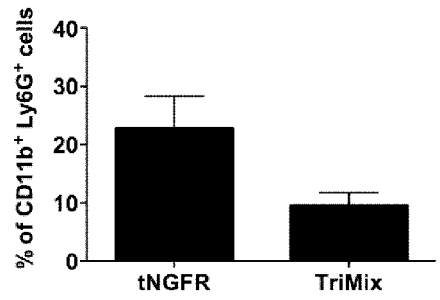
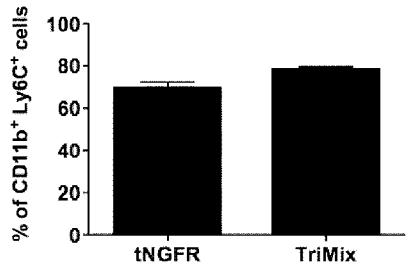

ENHANCING THE T-CELL STIMULATORY CAPACITY OF HUMAN ANTIGEN PRESENTING CELLS IN VITRO AND IN VIVO AND ITS USE IN VACCINATION

CROSS-REFERENCE TO RELATED APPLICATIONS

This application is a continuation-in-part of U.S. application Ser. No. 13/593,393, filed Aug. 23, 2012, which is incorporated herein by reference and which is the continuation-in-part of U.S. application Ser. No. 12/677,476, filed Mar. 10, 2010 and now patented as U.S. Pat. No. 8,476,419 on Jul. 2, 2013, which is the U.S. National Phase under 35 U.S.C. §371 of International Application PCT/EP08/62174, filed Sep. 12, 2008, which claims priority under 35 U.S.C. §119 (a)-(d) to Application No. PCT/EP2007/059732, filed Sep. 14, 2007.

REFERENCE TO SEQUENCE LISTING

This application incorporates by reference the sequence listing submitted as ASCII text filed via EFS-Web on Aug. 23, 2013. The Sequence Listing is provided as a file entitled "seq lst us decle69-12p2," created on Aug. 23, 2013, and which is approximately 3 kilobytes in size.

FIELD OF THE INVENTION

The invention is situated in the field of immunotherapy using antigen presenting cells (APCs) from a patient modified either in vitro or in vivo (in situ) so they are capable of presenting a target-specific antigen in the patient, leading to a host-mediated immune response to the target-expressing cells. The invention is especially related to increasing the immunostimulatory effect of the APCs either in vitro or in vivo (in situ) in view of vaccination of patients suffering from cancer or infectious disorders.

BACKGROUND OF THE INVENTION

Over the years, APCs such as Dendritic Cells (DCs) have emerged as key players in orchestrating immune responses and in particular in inducing primary responses in patients in general. Nowadays, DCs can be generated on a large scale in closed systems, yielding sufficient numbers of cells for use in clinical trials. Simultaneously, antigens derived from infectious microorganisms and many different tumor-associated antigens, which are either selectively or preferentially expressed by tumor cells have been identified. Also, a whole range of strategies to load DCs with such antigens have been designed. Together, these findings enabled the start of clinical studies with antigen-loaded DCs in cancer patients and in patients suffering from infections. Nonetheless, satisfying immunological responses and clinical outcomes are difficult to achieve.

One major problem using DCs loaded with a target-specific antigen as APCs is that they are insufficient for eliciting a strong immune response both in vitro and in vivo. One cause of this insufficient immunostimulation is the complicated in vitro manipulation of the DCs prior to their use, leading to loss of their characteristic properties such as secretion of cytokines and other factors triggering immune responses. Another problem is that artificially made DCs often do not express the necessary cellular markers on their cell-surface needed to activate a T-cell response to the target-specific antigen presented by the DCs thereby overcoming the often occurring T-cell tolerance towards the target-specific antigens.

Different approaches can be used to transfect DCs including an extensively studied ex vivo approach in which DCs are modified ex vivo with subsequent adoptive transfer of transfected DCs to the patient. Direct administration of mRNA and uptake in vivo is a more recent approach that has advantages over the ex vivo approach. The most important advantage is that it allows a decrease in the amount of manipulation steps and time. When antigens are administered in vivo, for example into the lymph nodes through intranodal injection, they are not easily presented by APCs such as DCs in an immunostimulatory fashion. When combining the in vivo approach with a maturation stimulus, for example through the stimulation of the DCs with e.g. LPS in order to mature them, this furthermore usually blocks the uptake and presentation of the actual antigens, resulting in poor antigen presentation of the target antigens.

It is therefore the object of the current invention to provide a solution to the above stated problems.

SUMMARY OF THE INVENTION

The inventors have established that the T cell stimulatory capacity of antigenic-peptide pulsed APCs or APCs can be greatly enhanced by providing them with specific molecular adjuvants in the form of a mixture of mRNA or DNA molecules encoding the immunostimulatory factor CD40L and one or more of CD70 and caTLR4, either in vivo or in vitro.

Said stimulation with immunostimulatory factors can be done in vitro, e.g. through co-electroporation or other means of introducing the mRNA or DNA molecules into the APCs, such as DCs. Said stimulation with immunostimulatory factors can also be done in vivo (in situ) through intranodal, intradermal, subcutaneous, intratumoral injection or intravenous administration of mRNA or DNA molecules encoding said immunostimulatory factors and optionally the tumor antigen mRNA, DNA or protein. Said mRNA or DNA can be naked or can be protected as described below. Said mRNA or DNA can be protected when administered for example intravenously.

It is known that the efficacy of immunization by mRNA administered into lymph nodes of subjects, e.g. through intranodal injection, depends on its uptake and its ability to create a cytotoxic T lymphocyte-inducing environment. The inventors have shown that these prerequisites are met through the codelivery of mRNA molecule(s) encoding the immunostimulatory factor CD40L and one or more of CD70 and caTLR4, as it allows antigen mRNA uptake, confers a high T-cell stimulatory capacity to DCs, and as such enhances their ability to stimulate antigen-specific immunity.

With prior art methods, antigen loading and maturation of DCs occurs in a consecutive fashion, which leads to either a reduced antigen loading efficiency or to DCs with a severely reduced cytokine secretion capacity (exhausted DCs). Using the methods and kits according to the present invention, mRNA encoding activation markers (e.g. TriMix) and antigen (either administered, or residing at the place of administering the mRNA encoding activation markers) are taken up simultaneously by resident immature DCs resulting in a contemporaneous maturation and antigen processing, thus ensuring that both processes occur in optimal circumstances. Maturation of the DCs and presentation of the antigens go hand in hand instead of excluding each other.

The inventors found that intranodal delivery of target antigen mRNA together with TriMix, (a mix of mRNA encoding CD40 ligand, constitutive active toll-like receptor 4 and CD70), results in the in situ modification and maturation of DCs hence priming of TAA-specific T-cells. Selective uptake and translation of mRNA in vivo by lymph node resident CD11c+ cells was shown. This process was hampered by co-delivery of classical maturation stimuli but not by TriMix mRNA. Importantly, TriMix mRNA induced a T-cell attracting and stimulatory environment, including recruitment of antigen-specific CD4+ and CD8+ T-cells and cytotoxic T lymphocytes (CTLs) against various TAAs. In several mouse tumor models, mRNA vaccination was as efficient in CTL induction and therapy response as vaccination with mRNA electroporated DCs.

The invention provides the proof of concept that such modified APCs pulsed with a target-specific peptide or co-electroporated with mRNA encoding a target-specific antigen can stimulate antigen-specific T cells both in vitro and after vaccination and thus form a promising new approach for anti-tumor, anti-viral, anti-bacterial or anti-fungal immunotherapy.

In addition, the invention provides proof of concept that direct administration of mRNAs encoding immunostimulatory factors CD40L, and CD70, caTLR4, or both, induces maturation of the APCs or DCs in situ, enabling them to present target specific antigens and elicit a genuine immune-response against the target. This was tested either using co-administration of target specific antigens, or without and it was found that the antigens present in the tumor environment were sufficient to provoke a specific immuneresponse towards said tumor. The inventors found that direct injection of the mRNAs encoding immunostimulatory factors CD40L, and CD70, caTLR4, or both into the tumor not only induced an immuneresponse towards said tumor, but also towards other, peripheral tumors.

The invention thus provides for a method for improving the immunostimulatory characteristics of APCs comprising the introduction of at least two different mRNA or DNA molecules encoding proteins that modify the functionality of the APCs. The invention hence also provides a method for loading APCs, preferably DCs with at least two different mRNA or DNA molecules encoding proteins that modify the functionality of the APCs. Said loading can be done in vitro through e.g. transfection or electroporation, or in vivo, through direct administration of said mRNA or DNA—either naked or in a protected form—in the subject or patient.

Preferably, said proteins are immunostimulatory factors CD40L and one or more of CD70 and caTLR4. More preferable, said proteins are the immunostimulatory factors CD40L, CD70 and caTLR4.

Optionally, one or more additional factors are introduced, selected from the group comprising or consisting of: secreted molecules such as IL-12p70, DC migration mediating molecules such as EL-selectin and CCR7, and/or further co-stimulatory molecules such as 4-1BBL.

Optionally, molecules influencing signaling pathways such as SOCS, STAT3, or A20, and/or molecules influencing inhibitory pathways such as PD-L1/PD-1/CTLA4 can be added to the APCs, preferably DCs.

In a specific embodiment, the antigen-specific stimulations are performed without the addition of any exogenous IL-2 and/or IL-7 to support T-cell proliferation and survival.

In certain embodiments, the APCs are additionally stimulated with soluble factors selected from the group comprising TLR ligands, IFN-gamma, TNF-alpha, IL-6, IL-1beta and/or PGE2.

Preferably, the method used for in vitro introduction of said mRNA or DNA molecules in APCs or DCs is selected from the group consisting or comprising of: (co)electroporation, viral transduction, lipofection and transfection of mRNA or DNA encoding the immunostimulatory antigens.

Preferably, the method used for in vivo (in situ) introduction of said different mRNA or DNA molecules in APCs or DCs is done by intranodal injection, intradermal injection, subcutane injection, intratumoral injection or by intravenous administration. For intradermal injection, or subcutane injection (and possibly also for intratumoral injection), pre-treatment can be done with for example GM-CSF, Flt3L or imiquimod to enhance the effect. For intravenous administration, the use of protected mRNA or DNA molecules is preferred.

The invention provides a method of vaccinating, or inducing an immune-response in a subject, by intranodal, intradermal, subcutaneous, intratumoral injection or intravenous administration of mRNA or DNA encoding the immunostimulatory factor CD40L and one or more of CD70 and caTLR4, optionally in combination with antigens or mRNA or DNA molecules encoding target-specific antigens, e.g. derived from a tumor cell, or from any infectious agent, such as a bacterium, a virus, a fungus, a toxin or venom, etc.

The invention also provides a method of treating an infection in a patient comprising the step of intranodal, intradermal, subcutane, or intratumoral injection intravenous administration of mRNA or DNA encoding the immunostimulatory factor CD40L and one or more of CD70 and caTLR4, optionally in combination with antigens or mRNA or DNA molecules encoding antigens derived from any infectious agent, such as a bacterium, a virus, a fungus, a toxin or venom, etc. Alternatively, the administration can be done at the site of infection. Adding the antigens or RNA or DNA molecules encoding them is optional because said antigens are present in circulation or at the site of infection.

The invention also provides a method of anti-cancer treatment of a patient comprising the step of intranodal, intratumoral, intradermal, subcutaneous, or intratumoral injection intravenous administration of mRNA or DNA encoding the immunostimulatory factor CD40L and one or more of CD70 and caTLR4, optionally in combination with antigens or mRNA or DNA molecules encoding tumor antigens. Adding the tumor antigens or RNA or DNA molecules encoding them is optional because said antigens are present in the tumor environment.

The invention further provides a method of improving antigen mRNA-based immunization of a subject, comprising the steps of administering mRNA or DNA encoding the immunostimulatory factor CD40L and one or more of CD70 and caTLR4 to said subject. Preferably, said administration is done in the lymph nodes, e.g. through intranodal injection. Alternatively, said administration is done intradermally, subcutaneously or intratumorally, through injection or done through intravenous administration. The antigens present at the site of administration will be effectively engulfed by the activated APCs and subsequently presented to the immune system, triggering a specific immune response.

The invention further provides a vaccine or composition comprising one or more mRNA or DNA molecules encoding the immunostimulatory factor CD40L and one or more of CD70 and caTLR4, optionally in combination with antigens or mRNA or DNA molecules encoding tumor antigens.

The invention further provides a method for preparing an immunotherapy agent comprising the steps of:
a) obtaining or providing APCs,
b) in vitro modifying said pool of APCs of step a) with at least 2 immunostimulatory molecules selected from the group comprising CD40L, CD70, caTLR4, IL-12p70, EL-selectin, CCR7, and/or 4-1 BBL; and/or SOCS, A20, PD-L1 or STAT3 inhibition, and c) in vitro modifying the pool of APCs from step b) such that they present target-specific antigen derived epitopes.

In preferred embodiments, the method of modification used in step b) and/or c) is selected from the group of electroporation, viral transduction, lipofection or transfection of mRNA or DNA encoding the immunostimulatory antigens.

Preferably, the specific immunostimulatory proteins and the target antigens are introduced through a one-step mechanism. In a preferred embodiment, co-electroporation of the mRNA or DNA encoding a target-specific antigen with the mRNA or DNA encoding the immunostimulatory factors, is used.

In another embodiment, protein or peptide pulsing is used to load the target-specific antigen or its derived antigenic peptides onto the APCs.

A preferred combination of immunostimulatory factors used in the methods of the invention is CD40L and CD70. In other preferred embodiments, the combination of CD40L, CD70 and caTLR4 immunostimulatory molecules is used, which is called the "TriMix" hereinafter.

The APCs used in the methods of the invention are selected from the group consisting of patient-specific DCs or B-cells; or established dendritic cell lines or B-cell lines.

The invention further provides a vaccine comprising the immunotherapy agent obtained by any of the methods of the invention mentioned above, further comprising pharmaceutically acceptable adjuvant(s).

In a specific embodiment, the immunotherapy agent is directed to a target-specific antigen which can be a tumor antigen, or a bacterial, viral or fungal antigen. Said target-specific antigen can be derived from either one of: total mRNA isolated from (a) target cell(s), one or more specific target mRNA molecules, protein lysates of (a) target cell(s), specific proteins from (a) target cell(s), or a synthetic target-specific peptide or protein and synthetic mRNA or DNA encoding a target-specific antigen or its derived peptides.

The invention further encompasses the use of a preparation of APCs obtained by the method of the invention or the immunotherapy agent obtained by the method of the invention in the manufacture of a vaccine capable of eliciting an immune response in a patient in need thereof.

The invention further provides for a method to screen for new target-specific epitopes that can be used for vaccination of patients, using APCs obtained by the immunostimulation method of the invention comprising;
a) stimulating T cells from healthy donors or patients (previously vaccinated or not with an anti-target vaccine) with APCs obtained by the immunostimulation method of the invention;
b) identifying T cells specific for the used target-antigen; and
c) identifying the target-antigen derived epitope for which the T cell is specific.

In addition, the invention provides for a method of following the effects of the treatment with an anti-target vaccine in a patient; comprising the detection and analysis of the immune response towards the target-specific antigen elicited in the subject previously injected with the anti-target vaccine obtained by any of the methods of the invention. In preferred embodiments, the patient is suffering from a disease or disorder selected from the group of: cancer, bacterial, viral or fungal infection, e.g. HIV infection or hepatitis.

The invention also provides a kit for improving the immunostimulatory characteristics of APCs comprising a combination of at least two different mRNA or DNA molecules encoding functional immunostimulatory proteins selected from the group consisting of CD40L, CD70, caTLR4, IL-12p70, EL-selectin, CCR7, and/or 4-1BBL, and optionally comprising molecules inhibiting SOCS, A20, PD-L1 or STAT3 expression or function. In a preferred embodiment, the kit comprises mRNA or DNA molecules encoding CD40L and CD70. In a more preferred embodiment, the kit of the invention can additionally comprise the mRNA or DNA encoding for the caTLR4, resulting in the so-called "TriMix". In certain embodiments, the kit of the invention comprises a single mRNA or DNA molecule, wherein said two or more mRNA or DNA molecules encoding the immunostimulatory proteins are combined. Preferably, the single mRNA or DNA molecule is capable of expressing the two or more immunostimulatory proteins simultaneously e.g. the two or more mRNA or DNA molecules encoding the immunostimulatory proteins are linked in the single mRNA or DNA molecule by an internal ribosomal entry site (IRES) or a self-cleaving 2a peptide encoding sequence.

In addition, the invention provides an ex vivo method of amplifying antigen-specific T-cells from a patient. The patient can be previously vaccinated or not. The amplified pool of T-cells can then be used for new or additional vaccination (boosting) of the patient. The invention thus provides a method for the ex vivo amplification of a pool of T-cells from a patient comprising;
a) obtaining T-cells from a patient who was vaccinated prior to the isolation or not
b) bringing the T-cells into contact with the immunotherapy agent of the invention, comprising APCs of the invention, and
c) identifying, isolating and expanding T-cells ex vivo that are specific for the antigen presented by the APCs they were contacted with. Optionally, the method comprises the following additional step:
d) administration of these in vitro stimulated and expanded antigen-specific T cells to the patient in a setting of adoptive T cell transfer.

The invention further provides for methods of using the modified APCs of the invention for treating neoplasms, cancer, infectious diseases such as viral, bacterial or fungal infections e.g. with HIV and hepatitis, or immunological disorders such as immunodeficiency, SCIPD, or AIDS. In cases of active immunotherapy for cancer or infectious or immunological diseases, the treatment with the vaccine, immunotherapy agent or APCs of the invention can be combined or followed by a non-specific treatment of immunomodulation in order to boost the immune system of the patient. In cases of cancer treatment, this can be anti-CTLA4 antibodies or IFN-alpha or other methods of immunomodulation in order to boost the immune system of the patient.

Providing the APCs such as DCs, B-cells, dendritic cell-lines, or B-cell-lines with a maturation signal through mRNA electroporation offers several advantages:

First there is no need to preincubate the APCs for up to 48 hours with soluble maturation signals like pro-inflammatory cytokines or TLR ligands to achieve activation of the antigen presenting cell, which can render the cells "exhausted" and inferior for vaccination purposes. As a result, APCs electroporated with mRNA or DNA encoding two or more immunostimulatory factors (e.g. the TriMix of CD40L, CD70 and caTRLA4), which can be injected into the patient within a few hours after electroporation, will mature and secrete most of their immunostimulatory cytokines and chemokines in situ.

Second, it has been postulated that maturation of APCs in situ resembles more closely the physiological process involved in response to pathogen infection, and therefore that in situ maturation may lead to enhanced T cell immunity. Pulsing said APCs with a target-specific peptide results in presentation of said peptide to the immune system of the patient.

Further, the inventors show that APCs electroporated with mRNA or DNA encoding two or more immunostimulatory factors (e.g. the TriMix of CD40L, CD70 and caTRLA4), can be co-electroporated with antigen-encoding mRNA instead of being pulsed with antigenic peptides. This approach offers several further advantages:

First, the maturation and antigen-loading of the APCs can be combined in one simple step. Obviating the peptide pulsing step in the vaccine production thus results in less manipulation of the cells and in less cell-loss and contamination-risk.

Second, by using full length antigen-encoding mRNA all possible antigenic epitopes of the TAA will be presented instead of some selected epitopes. Consequently, this strategy might induce a broader antigen-specific T cell response and it is not dependent on (the knowledge of) each patient's Human Leukocyte Antigen (HLA) type or on the prior identification of antigen-derived epitopes.

Third, the antigen-encoding plasmid can be genetically modified by adding an HLA class II targeting sequence. This not only routes the antigen to the HLA class II compartments for processing and presentation of HLA class II restricted antigen-derived peptides, but also enhances processing and presentation in the context of HLA class I molecules.

It was further established, that TriMix APCs (i.e. electroporated with mRNA encoding CD40L, CD70 and caTLR4) can almost equally well stimulate MelanA-specific T cells when co-electroporated with whole MelanA-encoding mRNA than when being pulsed with MelanA-derived peptide. Moreover, TriMix APCs can stimulate T cells specific for other antigens with a lower precursor frequency both in vitro and in vivo.

The invention thus provides for a method for inducing an antigen-specific immune response in a subject, comprising the step of administering to said subject:

a) one or more mRNA or DNA molecule(s) encoding the functional immunostimulatory proteins CD40L, CD70, and caTLR4.

In an embodiment, said method additionally comprises the step of administering target-specific antigen(s) before, after, or simultaneously with the one or more mRNA or DNA molecules added in step a).

Preferably, said mRNA or DNA molecules and optionally target-specific antigens are administered to the lymph node(s), to the tumor, or wherein said mRNA or DNA molecules are administered subcutaneously, intradermally or intravenously.

More preferably, said mRNA or DNA molecules and optionally target-specific antigens are administered through intranodal, intratumoral, subcutaneous or intradermal injection or through intravenous administration.

In a preferred embodiment, said target-specific antigen is a tumor antigen. Preferably, prior to said administration, the tumor was treated by ablation such as radiofrequency or cryoablation, thereby freeing antigens. In preferred embodiments, said immuneresponse leads to the treatment of a proliferative disorder.

In an alternative embodiment, said target-specific antigen is a bacterial, viral or fungal antigen. Preferably, said immuneresponse leads to the treatment of an infection or an inflammatory disorder.

In an embodiment, said target-specific antigen is selected from the group consisting of: total mRNA isolated from (a) target cell(s), one or more specific target mRNA molecules, protein lysates of (a) target cell(s), specific proteins from (a) target cell(s), a synthetic target-specific peptide or protein, and synthetic mRNA or DNA encoding a target-specific antigen or its derived peptide(s).

In an embodiment, said subject is suffering from a disease or disorder selected from the group consisting of: neoplastic disorders, infectious disorders, or immunological disorders.

In another embodiment, said subject is suffering from a disease or disorder selected from the group consisting of: tumor presence, cancer, melanoma presence, bacterial infection, viral infection, fungal infection, HIV infection, hepatitis infection, immunosuppression, SCID, and AIDS.

In a preferred embodiment, said method additionally comprises the administration of mRNA or DNA encoding one or more of the following molecules: IL-12p70, EL-selectin, CCR7, and/or 4-1BBL. In a further preferred embodiment, said method additionally comprises the administration of molecules inhibiting SOCS, A20, PD-L1 or STAT3 expression or function.

Preferably, said mRNA or DNA molecules encoding the immunostimulatory proteins are part of a single mRNA or DNA molecule. Preferably, the single mRNA or DNA molecule is capable of expressing the two or more proteins simultaneously. In one embodiment, the mRNA or DNA molecules encoding the immunostimulatory proteins are separated in the single mRNA or DNA molecule by an internal ribosomal entry site (IRES) or a self-cleaving 2a peptide encoding sequence. Optionally, said mRNA is protected.

The invention further provides for methods of treatment of a subject having cancer, being infected with an infectious agent, or suffering from an immunological disorder, comprising the administration of a vaccine comprising DCs that have been in vitro modified with the immunostimulatory factors such as CD40L, CD70 and/or caTLR4.

The invention also provides for a method of inducing an immuneresponse in a subject or a method of vaccinating a subject against an antigen, comprising the administration of a vaccine comprising DCs that have been in vitro modified with the immunostimulatory factors such as CD40L, CD70 and/or caTLR4.

Said administration can be done intravenously or intradermally, or through a combination thereof in any one of the methods using in vitro modified DCs according to the invention (e.g. TriMix-DCs).

Said methods of treatment or vaccination using in vitro modified DCs according to the invention (e.g. TriMix-DCs) can be combined with any other chemotherapeutic or otherwise beneficial treatment to said subject.

The in vivo modification of APCs or DC's, is also part of the invention and encompasses the direct administration of one or more mRNA or DNA molecule(s) encoding the immunostimulatory factor CD40L and one or more of CD70 and caTLR4.

Optionally, mRNA or DNA molecules encoding target-specific antigens can be administered as well.

The mRNA or DNA mentioned in any one of the embodiments defined herein can either be naked mRNA or DNA, or protected mRNA or DNA. Protection of DNA or mRNA increases its stability, yet preserving the ability to use the mRNA or DNA for vaccination purposes, since it is still able to be presented by APCs or DCs. Non-limiting examples of mRNA or DNA protection can be: liposome-encapsulation, protamine-protection, (Cationic) Lipid Lipoplexation, lipidic, cationic or polycationic compositions, Mannosylated Lipoplexation, Bubble Liposomation, Polyethylenimine (PEI) protection, liposome-loaded microbubble protection etc.

The administration of the components of the vaccine, immunotherapy agent, or composition can be done simultaneously or sequentially, i.e. components can be administered to the subject one at the time. For example, the mRNA or DNA molecules encoding CD40L, and caTLR4 or CD70 can be administered simultaneously together with the target antigen. Alternatively, the antigen can be added after a small time interval. In another embodiment, each mRNA or DNA molecule encoding an immunostimulatory factor (i.e. CD40L, caTLR4, and CD70) can be added sequentially, with a small time interval in between the subsequent administrations, followed or preceeded optionally by addition of the target antigen.

Similarly, the DCs or APCs can be in vitro modified by adding the components of the kit or composition simultaneously or sequentially, i.e. component can be added one at a time. For example, the mRNA or DNA molecules encoding CD40L, and caTLR4 or CD70 can be added to the APCs or DCs simultaneously together with the target antigen. Alternatively, the antigen can be added after a small time interval. In another embodiment, each mRNA or DNA molecule encoding an immunostimulatory factor (i.e. CD40L, caTLR4, and CD70) can be added sequentially to the APCs or DCs, with a small time interval in between the subsequent administrations followed or proceeded optionally by addition of the target antigen.

In addition, the inventors have seen that modifying APCs or DCs with the immunostimulatory agents also reduces the activity of regulatory T cells in vitro. Regulatory T cells are important mediators of peripheral tolerance, thus preventing the occurrence of autoimmune responses. During chronic infections and cancer these regulatory T cells accumulate and dampen the infection- or cancer-specific immune response. Reducing the activity of regulatory T cells at the site of infection or within the tumor environment is therefore highly beneficial, since it will increase the immune response towards the antigens present at the site of infection or within the tumor. We demonstrated that TriMix mRNA modified human DCs do not induce Treg induction starting from CD4$^+$ CD25$^-$ T cells. More importantly, the stimulation of CD8$^+$ T cells by TriMix-DCs was only marginally influenced by the presence of Tregs. In addition, we observed that CD8$^+$ T cells that had been pre-cultured with TriMix-DCs were partially protected against subsequent Treg suppression. Besides desensitization of CD8$^+$ T cells to Tregs, we further showed that Tregs co-cultured in the presence of TriMix-DCs partially lost their suppressive capacity, a phenomenon that was accompanied by a decrease in CD27 and CD25 expression on these Tregs, as well as an increase in the expression of the transcription factor T-bet and secretion of cytokines linked to a $T_H1$ phenotype.

Thus, the invention provides mRNA or DNA molecules encoding CD40L, and caTLR4, CD70, or both, which can be used to locally reduce the activity of Regulatory T cells, comprising the step of administering said mRNA or DNA molecules to the subject, preferably to the site of infection or to the tumor, or intranodally or intradermally.

Alternatively, the invention therefore further provides for a method of locally reducing the activity of regulatory T cells, comprising the step of administering antigen-presenting or DCs modified by introduction of mRNA or DNA molecules encoding CD40L, and caTLR4, CD70, or both, to the site of infection or to the tumor.

The invention further provides antigen-presenting cells or DCs modified by introduction of mRNA or DNA molecules encoding CD40L, and caTLR4, CD70, or both, for use in locally reducing the activity of regulatory T cells, comprising the step of administering said antigen-presenting cells or DCs to the site of infection or to the tumor.

The following section will describe the invention in more detail.

DESCRIPTION OF THE FIGURES

FIG. 4. FIG. 4B-1 to 4B-4.

Cytolytic activity of MelanA-specific T-cells was determined by a CD107a mobilization assay. Primed T-cells were restimulated with T2 cells pulsed with gag or MelanA peptide in the presence of anti-CD107-PE-Cy5mAb and Golgi-stop. After overnight culture, cells were harvested, stained with anti-CD8-FITC and analyzed by flow cytometry. T-cells were gated on FSC/SSC characteristics and CD8 positivity. FIG. 4C-1 to 4C-4. Intracellular IFN-gamma/TNF-alpha production by MelanA primed CD8$^+$T-cells was measured by flow cytometry. Primed T-cells were restimulated with T2 cells pulsed with gag or MelanA peptide in the presence of Golgi-plug. After overnight culture, T-cells were stained for CD8, IFN-gamma and TNF-alpha positivity. T-cells were gated on FSC/SSC characteristics and CD8 positivity. The percentage of IFN-gamma and/or TNF-alpha secreting cells is given, after subtraction of background response induced by T2 pulsed with gag peptide. Results in panels (B) and (C) are given for Experiment 2 (see Table 2). The percentage of MelanA-A2 tetramer positive cells is indicated. For all other experiments, CD107a positivity and IFN-gamma/TNF-alpha secretion correlated with the percentage of MelanA-specific T-cells present in the culture. FIG. 4D-1 to 4D-3. Phenotype of MelanA-specific CD8$^+$T-cells. T-cells were stained for CD8 and MelanA-A2 tetramer positivity in combination with the following T-cell markers: CD45RA, CD45RO, CD27, CD28, CCR7 and CD62L. Results are shown for the MelanA-specific CD8$^+$T-cells induced by DCs electroporated with CD4OL, CD70 and caTLR4mRNA and are representative for all MelanA-specific CD8$^+$T-cells, irrespective of which DCs were used for stimulation.

FIG. 5A-1 to 5A2. DCs were electroporated with TriMix (mRNA encoding CD4OL, CD70 and caTLR4) mRNA alone or in combination with tumorantigen mRNA. Twenty-four hours later, electroporation efficiency was investigated by staining for surface CD70 expression. Immature DCs electroporated with irrelevant NGFR mRNA were used as negative control. Results are representative for at least 5 independent experiments. FIG. 5B-1 to 5B-12. Twenty-four hours after electroporation, DCs were stained for costimulatory molecules CD40, CD80, CD83and CD86 and for HLA class I and II molecules. Percentage of positive cells and mean fluorescence intensity are indicated. Phenotype is compared to immature and cytokine cocktail matured DCs electroporated with irrelevant NGFR mRNA. Results are representative for at least 5 independent experiments.

FIG. 6. In vitro induction of HLA-A2 restricted MelanA-specific CD8$^+$ T cells, activated/cytolytic CD8$^+$ T cells and IFN-gamma/TNF-alpha secreting CD8$^+$ T cells by DCs electroporated with TriMix mRNA (mRNA encoding CD40L, CD70 and caTLR4) pulsed with antigenic peptide or co-electroporated with tumorantigen mRNA. (A) Naive CD8$^+$ T cells were stimulated 3 times, with a weekly interval with TriMix DCs, i.e. DCs electroporated with a mixture of mRNA molecules encoding CD40L, CD70 and caTRLA4 immunostimulatory proteins). Every week, T cells were counted, stained for CD8 and MelanA specificity and the absolute number of MelanA-specific CD8$^+$ cells present in the culture was calculated. Relative percentage in comparison with the number of MelanA-specific CD8$^+$ T cells obtained after 3 stimulations with TriMix DCs pulsed with MelanA-A2 peptide (set at 100%) is shown. (B) Activation status and cytolytic activity of MelanA-specific T cells was determined by a CD137/CD107a assay. Primed T cells were restimulated with T2 cells pulsed with gag or MelanA peptide in the presence of anti-CD107-PE-Cy5 mAb and Golgi-stop. After overnight culture, cells were harvested, stained with anti-CD8-FITC, CD137-PE and analyzed by flow cytometry. T cells were gated on FSC/SSC characteristics and CD8 positivity. The percentage of CD137/CD107a double positive cells is given, after subtraction of background response induced by T2 pulsed with gag peptide. (C) Intracellular IFN-gamma/TNF-alpha production by MelanA primed CD8$^+$ T cells was measured by flow cytometry. Primed T cells were restimulated overnight with T2 cells pulsed with gag or MelanA peptide in the presence of Golgi-plug. Then, T cells were stained for CD8, IFN-gamma and TNF-alpha positivity. T cells were gated on FSC/SSC characteristics and CD8 positivity. The percentage of IFN-gamma and/or TNF-alpha secreting cells is given, after subtraction of background response induced by T2 pulsed with gag peptide. Results in panels B and C are given for Experiment 1 (see Table 3). In each experiment, CD137/CD107a positivity and IFN-gamma/TNF-alpha secretion correlated with the percentage of MelanA-specific T cells present in the culture.

FIG. 7. CD4$^+$ T cell stimulatory capacity of TriMix DCs pulsed with antigenic peptide or co-electroporated with tumorantigen mRNA. DCs were either pulsed with Mage-A3-DP4 peptide or co-electroporated with MageA3-DCLamp mRNA. Four hours later, the cells were cocultured with Mage-A3-specific, HLA-DP4-restricted T cells for 20 h. Immature DCs electroporated with irrelevant NGFR mRNA were used as a negative control. IFN-gamma production is shown. Each dot represents one individual experiment and the mean is indicated by a horizontal line.

FIG. 8. Induction of CD8$^+$T cells specific for other antigens than MelanA in melanoma patients both in vitro and in vivo. FIG. 8A-1 to 8A-3. TriMix DCs as prepared for vaccination were used to stimulate CD8$^+$T cells isolated from the blood of HLA-A2$^+$melanoma patients prior to vaccination. Cytokine cocktail matured DCs pulsed with HLA-A2restricted, Mage-A3, Mage-C2, Tyrosinase or gp100-specific peptide were used as control. After 3 weekly stimulations, the cells were stained with a panel of HLA-A2 tetramers loaded with different Mage-A3, Mage-C2, Tyrosinase or gp100-specific peptides and anti-CD8 Ab. TAA-specific CD8$^+$T cells were then identified by flow cytometry. Background staining with NY-ESO-1-specific HLA-A2 tetramers was subtracted. FIG. 8B-1 to 8B-12. Activation status and cytolytic activity of CD8$^+$T cells from melanoma patients before or after vaccination with TriMix DCs was determined by a CD107a/137 assay. CD8$^+$T cells isolated from the blood of HLA-A2$^+$ melanoma patients before or after vaccination with TriMix DCs were stimulated 2 times in vitro with the same DCs as used for vaccination. One week after the last stimulation, cells were restimulated overnight with mature DCs electroporated with TAA mRNA or NGFR as irrelevant control in the presence of anti-CD107-PE-Cy5 mAb and Golgi-stop. Cells were harvested, stained with anti-CD8-FITC, CD137-PE and analyzed by flow cytometry. T cells were gated on FSC/SSC characteristics and CD8 positivity. The percentage of CD137/CD107a double positive cells is given. FIG. 8C-1 to 8C-12. Cytokine production of CD8$^+$T cells from melanoma patients before or after vaccination with TriMix DCs was determined by intracellular cytokine staining. CD8$^+$T cells isolated from the blood of HLA-A2$^+$melanoma patients before or after vaccination with TriMix DCs were stimulated 2 times in vitro with the same DCs as used for vaccination. One week after the last stimulation, cells were restimulated overnight with mature DCs electroporated with TAA mRNA or NGFR as irrelevant control in the presence of Golgi-plug. Then, T cells were stained for CD8, IFN-gamma and TNF-alpha positivity. T cells were gated on FSC/SSC characteristics and CD8 positivity. The percentage of IFN-gamma and/or TNF-aplha secreting cells is given.

FIG. 9. DCs matured through electroporation of TriMix efficiently stimulate antigen-specific T cells. The histogram overlays in (A) show the phenotype of DCs electroporated with tNGFRmRNA and left immature or matured by coelectroporation of TriMix or addition of LPS (n=10). The graphs in (B) show the cytokines secreted by these DCs (n=6). The graph in (C) depicts the incorporation of 3H thymidine by allogeneic spleen cells cultured with these DCs (n=3). D-F, mice were immunized intravenously with 5×105 DCs electroporated with OVA mRNA and matured by coelectroporation of TriMix mRNA or addition of LPS. Five days later, the expansion of functional OVA-specific CD8$^\pm$ T cells was assessed. The results of (D) the pentamer staining, (E) the in vivo cytotoxicity assay, and (F) the intracytoplasmatic staining of IFN-gamma on spleen cells restimulated with SIINFEKL-presenting DCs are shown (n=2). G, mice, immunized with Trp2-presenting DCs, were subjected to an in vivo cytotoxicity assay to evaluate the stimulation of Trp2-specific CD8$^+$ T cells (n=2).

FIG. 10. Formulation and pharmacokinetics of mRNA. A, mouse DCs were pulsed with FLuc mRNA in the indicated buffer. Luminescence was measured 4 hours later. The graph depicts the photon emission (n=4). B and C, mice were injected intranodally with FLuc mRNA. B, in vivo bioluminescence imaging was conducted at the indicated time points (n=4). C, to evaluate the stability of FLuc mRNA in vivo, lymph nodes were isolated 6, 12, and 24 hours after injection and PCR carried out on cDNA synthesized from extracted mRNA (n=4). D, mice received an intranodal injection of eGFP mRNA formulated in 0.8 RL. Four hours later, the lymph node was resected, a single-cell suspension prepared and stained for CD11c. The photograph obtained by fluorescence microscopy shows eGFP (green) expression by CD11c$^\pm$ cells (red, n=4). E, transgenic CD11c-DTR mice, which were pretreated with PBS or DT, received an intranodal injection with FLuc mRNA. In vivo bioluminescence imaging was conducted 4 hours later. Single-cell suspensions were prepared from the lymph nodes and analyzed by flow cytometry for the presence of CD11c$^\pm$ cells (n=3). F, mice, of which the skin was pretreated with PBS or GM-CSF, were injected intradermally with FLuc mRNA. In vivo bioluminescence imaging was conducted 6 hours later (n=3).

FIG. 11. Intranodal delivery of TriMix generates an immunostimulatory environment. A and B, DCs were pulsed with FLuc mRNA in the presence of activation stimuli after which uptake of mRNA and the DCs' phenotype was analyzed (n=4). The graph in (A) shows the photon emission as mean SEM of 4 experiments. The histogram overlays in (B) show the expression of CD70, CD40, CD80, and CD86 by DCs pulsed in the absence of a maturation stimulus, in the presence of LPS, poly[I:C], or TriMix. C, mice were injected intranodally with FLuc mRNA alone or combined with TriMix or LPS after which in vivo bioluminescence imaging was conducted (n=5). D, activation of DCs in mice pretreated with Flt3-L and injected with FLuc mRNA alone or combined with LPS or TriMix was evaluated by flow cytometry. The histograms depict the expression of CD40, CD80, and CD86 by CD11c$^\pm$ cells obtained from lymph nodes injected with FLuc mRNA alone or the latter together with TriMix mRNA or LPS (n=3).

FIG. 12. Intranodal delivery of TriMix but not LPS together with OVAmRNA results in Ssimulation of OVA-specific CD4$^\pm$ and CD8$^\pm$ T cells. CFSE-labeled CD4$^\pm$ OT-II or CD8$^\pm$ OT-I cells were adoptively transferred 1 day before immunization of mice with tNGFR mRNA, OVA mRNA alone, or combined with TriMix or LPS. The amount of mRNA was kept constant by addition of tNGFR mRNA. Five days postimmunization, stimulation of T cells within the lymph node was analyzed. A, proliferation of CD4$^\pm$ OT-II cells was analyzed by flow cytometry (n=3). B and C, stimulation of CD8$^\pm$ OT-I cells was analyzed by (B) pentamer staining (n=5) and (C) in vivo cytotoxicity assay (n=3). D, stimulation of CTLs after immunization with OVA and Tri-Mix mRNA either delivered intradermally in mice pretreated with GM-CSF or intranodally was analyzed by in vivo cytotoxicity assay (n=2).

B) A human lymph node of a non-heartbeating organ donor was injected with 50 µg FLuc mRNA dissolved in Ringer Lactate. After 4 h of incubation in PBS, in vivo bioluminescence imaging was performed to obtain bioluminescent images, in which high luminescence [a measure for the amount of FLuc+ cells] is shown by the arrow.

Figure 16:
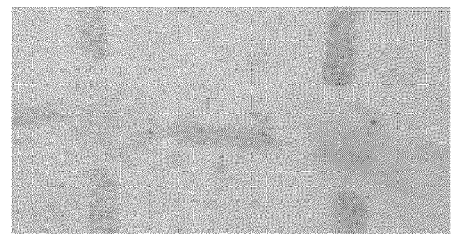
Figure 16:
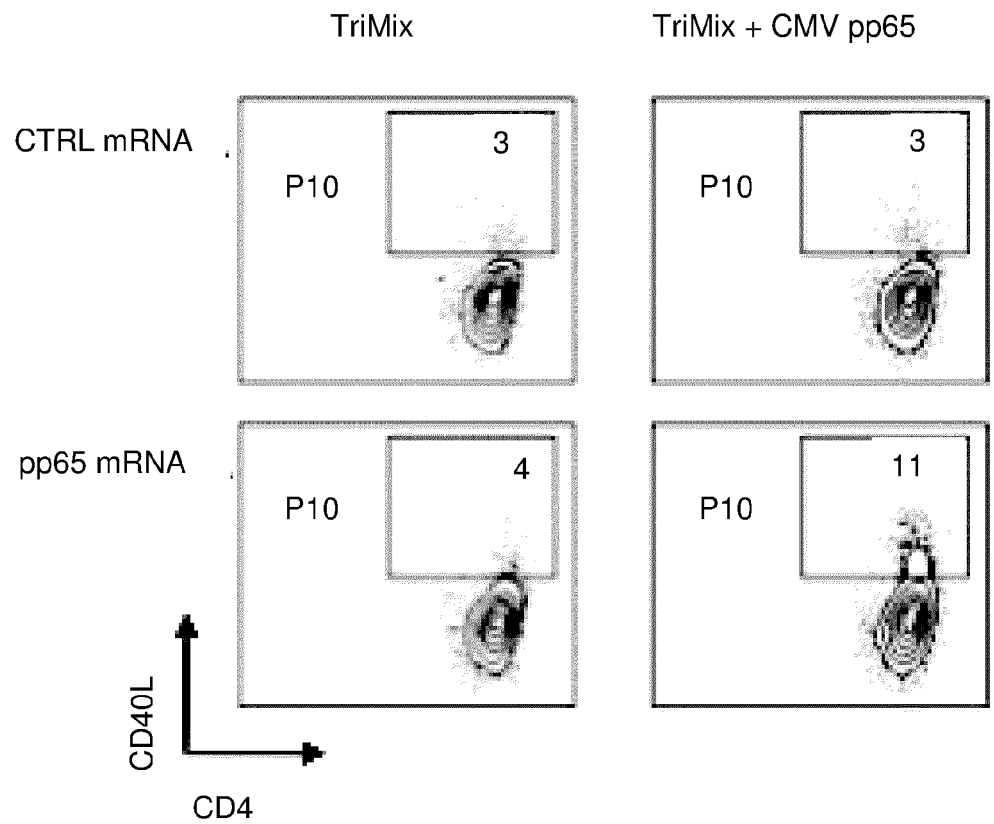

FIG. 16. Intradermal injection of TriMix mRNA and CMV pp 65 mRNA stimulates a specific immune response. TriMix mRNA alone or in combination with pp 65 CMV mRNA was injected intradermally in the lower back of a subject. A) 72 h after injection, a DTH reaction is visible on both injection places (redness and induration), but more pronounced where the CMV antigen is present. B) A CMV-specific CD4+ T cell response was observed in the cells derived from a skin biopsy after injection of TriMix+CMV mRNA.

Figure 17:
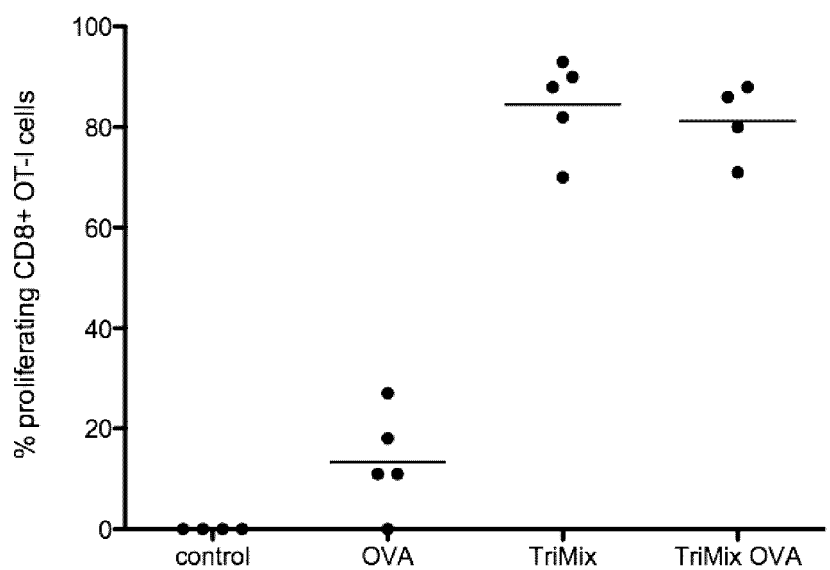

FIG. 17. Intratumoral delivery of TriMix results in the induction of antigen-specific immune responses. CFSE-labeled CD8+ OT-I cells were adoptively transferred 1 day before immunization of mice with tNGFR mRNA, OVA or TriMix mRNA alone, or its combination. Five days postimmunization, stimulation of T cells within the tumor was analyzed. Proliferation of CD8+ OT-I cells was analyzed by flow cytometry.

Figure 18:
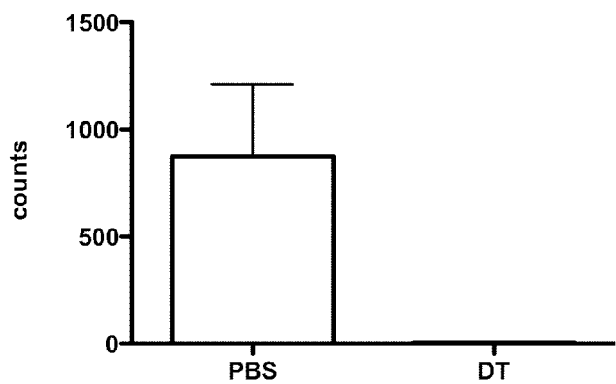
Figure 18:
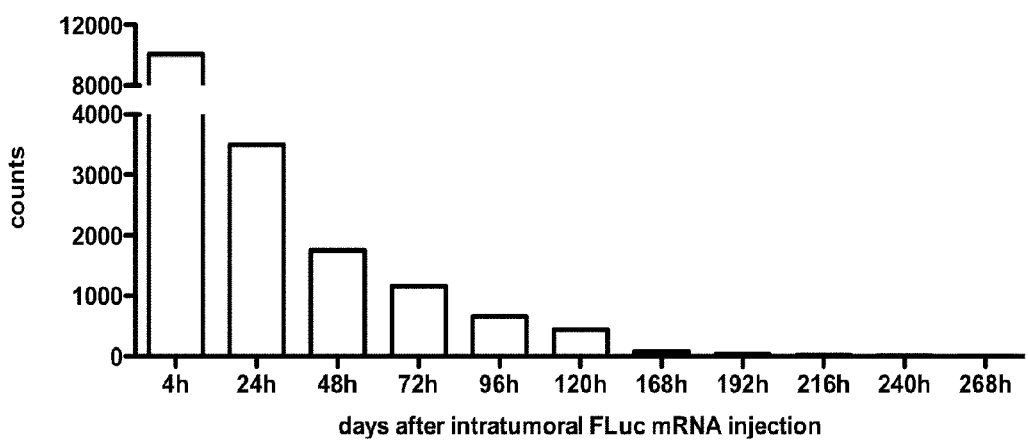

FIG. 18. Tumor-resident CD11c+ cells engulf intratumorally administered mRNA. Transgenic CD11c-DTR mice, which were pre-treated with PBS or DT, received an intratumoral injection with FLuc mRNA. In vivo bioluminescence imaging was performed 4 hours after administration of FLuc mRNA. Subsequently single cell suspensions were prepared from the tumors and analyzed by flow cytometry for the presence of CD11c+ cells (A). Kinetics of bioluminescence was performed until 11 days after intratumoral injection (B).

Figure 19A:
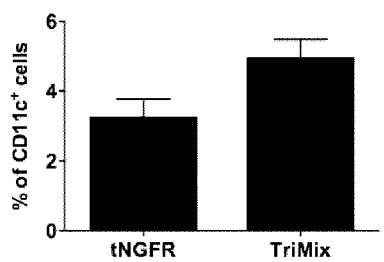
Figure 19B:
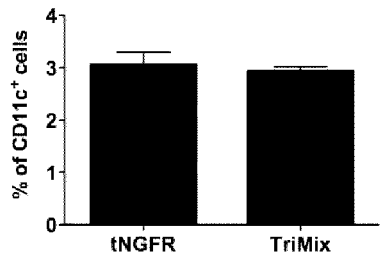

FIG. 19. The tumor environment of mice treated with TriMix mRNA contains a higher number of CD11c+ cells, which have a similar maturation status as CD11c+ cells from tNGFR treated mice (A). In contrast, the number of CD11c+ cells in tumor draining lymph nodes does not differ between TriMix or tNGFR treated mice, whereas the maturation status of the former is increased (B).

FIG. 20. The tumor environment of mice treated with TriMix contains a lower number of CD11b+ cells, in particular CD11b+ Ly6G+ cells. These cells are immunosuppressive MDSC (myeloid derived suppressor cells).

Figure 21:
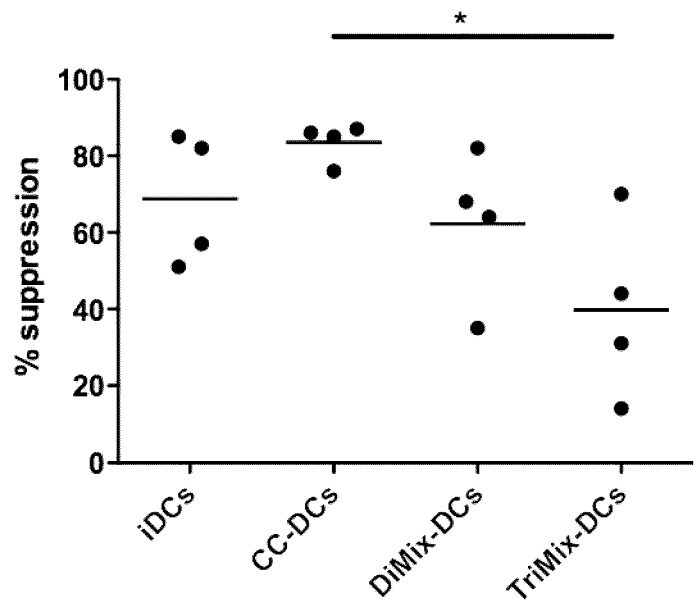

FIG. 21. Alleviation of Treg inhibition of unstimulated CD8+ T cells

Differentially modified DCs (iDCs=immature dendritic cells; CC-DCs=cytokine cocktail maturated DCs; DiMix-DCs=DCs electroporated with caTLR4 and CD40L; TriMix-DCs=DCs electroporated with caTLR4, CD40L and CD70), freshly purified $T_{reg}$ and unstimulated CFSE labeled CD8$^+$ T cells (DC-CD8$^+$ T cell ratio of 1:10 and CD8$^+$ T cell:$T_{reg}$ ratio of 1:1) were cocultured together for 6 days in the presence of anti-CD3 coated beads (left panel). Suppression of proliferation was calculated as 1−(the % of CD8$^+$ T cell proliferation in the presence of $T_{reg}$ divided by the % of CD8$^+$ T cell proliferation without $T_{reg}$)×100. The horizontal bars indicate the mean of 6 independent experiments, one representative experiment shown (right panel) with filled histograms indicating proliferation in the presence of $T_{reg}$ and empty histograms the absence of $T_{reg}$ in the CD8$^+$ T cell cocultures. A one-way ANOVA was used to compare different groups and a Bonferroni correction for post hoc pairwise comparison.

Figure 22:
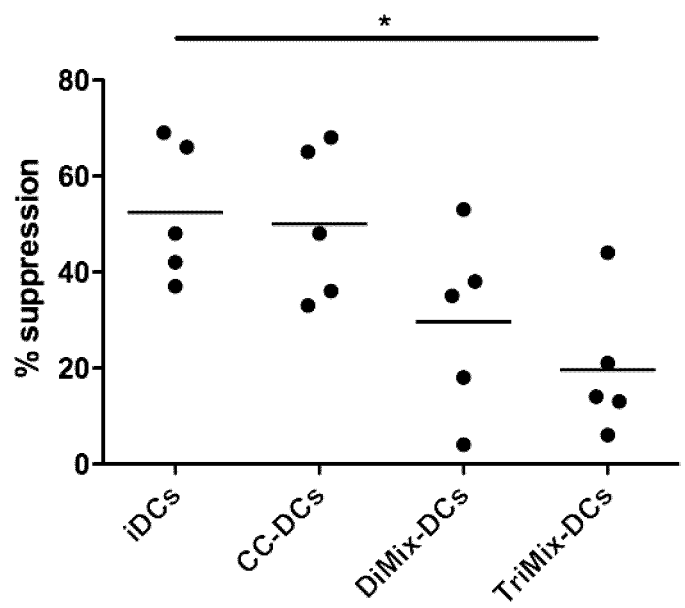

FIG. 22. Protection against Treg suppression of effector CD8+ T cells

Unstimulated CD8$^+$ T cells were first cultured with differentially modified DCs (iDCs=immature dendritic cells; CC-DCs=cytokine cocktail maturated DCs; DiMix-DCs=DCs electroporated with caTLR4 and CD40L; TriMix-DCs=DCs electroporated with caTLR4, CD40L and CD70) for 6 days after which the CD8$^+$ T cells were harvested and cocultured with freshly purified $T_{reg}$ for 6 days in the presence of anti-CD3 and anti-CD28 coated beads; cell ratios and calculation of suppression were as described in FIG. 21. The horizontal bars indicate the mean of 5 independent experiments, one representative experiment shown with filled histograms indicating the proliferation in the presence of $T_{reg}$ and empty histograms in the absence of $T_{reg}$ in the T-cell cocultures. A one-way ANOVA was used to compare different groups with a Bonferroni correction for post hoc pairwise comparison.

Figure 23:
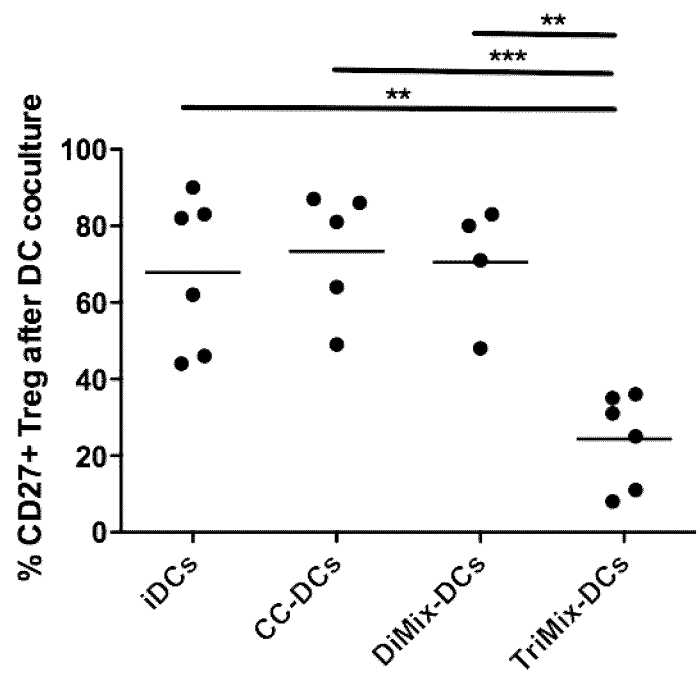

FIG. 23. Influence of DCs on the suppressive capacity of regulatory T cells

Differentially modified DCs (iDCs=immature dendritic cells; CC-DCs=cytokine cocktail maturated DCs; DiMix-DCs=DCs electroporated with caTLR4 and CD40L; TriMix-DCs=DCs electroporated with caTLR4, CD40L and CD70) were cocultured with $T_{reg}$ for 3 days after which the phenotype and function of the $T_{reg}$ was assessed. A, CD27 expression as of positive cells is shown in the upper left panel, CD27 MFI is shown in the lower left panel. n=at least 4 for each condition, one representative experiment shown in the right panel. $T_{reg}$ were determined by first gating on CD3$^+$CD4$^+$ cells, and subsequently on the CD25$^{high}$, CD127$^-$ and Foxp3$^+$ population. B, After preculture with DCs for 3 days, $T_{reg}$ were purified and cocultured with CFSE labeled unstimulated CD8$^+$ T cells for 6 days. Suppression was again calculated as in FIG. 21 (n=3, one representative experiment shown with filled histograms indicating proliferation in the presence of $T_{reg}$ and empty histograms the absence of $T_{reg}$ in the CD8$^+$ T cell cocultures). A one-way ANOVA was used to compare different groups with a Bonferroni correction for post hoc pairwise comparison.

FIG. 24. Differentiation of regulatory T cells towards Th cells upon coculture with DCs After preculture with differentially modified DCs (iDCs=immature dendritic cells; CC-DCs=cytokine cocktail maturated DCs; DiMix-DCs=DCs electroporated with caTLR4 and CD40L; TriMix-DCs=DCs electroporated with caTLR4, CD40L and CD70) for 5 days, $T_{reg}$ were assessed for CD25 expression (A), as well as expression of transcription factor Foxp3 (B) (n=4, except for control conditions, one representative experiment shown for each panel). Supernatant was taken from these cultures and assessed for the cytokines IFN-γ, TNF-α, IL-5, IL-13, IL-17, IL-2 and IL-10 (C, only IFN-γ, IL-10 and TNF-α shown, from left to right) (n=3). D, expression of T-bet, MFI in the left panel and % in the right panel of $T_{reg}$ that have already been selected on the CD3$^+$CD4$^+$CD25$^{high}$CD127$^-$ phenotype. (n=4, except for extra control conditions, one representative experiment shown for each panel) A one-way ANOVA was used to compare different groups and a Bonferroni correction for post hoc pairwise comparison.

Figure 25:
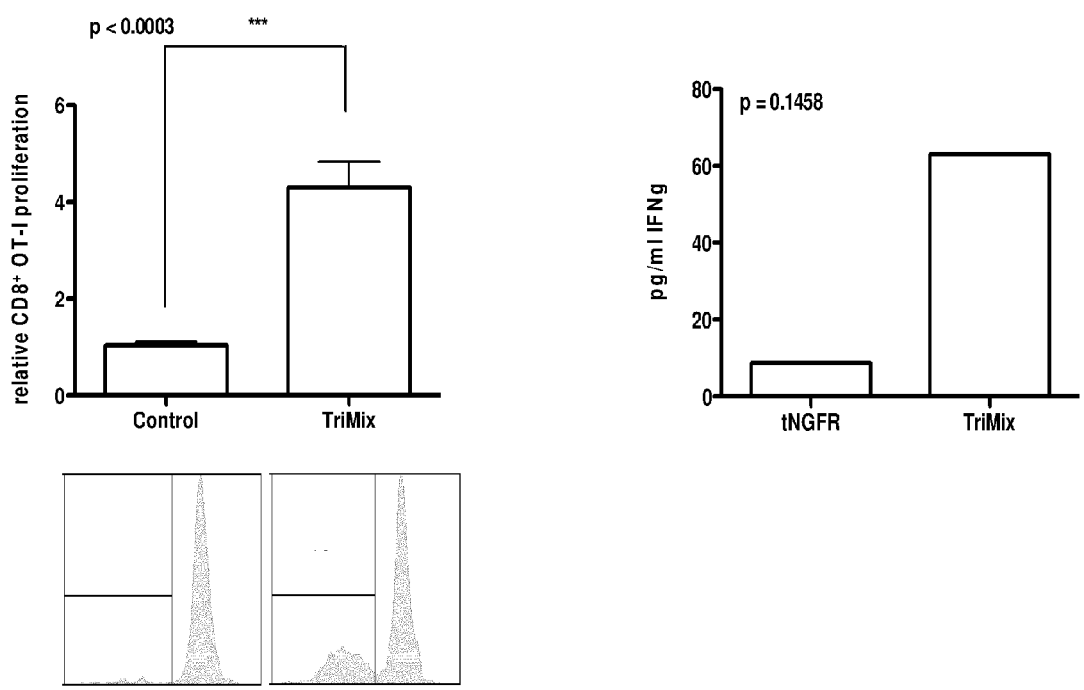
Figure 25:
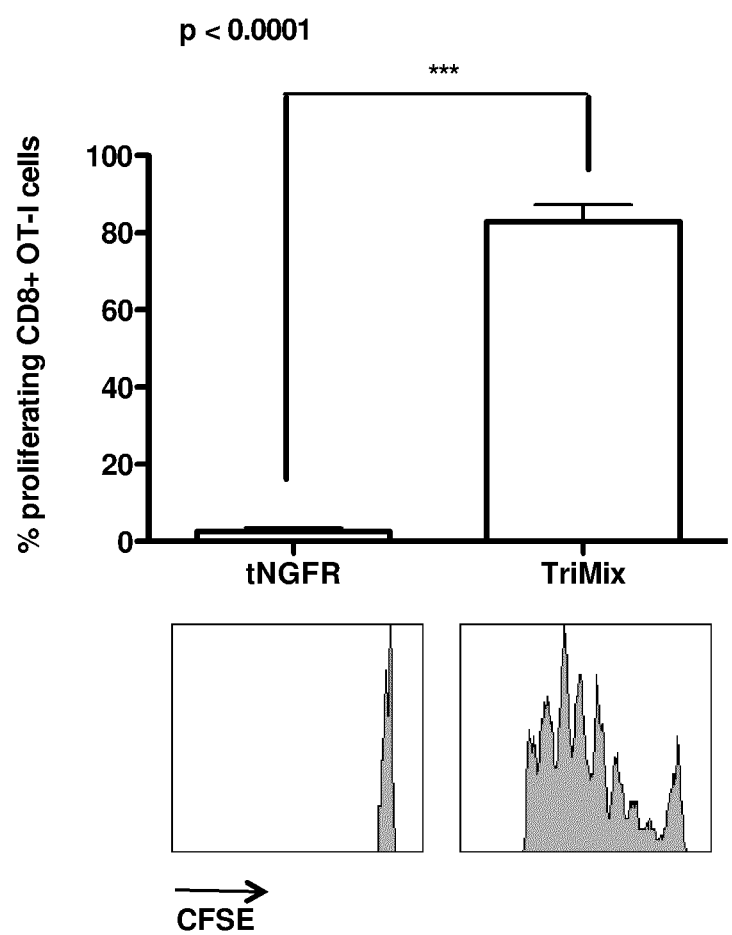
Figure 25:
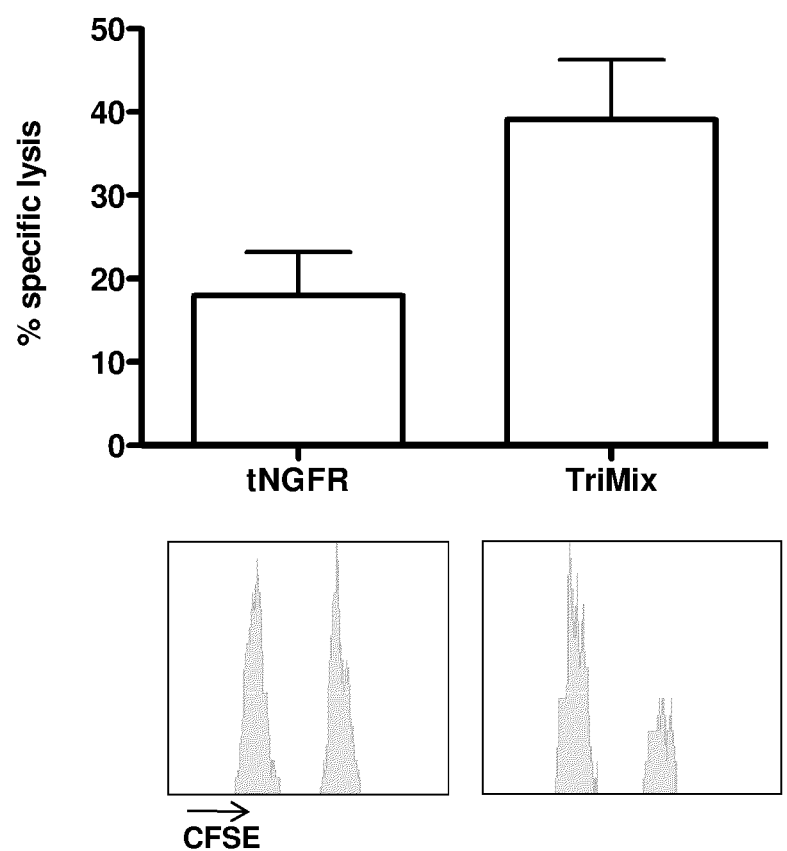

FIG. 25: Effect of intratumoral TriMix mRNA on tumor environment

C57Bl/6 mice were inoculated subcutaneously with tumor cells (ovalbumin expressing EL-4 thymoma cells (E.G7-OVA)). A) Control or TriMix mRNA was injected into the tumor nodules when the tumor reached a volume of about 150 mm$^3$. Three days later, the tumor draining lymph nodes were resected and a single cell suspension was made. The CD11c+ cells present in this cell suspension were enriched by MACS and co-cultured with OT-I CD8+ T cells recognizing an ovalbumin derived epitope. The induction of T cell proliferation and the secretion of interferon-g by these T cells was analyzed. The induction of proliferation and the induction of IFN-g secretion by the OVA-specific T cells by the migrated tumor-resident DCs indicates that the tumor-resident DC have been loaded by tumor antigens present in the tumor microenvironment;

B) When the tumor reached a volume of about 150 mm$^3$, the mice were injected intravenously with OT-I CD8+ T cells recognizing an ovalbumin derived epitope. The next day, control (tNGFR) or TriMix mRNA was injected into the tumor nodules. Five days later, the tumor draining lymph nodes were resected and a single cell suspension was made. The induction of the T cell proliferation was analyzed and indicates that the tumor-resident DC have been loaded by tumor antigens present in the tumor microenvironment and are activated to migrate to the draining lymph nodes;

C) Control or TriMix mRNA was injected into the tumor nodules when the tumor reached a volume of about 150 mm$^3$. Five days later, the induction of an OVA-specific cytotoxic T cell response was analyzed. It is shown that Intratumoral administration of TriMix mRNA induces a tumor antigen specific immune response.

Figure 26:
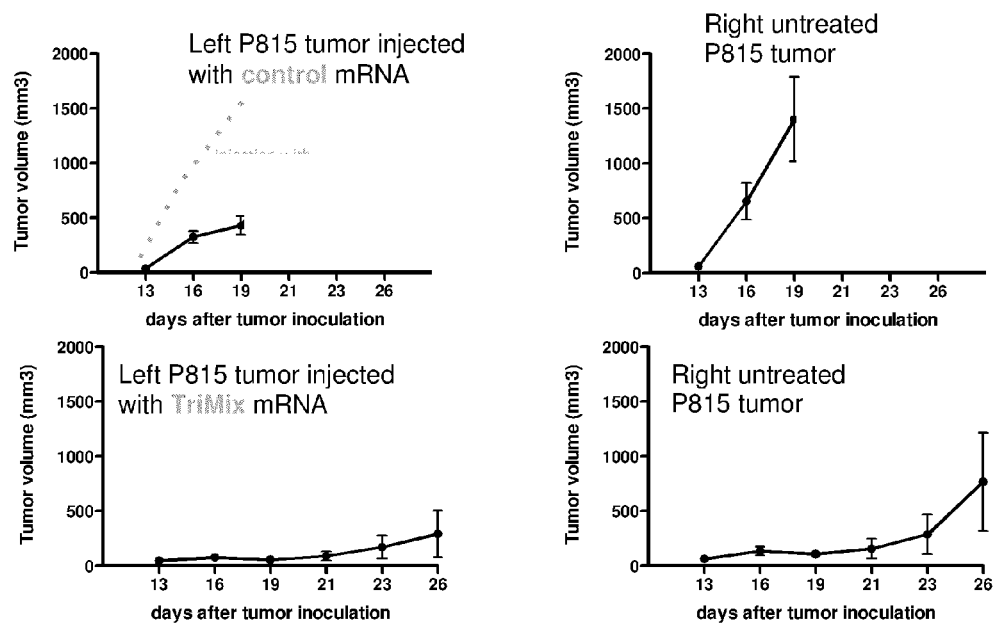
Figure 26:
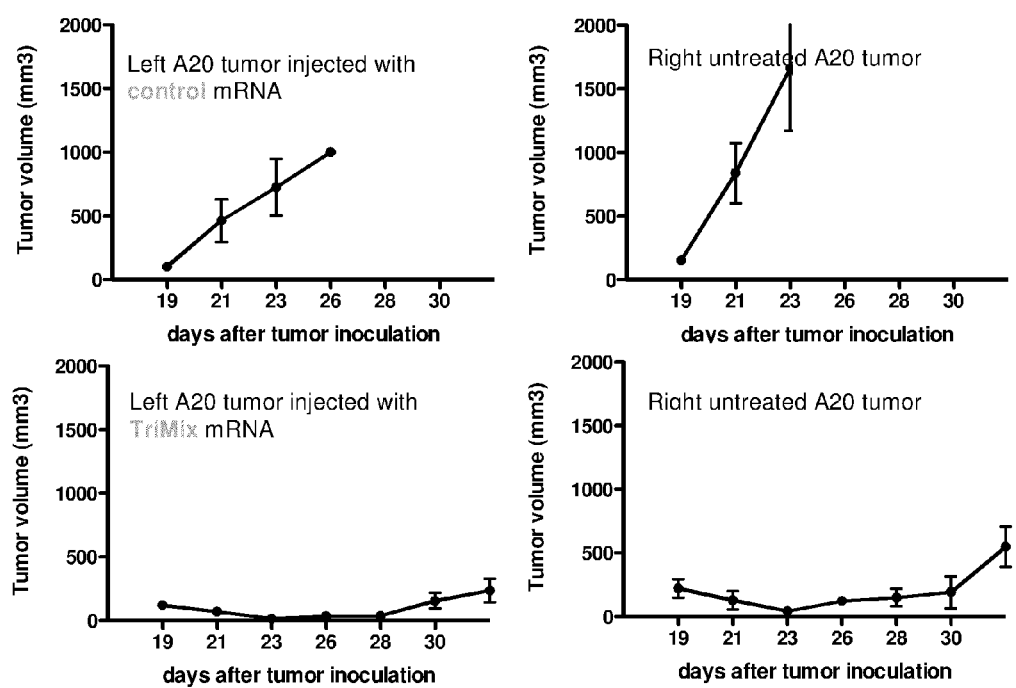

FIG. 26. Effect of intratumoral TriMix mRNA injection on tumor size, both at injected tumor and distal tumor A) DBA/2 mice were inoculated subcutaneously with P815 mastocytoma cells in the left and right flank. Control or TriMix mRNA was injected into left the tumor nodules when the tumor reached a volume of about 150 mm$^3$. Tumor volumes were measured over time. B) Balb/C mice were inoculated subcutaneously with A20 B lymphoma cells in the left and right flank. Control or TriMix mRNA was injected into left the tumor nodules when the tumor reached a volume of about 150 mm3. Tumor volumes were measured over time.

Figure 27:
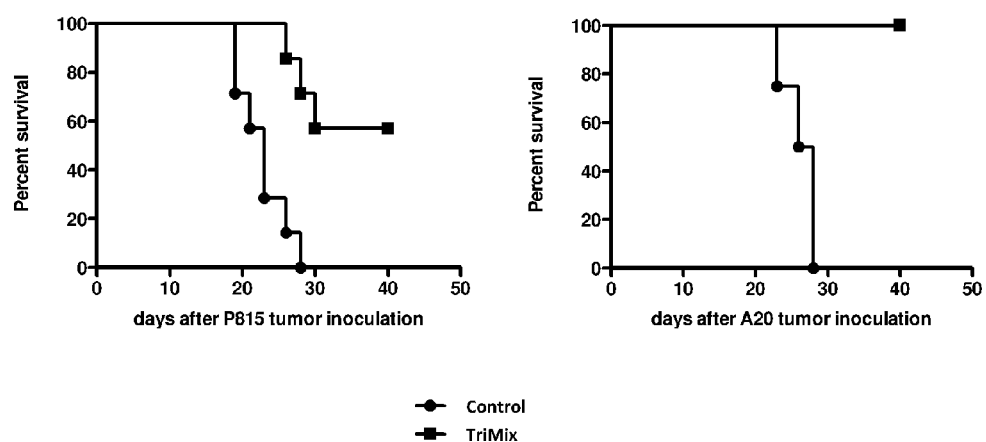

FIG. 27: Effect of intratumoral TriMix mRNA injection on iurvival

DBA/2 mice were inoculated with P815 mastocytoma cells and Balb/C mice with A20 B lymphoma cells in the left and right flank. Control or TriMix mRNA was injected into left the tumor nodules when the tumor reached a volume of about 150 mm$^3$. The survival of the animals was recorded.

DETAILED DESCRIPTION OF THE INVENTION

In search for new methods for making anti-cancer vaccines, the inventors investigated whether the activation state of DCs is a critical factor in determining whether the DCs presenting a target-specific antigen will be potent inducers of an anti-target immune response after vaccination or not. The inventors unexpectedly found that the effectiveness of currently used DC vaccination protocols could be significantly improved by providing the DCs with a more potent activation signal and by using a shorter manipulation process. The inventors moreover found that using a combination of mRNA or DNA molecules encoding a set of specific immunostimulatory proteins could be used to mature DCs both in vitro and in vivo, i.e. through in situ administration to the subject in e.g. the lymph nodes or directly at the site of infection or in the tumor.

Throughout the invention, the term "TriMix" stands for a mixture of mRNA molecules encoding CD40L, CD70 and caTLR4 immunostimulatory proteins.

Throughout the invention the term "TriMix DCs" or "TriMix APCs" stands for respectively DCs or APCs that have been modified to express the TriMix mixture of mRNA or DNA molecules encoding CD40L, CD70 and caTLR4 immunostimulatory proteins.

The mRNA or DNA used or mentioned herein can either be naked mRNA or DNA, or protected mRNA or DNA. Protection of DNA or mRNA increases its stability, yet preserving the ability to use the mRNA or DNA for vaccination purposes. Non-limiting examples of protection of both mRNA and DNA can be: liposome-encapsulation, protamine-protection, (Cationic) Lipid Lipoplexation, lipidic, cationic or polycationic compositions, Mannosylated Lipoplexation, Bubble Liposomation, Polyethylenimine (PEI) protection, liposome-loaded microbubble protection etc.

The term "target" used throughout the description is not limited to the specific examples that may be described herein. Any infectious agent such as a virus, a bacterium or a fungus may be targeted. In addition any tumor or cancer cell may be targeted.

The term "target-specific antigen" used throughout the description is not limited to the specific examples that may be described herein. It will be clear to the skilled person that the invention is related to the induction of immunostimulation in APCs, regardless of the target-specific antigen that is presented. The antigen that is to be presented will depend on the type of target to which one intends to elicit an immune response in a subject. Typical examples of target-specific antigens are expressed or secreted markers that are specific to tumor, bacterial and fungal cells or to specific viral proteins or viral structures. Without wanting to limit the scope of protection of the invention, some examples of possible markers are listed below.

The term "antigen presenting cell" used throughout the description includes all APCs. Specific non limiting examples are DCs, dendritic cell-lines, B-cells, or B-cell-lines. The DCs or B-cells can be isolated or generated from the blood of a patient or healthy subject. The patient or subject can have been the subject of prior vaccination or not.

The terms "neoplasms", "cancer" and/or "tumor" used throughout the description are not intended to be limited to the types of cancer or tumors that may have been exemplified. The term therefore encompasses all proliferative disorders such as neoplasma, dysplasia, premalignant or precancerous lesions, abnormal cell growths, benign tumors, malignant tumors, cancer or metastasis, wherein the cancer is selected from the group of: leukemia, non-small cell lung cancer, small cell lung cancer, CNS cancer, melanoma, ovarian cancer, kidney cancer, prostate cancer, breast cancer, glioma, colon cancer, bladder cancer, sarcoma, pancreatic cancer, colorectal cancer, head and neck cancer, liver cancer, bone cancer, bone marrow cancer, stomach cancer, duodenum cancer, oesophageal cancer, thyroid cancer, hematological cancer, and lymphoma. Specific antigens for cancer can e.g. be MelanA/MART1, Cancer-germline antigens, gp100, Tyrosinase, CEA, PSA, Her-2/neu, survivin, telomerase.

The term "infectious disease" or "infection" used throughout the description is not intended to be limited to the types of infections that may have been exemplified herein. The term therefore encompasses all infectious agents to which vaccination would be beneficial to the subject. Non-limiting examples are the following virus-caused infections or disorders: Acquired Immunodeficiency Syndrome-Adenoviridae Infections-Alphavirus Infections-Arbovirus Infections-Bell Palsy-Borna Disease-Bunyaviridae Infections-Caliciviridae Infections-Chickenpox-Common Cold-Condyloma Acuminata-Coronaviridae Infections-Coxsackievirus Infections-Cytomegalovirus Infections-Dengue-DNA Virus Infections-Contagious Eethyma, -Encephalitis-Encephalitis, Arbovirus-Encephalitis, Herpes Simplex-Epstein-Barr Virus Infections-Erythema Infectiosum-Exanthema Subitum-Fatigue Syndrome, Chronic-Hantavirus Infections-Hemorrhagic Fevers, Viral-Hepatitis, Viral, Human-Herpes Labialis-Herpes Simplex-Herpes Zoster-Herpes Zoster Oticus-Herpesviridae Infections-HIV Infections-Infectious Mononucleosis-Influenza in Birds-Influenza, Human-Lassa Fever-Measles-Meningitis, Viral-Molluscum Contagiosum-Monkeypox-Mumps-Myelitis-Papillomavirus Infections-Paramyxoviridae Infections-Phlebotomus Fever-Poliomyelitis-Polyomavirus Infections-Postpoliomyelitis Syndrome-Rabies-Respiratory Syncytial Virus Infections-Rift Valley Fever-RNA Virus Infections-Rubella-Severe Acute Respiratory Syndrome-Slow Virus Diseases-Smallpox-Subacute Sclerosing Panencephalitis-Tick-Borne Diseases-Tumor Virus Infections-Warts-West Nile Fever-Virus Diseases-Yellow Fever-Zoonoses-Etc. Specific antigens for viruses can be HIV-gag, -tat, -rev or -nef, or Hepatitis C-antigens.

Further non-limiting examples are the following bacteria- or fungus-caused infections or disorders: Abscess-Actinomycosis-Anaplasmosis-Anthrax-Arthritis, Reactive-Aspergillosis-Bacteremia-Bacterial Infections and Mycoses-*Bartonella*

Infections-Botulism-Brain Abscess-Brucellosis-*Burkholderia* Infections-*Campylobacter* Infections-Candidiasis-Candidiasis, Vulvovaginal-Cat-Scratch Disease-Cellulitis-Central Nervous System Infections-Chancroid-*Chlamydia* Infections-Chlamydiaceae Infections-Cholera-*Clostridium* Infections-Coccidioidomycosis-Corneal Ulcer-Cross Infection-Cryptococcosis-Dermatomycoses-Diphtheria-Ehrlichiosis-Empyema, Pleural-Endocarditis, Bacterial-Endophthalmitis-Enterocolitis, Pseudomembranous-Erysipelas-*Escherichia coli* Infections-Fasciitis, Necrotizing-Fournier Gangrene-Furunculosis-*Fusobacterium* Infections-Gas Gangrene-Gonorrhea-Gram-Negative Bacterial Infections-Gram-Positive Bacterial Infections-Granuloma Inguinale-Hidradenitis Suppurativa-Histoplasmosis-Hordeolum-Impetigo-*Klebsiella* Infections-Legionellosis-Leprosy-Leptospirosis-*Listeria* Infections-Ludwig's Angina-Lung Abscess-Lyme Disease-Lymphogranuloma Venereum-*Maduromycosis*-Melioidosis-Meningitis, Bacterial-*Mycobacterium* Infections-*Mycoplasma* Infections-Mycoses-*Nocardia* Infections-Onychomycosis-Osteomyelitis-Paronychia-Pelvic Inflammatory Disease-Plague-Pneumococcal Infections-*Pseudomonas* Infections-Psittacosis-Puerperal Infection-Q Fever-Rat-Bite Fever-Relapsing Fever-Respiratory Tract Infections-Retropharyngeal Abscess-Rheumatic Fever-Rhinoscleroma-*Rickettsia* Infections-Rocky Mountain Spotted Fever-*Salmonella* Infections-Scarlet Fever-Scrub Typhus-Sepsis-Sexually Transmitted Diseases, Bacterial-Sexually Transmitted Diseases, Bacterial-Shock, Septic-Skin Diseases, Bacterial-Skin Diseases, Infectious-Staphylococcal Infections-Streptococcal Infections-Syphilis-Syphilis, Congenital-Tetanus-Tick-Borne Diseases-Tinea-Tinea Versicolor-Trachoma-Tuberculosis-Tuberculosis, Spinal-Tularemia-Typhoid Fever-Typhus, Epidemic Louse-Borne-Urinary Tract Infections-Whipple Disease-Whooping Cough-*Vibrio* Infections-Yaws-*Yersinia* Infections-Zoonoses-Zygomycosis-Etc.

The term "immunological disorder" encompasses any immunological disorder, including all disorders or syndromes involving impaired or reduced immunological response. Non-limiting examples of disorders or syndromes involving impaired or reduced immune response are so-called Primary Immune Deficiencies such as: congenital defects of the immune system, Selective IgA Deficiency, Common Variable Immunodeficiency, X-Linked Agammaglobulinemia (Bruton type, X-linked infantile, or congenital agammaglobulinemia), Chronic Granulomatous Disease, Hyper-IgM Syndrome, and SCID (the classic "bubble boy" disease). In addition, acquired immunodeficiencies can occur, such as, but not limited to: AIDS, or to subjects receiving chemotherapy or immunosuppressive medications such as subjects having cancer and subjects that underwent an organ transplant, or for various other conditions. Furthermore, diabetes patients might suffer from mild immune suppression and elderly people or children and newborns can have a weakened or weaker immune system. All said conditions, syndromes or disorders are meant to be covered by the term "immunological disorders".

The current invention provides new methods of enhancing the immunostimulatory capacities of human DCs through transfection with at least two different mRNA or DNA molecules encoding molecular adjuvants selected from the list of CD40L, CD70, caTLR4, IL-12p70, EL-selectin, CCR7 and/or 4-1BBL; or in combination with the inhibition of the expression or function of SOCS, A20, PD-L1 or STAT3, for example through siRNA transfection.

In addition, the invention provides for methods of enhancing the immunostimulatory capacities of human DCs in situ in a subject, by administering mRNA or DNA molecules encoding molecular adjuvants CD40L and CD70, caTLR4, or both to said subject, preferably in the lymph nodes, where DCs reside and mature. Alternatively, said mRNA or DNA molecules can be administered intratumorally, subcutane, or intradermally.

Optionally, additional mRNA or DNA molecules encoding any one or more of the following proteins: IL-12p70-, EL-selectin, CCR7 and 4-1BBL can be co-administered.

The use of the combination of CD40L and caTLR4 in monocyte derived immature DCs through mRNA electroporation generates mature, cytokine/chemokine secreting DCs, as has been shown for CD40 and TLR4 ligation through addition of soluble CD40L and LPS.

The introduction of CD70 into the DCs provides a co-stimulatory signal to $CD27^+$ naive T-cells by inhibiting activated T-cell apoptosis and by supporting T-cell proliferation.

As an alternative to caTLR4, other Toll-Like Receptors (TLR) could be used. For each TLR, a constitutive active form is known, and could possibly be introduced into the DCs in order to elicit a host immune response. In our view however, caTLR4 is the most potent activating molecule and is therefore preferred.

Introduction of mRNA encoding an additional cytokine such as IL-12p70 in the DCs could be beneficial to further increase the cytokine excretion of the DCs, subsequently further stimulating the host immune response.

Additional introduction of EL-selectin or CCR7 into the DCs could be beneficial to promote the in vivo migration of the manipulated DCs towards the lymph nodes, the place where the immune response is naturally initiated in the host.

Further co-stimulatory molecules such as 4-1BBL or a constitutively active form of Akt could also be introduced in the DCs or co-administered in situ.

In addition, the expression and/or function of inhibitory molecules such as SOCS, A20, PD-L1, STAT3 could be lowered or halted through additional introduction of specific inhibitory molecules such as specific siRNA molecules in the DCs, or can be co-administered in situ.

Additional in vitro incubation of the DCs with soluble factors such as TLR ligands, IFN-gamma, TNF-alpha, IL-6, PGE2 and/or IL-1 beta could also be utilised for the maturation of the DCs. Alternatively, in situ administration of said factor(s) could be done in order to mature the DCs in vivo in a subject.

The invention preferably uses DCs derived from peripheral blood mononuclear cells (PBMCs) directly isolated from the patient's blood, but alternatives such as DCs differentiated out of CD34-positive cells or commercially available dendritic cell-lines could be used as well.

The in vitro method of the invention uses either mRNA electroporation, viral transduction (e.g. through lentivirus, adenovirus, or vaccinia virus), mRNA lipofection or DNA transfection to introduce immunostimulatory molecules and target-specific antigens into the DCs. mRNA electroporation is especially preferred due to its high efficiency and its wide accepted use in clinical settings in contrast to viral transduction. For introduction of the target-specific antigens, pulsing of the cells with the antigen-specific peptides or with protein can be used as an alternative to mRNA electroporation. The introduced mRNA can be a specifically synthesized sequence based on known tumor-specific markers, or can be isolated from (a) tumor cell line(s) or from a tumor-biopsy of the patient.

For the production of the DCs, the invention preferably uses autologous plasma obtained from the patient, but human AB serum, which is commercially available, can also be used.

The in vivo or in situ methods preferably encompass intranodal injection of the mRNA or DNA molecules encoding the immunostimulatory factors as explained above. Alternatively, intratumoral or intradermal injection can be used to target the DCs in vivo. In a preferred embodiment, said intradermal injection is preceded by intradermal injection with GM-CSF, FLT3L or local treatment with imiquimod.

In a preferred embodiment, the invention lies in the combined administration of CD40L and CD70 to DCs, either in vitro or in vivo, thereby leading to increased immunostimulatory effects of the DCs. In a further preferred embodiment, the specific combination of CD40L, CD70 and caTLR4 is administered to the DCs, again in vitro or in vivo, to improve the immunostimulatory effects of the DCs. In both of these embodiments, any of the following markers could be administered additionally: IL-12p70, EL-selectin, CCR7, 4-1BBL for increased expression or SOCS, A20, PD-L1 or STAT3 inhibition. In addition to the molecular adjuvants, a target-specific antigen or its derived epitopes are introduced into the DCs in order to enable them to elicit a T-cell immune response towards the target-specific antigen. Several of the combinations listed above were shown to have unexpectedly high immunostimulatory effects on the DCs.

Several hurdles had to be taken in order to make the method work. First we assessed transgene expression of CD40L after electroporation into K562 cells and DCs. Although CD40L could be readily detected on the membrane of electroporated K562 cells until 24 h after electroporation, we were unable to detect it on the DC membrane. This is probably due to the fact that newly synthesized CD40L protein rapidly encounters CD40 on the DC membrane and is re-internalized, a process that cannot take place in CD40-negative K562 cells. Indeed, when the trans-Golgi trafficking of CD40L was blocked with brefeldin A, we were able to detect CD40L protein intracellularly in the DCs.

Although strong expression of CD70 on mature murine DCs had been reported after CD40 and TLR ligation alone or in combination, very little is known about the expression of CD70 on human DCs. In our hands, immature DCs, cytokine cocktail matured DCs or DCs electroporated with CD40L and/or TLR4 did not express CD70. Even after combined CD40 ligation through 3T6-associated CD40L and TLR ligation through LPS or dsRNA only a minor percentage of DCs showed CD70 expression. Whether this low CD70 expression by human DCs is a general phenomenon or could be related to our DC generation protocol remains to be established.

Human DCs were matured with different maturation stimuli and were put in coculture with CD40L expressing 3T6 cells with or without IFN-gamma. Twenty-four and 48 hours later, CD70 expression was assessed, showing very little CD70 upregulation. These data show that even very strong, combined maturation stimuli (including CD40 ligation, TLR ligation and IFN-gamma) are unable to induce upregulation of CD70 on human DCs. This is in clear contrast with the data published on murine DCs, where CD70 is readily upregulated after CD40 and/or TLR ligation. For human DCs, CD70 expression needs to be forced through mRNA electroporation. These experiments clearly show that the mere extrapolation of the mouse immunostimulatory concept to the human situation is in no way straightforward. In contrast, we had to explicitly induce CD70 expression through electroporation of CD70 mRNA in human DCs. Only then we could establish a strong expression that persisted for several days, which should enable the DCs to interact with CD27$^+$ T-cells for a prolonged period of time. From the experimental results outlined herein, it will become clear that TriMix-modified DCs are much more potent in stimulating the immune system than DiMix-modified DCs, modified with CD40L and caTLR4 only, again pointing towards an important contribution of CD70.

Although it was technically unable to investigate the expression of the caTLR4 protein, the NF-kappaB activation assay indicates that the mRNA electroporation of our caTLR4 plasmid leads to the expression of a functional protein. In parallel we could also show that the CD40L and CD70 plasmids encode functional proteins since CD40L and CD70 electroporated DCs activate the NF-kappaB signaling pathway after CD40 and CD27 ligation, respectively.

In a further experiment, the inventors investigated the effect of CD40L, CD70 and caTLR4 in vitro electroporation in different combinations on the DC phenotype, its cytokine/chemokine secretion pattern and its ability to stimulate naive CD4$^+$ T-cells. For all three properties tested, the same conclusions can be drawn:

[1] Both CD40L and caTLR4 electroporation in DCs induced phenotypical maturation, enhanced cytokine/chemokine secretion and these electroporated DCs stimulated naive CD4$^+$ T-cells to become IFN-gamma producing, Th1 type T-cells,

[2] Combination of CD40L with caTLR4 electroporation boosted the effect even further, while

[3] CD70 (co-)electroporation had no effect on phenotype & chemokine/cytokine secretion (which is as expected because the DC don't express the ligand of CD70 (CD27).

On the phenotype level, we observed an enhanced expression of the costimulatory molecules CD40, CD80, CD83, CD86 and of the HLA class 1 molecules. Of note, CD40 engagement through CD40L electroporation did not impair the upregulation of CD40 expression. On the cytokine secretion level, we found a marked upregulation in the secretion of the Th1 cytokine IL-12p70, several pro-inflammatory cytokines (IL-1beta, IL-6, TNF-alpha), hematopoietic growth factors (G-CSF, GM-CSF), IFN-gamma, and IL-10. On the chemokine secretion level, enhanced secretion of IL-8 (recruitment of neutrophils), MIP-1 alpha (recruitment of monocytes and T-cells), IP-10 (IFN-gamma inducible 10 kDa protein; recruitment of monocytes and T-cells) and RANTES (recruitment of T-cells, basophils and eosinophils) was observed. MIP-1 alpha, RANTES and IP-10 are all chemotactic for T-cells, but it has been shown that MIP-1 alpha and RANTES are produced by Th1/Th2-promoting DCs, while IP-10 production is restricted to Th1-promoting DCs. CD70 (co-)electroporation does not induce phenotypical changes or enhanced cytokine/chemokine secretion by DCs, because DCs lack expression of its signaling ligand CD27.

The cytokine and chemokine secretion pattern suggests that DCs electroporated with CD40L and/or caTLR4 mRNA would preferentially induce IFN-gamma producing Th1 cells, a finding that was confirmed in the allogeneic stimulation of CD45RA$^+$ CD4$^+$ T-cells. Indeed, T-cells stimulated with DCs electroporated with CD40L and caTLR4, alone or in combination, produced very high amounts of IFN-gamma, but almost no IL-4 and IL-10, secretion of which was not increased in comparison to T-cells stimulated with DCs electroporated with irrelevant mRNA. We did not observe an increased IFN-gamma secretion by CD4' T-cells stimulated with CD70 (co-)electroporated DCs, demonstrating that DCs expressing human CD70 do not directly instruct for Th1 development and IFN-gamma secretion. Nonetheless, DCs expressing human CD70 might sensitize naive CD4' T-cells towards Th1 development through the induction of T-bet and IL-12Rbeta2.

In a following experiment, the inventors analyzed whether DCs electroporated with different combinations of CD40L, CD70 and caTLR4 mRNA exerted costimulatory functions in an antigen-specific setting. We could indeed show that MelanA-A2 peptide pulsed DCs expressing CD40L, CD70 and caTLR4 in different combinations induced increased numbers of MelanA-specific CD8$^+$ T-cells, with the combination of all three molecules yielding the best stimulation. DCs electroporated with CD70 alone did not stimulate an increased number of MelanA-specific CD8$^+$ T-cells in comparison to DCs electroporated with NGFR mRNA. In contrast, CD70 co-electroporation with CD40L, together or not with caTLR4, induced an additional increase of MelanA-specific T-cells when compared to DCs electroporated with CD40L together or not with caTLR4. This is probably due to a survival-effect induced by the ligation of CD70 on the DCs with CD27 on the T-cells during stimulation.

After having established that CD40L, caTLR4 and CD70 expression by DCs increases their ability to stimulate MelanA-specific CD8$^+$ T-cells, the inventors investigated the functional and phenotypical properties of the stimulated T-cells. In correlation with the increased number of MelanA-specific CD8$^+$ T-cells, more IFN-gamma/TNF-alpha producing cells were generated and a greater number of CD8$^+$ T-cells with a cytolytic capacity could be detected. When analyzing the phenotype of the MelanA-specific CD8$^+$ T-cells, all cells appeared to be CD45RA$^-$CD45RO$^+$CD27$^+$CD28$^+$, together with a variable expression of CD62L and CCR7. This indicates that central memory T-cells (CD62L$^+$ and CCR7$^+$) have been induced as well as early effector memory T-cells or EM$_1$ cells (CD62L$^-$ and CCR7$^-$), depending on the nomenclature.

The results of the experiments listed below in the examples clearly establish a proof-of-principle that DCs co-electroporated with mRNA encoding multiple stimulating proteins and pulsed with antigenic peptide are better T-cell stimulators than immature or cytokine cocktail matured DCs. Moreover, it is possible to co-electroporate these DCs with target-specific antigen encoding mRNA, thus providing its full antigenic spectrum. Additional data where DCs were co-electroporated with CD40L, CD70, and caTLR4 mRNA together with mRNA encoding the MelanA antigen linked to the HLA class II targeting signal of DC-LAMP indicate that these cells are also superior in inducing MelanA-specific CD8$^+$ T-cells, leading to a fold increase of 300 in comparison to immature DCs. Data suggest that DCs co-electroporated with CD40L, CD70 and caTLR4 mRNA are also able to prime T cells specific for target-associated antigens other than MelanA, in particular for MAGE-A3, gp100 and tyrosinase; antigens for which lower T cell precursor frequencies have been reported. It is clear that the present invention should not be regarded as being limited to the examples used to proof the concept of using the APCs of the invention to create an immune response in a subject. Any possible antigen to which an immune response could be beneficial for a subject can be envisaged and is an integral part of the invention. Markers can be tumor-specific markers or can be virus-specific, bacterium-specific or fungal specific.

The invention provides for the first time evidence that genetically modified DCs expressing at least two stimulating molecules selected from the lot of CD40L, CD70 and caTLR4, IL-12p70, EL-selectin, CCR7, 4-1BBL; or in combination with suppression of SOCS, A20, PD-L1 or STAT3 offer a DC based vaccine possessing all the features considered necessary for induction of optimal target-reactive immune responses. In a preferred embodiment of the invention the combination of stimulating molecules is CD40L and CD70. In a further preferred embodiment, the specific combination of stimulating molecules is the TriMix of CD40L, CD70 and caTLR4.

Of importance is that in the methods of the invention, all antigen-specific stimulations were performed without the addition of any exogenous IL-2 and/or IL-7 to support T-cell proliferation and survival, which is in contrast to most studies reporting in vitro stimulations. In our opinion, omitting exogenous cytokines creates a less artificial environment and is closer to the situation in vivo. Indeed, it has been shown that addition of 50 IU/ml IL-2 during antigen-specific stimulation had no effect on the number of antigen-specific T-cells induced, but did influence the functional profile of the induced specific T-cells, namely by increasing both the number of lytic and of IFN-gamma/TNF-alpha secreting T-cells, indicating that addition of exogenous cytokines to T-cell stimulations can alter the outcome of monitoring techniques.

The use of the methods of the invention has a further advantage over the prior art in that the in vitro manipulation of the DCs is reduced to a minimum in order to prevent the excretion of physiologically relevant cytokines in the in vitro culture medium. This is achieved by using a highly efficient one-step transduction method, preferably through mRNA electroporation, enabling the simultaneous introduction of at least two mRNA molecules encoding molecular adjuvants (possibly in combination with a target-specific antigen). This enables the DCs to release their natural cytokines in their future environment, be it in vitro for the experiments or in vivo in the patient, leading to an increased T-cell immune response.

In an additional embodiment, the DCs of the invention are useful in methods for identifying new target-specific markers. The modified DCs can be used to stimulate T cells from healthy donors or patients having cancer or an infectious disease, who were or were not previously vaccinated with a vaccine containing a target-specific antigen. Subsequently, after one or more stimulations with modified DCs, the target-antigen specific T cells can be identified and the target-antigen derived epitope against which the T cells are responding, can be characterized.

It was first shown that human, monocyte derived DCs electroporated with mRNA encoding CD40L, CD70 and caTLR4 mRNA (thus creating TriMix DCs), acquire a mature phenotype, enhance their cytokine and chemokine secretion and have an increased capacity to skew naive CD4$^+$ to a Th1 response and to induce MelanA-specific CD8$^+$ T cells when pulsed with the immunodominant MelanA-A2 peptide.

Further, the inventors show that TriMix DCs can be co-electroporated with (tumor)antigen-encoding mRNA instead of being pulsed with antigenic peptides. This approach offers several further advantages. First, the maturation and (tumor)antigen-loading of the DCs can be combined in one simple step. Obviating the peptide pulsing step in the vaccine production thus results in less manipulation of the cells and in less cell-loss and contamination-risk. Second, by using full-length tumorantigen-encoding mRNA all possible antigenic epitopes of the (tumor)antigen will be presented instead of some selected epitopes. Consequently, this strategy might induce a broader (tumor)antigen-specific T cell response and it is not dependent on the knowledge of each patient's HLA haplotype or on the prior identification of tumorantigen-derived epitopes. Third, the (tumor)antigen-encoding plasmid can be genetically modified by adding an HLA class II targeting sequence. This not only routes the (tumor)antigen to the HLA class II compartments for processing and presentation of HLA class II restricted (tumor)antigen-derived peptides, but also enhances processing and presentation in the context of HLA class I molecules. The same of course holds true for non-tumor antigens such as virus, bacterium or funus derived antigens.

The inventors confirmed that there were no differences in electroporation efficiency, maturation potential and cytokine secretion when TriMix DCs were prepared as such or co-electroporated with tumorantigen-mRNA.

Further, the inventors showed the capacity of TriMix DCs co-electroporated with tumorantigen mRNA to stimulate both HLA-A2-restricted, MelanA-specific CD8+ T cells and compared it to peptide pulsed TriMix DCs. It was observed that TriMix DCs co-electroporated with sig-MelanA-DCLamp mRNA were indeed able to prime MelanA-specific CD8+ T cells from the blood of healthy donors and that, like their peptide pulsed counterparts, they were much more potent than immature or cytokine cocktail matured DCs.

When compared to peptide pulsed TriMix DCs, the inventors observed that after 1 or 2 stimulations, TriMix DCs co-electroporated with tumorantigen mRNA were slightly less potent than peptide pulsed TriMix DCs, while after 3 stimulations they were equally potent in 2 out of 4 experiments. Although co-electroporated TriMix DCs seem to induce a lower number of epitope specific T cells than their peptide pulsed counterparts in this setting, this does not necessarily mean that they will be less efficient when used for vaccination purposes, and this for a number of reasons. First, when investigating the qualitative functionality of the induced T cells, we consistently observed that the T cells stimulated with co-electroporated TriMix DCs induced more cells secreting both IFN-gamma □and TNF-alpha. Moreover, the mean fluorescence intensity of the intracellular IFN-gamma staining was increased, indicating that more cytokine per cell had been produced. These data suggest that these T cells are multifunctional, which has been correlated with a better effector function. Second, as discussed before, by electroporating full-length tumorantigen mRNA linked to a HLA class II targeting signal into the DCs all antigenic epitopes are introduced, including unidentified epitopes and epitopes restricted to all possible HLA haplotypes being HLA class I as well as class II. Therefore, this approach is prone to induce a broader TAA-specific T cell response.

The HLA-A2 restricted immunodominant peptide of MelanA is an epitope for which a very high precursor frequency in the blood exists. We next evaluated whether TriMix DCs co-electroporated with other tumorantigens would be able to induce antigen specific CD8+ T cell responses. Since this work is part of the preclinical assessment of a vaccination study where TriMix DCs co-electroporated with Mage-A3, Mage-C2, Tyrosinase or gp100 mRNA will be injected into melanoma patients, we investigated whether responses specific for these antigens could be induced both in vitro in the blood of unvaccinated melanoma patients and in vivo after vaccination. We observed that in unvaccinated patients, TriMix DCs could indeed stimulate TAA-specific T cells and like for the MelanA antigen, they were more potent than cytokine cocktail matured DCs. Nevertheless, we could only observe specific responses for the HLA-A2 restricted Tyrosinase epitope, as demonstrated by tetramer staining. No responses were observed for the other HLA-A2 restricted Mage-A3, Mage-C2 or gp100 epitopes tested. Moreover, the functional assays did not show that the TriMix DCs had induced T cells specific for other epitopes than the ones tested in tetramer staining, although in these experiments positive results might have been concealed by the relatively high aspecific T cell activation induced by TriMix DCs. This aspecific T cell activation seems inherent to TriMix DCs and occurs both in vitro and in vivo. The reason for this observation remains unclear at this point. On the one hand, it might be due to the fact that DCs electroporated with CD40L and caTLR4 secrete quite high amounts of cytokines and chemokines, which might attract and activate T cells in an aspecific manner. On the other hand, it has been shown that chronic stimulation of naive T cells by APCs continuously expressing CD70, leads to activation of the T cell pool and conversion into effector-memory cells. In this CD70 transgenic mouse model, the T cell activation eventually led to exhaustion of the naive T cell pool and lethal immunodeficiency. Although we also use APCs continuously expressing CD70, we do not expect this in our vaccination study because the T cell pool is not continuously stimulated with CD70, since the DCs are injected bi-weekly and have a limited lifespan in vivo.

When compared to the massive induction of MelanA specific T cells by TriMix DCs, the induction of T cells specific for other target-specific antigens in vitro is rather poor. This is most probably due to the low precursor frequency of the latter. Overall, reports on the induction of Mage-A3, Mage-C3, Tyrosinase or gp100 specific CD8+ T cells by DCs are scarce and comparisons with our results are difficult to make because exogenous IL-2 and/or IL-7 are commonly added during these stimulations, which support T cell activation and proliferation and thus create an artificial T cell stimulatory environment.

Although the responses induced in CD8+ T cells of unvaccinated patients were quite poor, we observed that TriMix DCs are able to induce robust responses for the Mage-A3, Mage-C2 and Tyrosinase antigens through vaccination. Tetramer staining showed that these responses were not directed towards the known HLA-A2 restricted epitopes tested, evidencing the advantage of using full-length tumorantigen mRNA.

Although it is clear that TriMix DCs preferably induce Th1 CD4+ T cells, we had not investigated whether they were also able to process and present HLA class II restricted peptides from electroporated target-specific antigen encoding mRNA. The invention further shows that TriMix DCs co-electroporated with Mage-A3 linked to a HLA class II targeting sequence can indeed stimulate established HLA-DP4 restricted Mage-A3 specific CD4+ T cells. Moreover, their capacity to do so is similar to the CD4+ T cell stimulatory capacity of peptide pulsed cells.

The invention therefore clearly provides the proof of concept that TriMix DCs pulsed with a target-specific peptide or co-electroporated with mRNA encoding a target-specific antigen can stimulate antigen-specific T cells both in vitro and after vaccination and thus form a promising new approach for anti-tumor, anti-viral, anti-bacterial or anti-fungal immunotherapy.

The ultimate goal of the invention is to provide an anti-target vaccine that is capable of eliciting or enhancing a host-specific immune response in either a cancer patient or in a patient infected with a virus, bacteria or fungus. To this end, the DCs are modified with at least two immunostimulatory molecules and a target-specific antigen or target-antigen derived epitope(s) in vitro and reintroduced into the patient intradermally, intravenously, or through a combination thereof. In the patient, the DCs are able to stimulate T-cells and elicit a host-mediated immune response due to their specific immunostimulatory characteristics.

Alternatively, the DC stimulation can be done in situ, by injecting the immunostimulatory molecules (the TriMix) and the target-specific antigens, intranodally, intratumorally, subcutane, or intradermally in the cancer patient or in a patient infected with a virus, bacteria or fungus. The immunostimulatory agents or proteins are capable of in situ maturating the DCs naturally residing in the lymph nodes of the patient, resulting in the DCs presenting the antigens to the immune system and hence provoking an immune response in said subject.

The immune reaction in the host can then be analyzed through known techniques. Analyzing the increase of inflammatory markers point to the establishment of an immune reaction in the host, probably directed towards the target antigen. In order to check whether the immune response is specifically directed towards the target antigen presented by the DCs in the vaccine preparation, several known techniques such as intracellular cytokine staining through flow cytometry, ELISPOT or Enzyme Linked Immuno-Sorbent Assays (ELISA) using peptide fragments of the target antigen or the whole antigen in order to capture and detect antigen specific host T cells can be used. The immune response can be monitored both in the peripheral blood of the patient or in the skin, after the induction of a delayed type hypersensitivity (DTH)-reaction and subsequent biopsy of the DTH region."

The invention further provides for a vaccine comprising:

a) one or more mRNA or DNA molecule(s) encoding functional immunostimulatory protein CD40L, in combination with CD70, caTLR4, or both, and optionally b) target-specific antigen. Preferably, said target-specific antigen is selected from the group consisting of: total mRNA isolated from (a) target cell(s), one or more specific target mRNA molecules, protein lysates of (a) target cell(s), specific proteins from (a) target cell(s), a synthetic target-specific peptide or protein and synthetic mRNA or DNA encoding a target-specific antigen or its derived peptide(s).

In a preferred embodiment of the vaccine, said target-specific antigen is a tumor antigen. Alternatively, the target-specific antigen is a bacterial, viral or fungal antigen.

In a preferred embodiment of the vaccine of the invention, the mRNA or DNA molecule(s) encode(s) the CD40L and CD70 immunostimulatory proteins. In a particularly preferred embodiment of the vaccine of the invention, the mRNA or DNA molecule(s) encode(s) CD40L, CD70, and caTLR4 immunostimulatory proteins.

Said mRNA or DNA molecules encoding the immunostimulatory proteins can be part of a single mRNA or DNA molecule. Preferably, said single mRNA or DNA molecule is capable of expressing the two or more proteins simultaneously. In one embodiment, the mRNA or DNA molecules encoding the immunostimulatory proteins are separated in the single mRNA or DNA molecule by an internal ribosomal entry site (IRES) or a self-cleaving 2a peptide encoding sequence.

The invention further encompasses a method of following the effects of the treatment with an anti-cancer vaccine in a cancer patient, comprising the detection and analysis of the immune response towards the tumor-specific antigen elicited in the subject previously injected with the anti-cancer vaccine obtainable or obtained by the methods of the invention.

In addition, the invention further encompasses a method of following the effects of the treatment with an anti-viral, anti-bacterial or anti-fungal vaccine in a patient respectively infected or at risk of being infected with a virus, bacteria or fungus, comprising the detection and analysis of the immune response towards the target-specific antigen elicited in the subject previously injected with the vaccine obtainable or obtained by the methods of the invention.

The invention further provides a kit for improving the immunostimulatory characteristics of APCs comprising a combination of at least two different mRNA or DNA molecules encoding functional immunostimulatory proteins selected from the group consisting of CD40L, CD70, caTLR4, IL-12p70, EL-selectin, CCR7, and/or 4-1BBL; or in combination with molecules inhibiting SOCS, A20, PD-L1 or STAT3 expression or function. In a preferred embodiment, the combination comprises mRNA encoding CD40L and CD70. In a most preferred embodiment, the kit comprises the mRNA coding for the CD40L, CD70 and caTLR4 immunostimulatory molecules.

In a further embodiment, the two or more mRNA or DNA molecules encoding the immunostimulatory proteins are part of a single mRNA or DNA molecule. This single mRNA or DNA molecule is preferably capable of expressing the two or more proteins independently. In a preferred embodiment, the two or more mRNA or DNA molecules encoding the immunostimulatory proteins are linked in the single mRNA or DNA molecule by an internal ribosomal entry site (IRES), enabling separate translation of each of the two or more mRNA sequences into an amino acid sequence. Alternatively, a self cleaving 2a peptide-encoding sequence is incorporated between the coding sequences of the different immunostimulatory factors. This way, two or more factors can be encoded by one single mRNA or DNA molecule. Preliminary data where cells were electroporated with mRNA encoding CD40L and CD70 linked by an IRES sequence or a self cleaving 2a peptide shows that this approach is indeed feasible.

The invention thus further provides for an mRNA molecule encoding two or more immunostimulatory factors, wherein the two or more immunostimulatory factors are either translated separately from the single mRNA molecule through the use of an IRES between the two or more coding sequences. Alternatively, the invention provides an mRNA molecule encoding two or more immunostimulatory factors separated by a self cleaving 2a peptide-encoding sequence, enabling the cleavage of the two protein sequences after translation.

In addition, the invention provides an ex vivo method for amplifying antigen-specific T-cells from a patient. This patient could be previously vaccinated or not.

This ex vivo amplified pool of T-cells can then be used for the purpose of "adoptive cellular transfer". The adoptive cellular transfer of autologous immune cells that were amplified ex vivo with the aid of the invention could be performed in patients that did or did not undergo a conditioning treatment (such as but not restricted to non-myeloablative chemotherapy) and could be performed with or without concommitant administrations of the invention or with or without additional immunomodulatory treatments (such as but not restricted to the administration of cytokines or co-stimulatory signal modifying molecules). The invention thus provides a method for the ex vivo amplification of a pool of autologous immune cells from a patient comprising;

a) obtaining or providing T-cells from a patient which was vaccinated prior to the isolation or not, b) bringing the T-cells ex vivo into contact with APCs or immunotherapy agent obtained by the method according to the invention, c) identifying, isolating and expanding T-cells ex vivo that are specific for the antigen presented by the APCs they were contacted with (these antigens could either be defined or undefined as would be the case if total tumor RNA would be used as a source of antigen).

d) administration of these in vitro stimulated and expanded antigen-specific T cells to the patient is a setting of an adoptive T cell transfer treatment protocol involving either or not preconditioning regimens and concommitant immunomodulatory treatment.

Alternatively, the invention provides for a method of in vivo amplifying antigen-specific T-cells in a patient comprising the steps of stimulating DCs in situ (in vivo) with the TriMix mRNA or DNA mixture and target-specific antigen.

The invention further provides for methods of treating a patient in need thereof with a pool of APCs of the invention or with the vaccine of the invention.

The invention further provides for methods of using the modified APCs of the invention, or of using the vaccine of the invention as defined herein for treating cancer or infectious diseases (such as viral, bacterial or fungal infections e.g. HIV and hepatitis virus infections). In case of active immunotherapy for cancer or infectious diseases, the treatment with APCs of the invention can be preceded by, combined with or followed by any non-specific treatment of immunomodulation in order to improve the activity of the invention itself or to exploit any synergy between the different treatment modalities (e.g. by improving the immune response to the invention through non-specific stimulation of the patient's immune system with cytokines (e.g. interleukin-2 or Interferon alfa-2b) or TLR-ligands; or e.g. by combination of the invention with a co-stimulatory signal modifying drug such as ipilimumab or tremelimumab); or any other form of immunotherapy. The invention also provides for complex treatment regimens in which the invention itself and a defined number of other immunomodulatory treatments are used to result in a more active treatment plan (e.g. the sequential use of the invention with modality 1 (e.g. a cytokine) followed by the use of the invention for ex vivo expansion of vaccinal immune cells followed by an adoptive cellular transfer of these cells followed by a combination treatment of the invention with an additional modality (e.g. a costimulatory receptor signal modifier) or any possible combination of concomitant and/or sequential use of the invention and additional immunomodulatory treatments.

The inventors next have analysed the possibility to stimulate or mature the DCs in situ (in vivo), instead of in vitro. This has the advantage of circumventing the steps of: generating DCs from the patient's blood, keeping them into culture, stimulating them in vitro performing an extensive quality control and cryo-preservation cycle, and re-injecting them into the patient. Unexpectedly, the inventors have been able to show that the TriMix mRNA composition of CD40L, CD70 and caTLR4 is able to stimulate DCs in vivo, when injected intranodally, intratumorally, or intradermally. When co-injected with e.g. mRNA molecules encoding target-specific antigens, said mRNA was taken up by the DC's, was expressed and cytotoxic T-cells were produced against said target-specific antigen in the treated subject. In addition, the inventors could demonstrate that antigens that are automatically occurring at the tumor sites or sites of infection were successfully presented by tumor or infection site resident or infiltrating DCs, i.e. without the need of actually administering said target specific antigens. The experimental proof of this is outlined in the examples below.

The invention hence provides for a method for inducing antigen-specific immunity or immune response in a subject, comprising the step of administering to said subject:

a) one or more mRNA or DNA molecule(s) encoding functional immunostimulatory protein CD40L in combination with CD70, caTLR4, or both, and optionally b) target-specific antigens.

Preferably, said mRNA or DNA molecules and target-specific antigens are administered to the lymph node(s), or said mRNA or DNA molecules are administered intratumorally or intradermally, e.g. respectively through intranodal, intratumoral, or intradermal injection.

Preferably, said mRNA or DNA molecule(s) encode(s) for CD40L and CD70 immunostimulatory proteins, more preferably the mRNA or DNA molecule(s) encode(s) for CD40L, CD70 and caTLR4 immunostimulatory proteins (called the TriMix herein).

In a preferred embodiment of the in vivo method, the target-specific antigen is a tumor antigen. Alternatively, the target-specific antigen is a bacterial, viral or fungal antigen.

In any embodiment, said target-specific antigen is selected from the group consisting of: total mRNA isolated from (a) target cell(s), one or more specific target mRNA molecules, protein lysates of (a) target cell(s), specific proteins from (a) target cell(s), a synthetic target-specific peptide or protein and synthetic mRNA or DNA encoding a target-specific antigen or its derived peptide(s). Said target can be viral, bacterial, fungal, or tumor-cell derived proteins or mRNA.

The subject to be treated is preferably suffering from a disease or disorder selected from the group consisting of: neoplasma, tumor presence, cancer, melanoma presence, bacterial, viral or fungal infection, HIV infection, hepatitis infection, or immunological disorders such as acquired or not-acquired impaired immune response syndromes or diseases, such as AIDS, SCID, etc.

EXAMPLES

The invention is illustrated by the following non-limiting examples

Example 1

Generating Immature Dendritic Cells from Patient Blood Mononuclear Cells (PBMCs)

Day 0: In vitro manipulation of PBMCs: after the patient underwent a leukapheresis in order to obtain a significant number of PBMCs, the leukapheresis product is thoroughly washed and subsequently seeded into cultivation chambers to allow them to adhere to the plastic of the chambers for two hours at 37° C., in the appropriate medium, such as X-VIVO medium, supplemented with 1% autologous plasma, previously obtained from the same patient. After these two hours, the cultivation chambers are washed with e.g. phosphate saline buffer (PBS) in order to remove the non-adherent cells. The adherent cells in turn are further cultivated in culture medium comprising dendritic cell differentiation factors such as GM-CSF (in a concentration of about 1000 U/ml) and IL-4 (in a concentration of 500 U/ml) in an appropriate medium (e.g. RPMI1640) supplemented with 1% autologous patient plasma.

Day 2 and 4: On days 2 and 4, the medium is again supplemented with GM/CSF and IL-4, in the same amounts as on day 0.

Day 6: Immature DCs are harvested from the cultivation chambers and can either be cryopreserved for future use or utilized immediately.

Cryopreservation is done in an appropriate medium such as 1 ml autologous patient plasma complemented with 10% DMSO and 2% glucose. Between 5 and 20 $10^6$ DCs are frozen per container and freezing is performed according to standard techniques in liquid nitrogen at −192° C.

Example 2

Modifying the Obtained Dendritic Cells Such that they Express Both a Tumorantigen Derived Peptide and the CD40L, CD70 and TLR4 Immunostimulatory Factors to Obtain an Anti-Tumor Vaccine.

Materials and methods:
Genetic constructs.

The cloning of the pGEM4Z-NGFR plasmid encoding a truncated form of the nerve growth factor receptor (extracellular and transmembrane fragment) has previously been described. CD40L was amplified from activated CD4+ T cell cDNA with the following primers: CD40LS 5'-GATGGATC-CGTCATGATCGAAACATACAAC-3' (SEQ ID NO:3) and CD40LAS 5'-GCT CGGTACCCATCAGAGTTTGAG-TAAGCC-3' (SEQ ID NO:4) and was inserted in the pGEM4Z-A64 plasmid (kindly provided by Dr. N. Schaft, Department of Dermatology, University Hospital of Erlangen, Germany) as a BamHI-KpnI fragment. CD70 was amplified from the pIRESneo2-CD70 plasmid (a kind gift from Dr. S. Iwamoto, Department of Biochemistry, Showa University, Japan) with the following primers: CD70S 5'-AAAAGCT-TCCACCATGCCGGAGGAGGGTTC-3' (SEQ ID NO:5) and CD70AS 5'-GGGGGGAATTCTCAGGGGCGCAC-CCAC-3' (SEQ ID NO:6) and was inserted in the pGEM4Z-A64 plasmid as a HindIII-EcoRI fragment. For the cloning of the pGEM4Z-caTLR4-A64 plasmid, the leader sequence (sig) of LAMP1 was fused to human TLR4, truncated between aa M620 and P621, thus deleting the extracellular, LPS-binding domain and creating the constitutively active form of TLR4. caTLR4 was amplified from human mature DC cDNA with the following primers: caTLR4S 5'-GGG-GATCCTGTGCTGAGTTTGAATA TCACC-3' (SEQ ID NO:7) and caTLR4AS 5'-GGGAATTCTCAGATAGATGT-TCTTCCTG-3' (SEQ ID NO:8). caTLR4 cDNA was inserted into the pGEM4Z-sig-LAMP1-A64 as a BamHI-EcoRI fragment, hereby deleting the LAMP1 targeting sequence from the vector. In parallel the caTLR4 cDNA was also inserted as a BamHI-EcoRI fragment into the pcDNA3 vector containing sig.

In vitro transcription of capped mRNA and mRNA electroporation of DCs.

Capped mRNA encoding the different immunostimulatory molecules was transcribed from linearized plasmid DNA with T7 polymerase. On day 6, $4 \times 10^6$ DCs obtained as in example 1 were electroporated with 10 μg of each mRNA. Electroporation was performed in 200 μl Optimix solution B (Equibio) in a 4 mm electroporation cuvette, using the EQUI-BIO Easyject Plus® apparatus. The following conditions were used for electroporation: voltage 300 V, capacitance 150 μF and resistance 99Ω, resulting in a pulse time of about 5 ms. Immediately after electroporation, cells were transferred into IMDM containing 1% heat inactivated AB serum (PAA Laboratories, Linz, Austria), PSG, 0.24 mM L-asparagine and 0.55 mM L-arginine (both from Cambrex) (referred to as stimulation medium) at a concentration of $1 \times 10^6$ cells/ml for further use. No GM-CSF, IL-4 or maturation cytokines were added to the DCs after electroporation.

Synthetic peptides and peptide pulsing.

The HLA-A*0201 restricted MelanA/MART-1 derived peptide corresponding to the optimized immunodominant epitope (aa 26-35; ELAGIGILTV) was purchased from Thermo Electron (Thermo Electron Corporation, Ulm, Germany). The HLA-A2 restricted gag peptide (gag-A2 peptide, HXB2 gag peptidecomplete Set, NIH, AIDS Research & Reference Reagent Program, McKesson BioServices Corporation, Rockville, Md.) was used as a negative control. For peptide pulsing, DC were diluted to a final density of $2 \times 10^6$ cells/ml in IMDM containing 10 μg/ml peptide and were incubated for 2 h at 37° C.

Flow Cytometry.

Cells were stained using monoclonal antibodies (mAbs) against CD40L-PE or CD70-PE (Beckton Dickinson, BD, San Jose, Calif.). For CD40L staining, DCs were incubated with Golgi-plug (brefeldin A, BD, San Jose, Calif.) for 4 h, after which an intracellular staining for CD40L was performed using the BD Cytofix/Cytoperm plus kit.

Results:
Transgene expression after mRNA electroporation.

Figure 1A:
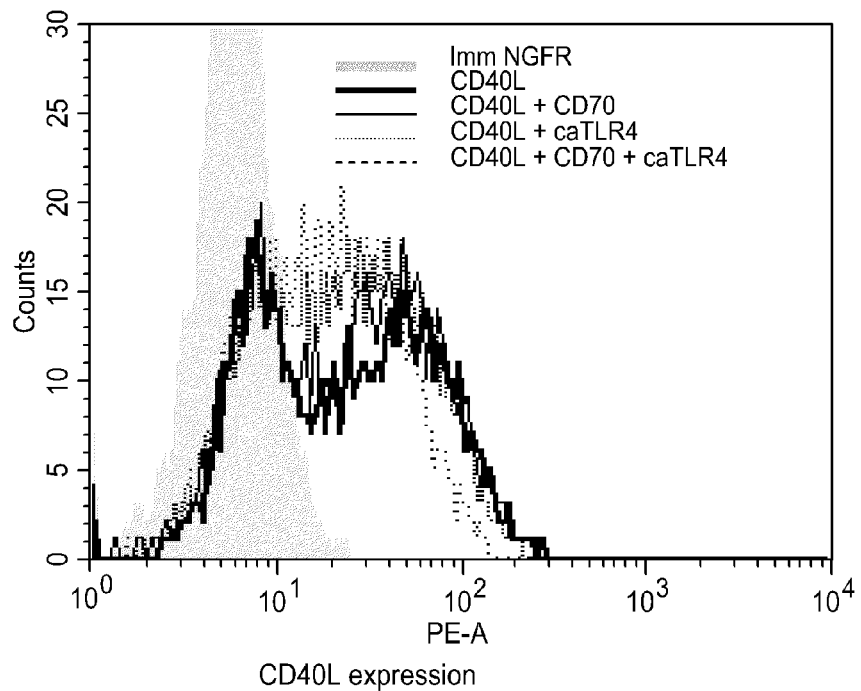
FIG. 1. Transgene expression after mRNA electroporation. (A) DCs were electroporated with CD40L alone or in combination with CD70 and/or caTLR4. Immediately after electroporation, protein transport was blocked with Golgi-plug and after 4 h, cells were stained intracellularly for CD40L. Immature DCs electroporated with irrelevant mRNA were used as negative control. Results are representative for 3 independent experiments. (B) DCs were electroporated with CD70 alone or in combination with CD40L and CD40L together with caTLR4. At several time points after electroporation, DCs were stained for CD70 expression. Immature DCs electroporated with irrelevant mRNA were used as negative control. Results are representative for 3 independent experiments.

When K562 cells were electroporated with CD40L mRNA, over 80% of the cells displayed a strong surface expression of CD40L after 4 h. After 24 h, more than 40% of the cells still expressed CD40L (data not shown). In contrast, when DCs were electroporated with CD40L mRNA, no membrane expression could be detected. CD40L could be detected intracellularly, but only when Golgi-plug was added immediately after electroporation to prevent trafficking to the cell membrane. Under these conditions, about 60% of the electroporated DCs expressed CD40L during the first 4 h after electroporation (FIG. 1A). The percentage of positive cells slightly decreased when CD40L mRNA was electroporated in combination with one or two other mRNAs.

Figure 1B:
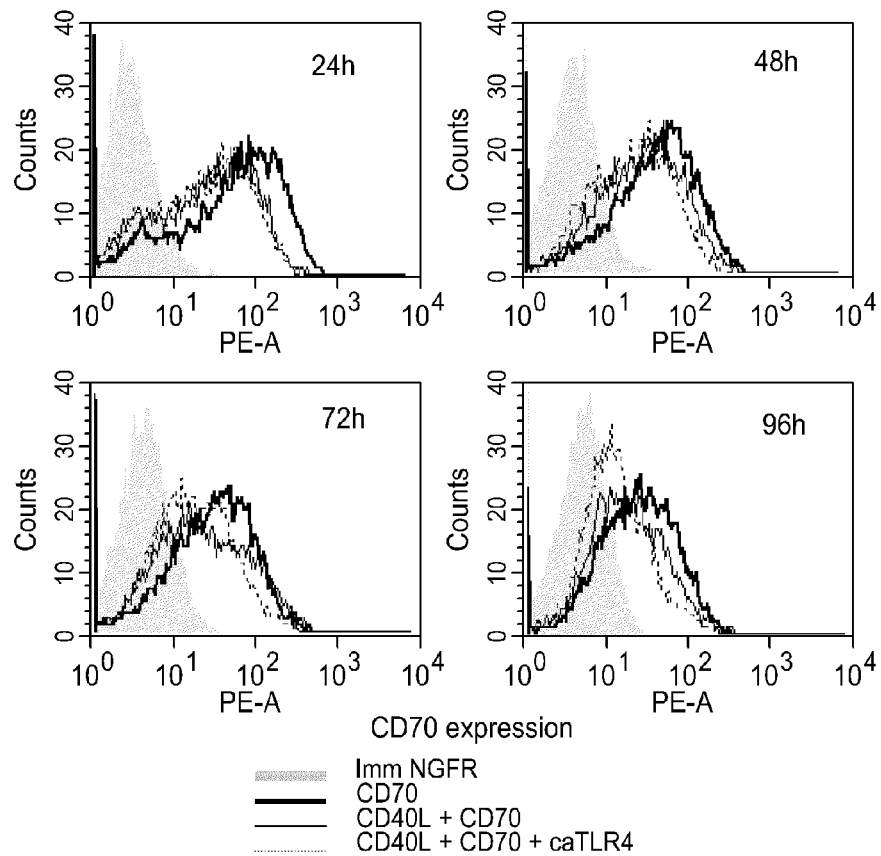

Immature or cytokine cocktail matured DCs showed no expression of CD70 as detected by FACS, nor did DCs electroporated with CD40L and/or caTLR4 mRNA. When these cells were plated on CD40L expressing 3T6 fibroblasts for 48 h, we observed a slight upregulation of CD70 expression in about 3±1.8% (n=2) of the immature DCs and 4.9±2.1% (n=2) of the cytokine cocktail matured DCs (data not shown). When the cells were matured with LPS or by passive pulsing or electroporation with the dsRNA analogue Ampligen, CD70 expression could be detected in about 5.8±0.3%, 9±3.3% and 11.2±3% of the DCs, respectively. On the other hand, DCs electroporated with CD70 mRNA showed a strong and long-lasting expression of CD70 on their membrane (FIG. 1B). Twenty-four hours after electroporation 78% of the electroporated DCs expressed CD70, while 96 h after electroporation, 67% still expressed CD70. Again, CD70 expression DCs slightly diminished when a combination of two or three different mRNAs was electroporated in comparison with CD70 mRNA alone.

DCs already express TLR4 and commercially available antibodies against TLR4 recognize the extracellular domain, which was deleted in the caTLR4 construct. Therefore, we were unable to assess the expression of caTLR4 after mRNA electroporation.

Example 3

Testing the Immunostimulatory Effect of the Obtained Anti-Tumor Vaccine In Vitro Materials and Methods:
Activation of the NF-kappaB pathway.

The genetic constructs used were as follows: the pNFcon-luc plasmid encoding the firefly luciferase gene driven by a minimal NF-kappaB-responsive promoter was kindly provided by Dr. R. Beyaert (VIB, Ghent University, Belgium). The CSCW-GLuc-YFP plasmid, encoding the humanized secreted Gaussia luciferase fused to yellow fluorescent protein was a kind gift from Dr. B. A. Tannous (Massachusetts General Hospital, Boston, Mass.). The GLuc-YFP was subcloned from this plasmid into the pHR-vector. CD27 was amplified from EBV-B cell cDNA with the following primers: CD27S 5'-AA AAAGCTTCCACCATGGCACGGCCA-CATCCCTG-3' (SEQ ID NO:1) and CD27AS 5'-CCCCTC-GAG TCAGGGGGAGCAGGCAGG-3' (SEQ ID NO:2) and was inserted in the pcDNA3 vector as a HindIII-XhoI fragment.

For NF-kappaB luciferase assay, 293T cells ($1\times10^5$ cells per well) were seeded in 24 well plates. After 24 h, cells were transfected with 10 ng of the pNFconluc reporter gene plasmid, 10 ng pHR-GLuc-YFP and with 100 ng of the pcDNA3-caTLR4 or pcDNA3-CD27 expression plasmid when indicated. Transfections were performed in triplicate with the FuGENE 6 transfection reagent (Roche) and the total amounts of plasmid were kept constant by adding empty pcDNA3 plasmid. Following transfection, $1\times10^5$ electroporated DCs were added to the wells when indicated. Cell extracts were prepared 24 h later, and reporter gene activity was determined by the luciferase assay system (Promega, Leiden, The Netherlands). Results were normalized for the secreted Gaussia luciferase activity.

Flow cytometry.

DCs were stained using monoclonal antibodies (mAbs) against CD40-PE, CD80-PE, CD83-FITC, CD86-FITC and HLA-ABC-FITC (all from Pharmingen, San Jose, Calif.).

T cells were phenotyped with mAbs against CD4-FITC, CD8-FITC, CD8-APC-Cy7, CD27-APC, CD28-APC, CD45RA-biotin, CD45RO-APC, CD62L-FITC (all from Pharmingen) and CCR7-APC (R&D Systems, Oxford, UK). Biotinylated CD45RA was detected with PerCP conjugated streptavidin.

Non-reactive isotype-matched mAbs (Pharmingen) were used as controls.

Data were collected using a FACSCanto flow cytometer and analyzed using FACSDiva or CellQuest software. Cells were electronically gated according to light scatter properties in order to exclude dead and contaminating cells.

Cytokine secretion assay.

The secretion of 27 different cytokines and chemokines by DCs during the first 24 h after electroporation was assessed with the Bio-Plex human cytokine 27-Plex A panel according to the manufacturer's instructions (Bio-Rad, Nazareth, Belgium).

Induction of a naive CD4$^+$ T-cell response by electroporated DCs.

Naive CD4$^+$ T-cells were isolated from the non-adherent fraction of peripheral blood mononuclear cells by immunomagnetic selection using the CD4$^+$ T-cell Isolation Kit II (Miltenyi Biotec, Bergisch Gladbach, Germany), after which CD45RA$^+$ T-cells were positively selected using CD45RA microbeads (Miltenyi Biotec). CD4$^+$ T-cells were consistently >85% pure and >90% CD45RA positive (data not shown). Next, $5\times10^4$ naive CD4$^+$ T-cells were co-cultured with $1\times10^4$ allogeneic DCs electroporated with the indicated mRNA. Each coculture was performed in 12-fold in 200 µl stimulation medium per round-bottom 96 well. After 6 days, stimulated T-cells were harvested, resuspended at a density of $1\times10^6$ T-cells/ml stimulation medium in the presence of $4.7\times10^4$ CD3/CD28 T-cell expander beads (Dynal, Invitrogen) and replated at 200 µl per 96-well with round bottom. After 24 h of incubation at 37° C., the supernatant was harvested and assayed for IFN-gamma (BioSource International, Camarillo, Calif.), IL-4 (Pierce Biotechnology, Aalst, Belgium) and IL-10 (R&D Systems) content using commercially available ELISA kits. Each coculture was tested in duplicate in ELISA.

Induction of MelanA-specific CD8$^+$ T-cells.

T cells and DCs were obtained from HLA-A2$^+$ healthy donors. DCs were electroporated with the indicated mRNA and immediately pulsed with MelanA-A2 peptide for 2 h. After washing, peptide-pulsed mRNA electroporated DC were co-cultured with $10\times10^6$ autologous CD8$^+$ T-cells purified through immunomagnetic selection by using CD8 microbeads (Miltenyi). CD8$^+$ T-cells were consistently >90% pure (data not shown). Stimulations were carried out at a DC:T cell ratio of 1:10 in 5 ml stimulation medium per 6 well. CD8$^+$ T-cells were restimulated weekly with the same stimulator DCs as used in the primary stimulation. After 3 rounds of stimulation, CD8$^+$ T-cells were harvested and their antigen specificity and function were determined.

Tetramer staining.

T cells were stained with 10 nM PE-labeled HLA-A2 tetramers containing either MelanA (ELAGIGILTV) or MAGE-A3 (FLWGPRALV) peptides. Tetramers were prepared in-house. Subsequently, cells were stained with a FITC-labeled anti-CD8 Ab and $1\times10^5$ cells were analyzed by flow cytometry.

Intracellular cytokine staining.

The ability of MelanA primed CD8$^+$ T-cells to produce cytokines upon specific restimulation was investigated using intracellular staining for IFN-gamma and TNF-alpha according to the manufacturer's instructions. T2 cells pulsed with MelanA-A2 or gag-A2 peptide were co-cultured with primed CD8$^+$ T-cells at a responder:stimulator ratio of 10:1 for 2-3 h at 37° C. Golgi-plug was then added to block cytokine secretion and cells were incubated for an additional 12 h at 37° C. CD8$^+$ T-cells were then stained with APC-Cy7-conjugated anti-CD8, washed, permeabilized and stained intracellularly with IFN-gamma-PE/TNF-alpha-FITC using the BD Cytofix/Cytoperm plus kit. One hundred thousand cells were analyzed by flow cytometry to assess the percentage of cytokine producing CD8$^+$ T-cells.

CD107a mobilization assay.

$1\times10^5$ primed CD8$^+$ T-cells were restimulated with $4\times10^4$ MelanA-A2 or gag-A2 peptide loaded T2 cells in the presence of Golgi-stop (monensin, BD) and either PE-Cy5-labelled anti-CD107a mAb or an irrelevant isotype control. After 12 h of incubation at 37° C., cells were harvested, stained with FITC-labeled anti-CD8 mAb and $1\times10^5$ cells were analyzed by flow cytometry to assess the percentage of CD8$^+$CD107a$^+$ T-cells.

Results:

Activation of the NF-kappaB pathway.

Figure 2:
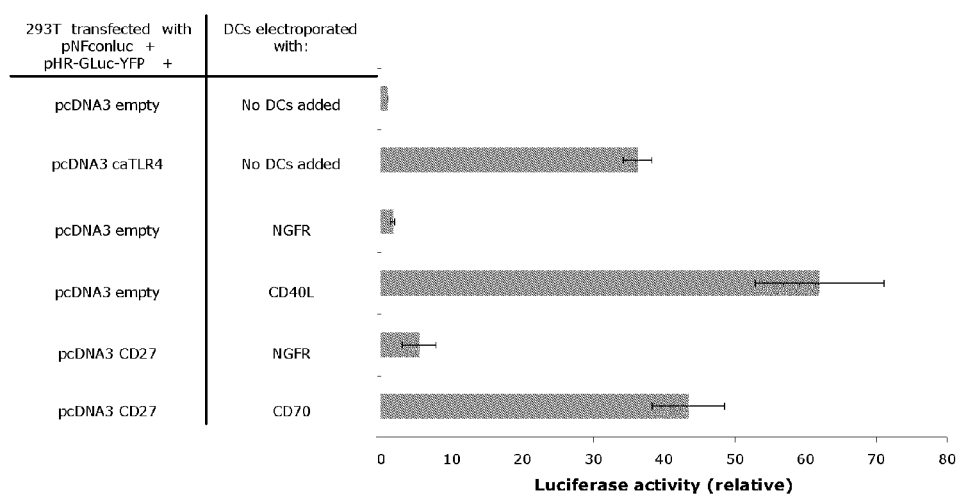
FIG. 2. NF-kappaB activation assay. 293T cells were transfected with the pNFconluc reporter gene plasmid (encoding the firefly luciferase gene driven by a minimal NF-kappaB-responsive promoter) and the pHR-GLuc-YFP plasmid (encoding the humanized secreted Gaussia luciferase fused to yellow fluorescent protein). When indicated, cells were co-transfected with the pcDNA3-caTLR4 or pcDNA3-CD27 expression plasmid. Of note, 293T cells endogenously express CD40. Transfections were performed in triplicate and the total amounts of plasmid were kept constant by adding empty pcDNA3 plasmid. Following transfection, $1 \times 10^5$ DCs electroporated with CD40L or CD70 mRNA were added when indicated. After 24 h, luciferase activities were determined and normalized on the basis of secreted Gaussia luciferase activity. Results are shown as mean±SD and are representative for 3 independent experiments.

As shown in FIG. 2, when compared to DCs electroporated with NGFR mRNA, both DCs electroporated with CD40L and CD70 mRNA led to NF-kappaB activation in 293T cells expressing CD40 or CD27, respectively. Although this type of experiment was not feasible with caTLR mRNA, we could show that 293T cells co-transfected with caTLR4 DNA (encoding the same protein as the caTLR4 mRNA) and NF-kappaB reporter plasmid also led to an activation of the NF-kappaB pathway when compared to 293T cells co-transfected with NF-kappaB reporter plasmid and empty pcDNA3 plasmid (FIG. 2). These data indicate that the CD40L, CD70 and caTLR4 mRNAs encode functionally active proteins.

Phenotype of differently electroporated DCs.

Figure 3A:
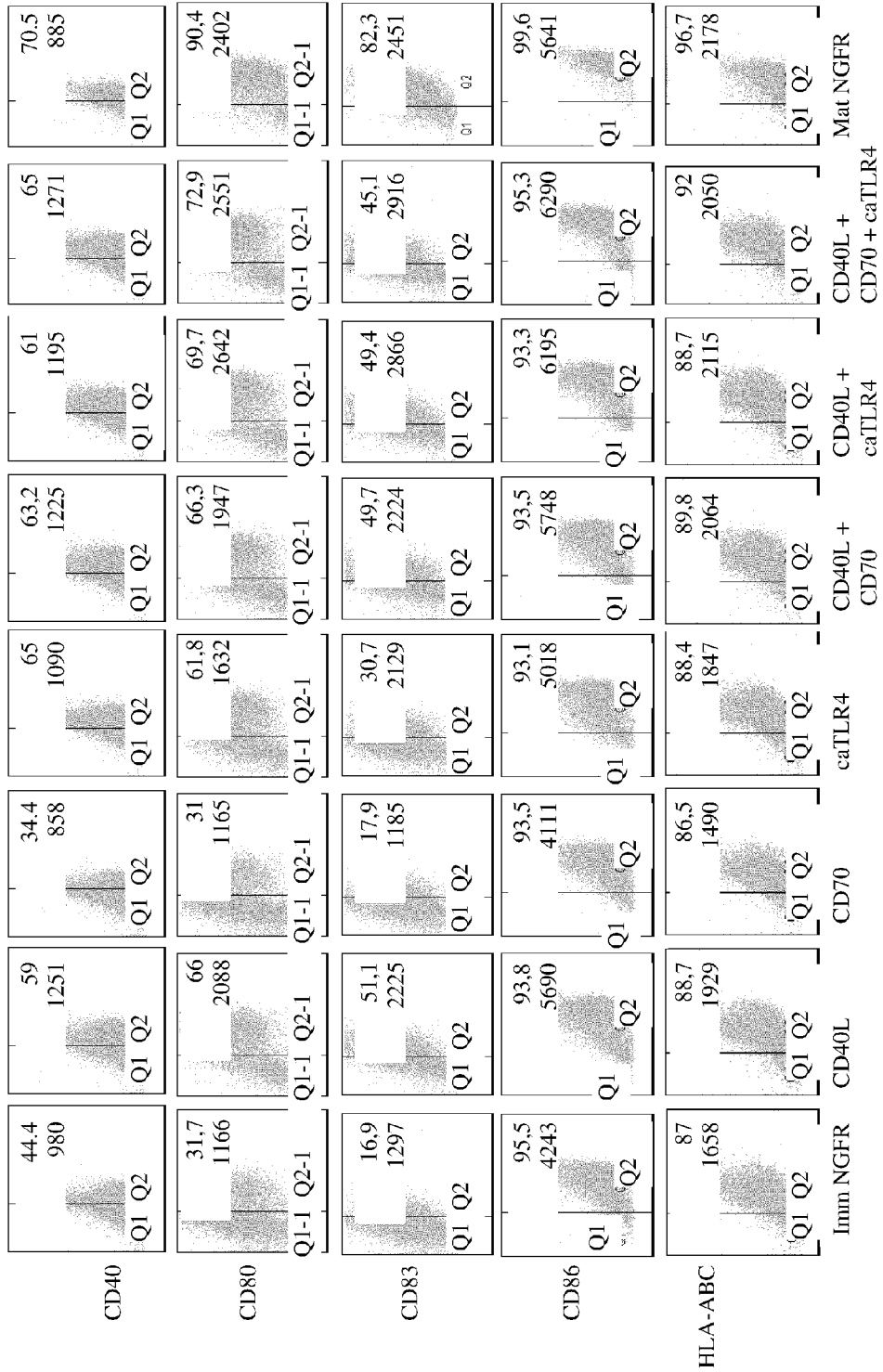
FIG. 3. Electroporating immature DCs with CD40L and/or caTLR4 mRNA induces phenotypic maturation, enhanced IL-12 secretion and stimulation of naive CD4$^+$ T-cells to differentiate into IFN-gamma secreting cells. (A) DCs electroporated with different combinations of CD40L, CD70 and caTLR4 mRNA were stained after 24 h for costimulatory molecules CD40, CD80, CD83 and CD86 and for HLA class I molecules. Percentage of positive cells and mean fluorescence intensity are indicated. Results are representative for at least 8 independent experiments. (B) IL-12p70 produced within 24 h after electroporation was dosed in the supernatant. Each dot represents one individual experiment and the mean is indicated by a horizontal line. (C) Electroporated DCs were used to stimulate allogeneic CD45RA$^+$ naive CD4$^+$ T-cells. Six days later, CD4$^+$ T-cells were restimulated with CD3/CD28 T-cell expander beads. After 24 h, IFN-gamma☐ secretion was assessed in the supernatant by ELISA. Each dot represents one individual experiment and the mean is indicated by a horizontal line.

We assessed the phenotype of DCs electroporated with the different combinations of CD40L, CD70 and caTLR4 mRNA and compared it to immature (1 mm) and cytokine cocktail matured (Mat) DCs electroporated with irrelevant NGFR mRNA as negative and positive controls, respectively. As shown in FIG. 3A, electroporation of immature DCs with CD40L and/or caTLR4 mRNA induced a marked upregulation of the costimulatory molecules CD40, CD80, CD83 and CD86 and of HLA class I molecules. Overall, caTLR4 mRNA electroporated DCs showed a slightly less pronounced phenotypical maturation than CD40L mRNA electroporated DCs whereas the combination of CD40L and caTLR4 mRNA induced the most pronounced phenotypical maturation, which was comparable with the maturation induced by the cytokine cocktail. In contrast, CD70 electroporation or co-electroporation had no effect on the DC's phenotype.

Cytokine/chemokine secretion by differently electroporated DCs.

Figure 3B:
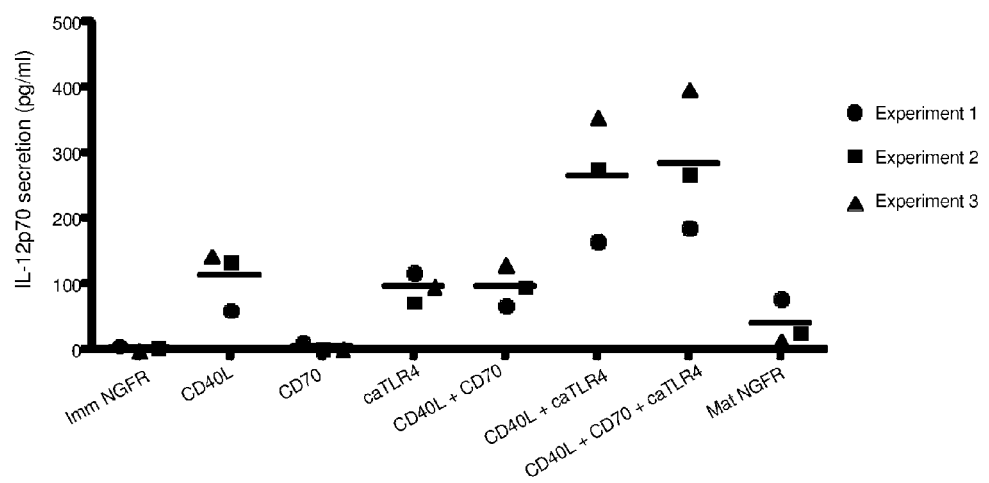

In addition to a phenotypical maturation, electroporation with CD40L or caTLR4 mRNA induced an enhanced secretion of bioactive IL-12p70. Combination of CD40L and caTLR4 boosted the IL-12p70 production even further. Again, CD70 electroporation or co-electroporation had no effect (FIG. 3B). We also investigated the secretion of several other cytokines and chemokines. Secretion by DCs co-electroporated with CD40L, CD70 and caTLR4 mRNA, compared to immature and cytokine cocktail matured DCs electroporated with irrelevant NGFR mRNA is shown in Table 1. For each cytokine/chemokine listed in Table 1, we found that CD70 (co-)electroporation had no effect, whereas CD40L and caTLR4 electroporation increased cytokine/chemokine secretion, and the combination of both yielded the highest secretion. Furthermore, we observed no secretion of IL-2, IL-4, IL-5, IL-7, IL-9, IL-13, IL-15, IL-17, eotaxin, FGF basic or PDGF by any of our DC preparations.

TABLE 1

Cytokine and chemokine production (pg/ml) by electroporated DCs. DCs were electroporated with irrelevant mRNA or the combination of CD40L, CD70 and caTLR4 mRNA. After electroporation, DCs were cultured for 24 h at a cell density of 1 × 10$^6$ cells/ml in stimulation medium without addition of supplemental cytokines. Cytokine and chemokine secretion were measured with the Bio-Plex human cytokine 27-Plex A panel. One out of 3 experiments shown.

|  |  | Imm NGFR | CD40L + CD70 + caTLR4 | Mat NGFR |
|---|---|---|---|---|
| Cytokines | IL-1beta | 7.2 | 146 | 3.5 |
|  | IL-6 | 754 | >20000 | 1093 |
|  | IL-10 | 43.4 | 902 | 54.1 |
|  | G-CSF | 140 | 8553 | 68 |
|  | GM-CSF | 9 | 101 | 10.3 |
|  | IFN-gamma | 51.5 | 508 | 71.6 |
|  | TNF-alpha | 87.2 | >20000 | 20 |
| Chemokines | IL-8 | 10521 | >30000 | 3143 |
|  | MIP-1alpha | 175 | 917 | 120 |
|  | IP-10 | 1076 | >20000 | 50.5 |
|  | RANTES | 1071 | >20000 | 598 |

Stimulation of naive CD4$^+$ T-cells by differently electroporated DCs.

Figure 3C:
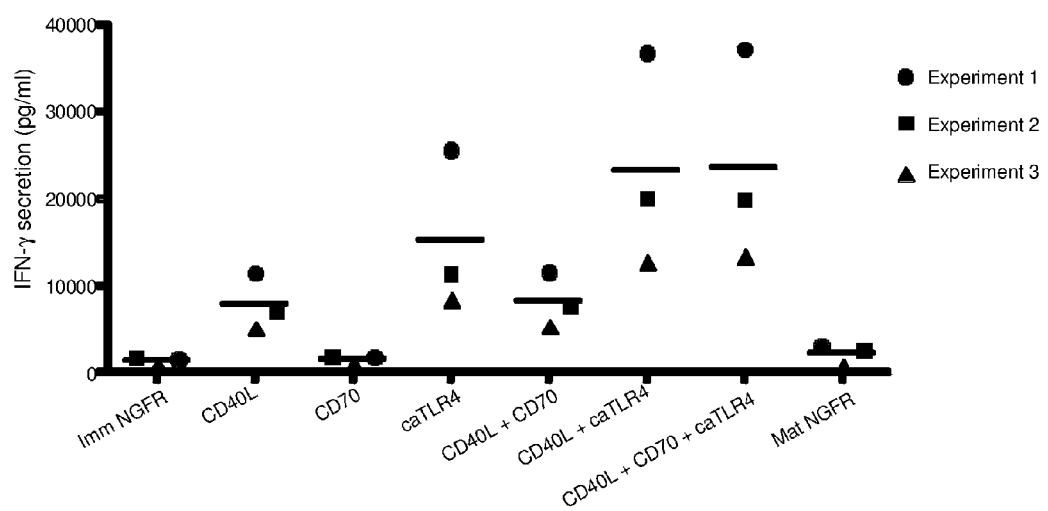

Next, it was investigated whether DCs electroporated with different combinations of CD40L, CD70 and caTLR4 mRNA could induce a naive CD4$^+$ T-cell response and whether skewing towards a Th1 or Th2 response was observed. Therefore, electroporated DCs were used to stimulate allogeneic CD45RA$^+$ CD4$^+$ T-cells and after restimulation with CD3/CD28 T-cell expander beads the supernatant was assessed for IL-4, IL-10 and IFN-gamma content. Overall, the stimulated T-cells secreted very low amounts of IL-4 (<50 pg/ml) and IL-10 (<200 pg/ml) and no differences were found between the differently stimulated T-cells (data not shown). On the other hand, DCs electroporated with CD40L and caTLR4 mRNA stimulated the CD4$^+$ T-cells to secrete high amounts of IFN-gamma. Here also, combination of CD40L with caTLR4 boosted the IFN-gamma secretion even further and CD70 (co-)electroporation had no effect (FIG. 3C), although FACS analysis confirmed that the CD4$^+$CD45RA$^+$ T-cells expressed CD27.

Induction of MelanA-specific CD8$^+$ T-cells by differently electroporated DCs.

Figure 4A:
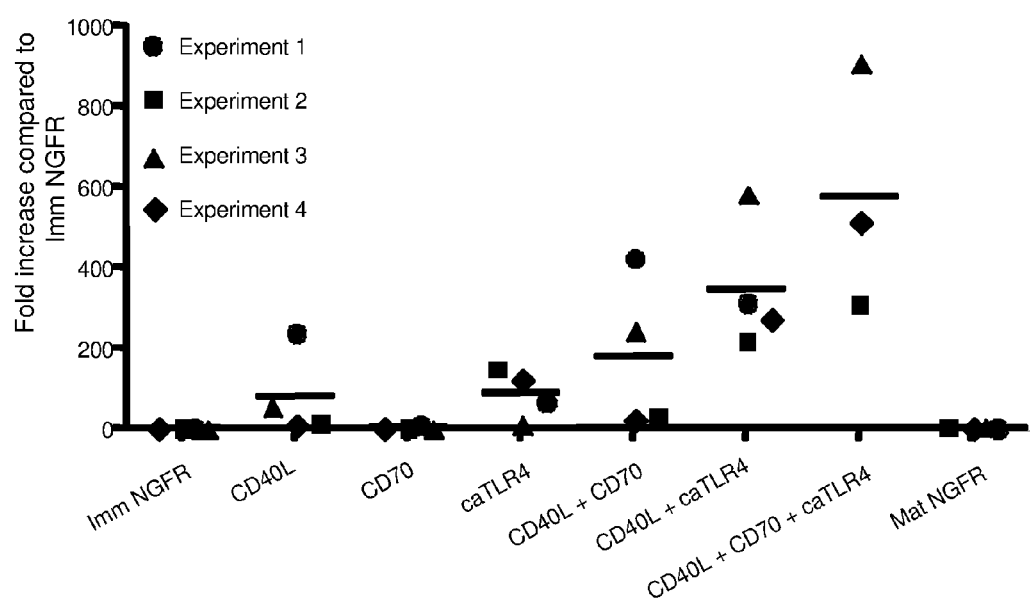
FIG. 4A. Increased induction of HLA-A2 restricted MelanA-specific CD8$^+$T-cells, cytolytic CD8$^+$T-cells and IFN-gamma/TNF-alpha secreting CD8$^+$T-cells by DCs electroporated with different combinations of CD4OL, CD70 and caTLR4 mRNA and pulsed with MelanA-A2peptide. (A) Naive CD8$^+$T-cells were stimulated 3 times with electroporated, peptide pulsed DCs. Then, T-cells were counted and stained for CD8 and MelanA specificity. Fold increase over immature DCs electroporated with irrelevant mRNA is shown. Each dot represents one individual experiment and the mean is indicated by a horizontal line.

In a next set of experiments, we investigated whether DCs electroporated with different combinations of CD40L, CD70 and caTLR4 mRNA could prime naive MelanA-specific CD8$^+$ T-cells. Therefore, DCs from HLA-A2$^+$ healthy donors were electroporated with different combinations of CD40L, CD70 and caTLR4 mRNA, pulsed with the immunodominant MelanA peptide and co-cultured with autologous CD8$^+$ T-cells. Immature and cytokine cocktail matured DCs, electroporated with irrelevant NGFR mRNA and pulsed with MelanA peptide, were used as controls. After 3 weekly stimulations, the number of remaining cells and the percentage of tetramer positive, MelanA-specific CD8$^+$ T-cells were determined (Table 2). From these data the absolute number of tetramer positive, MelanA-specific CD8$^+$ T-cells (Table 2) and the fold increase over immature DCs electroporated with irrelevant mRNA (FIG. 4A) were calculated. Our data show that electroporating DCs with CD40L or caTLR4 mRNA alone yielded a higher number of MelanA-specific CD8$^+$ T-cells, which was further increased by combining CD40L with CD70 or caTLR4 electroporation. Combination of all three molecules consistently resulted in the highest increase of antigen-specific T-cell numbers, with a mean fold increase of 573 and 203 over immature or cytokine cocktail matured DCs electroporated with NGFR mRNA, respectively.

TABLE 2

Induction of HLA-A2 restricted MelanA-specific CD8$^+$ T-cells by DCs electroporated with different combinations of CD40L, CD70 and caTLR4 mRNA and pulsed with MelanA peptide. Results are shown for 4 individual experiments from different healthy donors.

|  | % CD8$^+$ MelanA tetramer$^+$ T-cells/ number of CD8$^+$ T-cells (10$^6$)$^†$ | | | | Absolute number of CD8$^+$ MelanA tetramer$^+$ T-cells (10$^3$)$^‡$ | | | |
|---|---|---|---|---|---|---|---|---|
|  | Exp 1 | Exp 2 | Exp 3 | Exp 4 | Exp 1 | Exp 2 | Exp 3 | Exp 4 |
| Imm NGFR | 0.4/3.4 | 0.5/2.1 | 0.1/2.8 | 0.1/1.35 | 13.7 | 10.7 | 2.8 | 1.35 |
| CD40L | 60.2/5.4 | 6.7/2.1 | 5.6/2.8 | 1.1/1.5 | 3271 | 141 | 157 | 16.5 |
| CD70 | 3.3/3.6 | 0.9/1.7 | 0.2/2.2 | 0.2/1.65 | 120 | 15.4 | 4.4 | 3.3 |

TABLE 2-continued

Induction of HLA-A2 restricted MelanA-specific CD8+ T-cells by DCs electroporated with different combinations of CD40L, CD70 and caTLR4 mRNA and pulsed with MelanA peptide. Results are shown for 4 individual experiments from different healthy donors.

| | % CD8+ MelanA tetramer+ T-cells/ number of CD8+ T-cells $(10^6)$† | | | | Absolute number of CD8+ MelanA tetramer+ T-cells $(10^3)$‡ | | | |
|---|---|---|---|---|---|---|---|---|
| | Exp 1 | Exp 2 | Exp 3 | Exp 4 | Exp 1 | Exp 2 | Exp 3 | Exp 4 |
| caTLR4 | 20.8/4.3 | 40.3/4.0 | 1.3/2.2 | 9.3/1.8 | 892 | 1596 | 29.1 | 167 |
| CD40L + CD70 | 65/8.9 | 17.3/2.0 | 17.1/4.0 | 1.8/1.75 | 5792 | 348 | 677 | 31.5 |
| CD40L + caTLR4 | 64/6.7 | 49.5/4.7 | 39.9/4.0 | 16.8/2.2 | 4301 | 2317 | 1612 | 370 |
| CD40L + CD70 + caTLR4 | ND/ND | 60.5/5.5 | 40.2/6.2 | 63.2/1.1 | ND | 3303 | 2508 | 695 |
| Mat NGFR | 0.7/3.1 | 1.2/3.4 | 0.4/3.2 | 0.1/1.7 | 21.7 | 41.0 | 12.9 | 1.7 |

†The T-cell population generated after 3 weekly stimulations with electroporated, MelanA peptide pulsed DCs was stained with MelanA loaded HLA-A2 tetramers and anti-CD8 Ab. MelanA-specific CD8+ T-cells were then identified by flow cytometry. Background staining with MAGE-A3-specific HLA-A2 tetramers, which never reached higher than 0.5%, was subtracted. The number of living cells was determined by trypan blue exclusion.
‡Absolute number of MelanA-specific CD8+ T-cells was calculated with the following formula: (number of CD8+ T-cells/100) × % of CD8+ MelanA tetramer+ T-cells.

Functional and phenotypical properties of stimulated CD8+ T-cells.

Figures 2, 4B:
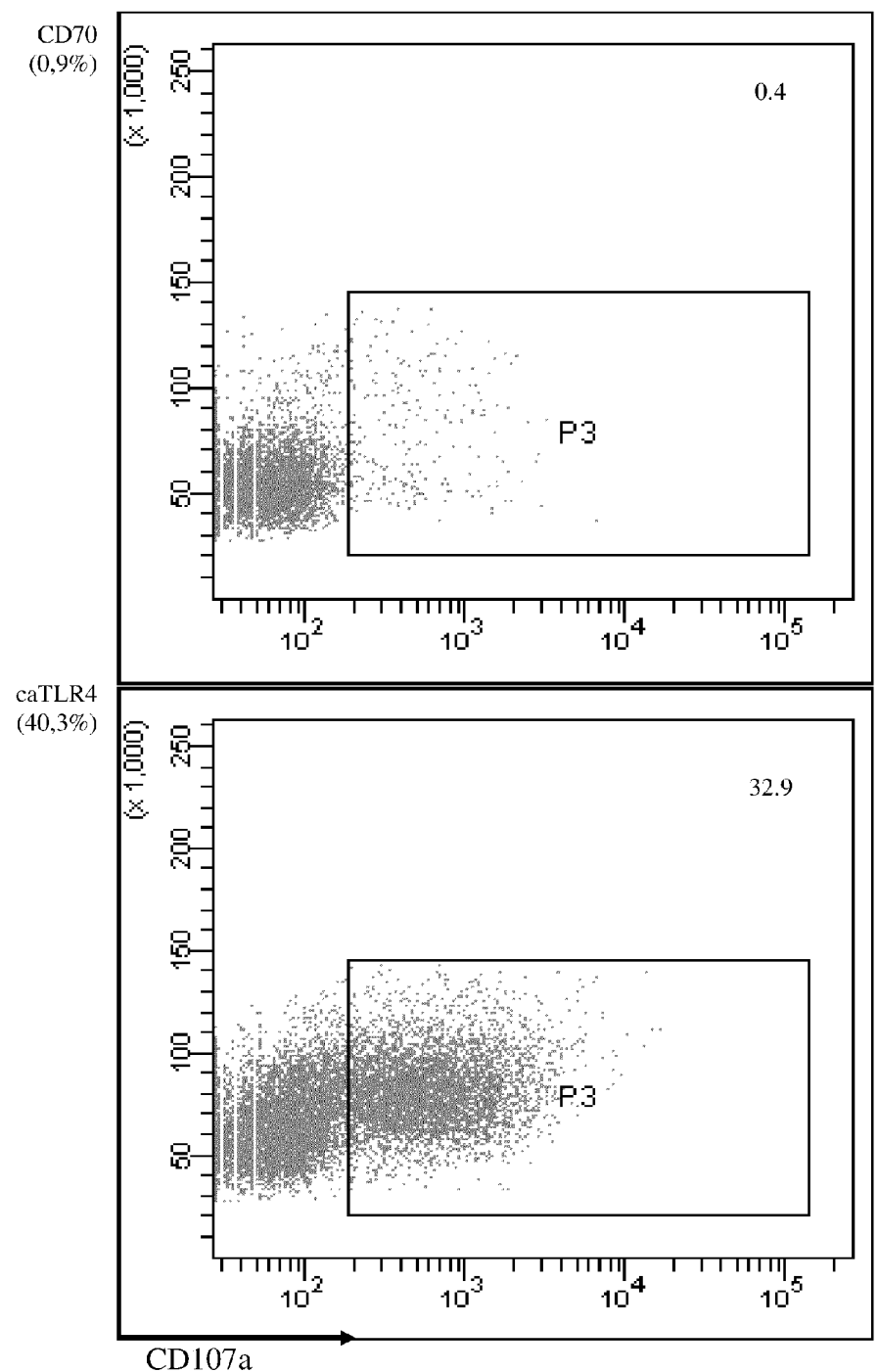
Figures 3, 4B:
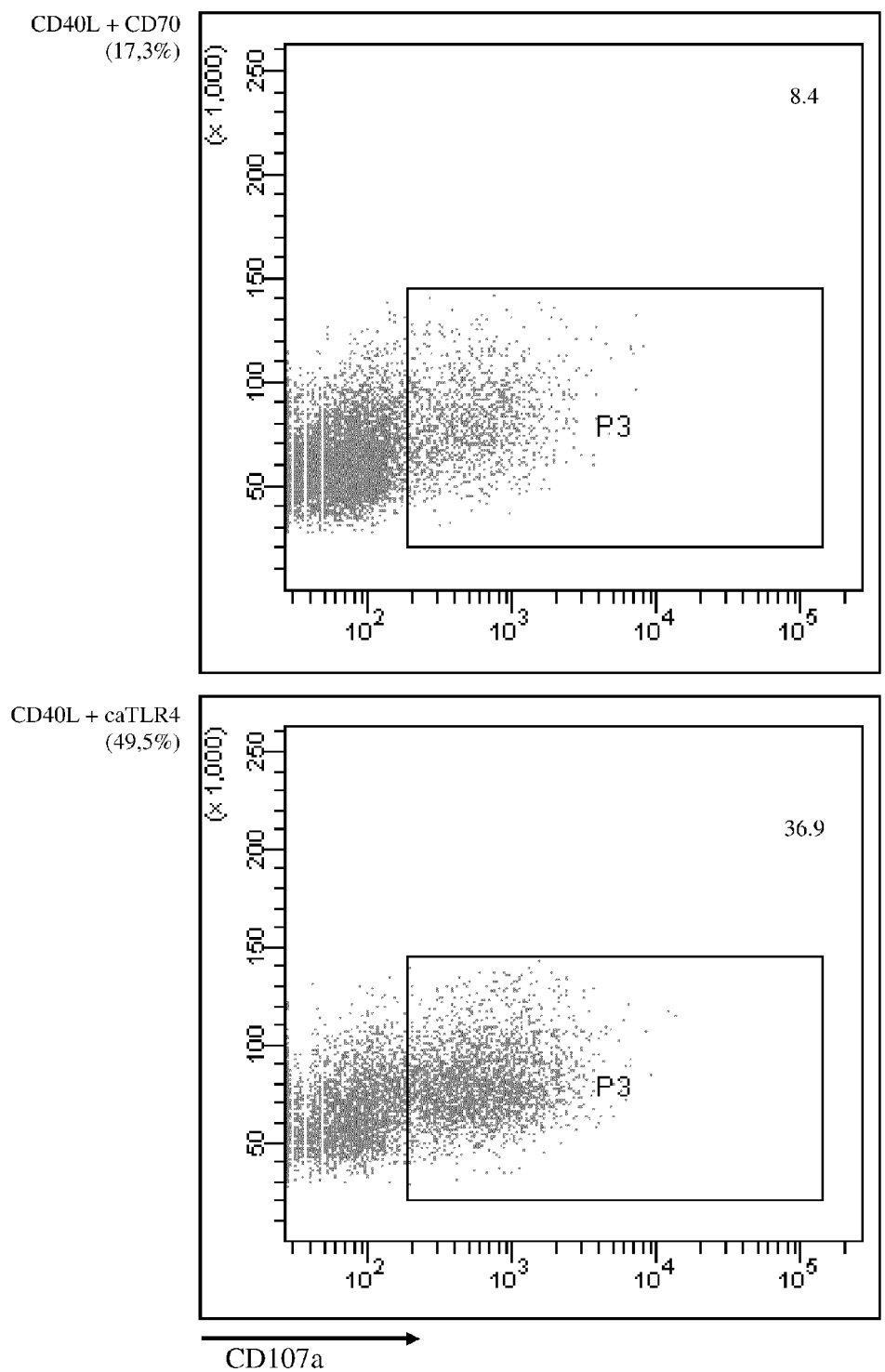
Figures 1, 4C:
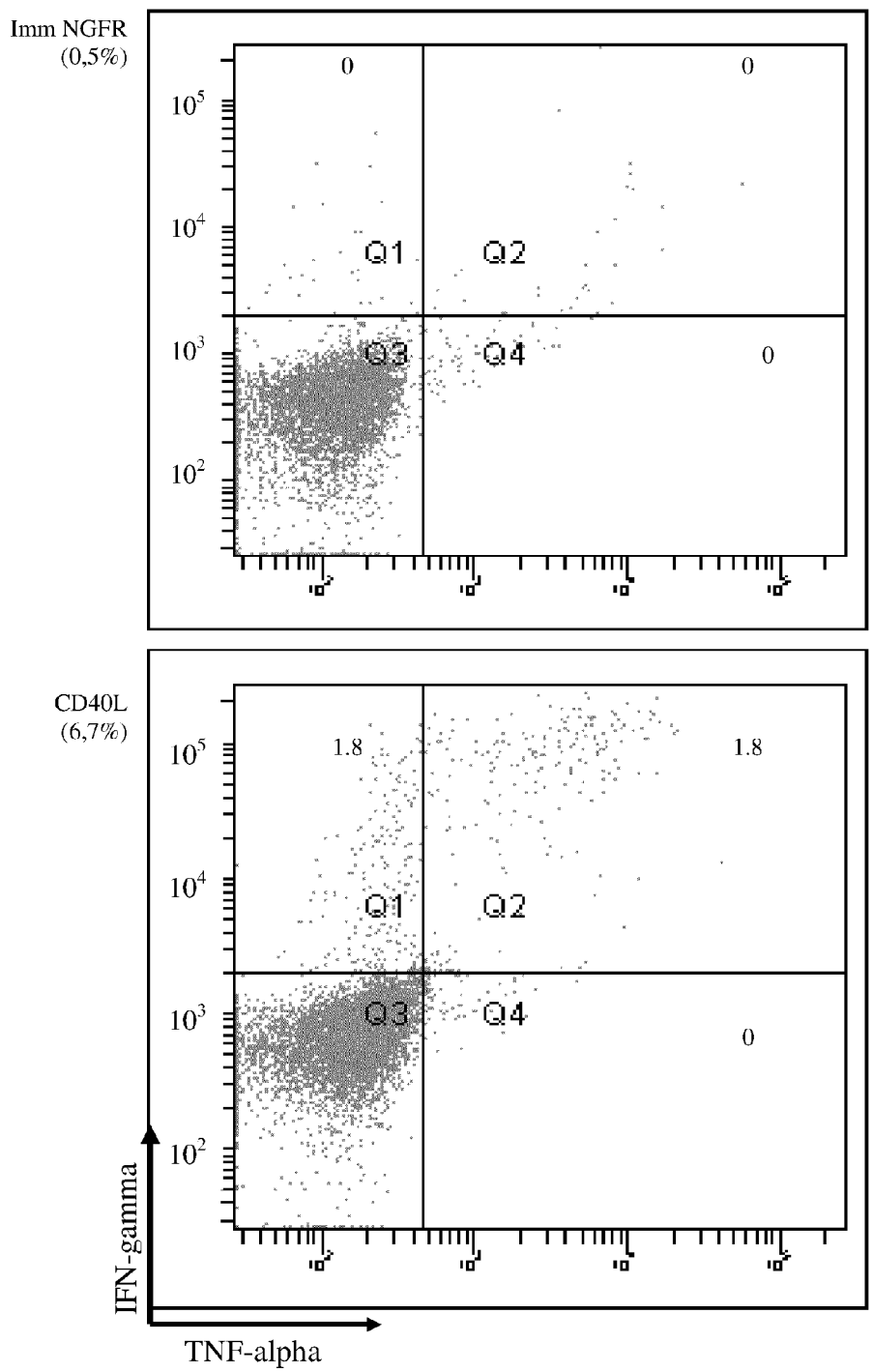
Figures 2, 4C:
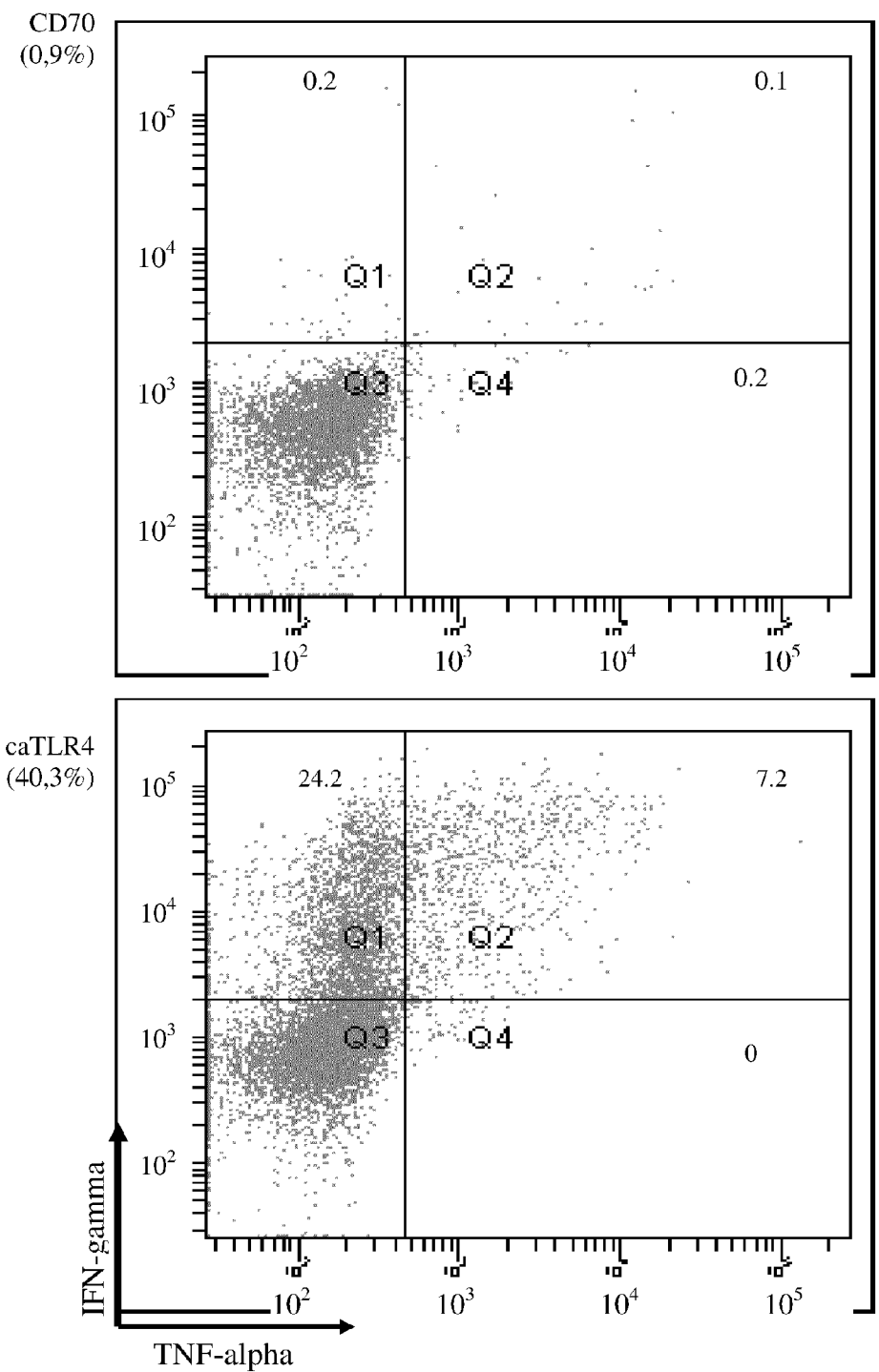
Figures 3, 4C:
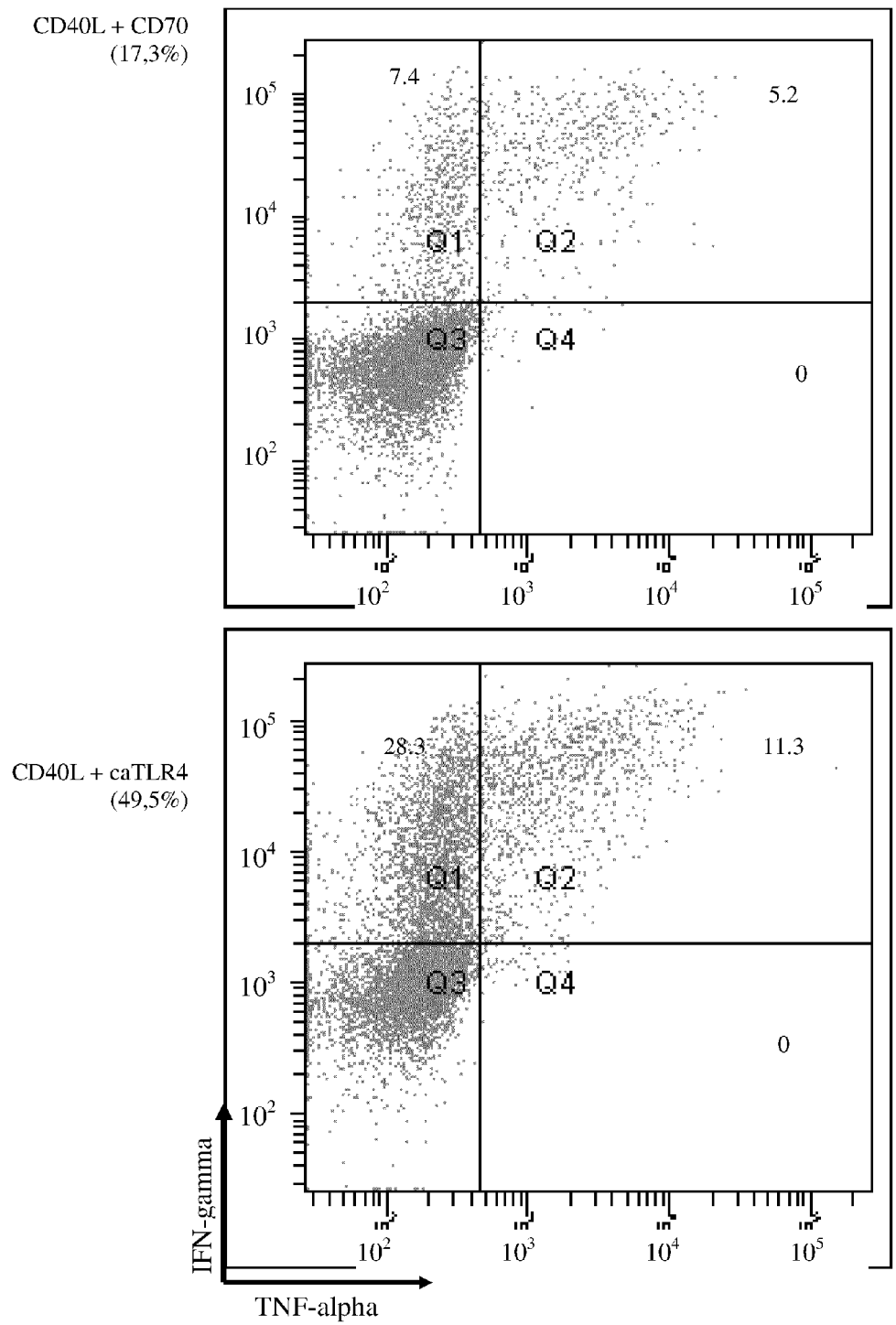
Figures 4, 4C:
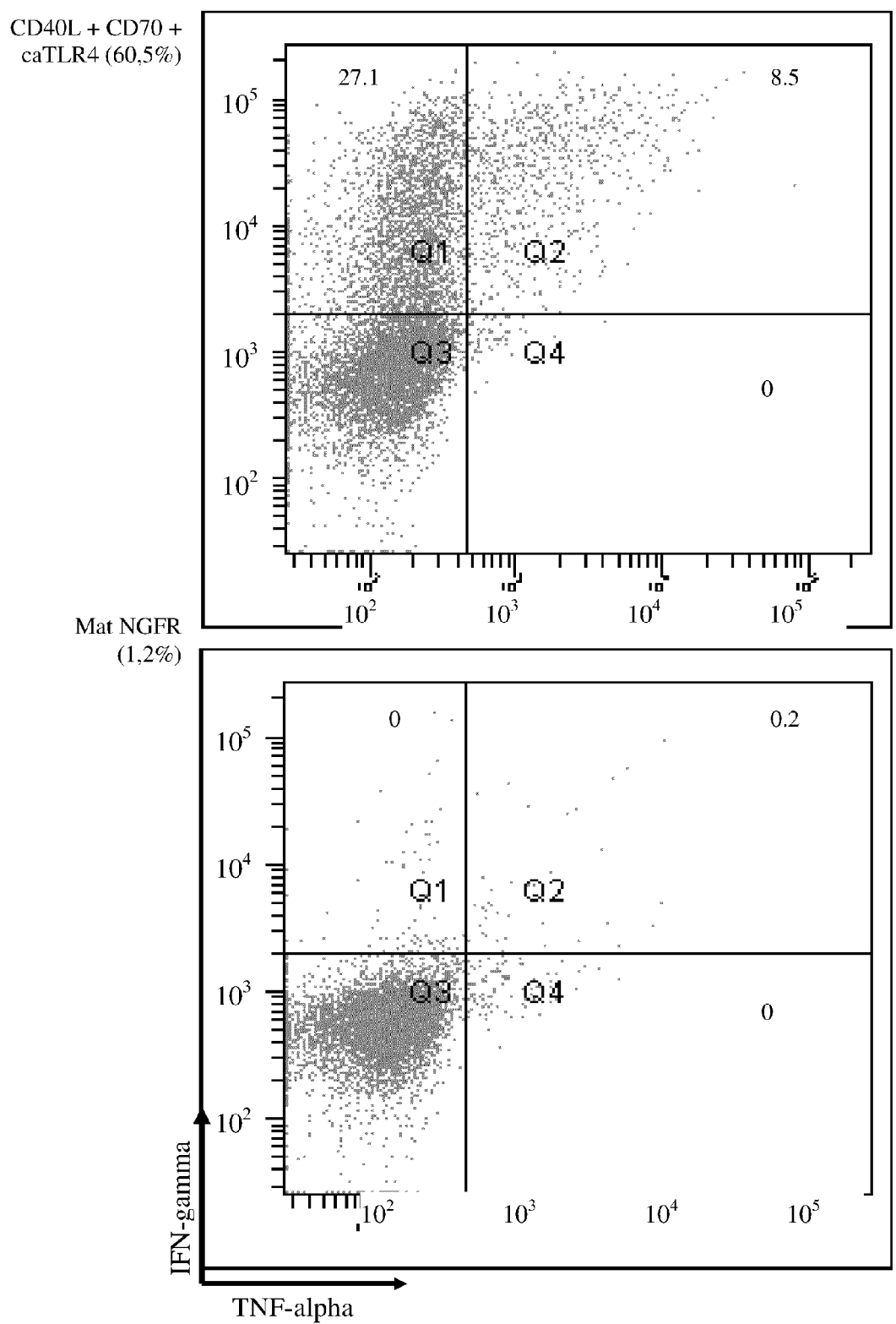
Figures 1, 4D:
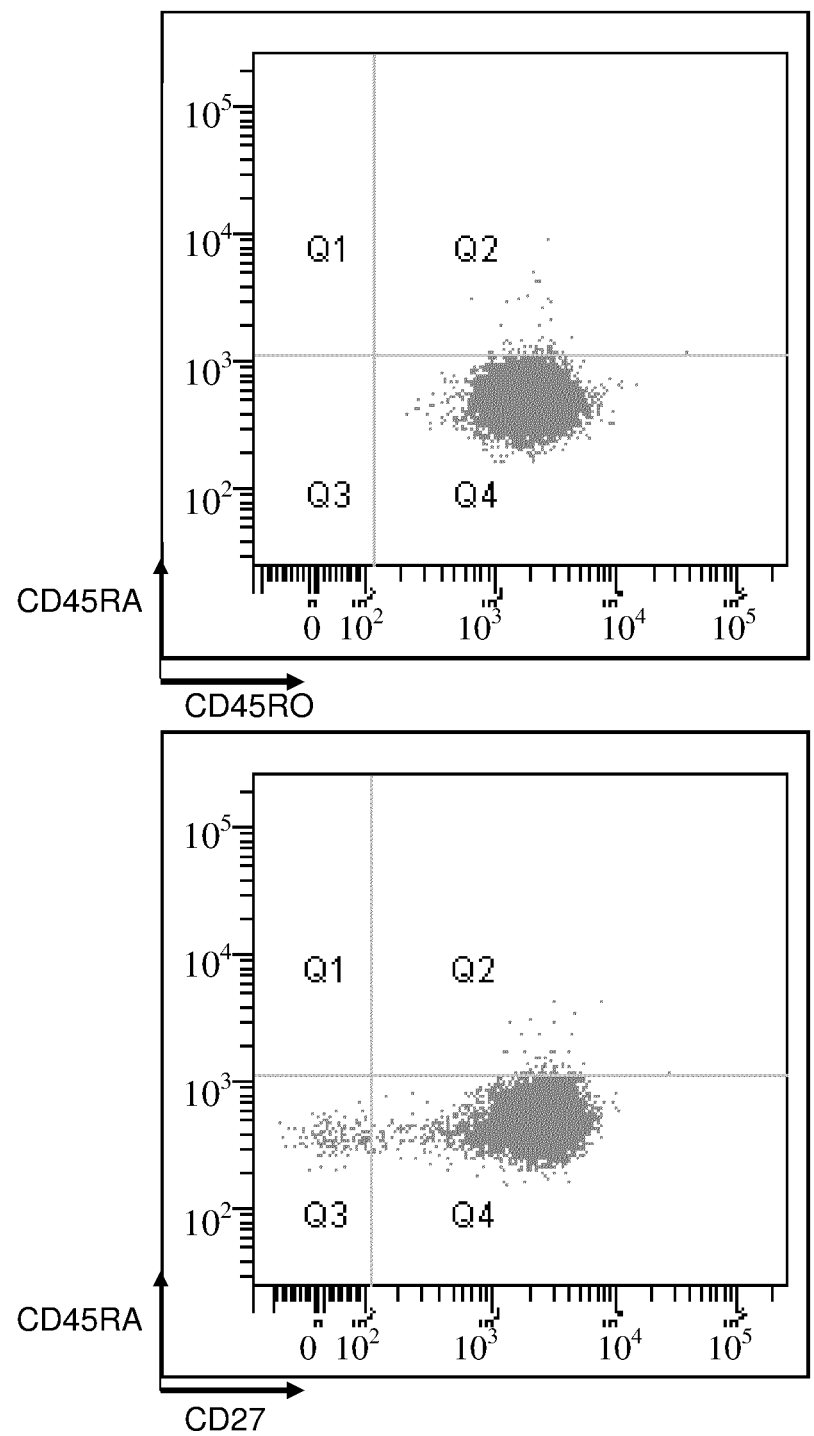
Figures 2, 4D:
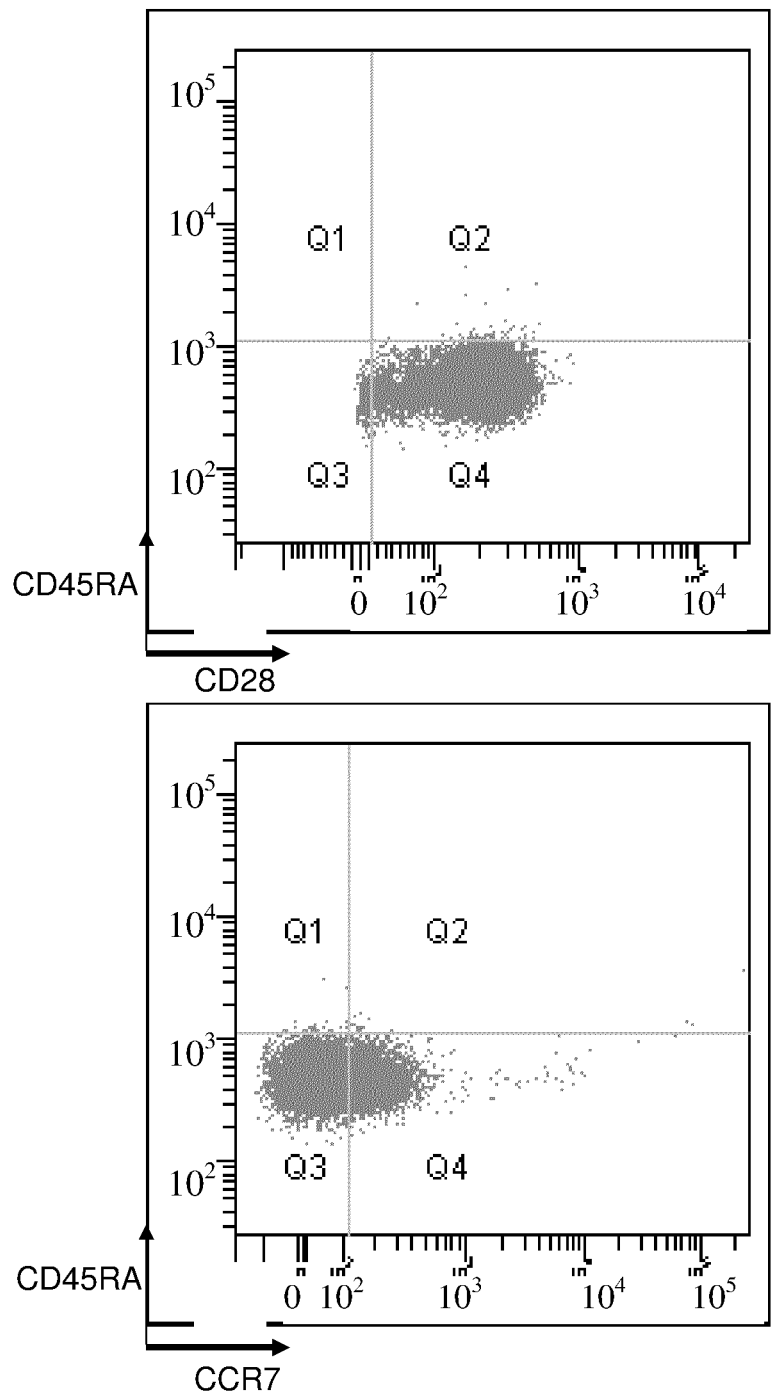
Figures 3, 4D:
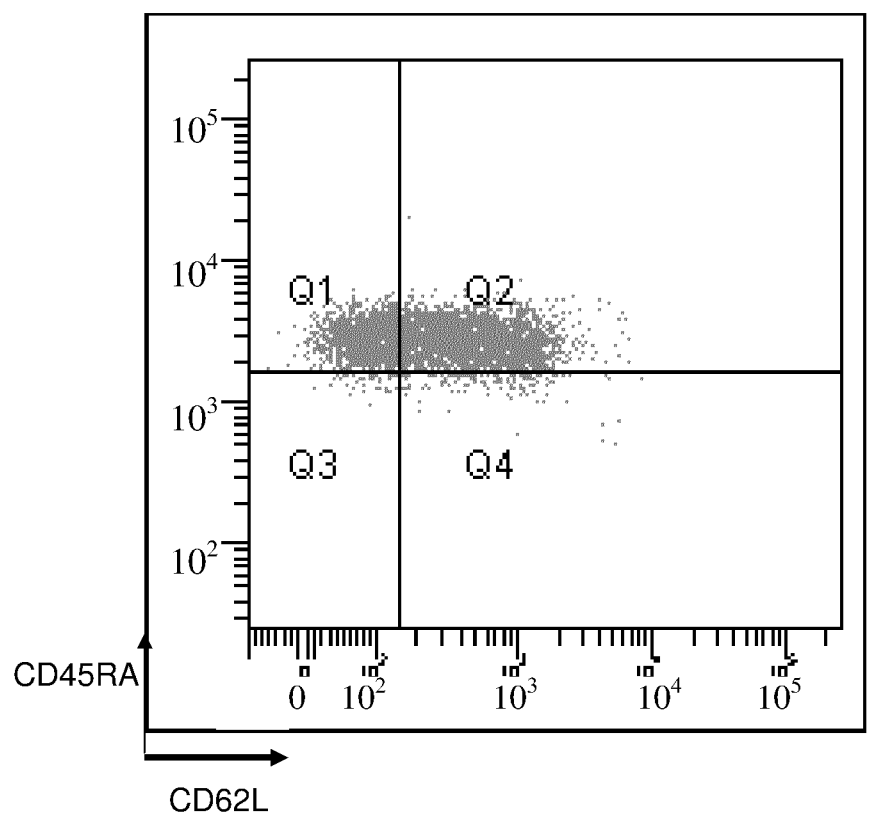

Finally, we assessed the functional and phenotypical properties of CD8+ T-cells stimulated 3 times with differently electroporated, MelanA-A2 peptide pulsed DCs. The main effector mechanisms of stimulated CD8+ T-cells, i.e. cytolysis and cytokine production, were investigated. First we performed a CD107a mobilization assay (FIG. 4B), which measures exposure of CD107a, present on the membrane of cytotoxic granules, onto the T-cell surface as a result of degranulation upon antigenic stimulation. It has been shown that CD107a mobilization can be used as a marker for lytic activity. Second we performed intracellular cytokine stainings to enumerate the number of cells secreting IFN-gamma and/or TNF-alpha, both major mediators of the immune response, upon antigenic stimulation (FIG. 4C). For all donors tested we observed that the percentage of MelanA-specific T-cells, correlated with the percentage of lytic T-cells and with the percentage of IFN-gamma/TNF-alpha producing T-cells. On the other hand, we also analyzed the phenotype of the induced MelanA-specific CD8+ T-cells. The primed CD8+ MelanA-specific T-cells were all CD45RA− CD45RO+CD27+CD28+, together with a variable expression of CD62L and CCR7 (FIG. 4D). Overall, there were no significant differences in the phenotype of the MelanA-specific CD8+ T-cells of the different donors, regardless of which DC type was used for stimulation.

Example 4

TriMix DCs can be Co-Electroporated with TAA mRNA without Affecting Their Electroporation Efficiency, Mature Phenotype and Cytokine Secretion Materials and methods:
Genetic constructs.

The pGEM-CD40L, pGEM-CD70, pGEM-caTLR4 plasmids encoding CD40L, CD70 and the constitutively active form of TLR4 (containing the intracellular and transmembrane fragments of TLR4), respectively; the pGEM-NGFR plasmid encoding a truncated form of the nerve growth factor receptor (NGFR, containing the extracellular and transmembrane fragments); and the pGEM-sig-MelanA-DCLamp plasmid encoding the full-length MelanA antigen, containing the optimized immunodominant MelanA-A2 epitope and linked to the DC-Lamp targeting signal have been described. In vitro generation of human monocyte derived DCs, in vitro transcription of capped mRNA and mRNA electroporation of DCs.

Generation, maturation and cryopreservation of immature and cytokine cocktail matured DCs, capped mRNA production and mRNA electroporation of TriMix DCs pulsed with MelanA peptide have been described above. For co-electroporation with tumorantigen mRNA, DCs were electroporated in the same manner as described in example 2, but 20 tumorantigen mRNA was included in the mRNA mixture.

Flow cytometry.

DCs were stained using the following mAbs: CD40-APC, CD70-PE, CD80-PE, CD83-PE, CD86-PE, HLA-ABC-FITC (all from BD Pharmingen, Erembodegem, Belgium) and HLA-DR (purified from clone L243). The anti-HLA-DR antibody was biotin labeled and detected through streptavidin-APC (BD Pharmingen). Non-reactive isotype-matched mAbs (BD Pharmingen) were used as controls. Data were collected using a FACSCanto flow cytometer and analyzed using FACSDiva software. Cells were electronically gated according to light scatter properties in order to exclude dead and contaminating cells.

Cytokine secretion assay.

IL-12p70 secretion by DCs during the first 24 h after electroporation was assessed by ELISA using a commercially available kit (eBioscience, Zoersel, Belgium).

Figures 1, 5A:
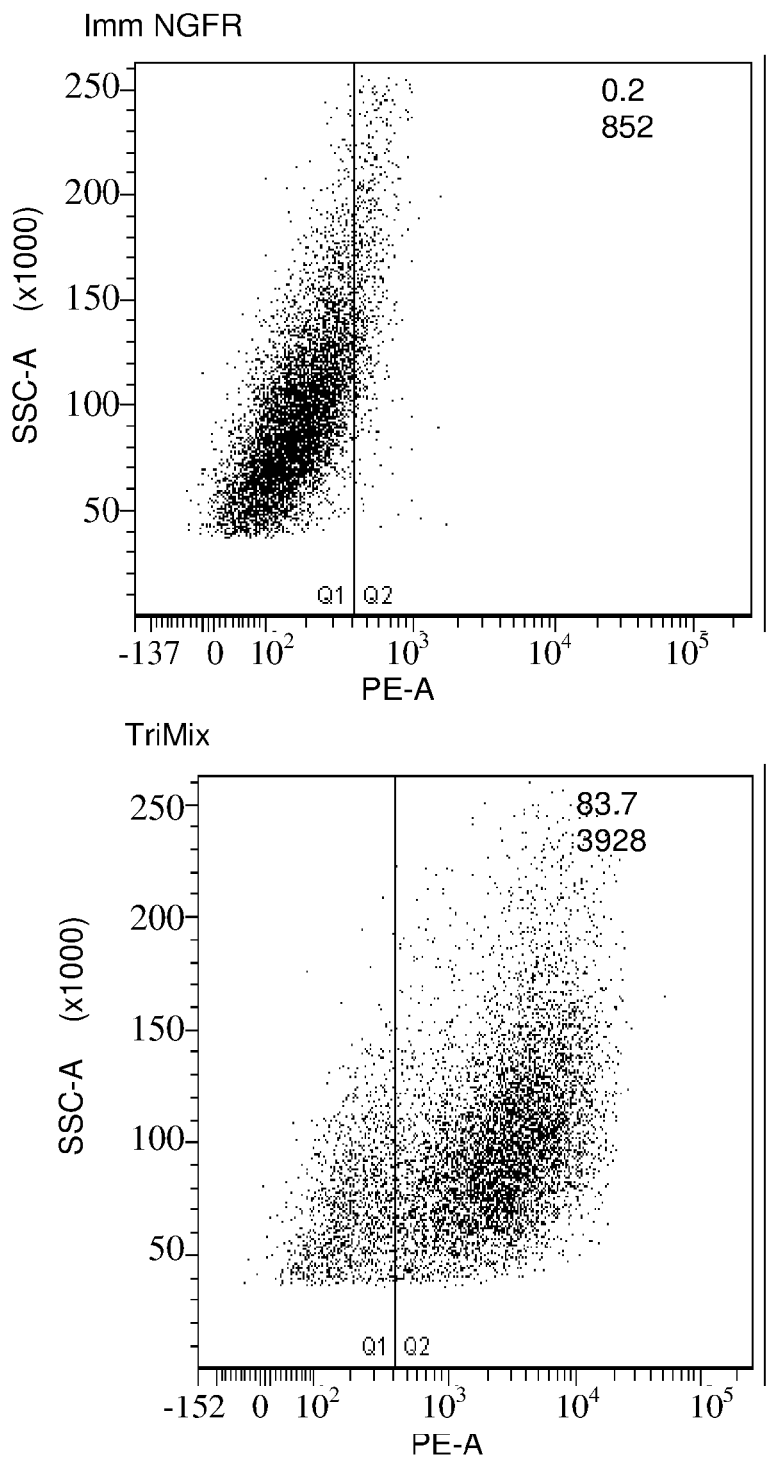
Figures 2, 5A:
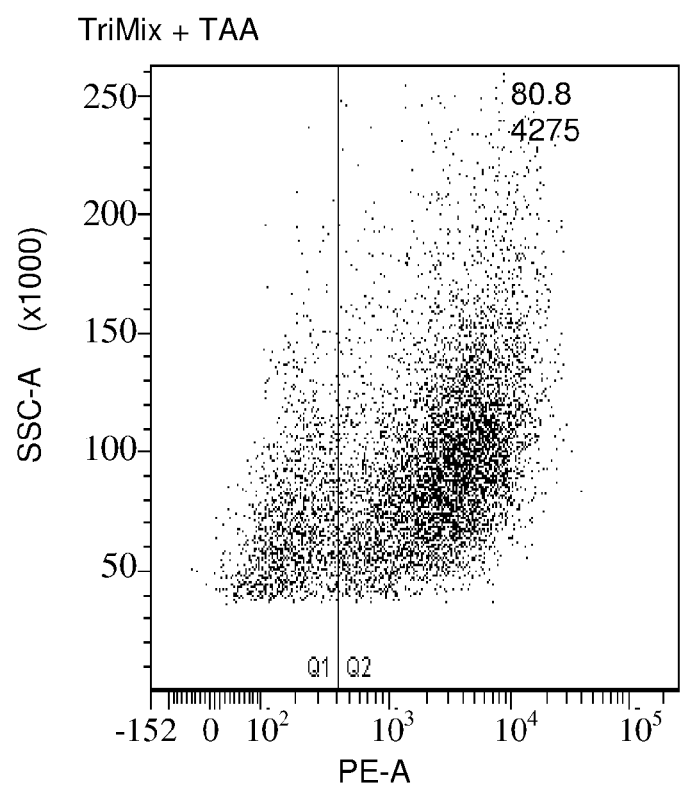

Results:

DCs electroporated with a TriMix of CD40L, CD70 and caTLR4 mRNA are typically very efficiently electroporated: on average, about 80% of the DCs express the CD70 molecule on their surface 24 h after electroporation. Because we observed that the electroporation efficiency slightly decreased when a combination of three different mRNAs was electroporated in comparison with a single mRNA, we investigated whether adding a fourth mRNA would affect electroporation efficiency. We found that, when TriMix DCs are co-electroporated with TAA mRNA, electroporation efficiency does not alter notably as demonstrated by CD70 expression 24 h after electroporation (FIG. 5A).

Figures 1, 5B:
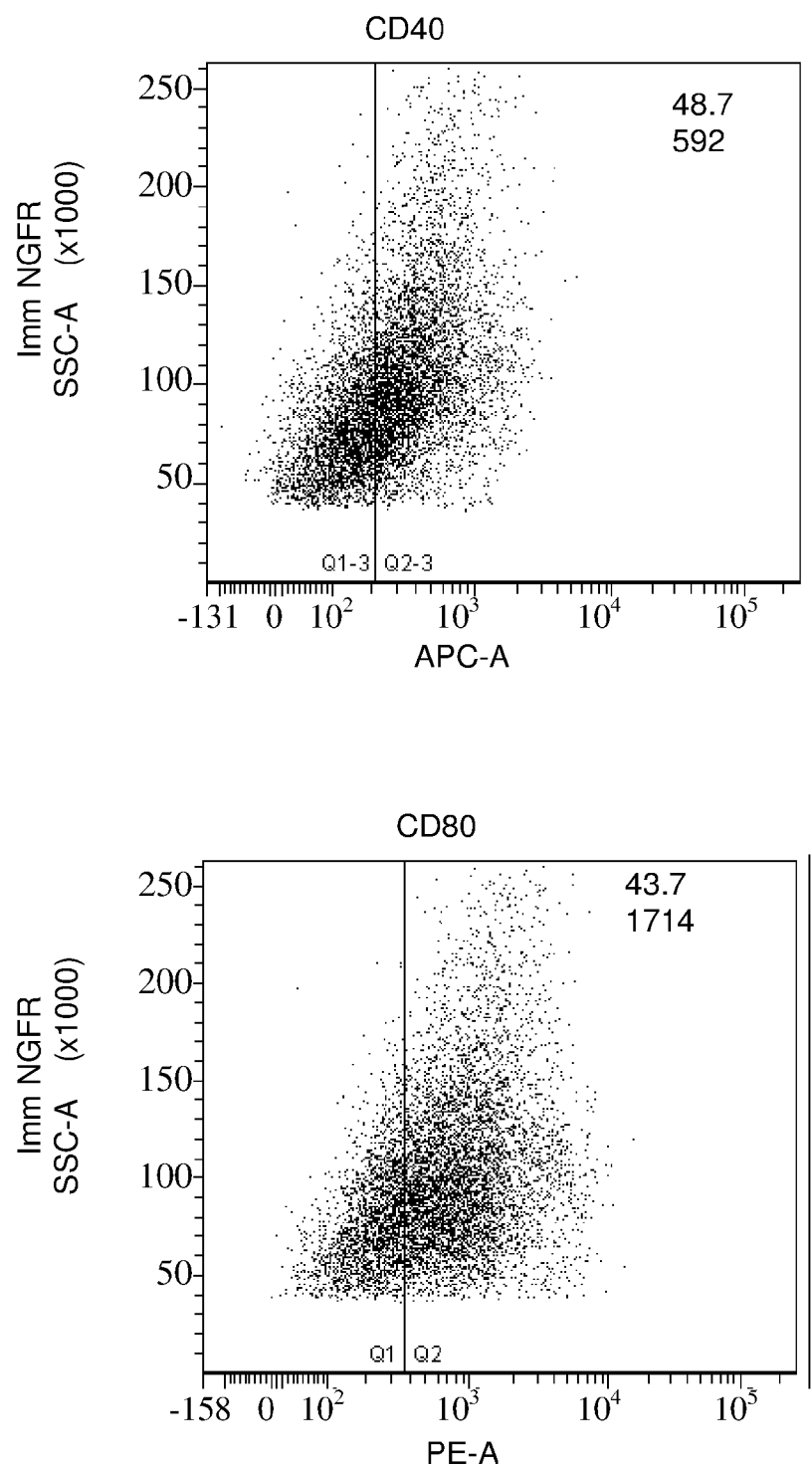
Figures 2, 5B:
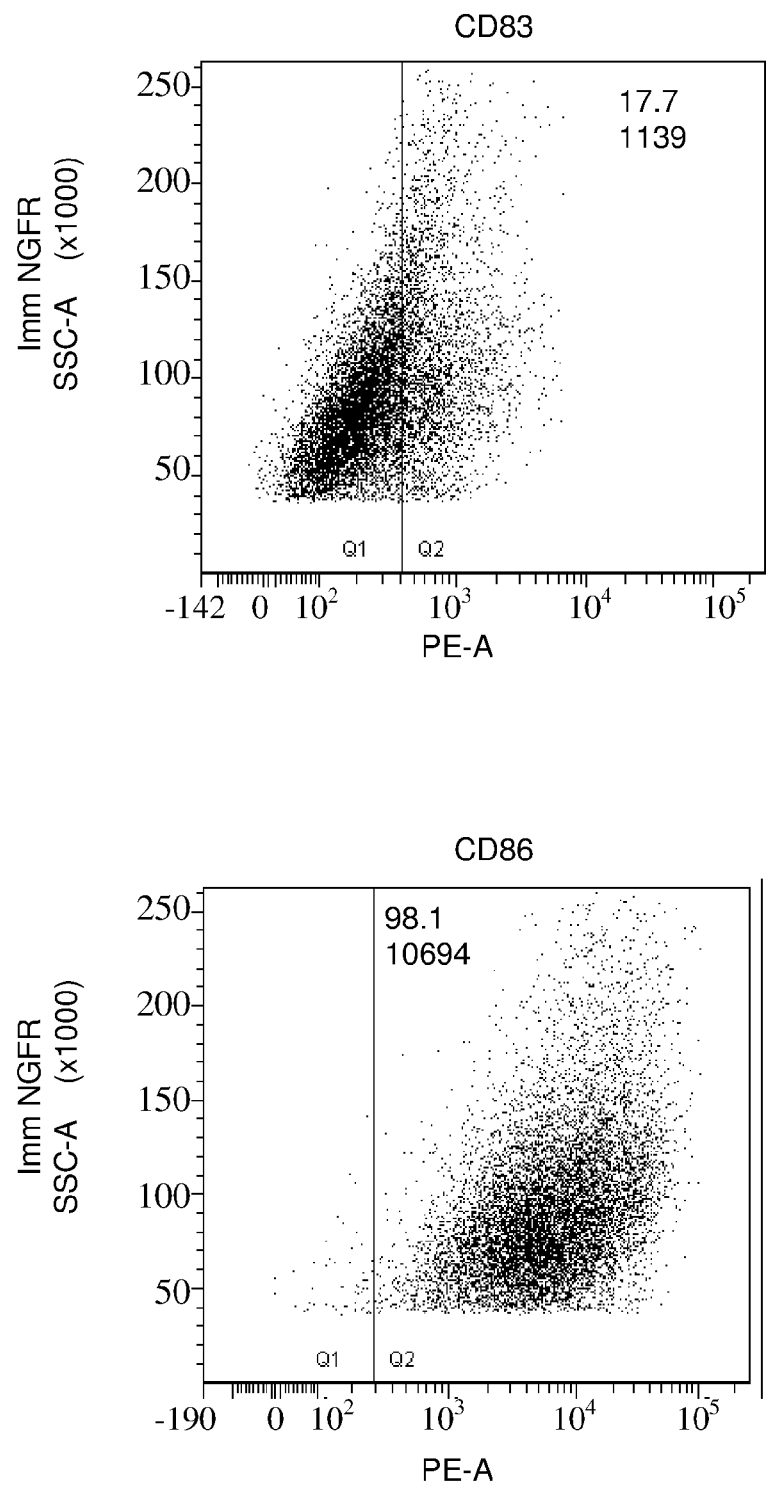
Figures 3, 5B:
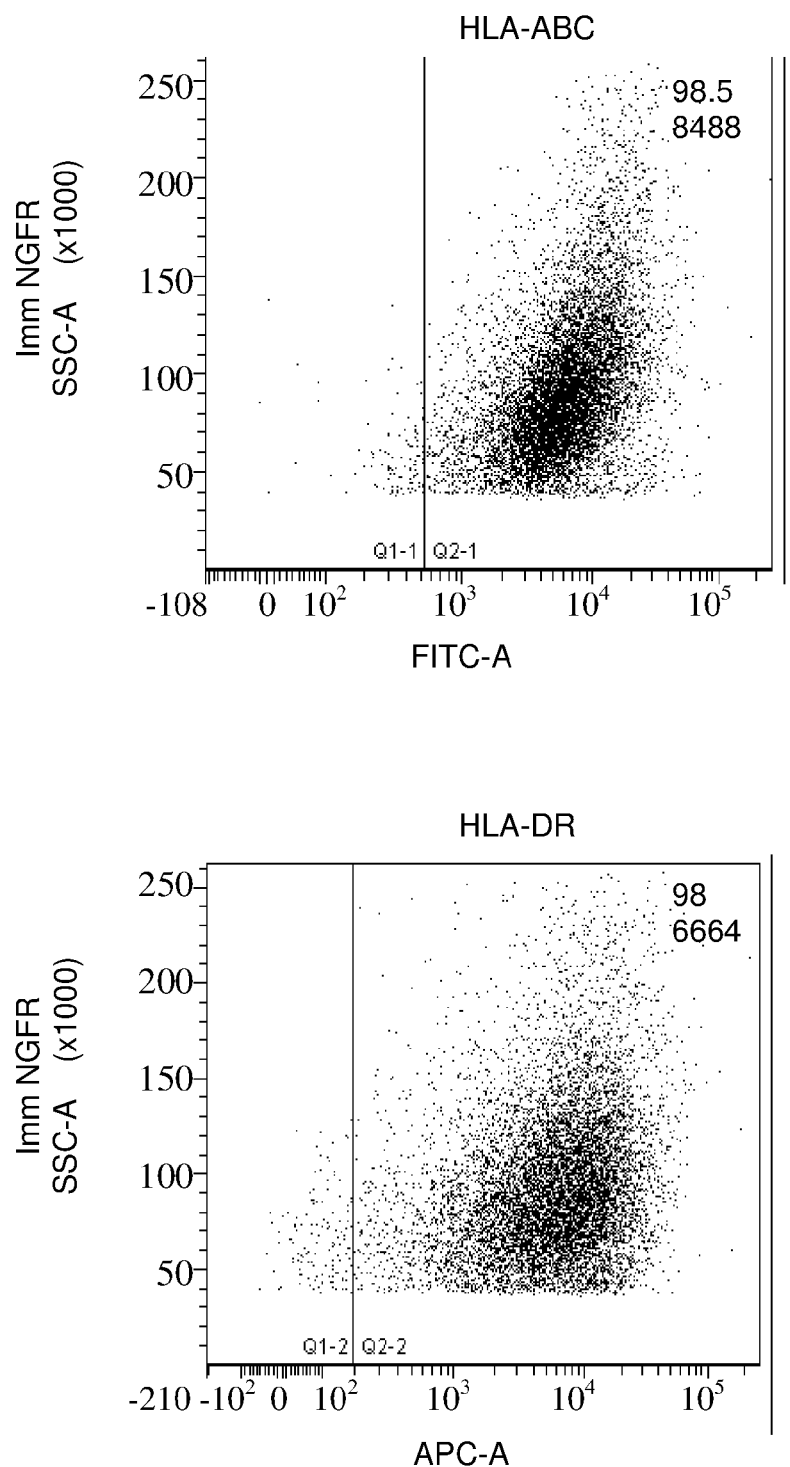
Figures 4, 5B:
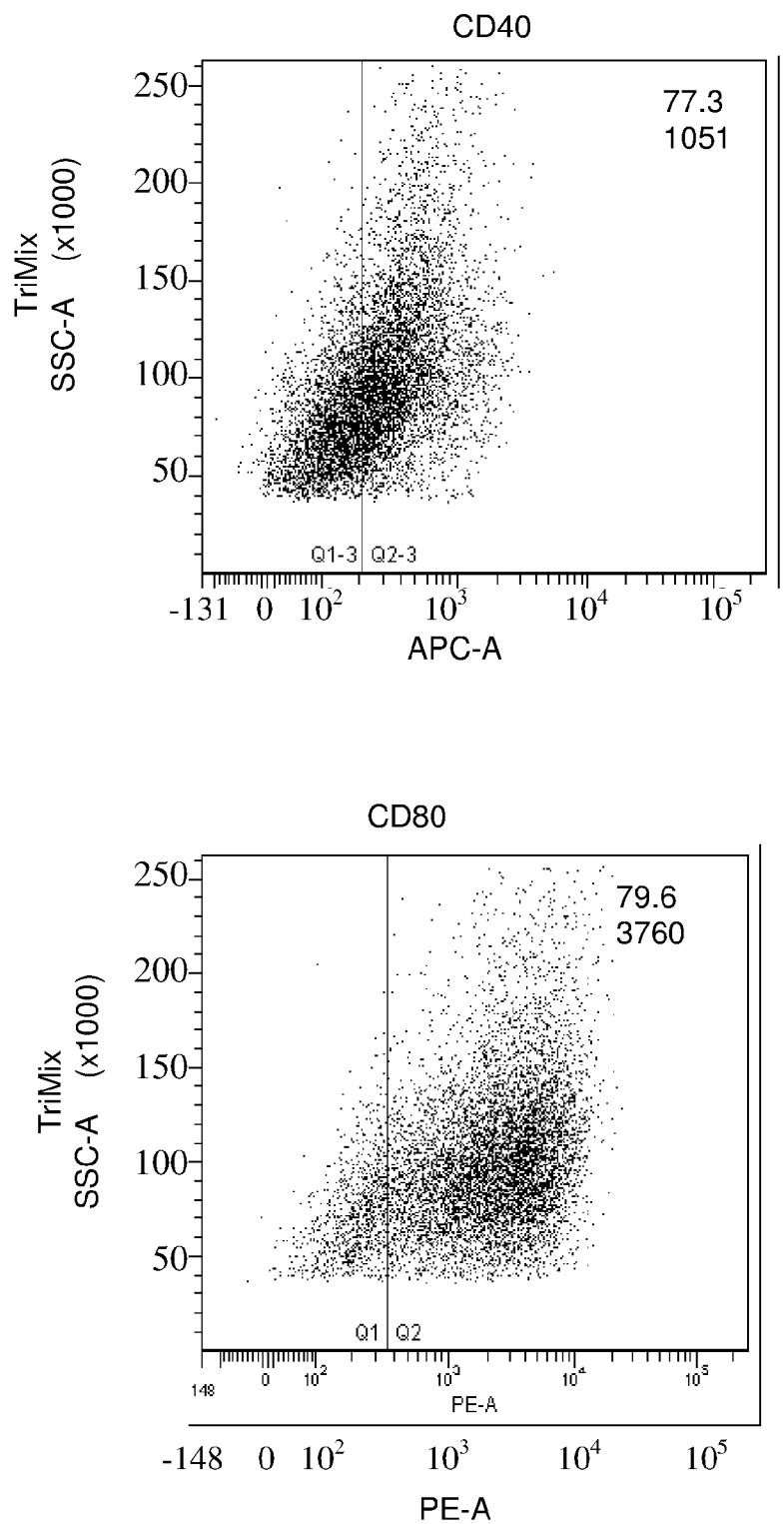
Figure 5B:
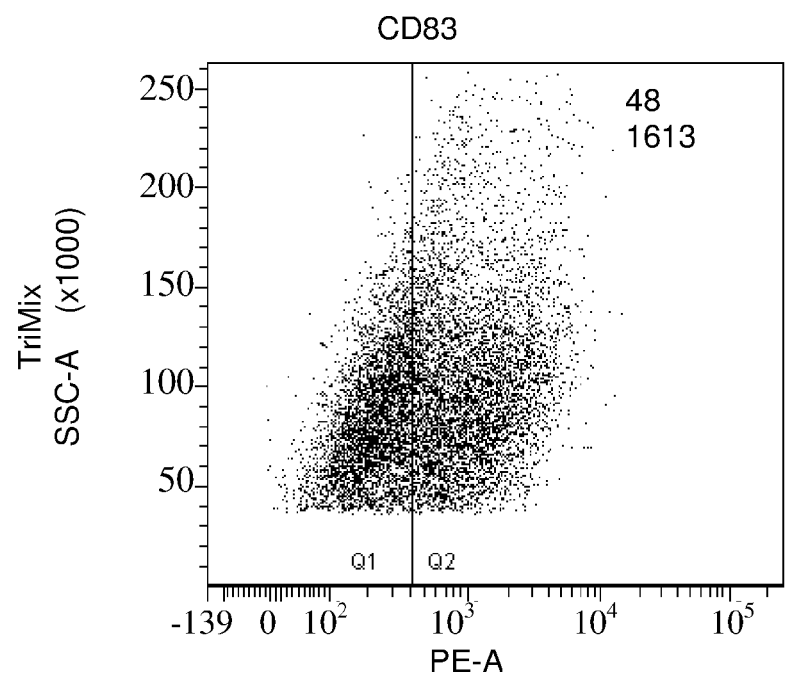
Figure 5:
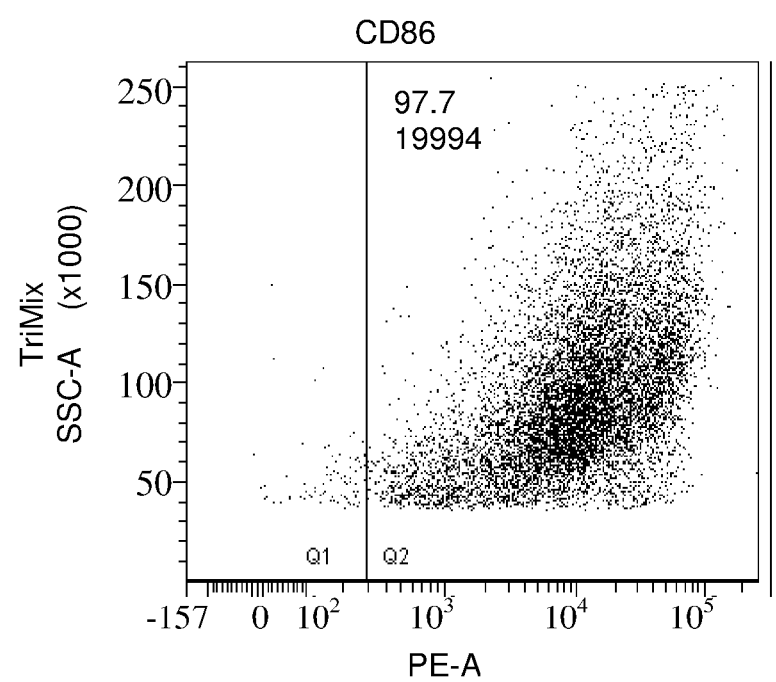
FIG. 5. Electroporation efficiency, phenotype and IL-12p70 secretion by DCs electroporated with TriMix mRNA alone or in combination with tumorantigen mRNA.

After electroporation with TriMix mRNA, immature DCs acquire a mature phenotype and enhance their cytokine secretion as demonstrated by upregulation of costimulatory molecules (CD40, CD80, CD83, CD86) and HLA-molecules, and IL-12p70 secretion, respectively. Here also, when TriMix DCs are co-electroporated with TAA mRNA the mature phenotype (FIG. 5B) and cytokine secretion (FIG. 5C) are not markedly altered.

Example 5

Induction of MelanA-Specific $CD8^+$ T Cells by TriMix DCs Pulsed with Peptide or Co-Electroporated with Whole Tumorantigen mRNA Materials and Methods:

TriMix DCs pulsed with peptide or co-electroporated with whole tumorantigen mRNA were prepared as described above, as well as the in vitro induction of MelanA specific $CD8^+$ T cells and tetramer staining.

Flow cytometry.

T cells were phenotyped with the following mAbs: CD8-FITC, CD8-APC-Cy7, CD27-APC, CD28-APC, CD45RA-biotin, CD45RO-APC, CD62L-FITC (all from BD Pharmingen) and CCR7-APC. Biotinylated CD45RA was detected with PerCP conjugated streptavidin (BD Pharmingen). Non-reactive isotype-matched mAbs (BD Pharmingen) were used as controls. Data were collected using a FACSCanto flow cytometer and analyzed using FACSDiva software. Cells were electronically gated according to light scatter properties in order to exclude dead and contaminating cells.

Intracellular cytokine staining and CD107a/CD137 assay.

For intracellular cytokine staining, $2 \times 10^5$ primed $CD8^+$ T cells were restimulated with $2 \times 10^4$ stimulator cells in the presence of Golgi-plug (brefeldinA, Becton Dickinson, BD, Erembodegem, Belgium). After 12 h of incubation at 37° C., $CD8^+$ T cells were then stained with FITC or APC-Cy7-conjugated anti-CD8 mAb, washed, permeabilized and stained intracellularly using the BD Cytofix/Cytoperm plus kit with IFN-gamma-PE/TNF-alpha-APC or IFN-gamma-PE/TNF-alfa-FITC, respectively. For the CD107a/CD137 assay, $1 \times 10^5$ primed $CD8^+$ T cells were restimulated with $2 \times 10^4$ stimulator cells in the presence of Golgi-stop (monensin, BD) and PE-Cy5-labelled anti-CD107a mAb (BD Pharmingen). After 12 h of incubation at 37° C., cells were harvested and stained with FITC-labeled anti-CD8 mAb and PE-labeled CD137 mAb (both from BD Pharmingen). As stimulator cells, TAP-deficient, $HLA-A2^+$ T2 cells pulsed with peptide or cytokine cocktail matured DCs electroporated with TAA-mRNA were used. Cells were analyzed by flow cytometry using a FACSCanto flow cytometer and FACSDiva software. Cells were electronically gated according to light scatter properties in order to exclude dead and contaminating cells.

Figure 6A:
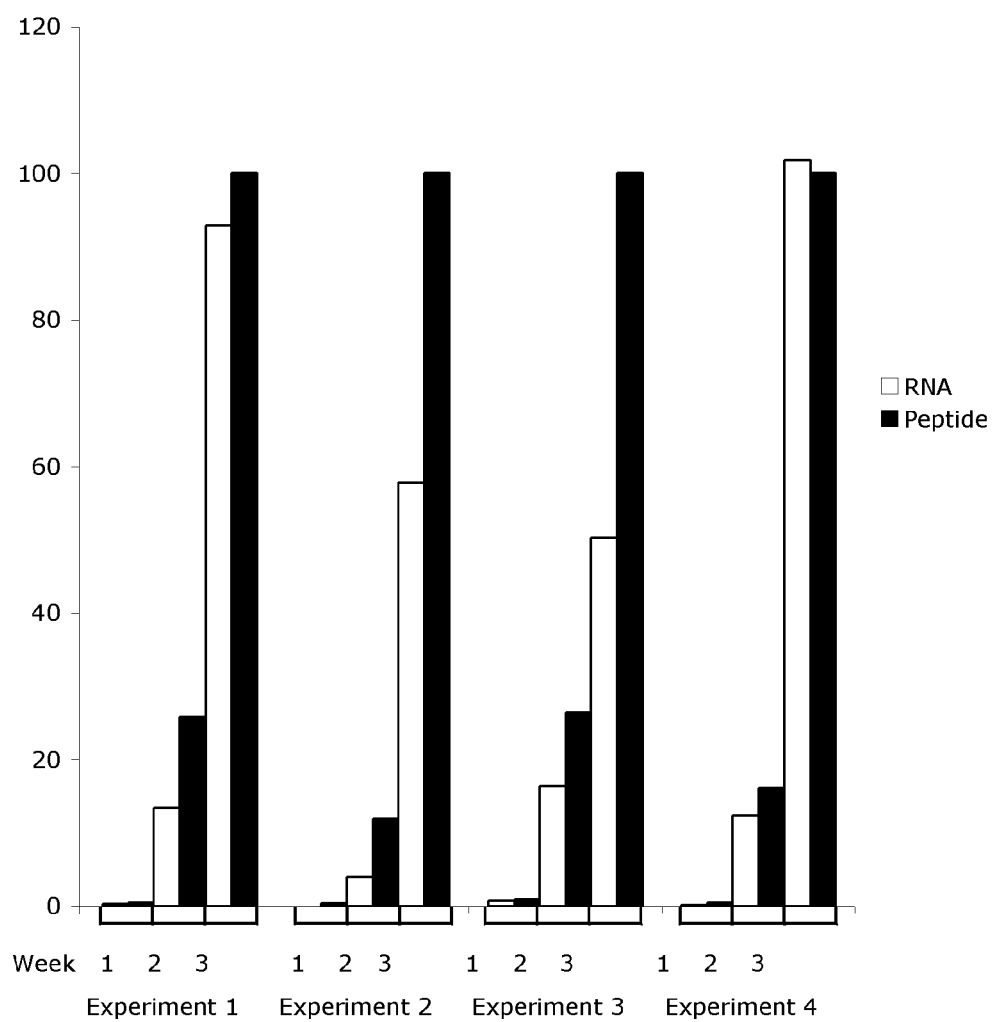
Figure 7:
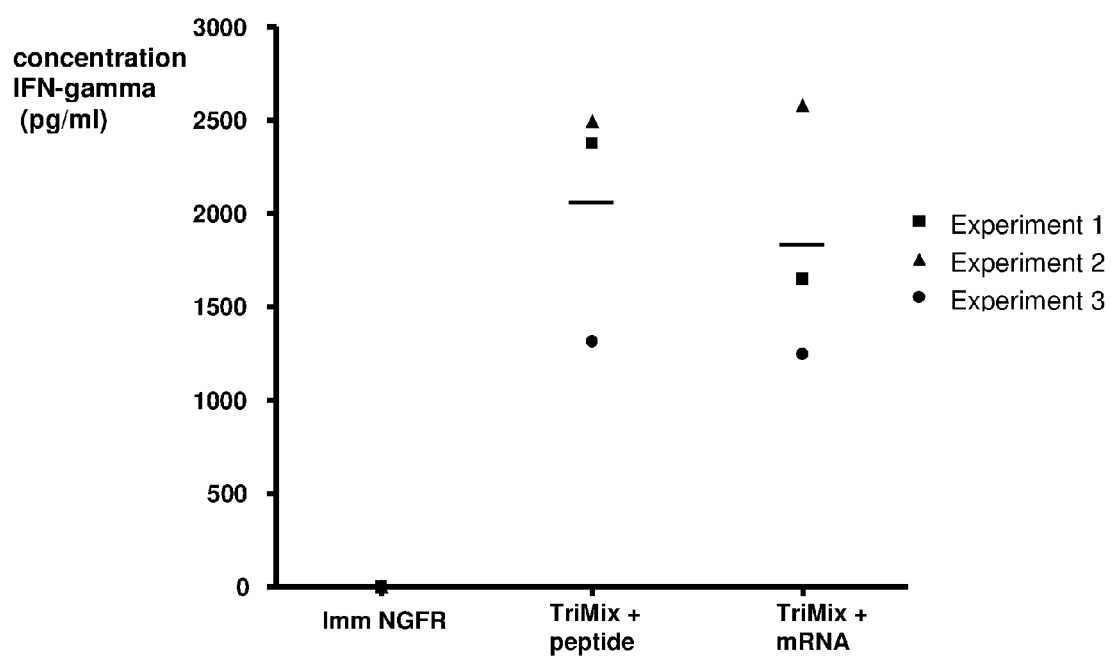

Results:

We investigated whether TriMix DCs co-electroporated with full length MelanA-encoding mRNA could prime naive MelanA-specific $CD8^+$ T cells. Therefore, DCs from $HLA-A2^+$ healthy donors were electroporated with TriMix mRNA and either pulsed with the immunodominant MelanA peptide or co-electroporated with MelanA-DCLamp mRNA. The DCs were then cocultured with autologous $CD8^+$ T cells without the addition of exogenous cytokines. Immature and cytokine cocktail matured DCs, electroporated with irrelevant NGFR mRNA and pulsed with MelanA peptide, were used as controls. Cells were stimulated 3 times with a weekly interval. After each stimulation round, the number of remaining cells and the percentage of tetramer positive, MelanA-specific $CD8^+$ T cells were determined and the absolute number of tetramer positive, MelanA-specific $CD8^+$ T cells was calculated (Table 3). Furthermore, the relative percentage of MelanA-specific T cells obtained after each stimulation was compared to the absolute number of MelanA-specific $CD8^+$ T cells obtained after 3 weekly stimulations with peptide-pulsed TriMix DCs (set at 100%) (FIG. 6A). We observed that, after 1 or 2 stimulations, TriMix DCs co-electroporated with TAA mRNA were slightly less potent than peptide pulsed TriMix DCs, while after 3 stimulations, they were equally potent in 2 out of 4 experiments.

Next, we assessed the functional and phenotypical properties of $CD8^+$ T cells stimulated 3 times with TriMix DCs pulsed with peptide or co-electroporated with TAA mRNA. The main effector mechanisms of stimulated $CD8^+$ T cells, i.e. activation, cytolysis and cytokine production, were investigated. T cells were restimulated overnight with T2 cells pulsed with MelanA-A2 peptide or gag peptide as a negative control. First we performed a CD107a mobilization assay combined with a CD137 activation assay (FIG. 6B), which respectively measure lytic activity (14) and T cell activation (15) upon antigenic stimulation. Second we performed intracellular cytokine staining to enumerate the number of cells secreting IFN-gamma and/or TNF-alpha upon antigenic stimulation; both major mediators of the immune response (FIG. 6C). For all donors tested we observed that the percentage of MelanA-specific T cells, correlated with the percentage of lytic/activated T cells and with the percentage of IFN-gamma/TNF-alpha producing T cells. Overall, no major differences were observed between T cells stimulated with peptide pulsed or TAA co-electroporated DCs, except a slight but reproducible increase in mean fluorescence intensity of IFN-gamma ☐staining and also in percentage of IFN-gamma/TNF-alpha ☐double positive cells, suggesting that T cells primed with co-electroporated TriMix DCs exert more functions at once (16). We also analyzed the phenotype of the induced MelanA-specific $CD8^+$ T cells. The primed $CD8^+$ MelanA-specific T cells were all $CD45RA^-CD45RO^+CD27^+CD28^+$, together with a variable expression of CD62L and CCR7 (data not shown), suggesting that both central memory T cells ($CD62L^+$ and $CCR7^+$) and early effector memory T cells ($CD62L^-$ and $CCR7^-$) have been induced (17). Overall, there were no significant differences in the phenotype of the MelanA-specific $CD8^+$ T cells of the different donors, regardless of whether peptide pulsed or TAA co-electroporated DCs were used for stimulation.

TABLE 3

Induction of HLA-A2 restricted MelanA-specific CD8+ T cells by TriMix DCs pulsed with MelanA-A2 peptide or co-electroporated with MelanA-DC Lamp mRNA*.

| | % CD8+ MelanA tetramer+ T cells/ number of CD8+ T cells ($10^6$)† | | | | Absolute number of CD8+ MelanA tetramer+ T cells ($10^3$)‡ | | | |
|---|---|---|---|---|---|---|---|---|
| | Exp 1 | Exp 2 | Exp 3 | Exp 4 | Exp 1 | Exp 2 | Exp 3 | Exp 4 |
| Imm + MelanA peptide | 0.3/1.2 | 0.1/1.35 | 1.2/4.2 | 0.5/3.5 | 3.5 | 1.3 | 50 | 19 |
| TriMix + MelanA peptide | 72.4/6.8 | 63.2/1.1 | 52.4/9.3 | 49.6/13 | 4922 | 695 | 4884 | 6478 |
| TriMix + MelanA mRNA | 72.5/6.3 | 25.9/1.6 | 43.3/5.7 | 44.8/14.7 | 4572 | 401 | 2455 | 6594 |
| Mat + MelanA peptide | ND | 0.1/1.5 | ND | 2.1/2.4 | ND | 1.5 | ND | 52 |

†The T cell population generated after 3 weekly stimulations with the different DCs was stained with MelanA peptide loaded HLA-A2 tetramers and anti-CD8 Ab. MelanA-specific CD8+ T cells were then identified by flow cytometry. Background staining with MAGE-A3-specific HLA-A2 tetramers was subtracted. The number of living cells was determined by trypan blue exclusion.
‡Absolute number of MelanA-specific CD8+ T cells was calculated with the following formula: (number of CD8+ T cells/100) × % of CD8+ MelanA tetramer+ T cells.
*Results are shown for 4 individual experiments from different healthy donors.
Abbreviations: Imm, immature DCs electroporated with irrelevant NGFR mRNA; Mat, cytokine cocktail matured DCs electroporated with NGFR mRNA; ND, not done.

Example 6

Figures 5, 5B, 6, 7:
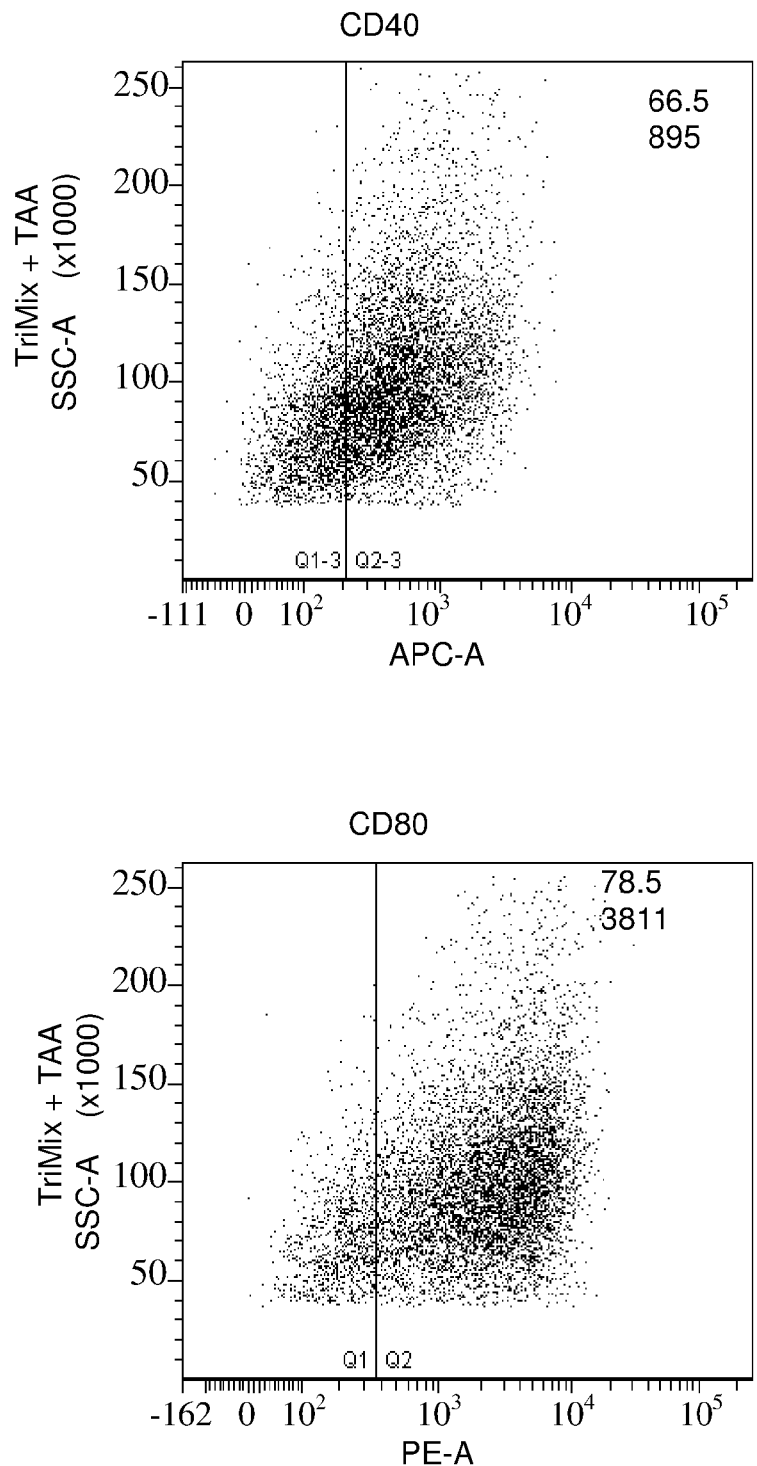
Figure 5C:
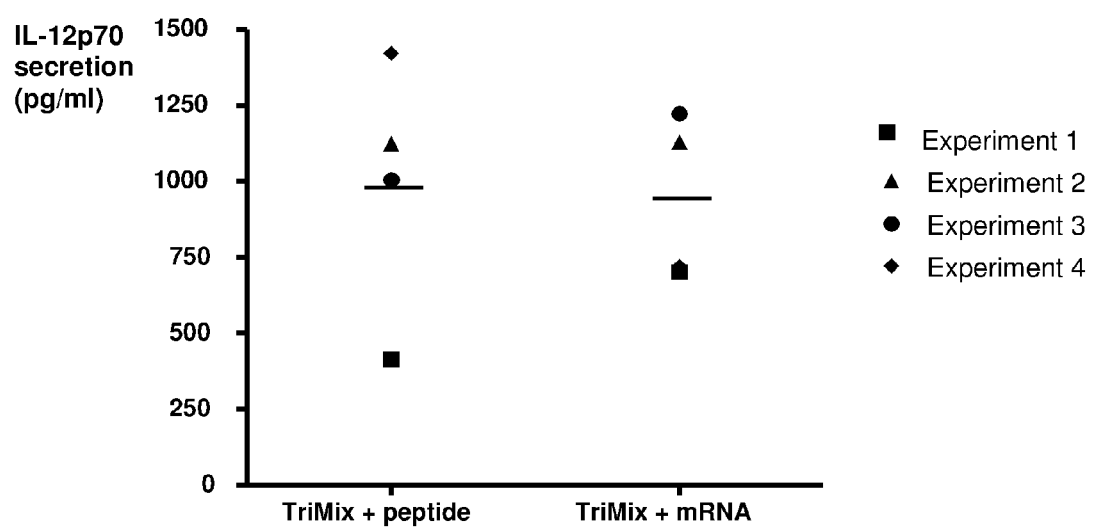
FIG. 5C. IL-12p70 produced within 24 h after electroporation was dosed in the supernatant. Each dot represents one individual experiment and the mean is indicated by a horizontal line.

Stimulation of Mage-A3-Specific CD4+ T Cells by TriMix DCs Pulsed with Peptide or Co-Electroporated with Whole TAA mRNA Because all TAA-constructs used contain an HLA class II targeting signal, we wanted to investigate whether TriMix DCs co-electroporated with TAA mRNA could stimulate established CD4+ T cells. Therefore, TriMix DCs were either pulsed with Mage-A3-DP4 peptide or co-electroporated with MageA3-DCLamp mRNA. Four hours later, the cells were cocultured with Mage-A3-specific, HLA-DP4-restricted T cells for 20 h. These T cells are HLA-DP4 (HLA-DPB1*0401) restricted and specific for the Mage-A3 epitope aa 243-258 with sequence KKLLTQHFVQENYLEY. Immature DCs electroporated with irrelevant NGFR mRNA were used as a negative control. IFN-gamma released in the supernatant during the coculture was measured by ELISA (FIG. 7). We observed that TriMix DCs are indeed capable of presenting antigenic epitopes in the context of HLA class II molecules, without remarkable differences between peptide pulsed and TAA co-electroporated cells.

Example 7

In Vitro Induction of CD8+ T Cells Specific for Other Antigens than MelanA in the Blood of Unvaccinated Melanoma Patients Materials and Methods:
Genetic constructs.
The pGEM-sig-MageA3-DCLamp plasmid encoding the full-length Mage-A3 antigen linked to the HLA class II targeting sequence of DC-Lamp (transmembrane/cytoplasmic region) has been described. The pGEM-sig-MageC2-DCLamp plasmid contains the full-length MageC2 gene, flanked by the signal sequence and the HLA class II targeting sequence of DC Lamp. The pGEM-sig-gp100-Lamp and pGEM-sig-Tyrosinase-Lamp plasmids contain the gp100 and Tyrosinase gene respectively, with their own signal sequence and with their transmembrane and cytosolic regions replaced by the HLA class II targeting sequence of Lamp-1.

Electroporation of DCs.
For co-electroporation with MageA3-DCLamp, MageC2-DCLamp, Tyrosinase-Lamp or gp100-Lamp mRNA, $50 \times 10^6$ DCs were electroporated with 20 μg of CD40L, CD70 and caTLR4 mRNA together with 60 μg of TAA-encoding mRNA in a 4 mm electroporation cuvette and the following conditions were used for electroporation: voltage 300 V, capacitance 450 μF and resistance 99Ω in a final volume of 600 μl.
Synthetic peptides and peptide pulsing.
The HLA-A*0201 restricted Mage-A3 (aa 112-120; KVAELVHFL), Mage-C2 (aa 336-344; ALKDVEERV), Tyrosinase (aa 369-377; YMDGTMSQV), gp100 (aa 209-217; ITDQVPFSV) and derived peptides were purchased from Thermo Electron (Ulm, Germany). The HLA-A2 restricted gag peptide (gag-A2 peptide, HXB2 gag peptide-complete Set, NIH, AIDS Research & Reference Reagent Program, McKesson BioServices Corporation, Rockville, Md.) was used as a negative control. For peptide pulsing, DC or T2 cells were diluted to a final density of $2 \times 10^6$ cells/ml in IMDM containing 10 μg/ml peptide and were incubated for 2 h at 37° C.
Induction of TAA-specific CD8+ T cells.
CD8+ T cells were isolated from the blood of HLA-A2+ melanoma patients. CD8+ T cells were purified through immunomagnetic selection by using CD8 microbeads (Miltenyi Biotec, Bergisch Gladbach, Germany) and were consistently >90% pure (data not shown). Twenty million CD8+ T cells were cocultured with autologous DCs at a DC:T cell ratio of 1:10 per 6 well in 7.5 ml stimulation medium consisting of IMDM medium containing 1% heat inactivated AB serum (PAA Laboratories, Linz, Austria), 100 U/ml penicillin, 100 μg/ml streptomycin, 2 mM L-glutamine, 0.24 mM L-asparagine and 0.55 mM L-arginine (all from Cambrex) without any further addition of exogenous cytokines such as IL-2 or IL-7. As stimulator DCs, DCs matured with the cytokine cocktail containing IL-1alpha, IL-6, TNF-alpha and $PGE_2$ and pulsed with a HLA-A2-restricted, Mage-A3, Mage-C2, Tyrosinase or gp100 derived peptide (sequences KVAELVHFL, ALKDVEERV, YMDGTMSQV and ITDQVPFSV, respectively; mixed at a 1:1:1:1 ratio); or TriMix DCs as prepared for vaccination were used. CD8+ T cells were restimulated weekly with the same stimulator DCs as used in the primary stimulation. After 2 rounds of stimulation, CD8+ T cells were harvested and their antigen specificity and function were determined.

Tetramer staining.

T cells were stained with a FITC-labeled anti-CD8 (BD Pharmingen) and with 10 nM PE-labeled HLA-A2 tetramers (prepared in-house). The tetramers contained one of the following HLA-A2 restricted, TAA-derived peptides: FLWGPRALV—SEQ ID NO:9- or KVAELVHFL—SEQ ID NO:10-(Mage-A3-derived); ALKDVEERV—SEQ ID NO:11-(Mage-C2-derived); YMDGTMSQV—SEQ ID NO:12-(Tyrosinase-derived); ITDQVPFSV—SEQ ID NO:13-, YLEPGPVTA—SEQ ID NO:14- or KTWGQYWQV—SEQ ID NO:15-(gp100-derived); or SLLMWITQC—SEQ ID NO:16-(NY-ESO-1-derived, negative control). Cells were analyzed by flow cytometry.

Intracellular cytokine staining and CD107a/CD137 assay were performed as described in example 5.

Figures 1, 8A:
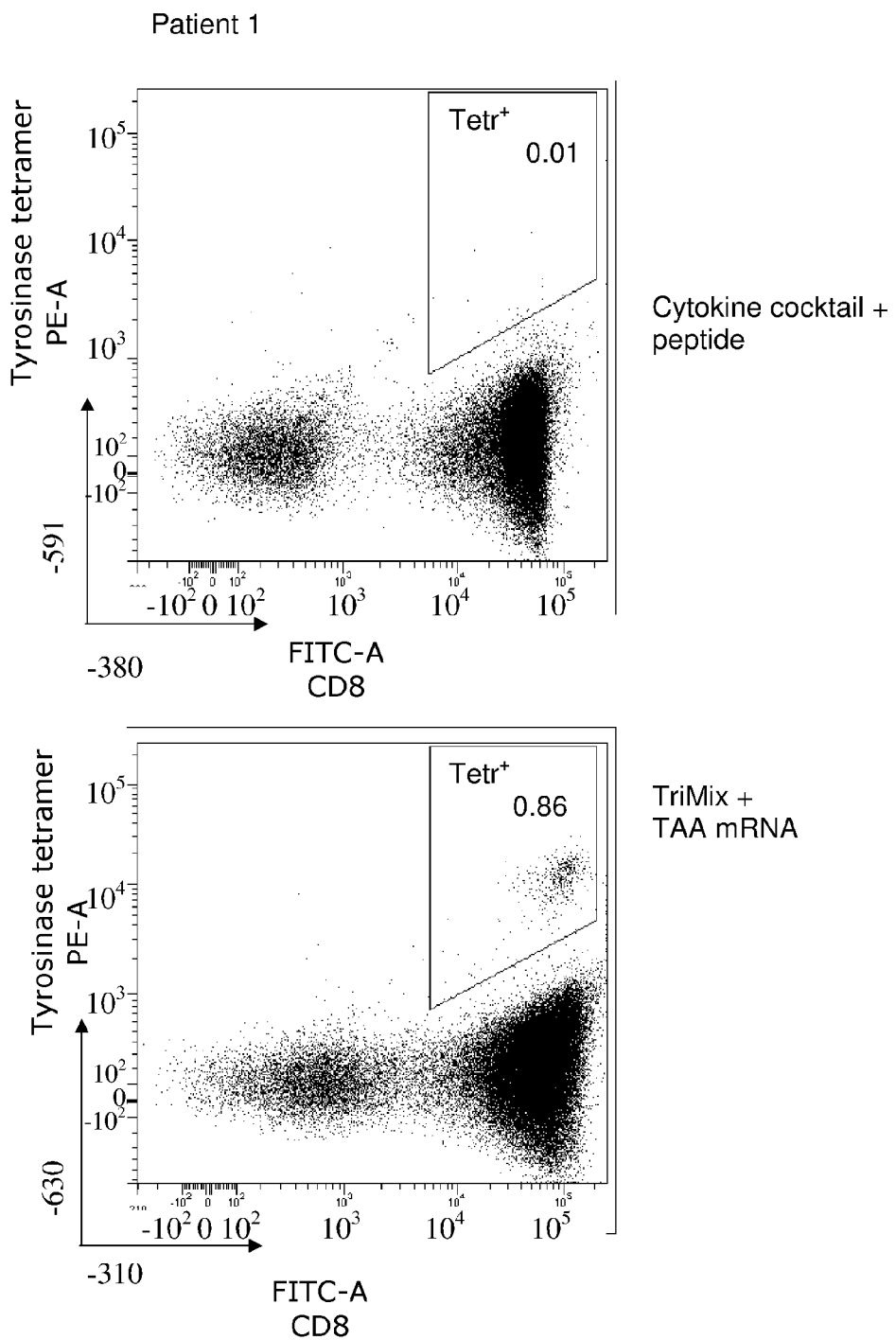
Figures 2, 8A:
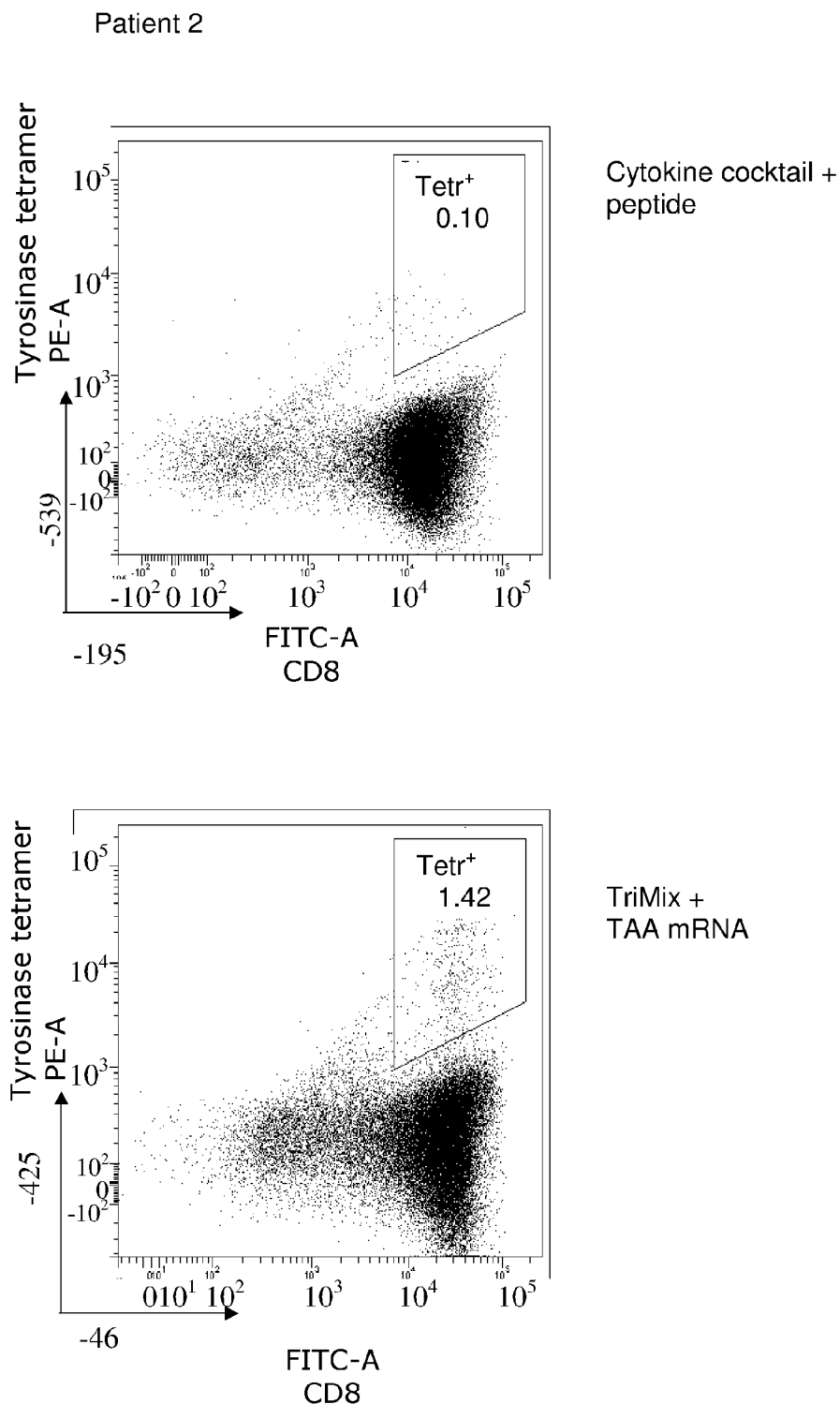
Figures 3, 8A:
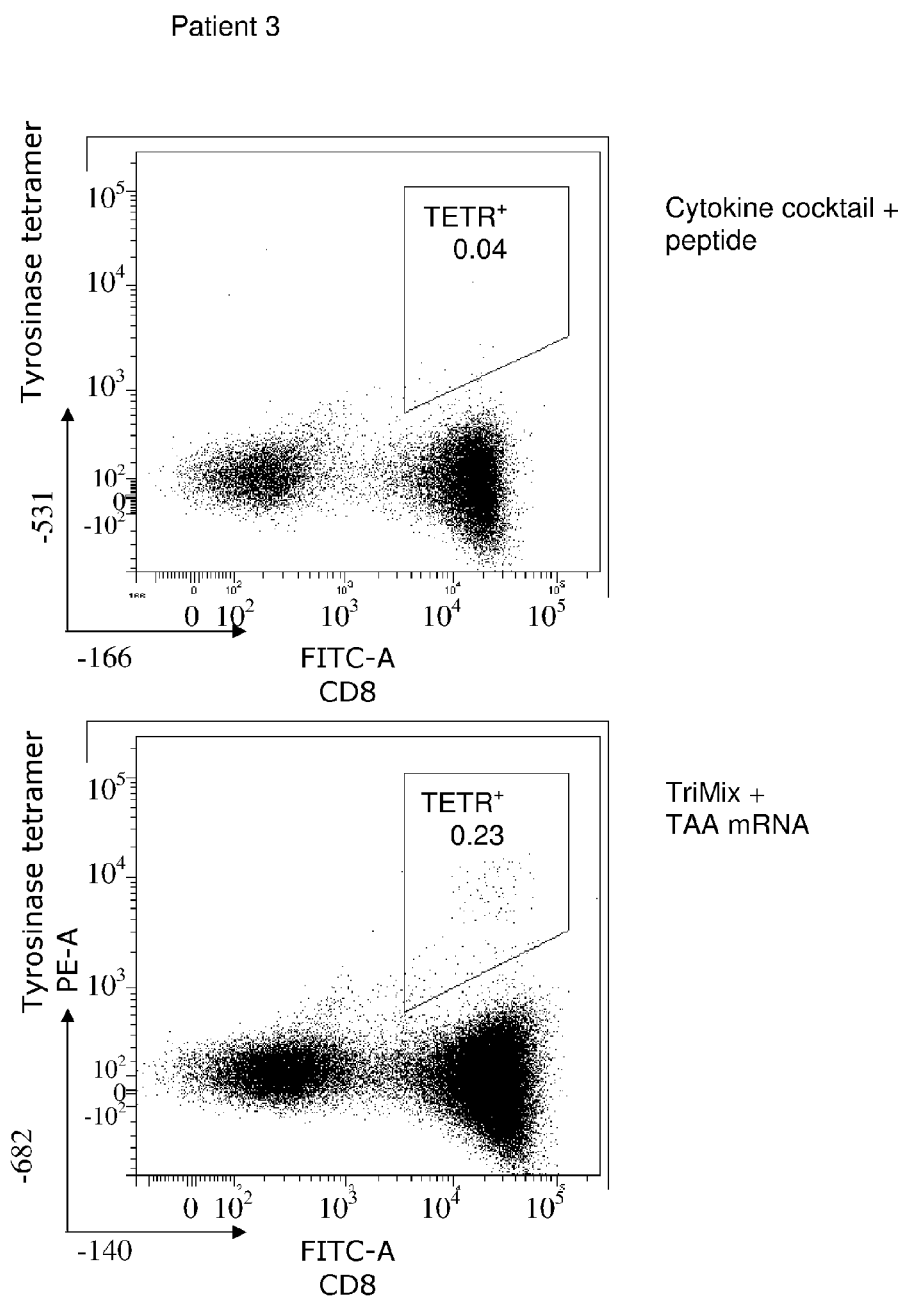
Figure 8B:
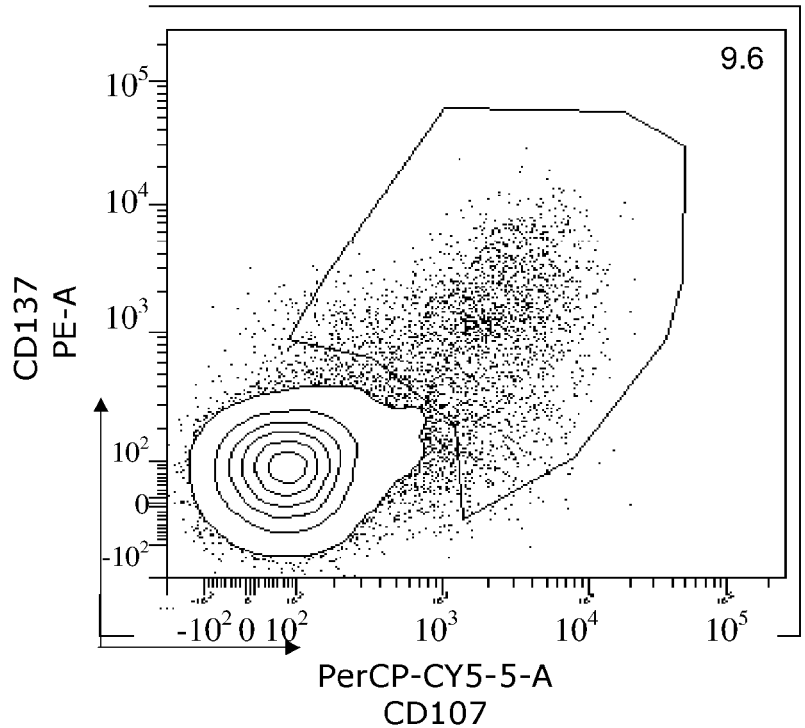
Figure 1:
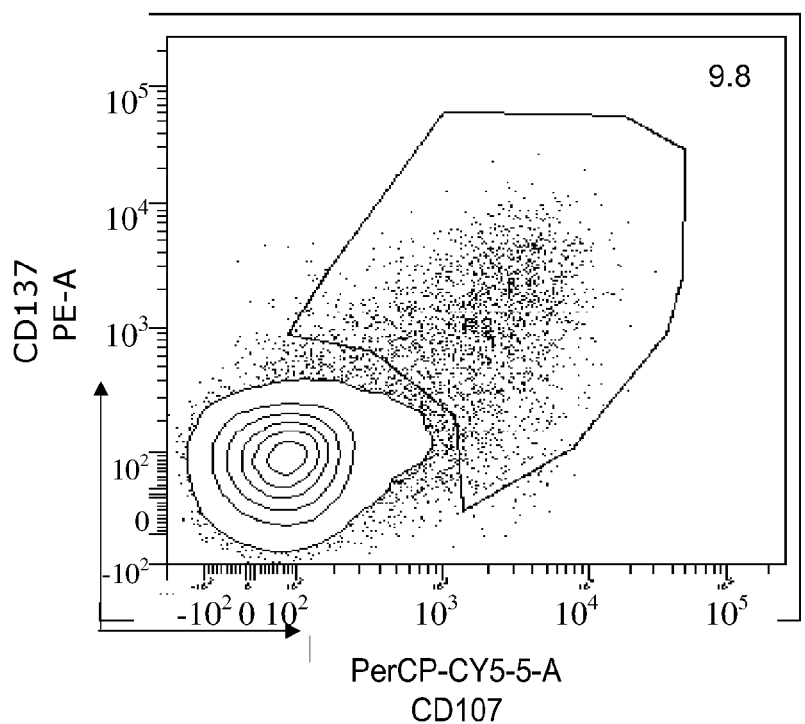
Figures 3, 8B:
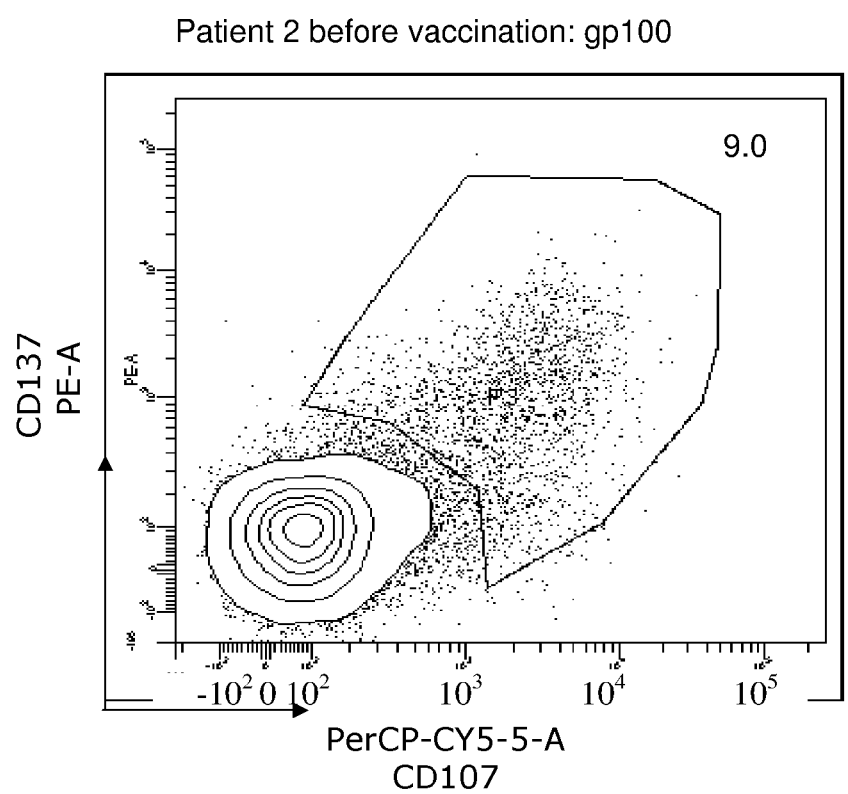
Figures 4, 8B:
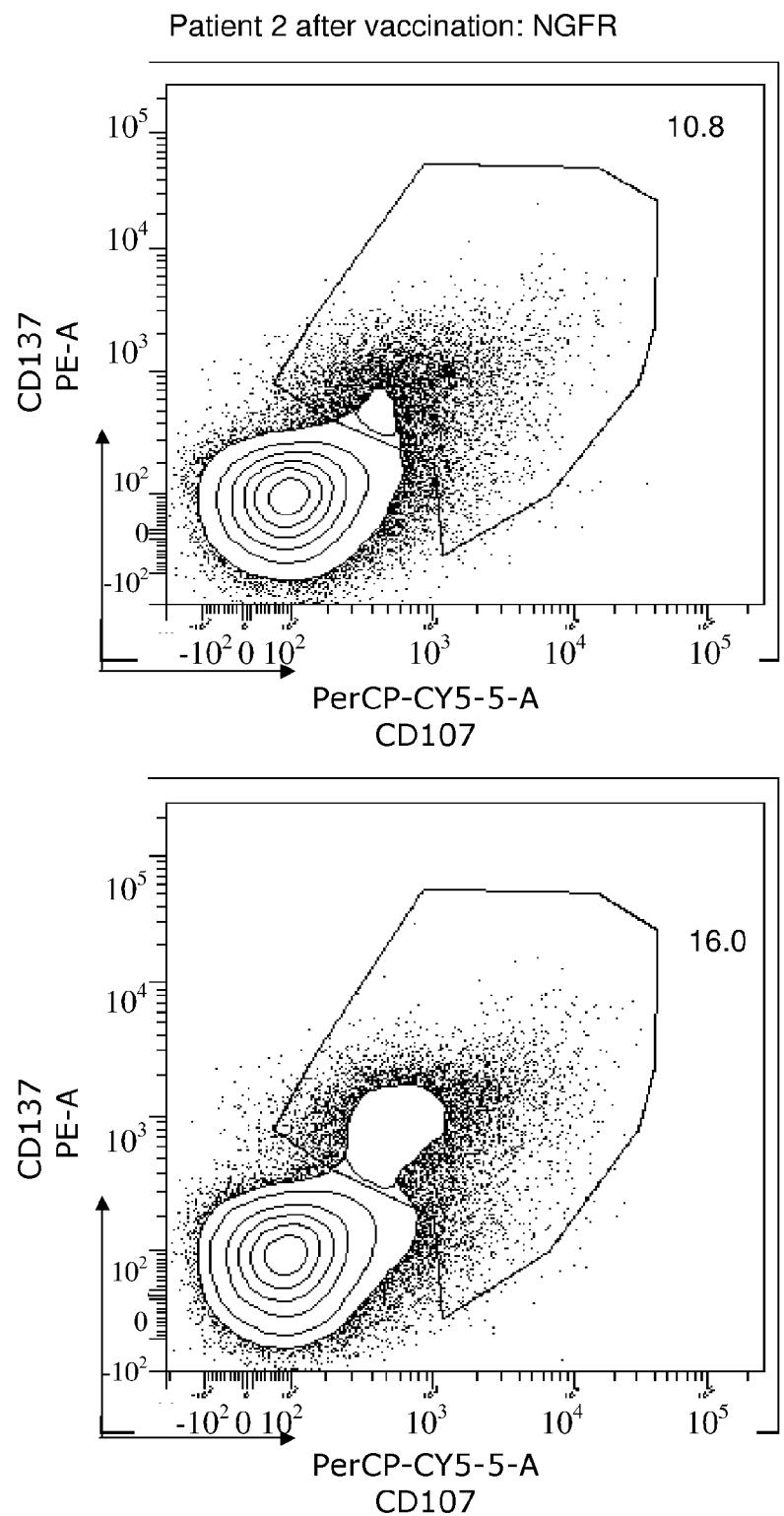
Figures 5, 8B:
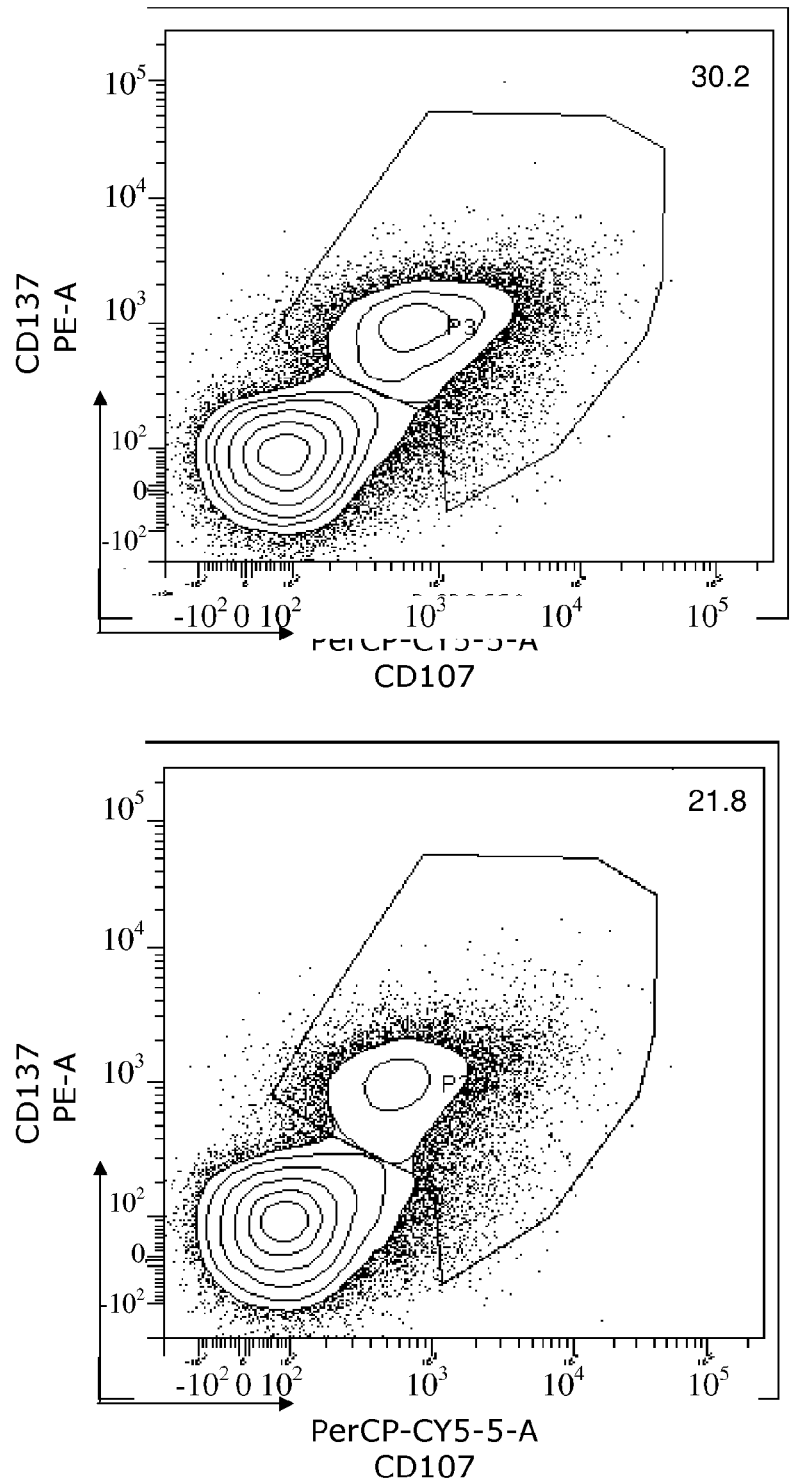
Figures 6, 8B:
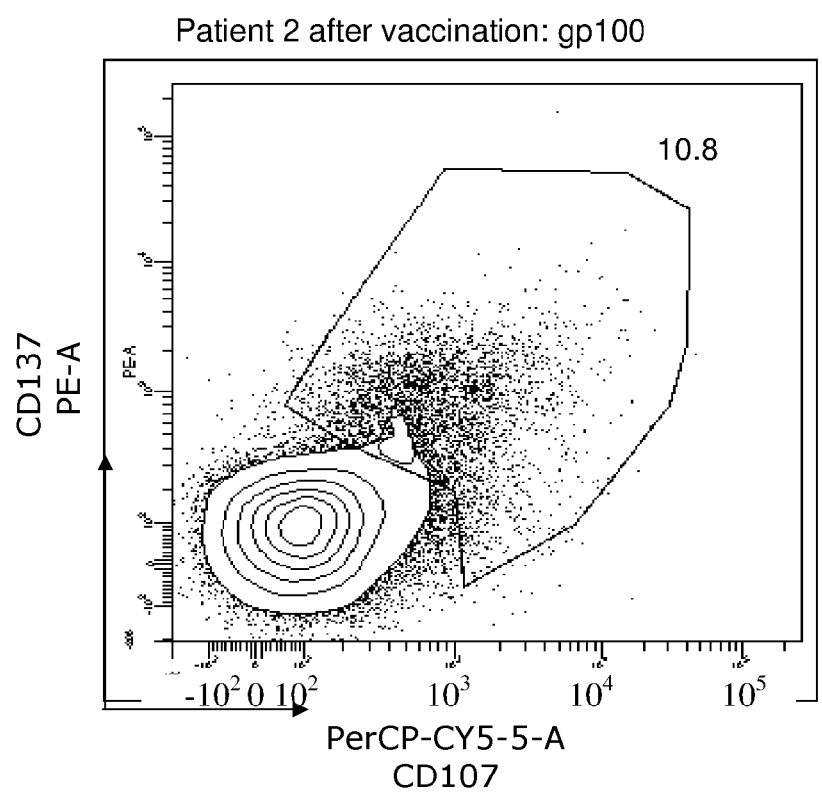
Figures 7, 8B:
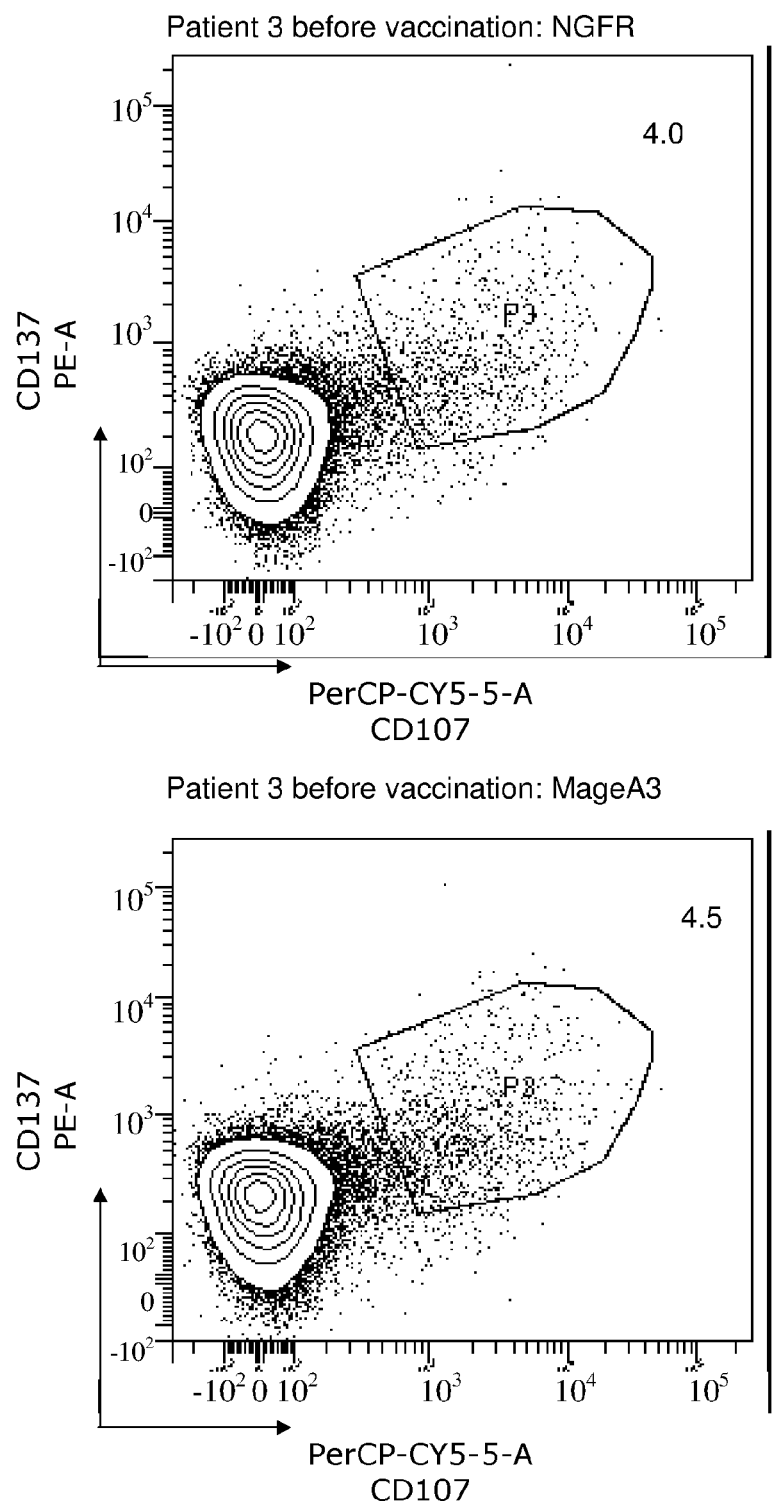
Figures 8, 8B:
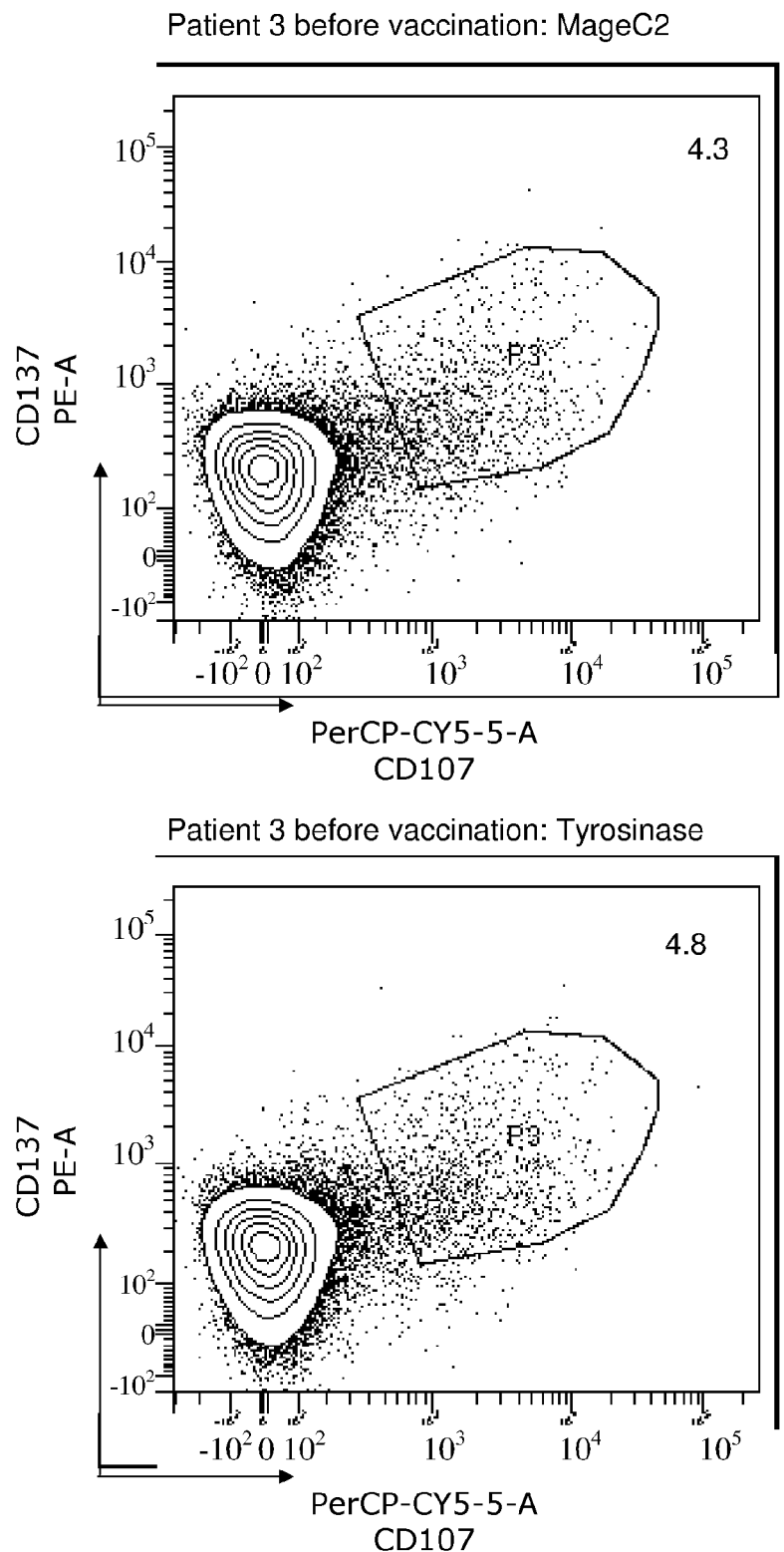

Results:

Because this work is part of the preclinical assessment of a vaccination study where TriMix DCs co-electroporated with Mage-A3, Mage-C2, Tyrosinase or gp100 mRNA will be injected into melanoma patients, we wanted to investigate whether these DCs are able to induce CD8+ T cells specific for these antigens in vitro in the PBMCs of unvaccinated melanoma patients. Therefore, CD8+ T cells from HLA-A2+ melanoma patients were cocultured with autologous DCs as prepared for vaccination, i.e. electroporated with TriMix mRNA together with one of four tumorantigen mRNAs, and mixed afterwards at equal amounts. Cytokine cocktail matured DCs pulsed with a HLA-A2-restricted, Mage-A3, Mage-C2, Tyrosinase or gp100 derived peptide (also mixed at equal amounts) were used as controls. During the whole stimulation period, no exogenous cytokines like IL-2 or IL-7 to support T cell proliferation and survival were added. After 3 weekly stimulations, the T cells were stained with a panel of tetramers recognizing 7 different HLA-A2 restricted, Mage-A3, Mage-C2, Tyrosinase or gp100-derived epitopes. For all 3 patients tested, we observed that TriMix DCs co-electroporated with TAA mRNA were able to induce HLA-A2-restricted Tyrosinase-specific T cells, while cytokine cocktail matured DCs pulsed with the Tyrosinase-A2 peptide failed to do so (FIG. 8A). We did not observe T cells recognizing the other Mage-A3, Mage-C2 or gp100-specific tetramers, neither when TriMix DCs nor cytokine cocktail matured DCs were used for in vitro stimulation (data not shown). Although TriMix DCs were co-electroporated with full-length TAA mRNA encoding all possible TAA-derived epitopes, we observed no induction of other Mage-A3, Mage-C2, Tyrosinase or gp100-specific T cells, as assessed by CD137/CD107a and intracellular cytokine staining assays (FIGS. 8B and C and data not shown), although low frequencies of specific T cells might have been concealed by the aspecific T cell activation induced by TriMix DCs.

Example 8

Induction of CD8+ T Cells Specific for Other Antigens than MelanA in the Blood of Melanoma Patients After Vaccination with TriMix DCs Co-Electroporated with TAA mRNA The ultimate goal of the invention is of course the provision of an anti-cancer vaccine comprising the manipulated DCs according to the invention, presenting tumor-specific antigen-derived epitope in the context of HLA class I or II molecules on their surface, that can be reintroduced into the patient, subsequently eliciting an immune response against the specific tumor marker. This immunovaccination procedure comprises the steps of (1) obtaining and manipulation of the DCs as outlined in examples 1 and 7 and (2) injecting the DCs into the subject. The subject will either be a mouse model for further analysis of the immunostimulatory effect of the vaccine in vivo, or the subject can be a cancer patient, in order to help establishing a host-mediated immune response towards the tumor-specific antigen. In short, a DC preparation preferably comprising 10-100 $10^6$ DCs, more preferably 10-50 $10^6$ DCs, resuspended in 250 µl phosphate-buffered saline (PBS), supplemented with human serum albumin is injected into the subject, preferably intradermally.

In the subject, the DCs are able to stimulate T-cells and elicit a host-mediated immune-response due to their specific immunostimulatory characteristics. The immune reaction in the host can then be analyzed through standard techniques. Analyzing the increase of inflammatory markers will point to the establishment of an immune reaction in the host, probably directed towards the tumor antigen. In order to check whether the immune response is specifically directed towards the tumor antigen presented by the DCs in the vaccine preparation, several known techniques such as intracellular staining through flow cytometry, ELISPOT or Enzyme Linked Immuno-Sorbent Assays (ELISA), using peptide fragments of the tumor antigen or the whole tumor antigen in order to capture and detect tumor-antigen specific host T cells can be used. The immune response can be monitored both in the peripheral blood of the patient or in the skin, after induction of a delayed type hypersensitivity (DTH)-reaction and subsequent biopsy of the DTH region.

Patients, vaccine preparation and vaccination schedule.

Three HLA-A2+ patients (2M/1F) with recurrent stage III or stage IV melanoma were recruited in an ongoing institutional (UZ Brussel) pilot trial with autologous TriMix-DC vaccine for patients with advanced melanoma. For vaccination purposes, DCs were electroporated with mRNA encoding one of four tumorantigens (Mage-A3, Mage-C2, Tyrosinase and gp100) and the TriMix-mRNA. After a rest period of one hour, the cells are mixed at equal ratios. The first vaccine was administered prior to cryopreservation of the DC-caccine, subsequent vaccines were performed with cells that were thawed at the day of vaccination. Vaccines consist of ±12.5 $10^6$ TriMix DC per antigen and are administered by 4 bi-weekly intradermal injections at 4 different injection sites (axillar and/or inguinal region).

Next it was investigated whether TriMix DCs co-electroporated with Mage-A3, Mage-C2, Tyrosinase or gp100 mRNA would be able to induce an antigen-specific CD8+ T cell-response in vivo. Therefore, 2 HLA-A2+ melanoma patients (patients 2 and 3) were vaccinated 4 times at bi-weekly intervals with TriMix DCs. Two weeks after the last vaccination, CD8+ T cells isolated from the blood of these patients were restimulated in vitro with autologous DCs, either with TriMix DCs as prepared for vaccination or with cytokine cocktail matured DCs co-electroporated with tumorantigen mRNA. Again, during the whole stimulation period, no exogenous cytokines were added. After 2 weekly stimulations, the antigen-specificity and functionality of the T cells was investigated by staining with the HLA-A2 tetramer panel and by the CD137/CD107a and intracellular cytokine staining assays; and this was compared to the response induced in the CD8+ T cells of the same patients, but before vaccination. For both patients, we observed no T cells specific for the known HLA-A2 restricted, Mage-A3, Mage-C2, Tyrosinase or gp100-derived epitopes in tetramer staining (data not shown), although we had been able to induce Tyrosinase-A2 specific T cells in the CD8+ T cells of these same patients before vaccination (FIG. 8A). This was still the case after the T cells had received an extra stimulation round in vitro (data not shown). Because the patients were vaccinated with DCs co-electroporated with full-length tumorantigen mRNA encoding all possible tumorantigen-derived epitopes, we investigated whether a T cell response specific for other epitopes than the known HLA-A2 restricted epitopes had been induced. Therefore, one week after the second restimulation in vitro, T cells were restimulated overnight with mature DCs electroporated with tumorantigen mRNA or NGFR as irrelevant control after which a CD137/CD107a (FIG. 8B) and an intracellular cytokine staining assay (FIG. 8C) were performed. Indeed, we observed strong, vaccine-induced responses against other Mage-A3 (patient 2), Mage-C2 (patient 2 and 3) and Tyrosinase-epitopes (patient 2), which were not present before vaccination. Overall, similar results were obtained when TriMix or cytokine cocktail matured DCs were used for restimulation in vitro, except for the fact that the latter induced less aspecific T cells (data not shown).

Example 9

Combining the Different mRNAs Encoding Immunostimulatory Factors in a Single mRNA Molecule for Electroporation For transfection of 2 or more mRNA or DNA molecules encoding functional immunostimulatory factors and/or factors inhibiting inhibitory molecules, separate mRNA or DNA preparations can be used as is shown in the above examples. In this case, each single factor is encoded by one single mRNA or DNA molecule. In this alternative example, several factors are linked to each other by means of an IRES (internal ribosomal entry site) sequence or a cleavable 2a peptide-encoding sequence. This way, two or more factors can be encoded by one single mRNA or DNA molecule. Preliminary data where cells were electroporated with mRNA encoding CD40L and CD70 linked by an IRES sequence or a cleavable 2a peptide show that this approach is indeed feasible. Extrapolation of this system to more than two immunostimulatory factors is of course also anticipated by this example.

Example 10

Figures 8, 8B, 9:
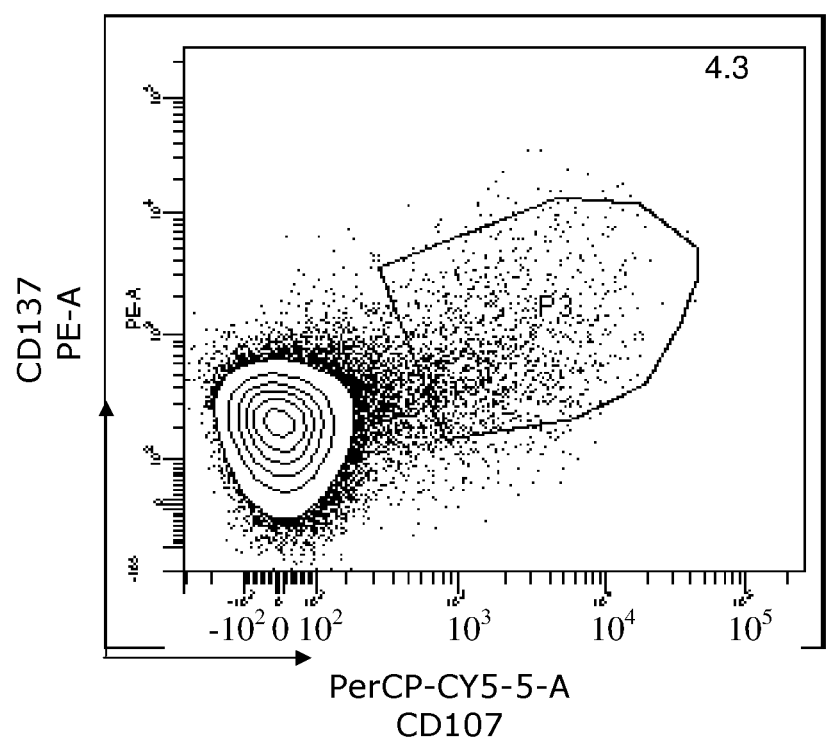

DCs Matured Through Electroporation with TriMix mRNA Efficiently Stimulate Antigen-Specific T Cells As they wanted to investigate the use of TriMix for the in situ modification of mouse DCs, the inventors evaluated whether electroporation of mouse DCs with TriMix results in immunogenic DCs. It was shown that TriMix-electroporated DCs displayed a phenotype (FIG. 9A), cytokine secretion profile (FIG. 9B), and allogeneic Tcell stimulatory capacity (FIG. 9C) comparable with that of LPS-activated DCs. Importantly, it was shown that TriMix-matured DCs were superior to LPS-matured DCs in stimulation of functional antigen-specific CD8± T cells in vivo. This was shown for OVA (FIG. 9D-F) and the TAA Trp2 (FIG. 9G).

Example 11

In Vivo Immunization Through Intranodal Injection of Antigen mRNA in Combination with the TriMix mRNA Composition Materials and Methods
Mice
    Female, 6- to 12-week-old C57BL/6, DBA/2, and BALB/c mice were purchased from Harlan. Transgenic mice were provided by B. Lambrecht (University of Ghent, Ghent, Belgium) and include OT-I mice that carry a transgenic CD8 T-cell receptor (TCR) specific for the MHC I-restricted ovalbumin (OVA) peptide SIINFEKL, OT-II mice that carry a transgenic CD4 TCR specific for the MHC II-restricted OVA peptide ISQAVHAAHAEINEAGR, and CD11c-diphtheria toxin receptor (DTR) mice in which CD11c+ cells are depleted upon treatment with 4 ng diphtheria toxin (DT)/g mouse (Sigma). Where indicated mice received an intravenous hydrodynamic injection with 10 microgram of a plasmid encoding Flt3 ligand (a gift from O. Leo, University Libre de Bruxelles, Brussels, Belgium) in 0.9 NaCl in a final volume equal to 10% of the mouse body weight. Animals were treated according to the European guidelines for animal experimentation. Experiments were reviewed by the Ethical committee for use of laboratory animals of the Vrije Universiteit Brussel (Jette, Belgium).
Mouse cell lines and DCs
    The melanoma MO4, the T-cell lymphoma EG7-OVA, the mastocytoma P815, and the myeloid leukemia C1498-WT1 were obtained from the American Type Culture Collection, C. Uytttenhove (Université Catholique de Louvain, Brussels, Belgium), and H. E. Kohrt (Stanford University Medical Centre, Stanford, Calif.), respectively. No full authentication was carried out. Cell lines were evaluated for the expression of MHC molecules and antigens (OVA, MO4 and EG7-OVA; P1A, P815; and WT1, C1498-WT1) by reverse transcriptase PCR (RT-PCR) or flow cytometry. Bone marrow-derived DCs were generated as described (Van Meirvenne et al., 2002, Cancer Gene Ther. 9:787-97).
Messenger RNA
    The vector, pST1 was provided by U. Sahin (Johannes-Gutenberg University, Mainz, Germany). The vectors pGEMIi80tOVA, pST1-tyrosinase-DC-LAMP, pST1-sig-WT1-DNLSDC-LAMP, pST1-caTLR4, and pGEM-tNGFR have been described (Benteyn and colleagues; manuscript in preparation; ref. Van Meirvenne et al., 2002, Cancer Gene Ther. 9:787-97). The sequence encoding firefly luciferase (FLuc) was cloned into pST1 with minor modifications. The vector pGEM-Ii80P1A was cloned analogous to the cloning of pGEMIi80tOVA. The codon-optimized cDNA encoding mouse CD40L or CD70 were obtained from Geneart and cloned as a SpeI-XhoI fragment in the pST1 vector. A fragment of the mouse Trp2 gene that encodes SVYDFFVWL was amplified with the following primers: 50-GGGGATC-CGGCCATCCTAAGACGG-30 and 30-GGGGGATCCGT-GCACACGTCACACTCGTTC-50 and cloned as a BamHI fragment in the BamHI linearized and shrimp alkaline phosphatase-treated pST1-sig-DC-LAMP. The sequence encoding enhanced GFP (eGFP) was isolated from p-eGFP-N1 as a HindIII-NotI fragment and cloned into the HindIII-NotI digested pST1 vector. All enzymes were purchased from Fermentas. Before in vitro transcription, pGEM and pST1 vectors were linearized with SpeI and SapI, respectively. In vitro transcription was carried out as described (Van Meirvenne et al., 2002 Cancer Gene Ther. 9:787-98). The mRNA was dissolved in PBS, Ca$^{2+}$-containing Hank's balanced salt solution (HBSS, Lonza), or 0.8 Ringer lactate (0.8 RL; Baxter).

Passive pulsing and electroporation of mRNA

To pulse DCs with mRNA, 5×10$^6$ DCs were pelleted and incubated for 15 minutes with 10 mg tNGFR or FLuc mRNA in 15 microliter. Where indicated pulsing was carried out in the presence of 1 ng/mL LPS from *Escherichia coli* serotype 055: B5 (Sigma-Aldrich), 10 mg/mL polyI:C (Sigma), or 100 ng/mL monophosphoryl lipid A (MPL; GlaxoSmithKline). DCs were cultured in RPMI-1640 medium supplemented with 5% FCI (Harlan), 50 micromol/L beta-mercaptoethanol, and 20 ng/mL mouse granulocyte macrophage colony-stimulating factor (GM-CSF; prepared in-house) at a cell density of 10$^6$ DCs per mL. Four hours later, DCs were lysed using the reporter lysis buffer from Promega. D-Luciferin (Xenogen) was added, luminescence measured with the Glomax 96-luminometer, and data analyzed with Glomax software (Promega). Electroporation of DCs with mRNA was carried out as described (Van Meirvenne et el., 2002, Cancer Gene Ther. 9:787-97). Where indicated, DCs were activated for 4 hours with 100 ng/mL LPS.

In situ delivery of mRNA

For intranodal delivery of mRNA, C57BL/6 mice were anesthetized with ketamine (70 mg/kg; Ceva) and xylazine (10 mg/kg; Bayer). The inguinal lymph node was surgically exposed and injected with the indicated amount of mRNA (and where indicated 1 ng LPS). Subsequently, the wound was closed. On 3 consecutive days before intradermal delivery of mRNA, mice were injected intradermally with PBS or 20 ng of mouse GM-CSF, after which the mRNA was administered.

RNA isolation, cDNA synthesis, and RT-PCR

RNA was extracted using the SV Total RNA Isolation System (Promega) and converted to cDNA by the RevertAid H-Minus First Strand cDNA Synthesis Kit (Fermentas). The sequence encoding FLuc was amplified with 50-AAGGTGTGGCCCTTCC-30 and 50-CCAAGAATGAAAAT-AGGGTTG-30, whereas the sequence encoding beta-actin was amplified with 50-TGCTATCCAGGCTGTGCTAT-30 and 50-GATGGAGTTGAAGGTAGTTT-30 using the following PCR program: 94° C. 50", 45(94° C. 30", 52° C. 30", 72° C. 30"), 72° C. 100, hold 4° C.

Immune array

RNA of lymph nodes injected with 0.8 RL, 10 mg antigen mRNA supplemented with 20 mg tNGFR mRNA or TriMix (10 microgram per component) was extracted and converted to cDNA. Quantitative RT-PCR by the TaqMan mouse immune response array (Applied Biosystems) and analysis was conducted according to the manufacturers instructions.

Flow cytometry

Allophycocyanin-conjugated anti-CD11c (HL3), -CCR7 (2H4), and phycoerythrin-conjugated anti-CD40L (MR1) and -CD70 (FR70) antibodies were purchased from Pharmingen. The antibodies against CD40 (FGK45), CD80 (16-10A1), and CD86 (GL-1) were prepared in-house. Nonreactive isotype matched antibodies served as controls (Pharmingen). Labeling of DCs was carried out as described (Van Meirvenne et al., 2002 Cancer Gene Ther. 9:787-98). Data were collected using the FACSCanto Flow Cytometer (Becton Dickinson) and analyzed with FACSDiva or FlowJo software.

Allogeneic mixed lymphocyte reaction

The ability of electroporated DCs to stimulate allogeneic CD90 purified (Miltenyi Biotec) T cells was assessed in a mixed lymphocyte reaction (Breckpot et al; 2010, J. Virol. 84:5627-36).

ELISA

Supernatants were screened in a sandwich ELISA for the presence of interleukin (IL)-6, IL-12p70, TNF-alpha, or IFN-gamma (eBioscience).

In Vivo Bioluminescence Imaging

In vivo bioluminescence imaging was conducted as described (Keyaerts et al., 2008 Eur. J. Nucl. Med Mol Imaging 35:999-1007).

Fluorescence Microscopy

Lymph nodes were injected with 10 mg eGFP mRNA, 1 day before isolation. Single-cell suspensions were prepared and stained with a phycoerythrin-conjugated anti-CD11c antibody. Expression of CD11c and eGFP was evaluated with the Evos$^{fl}$ fluorescence microscope.

Immunization of mice

Mice were immunized intravenously with 5×10$^5$ antigen presenting DCs activated with TriMix or LPS, or intranodally or intradermally with 10 microgram antigen mRNA supplemented with 30 mg tNGFR mRNA or TriMix (10 microgram per component). Immunization with DCs electroporated with tNGFR mRNA or with tNGFR mRNA as such served as a control. For assessment of therapeutic efficacy, 5×10$^5$ tumor cells were administered subcutaneously in the lower back, 7 days before immunization.

Intracytoplasmatic staining of IFN-g

Spleen cells of immunized mice were stimulated for 24 hours with DCs pulsed for 2 hours with 5 mmol/L SIINFEKL peptide and matured with LPS. GolgiPlug was added 24 hours before intracytoplasmatic staining of IFN-gamma.

Pentamer staining

The staining of CD8$^+$ T cells with H2-K$^b$/SIINFEKL pentamers (Immunosource) was carried out as described (Breckpot et al; 2010, J. Virol. 84:5627-36).

In vivo cytotoxicity assay

Spleen cells from syngeneic mice were labeled with 10 mmol/L carboxyfluorescein diacetate succinimidyl ester (CFSE) as described (Van Meirvenne et al., 2002 Cancer Gene Ther. 9:787-98). These were pulsed with the peptide SIINFEKL (OVA) or SVYDFFVWL (Trp2; Thermo Electron Cooperation) or a set of overlapping peptides covering WT1 (kind gift from V. Van Tendeloo, University of Antwerp, Edegem, Belgium) or tyrosinase (EMC microcultures) at 5 mmol/L for 2 hours. Peptide-pulsed cells were mixed at a 1:1 ratio with nonpulsed cells, labeled with 0.5 mmol/L CFSE. Specific lysis of target cells was analyzed 18 hours later by flow cytometry. The percentage of killing was calculated as described (Dullaers et al., 2006, Gene Ther. 13:630-40).

In vivo proliferation assay

One day before immunization, 10$^6$ purified and CFSE-labeled CD8$^+$ OT-I or CD4$^+$ OT-II spleen cells were transferred to mice by intravenous injection. Five days postimmunization, proliferation of T cells was analyzed in peripheral blood, spleen, and lymph nodes (Dullaers et al., 2006, Gene Ther. 13:630-40).

Statistical analyses

A one-way ANOVA followed by the Bonferroni multiple comparison test was conducted. Sample sizes and number of times experiments were repeated are indicated in the figure legends. Number of asterisks in the figures indicates the level of statistical significance as follows: *, P<0.05; , P<0.01; *, P<0.001. The results are shown in a scatter plot in which each mouse is depicted as a dot and the mean as a horizontal line or in a column graph or table as the mean+/−SEM. Survival was visualized in a Kaplan-Meier plot. Differences in survival were analyzed by the log-rank test.

Results:

11a. Formulation and pharmacokinetics of mRNA for vaccination purposes.

In this experiment, it was evaluated which buffer is best suited to deliver mRNA to DCs.

Figures 8, 8B, 9, 10:
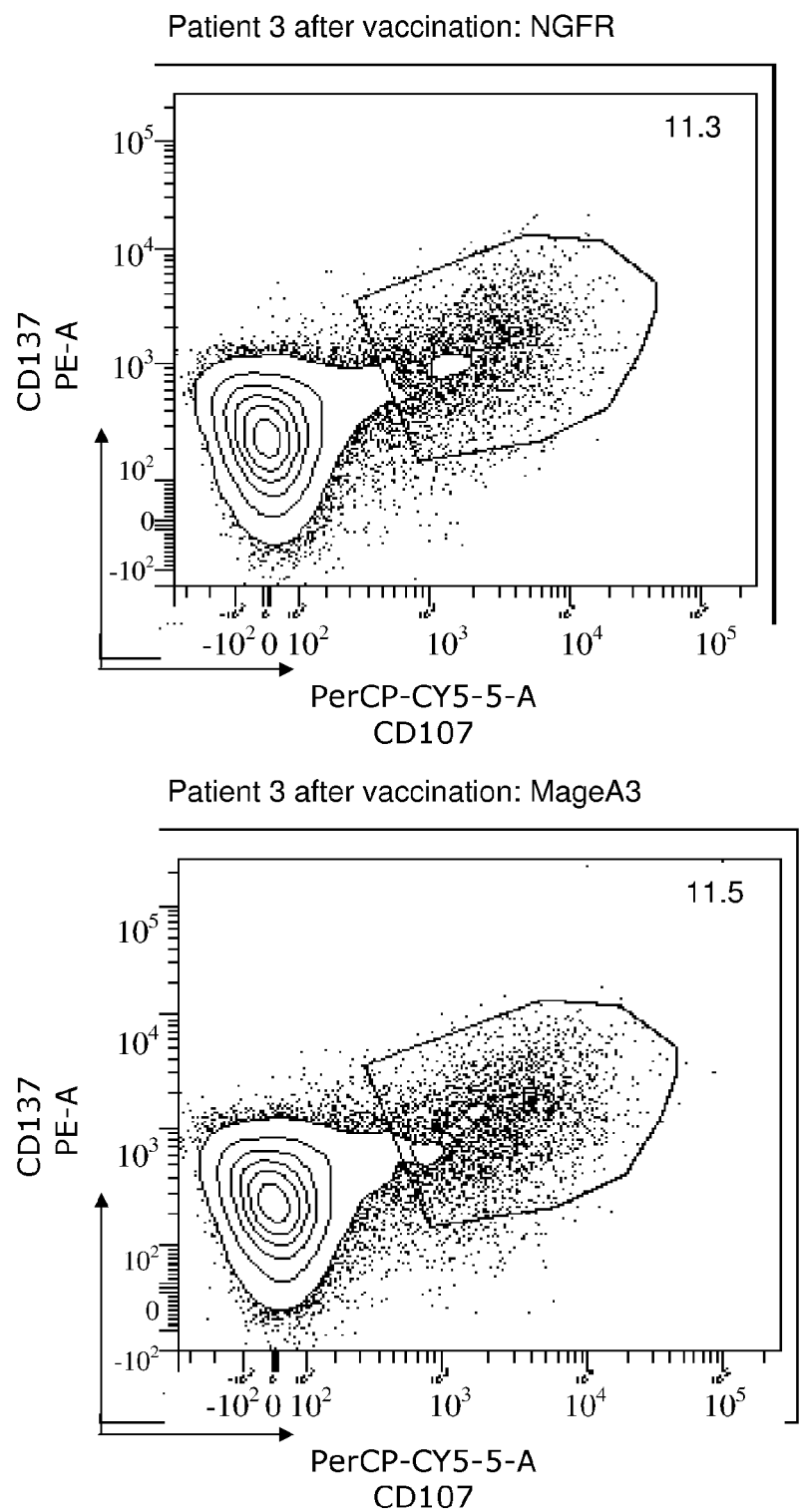

FLuc mRNA was dissolved in PBS, $Ca^{2+}$-containing HBSS, or 0.8 RL. Luminescence analysis of passively pulsed DCs showed high FLuc expression when the mRNA was dissolved in 0.8 RL or HBSS (FIG. 10A).

Next, FLuc mRNA was administered intranodally. In vivo bioluminescence imaging showed short-term FLuc expression when mRNA was formulated in PBS when compared with high and long FLuc expression when mRNA was formulated in HBSS or 0.8 RL (FIG. 10B). The latter was unexpected as naked mRNA is believed to have a short extracellular half-life. To analyze the stability of mRNA in vivo upon delivery in 0.8 RL, the inventors resected lymph nodes injected with FLuc mRNA 6, 12, and 24 hours after injection. RT-PCR showed the presence of FLuc mRNA up to 12 hours after injection. No FLuc mRNA was detectable at later time points (FIG. 10C).

Next, the role of DCs in the uptake of mRNA in vivo was evaluated. Lymph nodes were injected with eGFP mRNA 24 hours before their isolation. Single-cell suspensions were prepared and stained for CD11c. Fluorescence microscopy showed a small number of eGFP$^\pm$ cells. Importantly, all eGFP$^\pm$ cells were CD11c$^\pm$, showing uptake and translation of mRNA by DCs (FIG. 10D). To further evidence a role for DCs, the inventors used CD11c-DTR transgenic mice in which administration of DT results in the depletion of CD11c$^\pm$ cells. In vivo bioluminescence imaging showed the absence of FLuc expression in mice that were treated with DT before intranodal administration of FLuc mRNA. Mice treated with PBS served as a control (FIG. 10E). Flow cytometric analysis of the lymph nodes of these mice confirmed that the absence of luminescence was correlated with the depletion of DCs (FIG. 10E). As delivery of mRNA into the inguinal lymph node is technically challenging, the feasibility of delivering mRNA intradermally was finally examined. Because it was shown in the former experiment that CD11c$^\pm$ cells are responsible for the DC uptake, the mice were pretreated with an intradermal injection of PBS or GM-CSF on 3 consecutive days before the intradermal injection of FLuc mRNA. In vivo bioluminescence imaging, conducted 6 hours later, showed FLuc expression only in mice pretreated with GM-CSF (FIG. 10F).

11b. Intranodal delivery of TriMix generates an immune stimulatory environment

Figures 8, 8B, 9, 10, 11, 12:
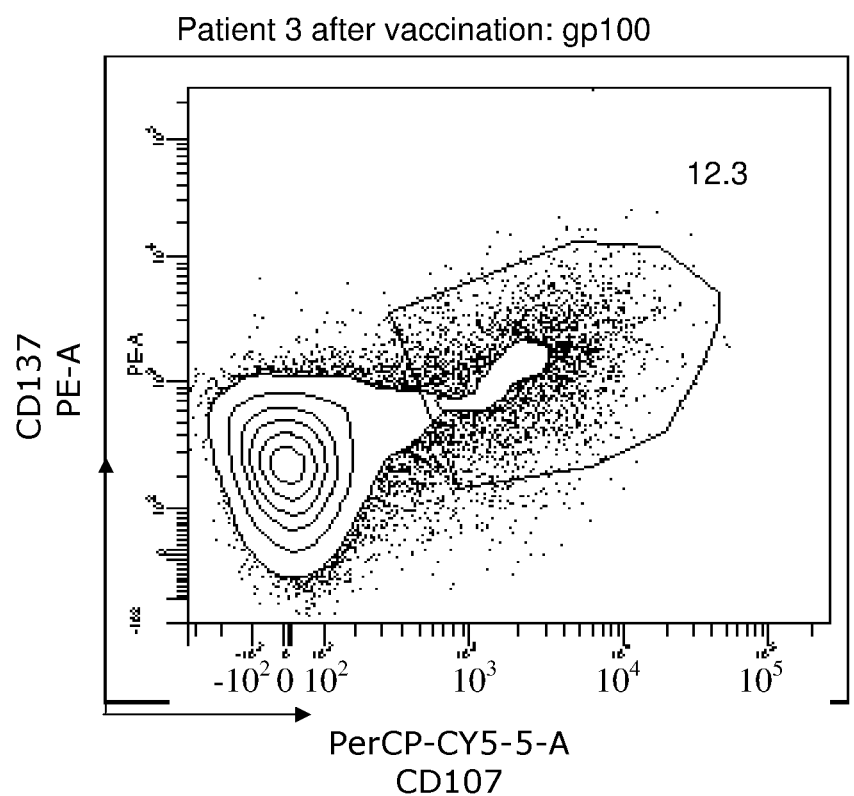
Figures 1, 8C:
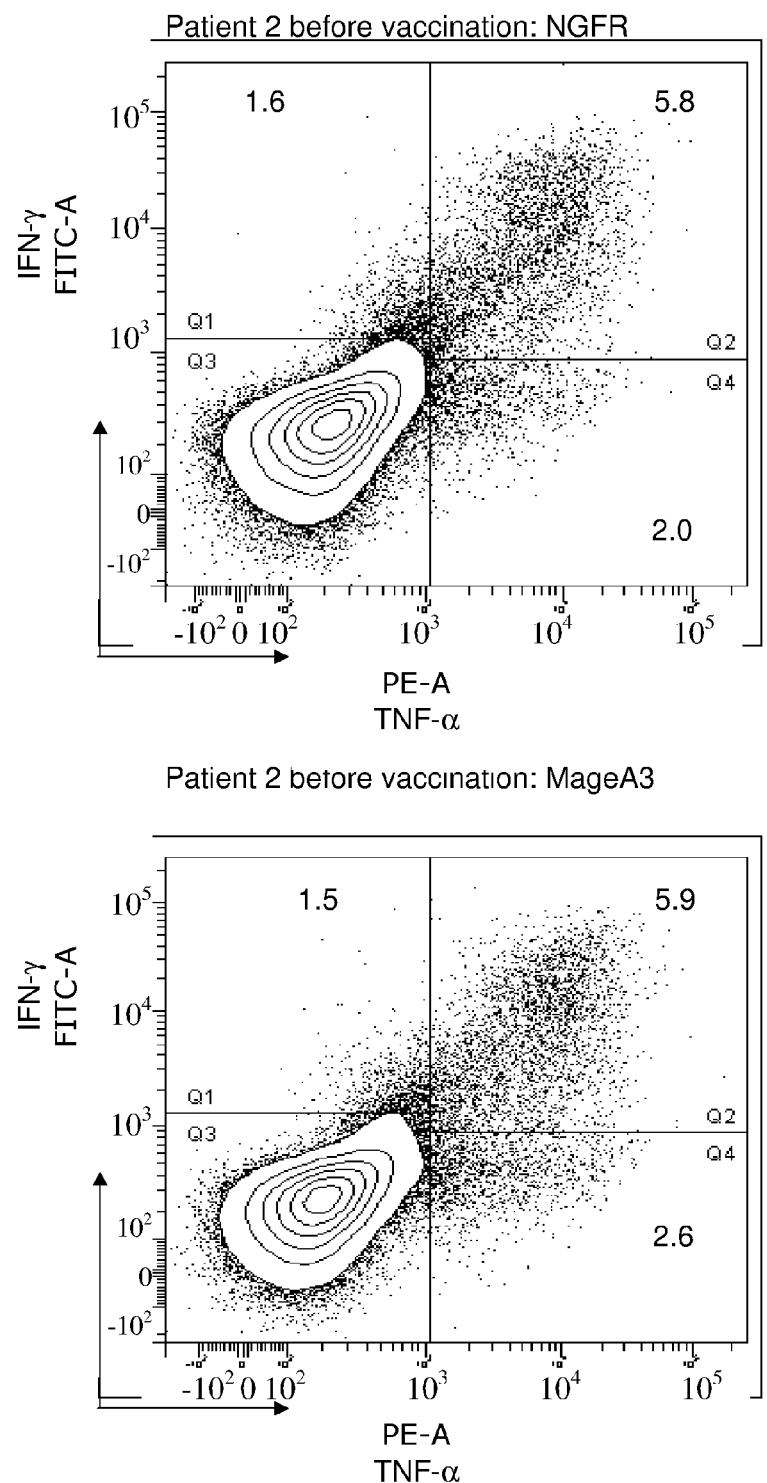
Figure 8C:
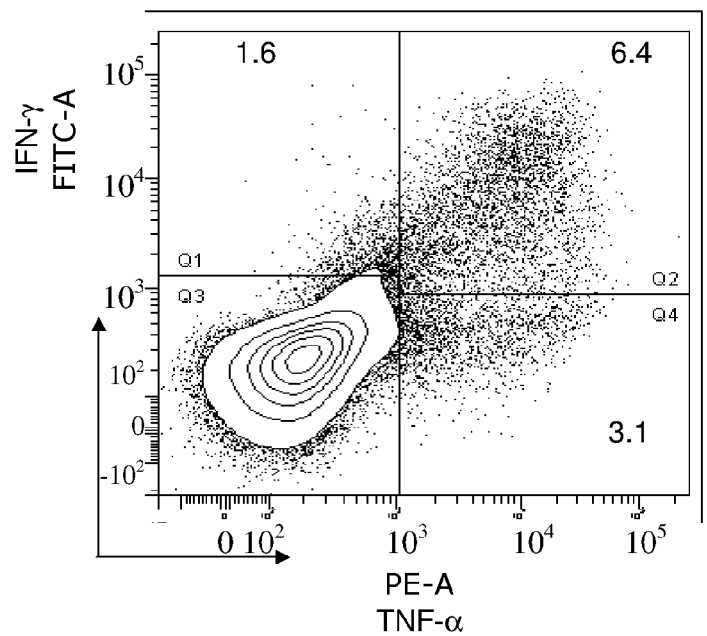
Figure 2:
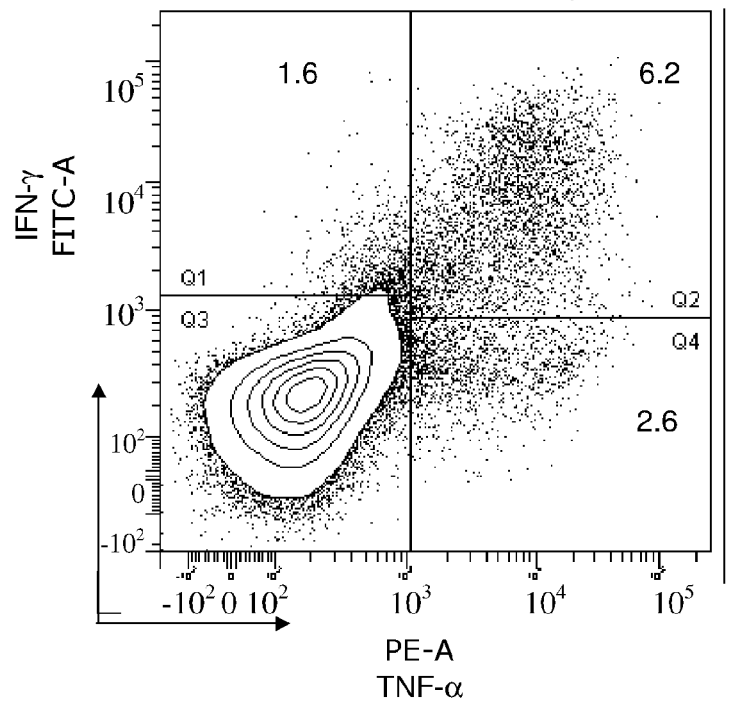
Figures 3, 8C:
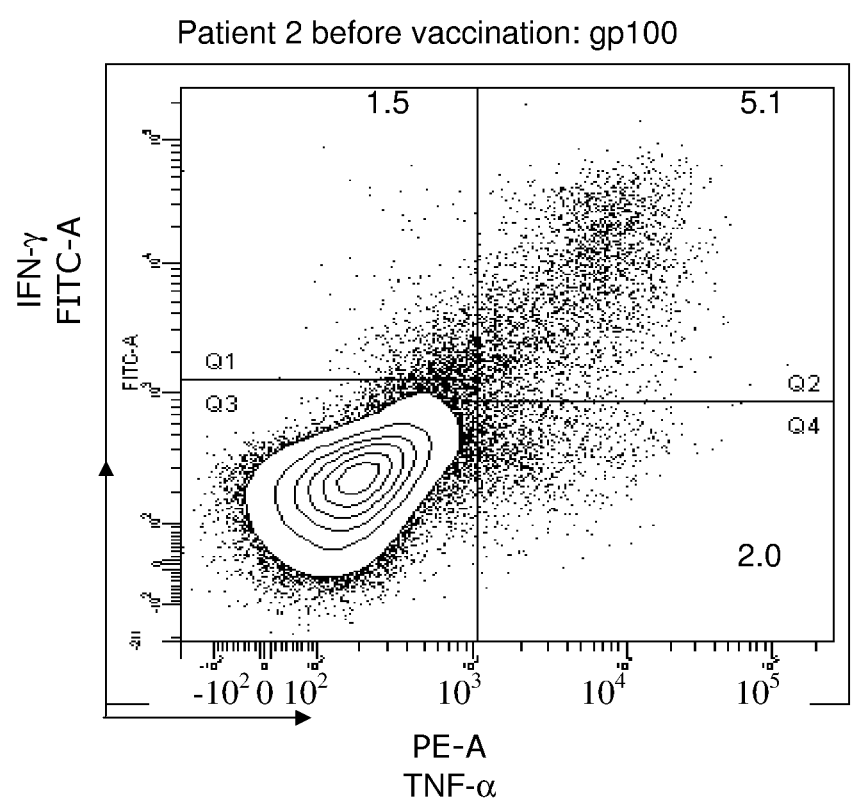
Figures 4, 8C:
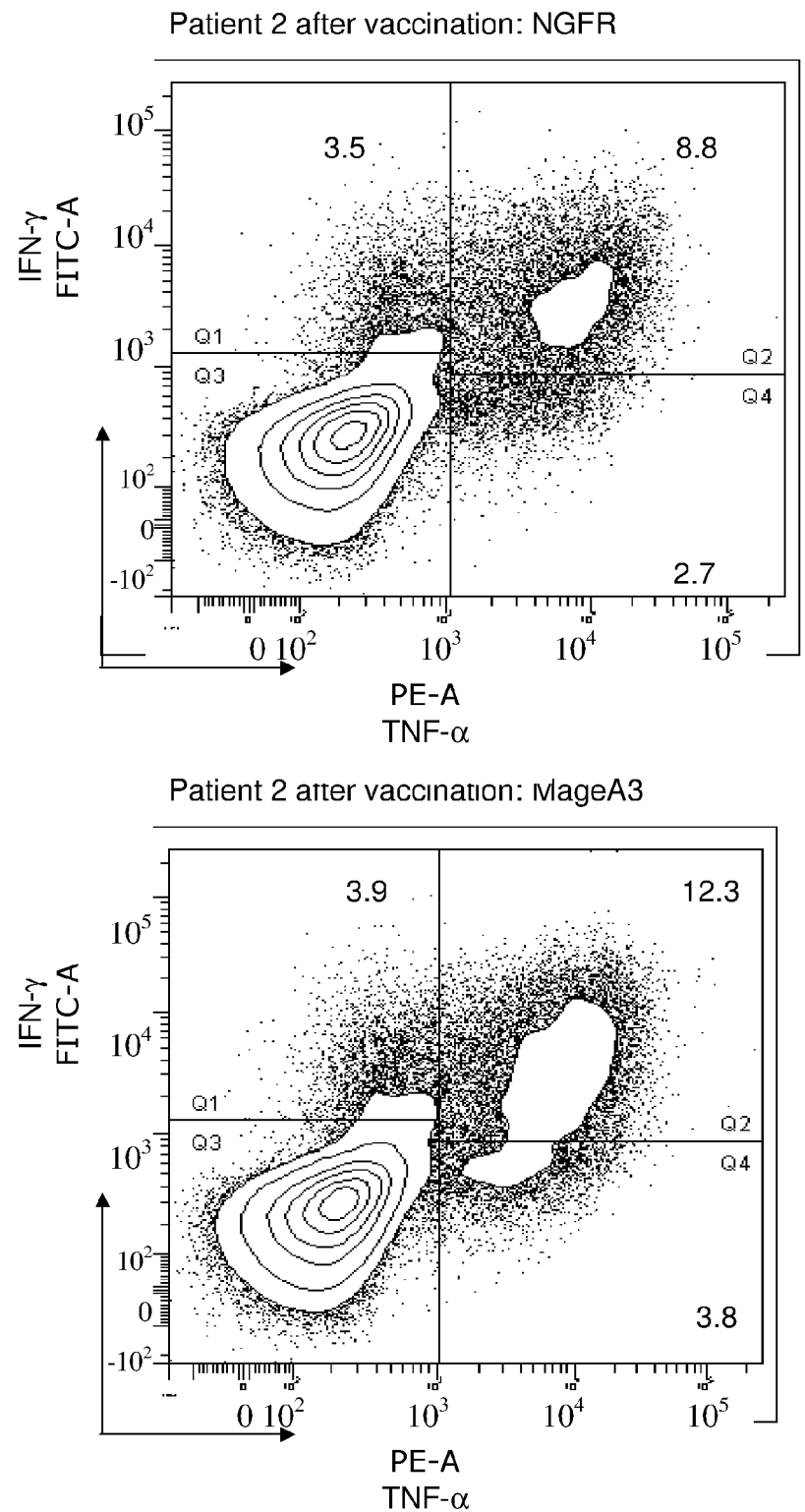
Figures 5, 8C:
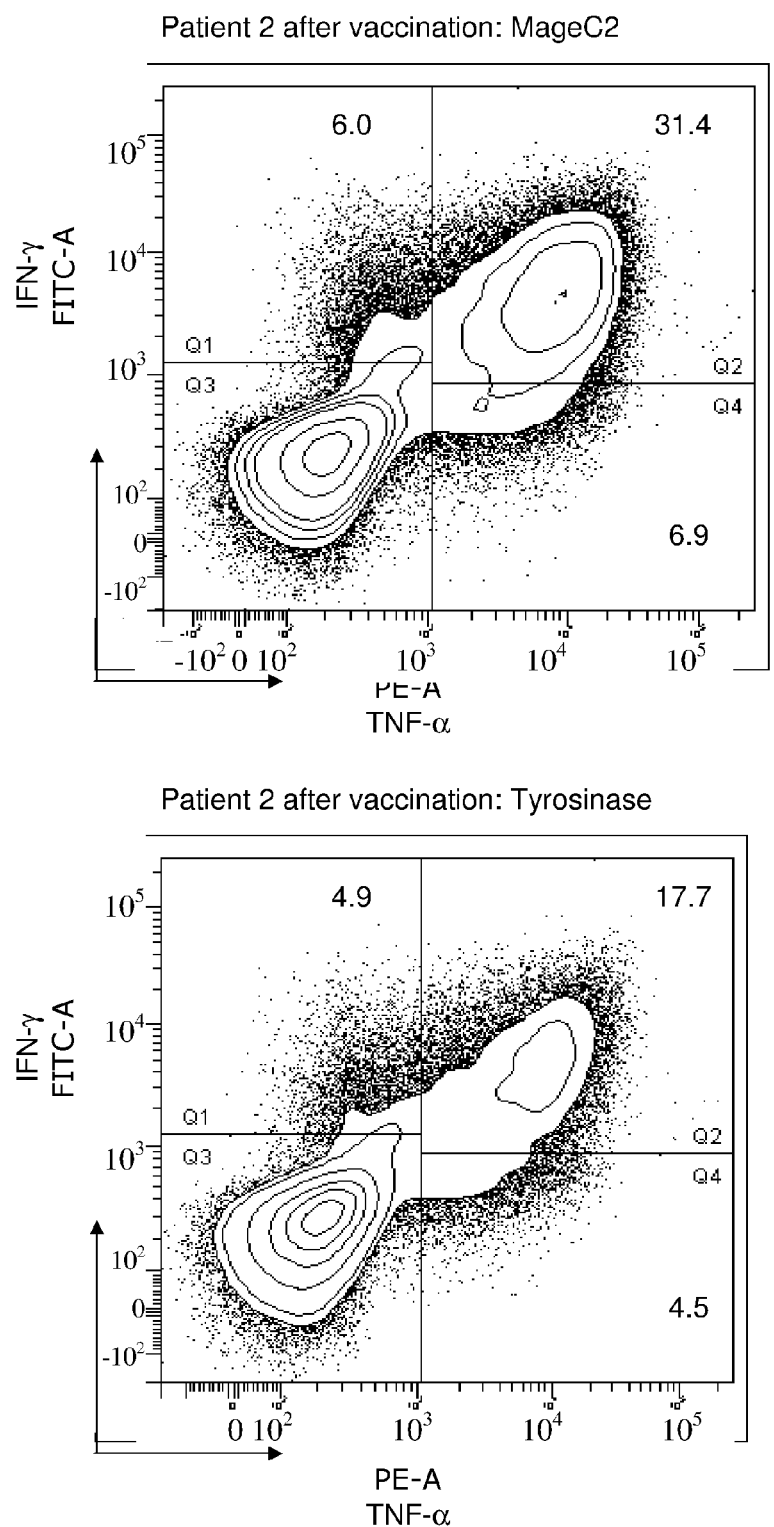
Figures 6, 8C:
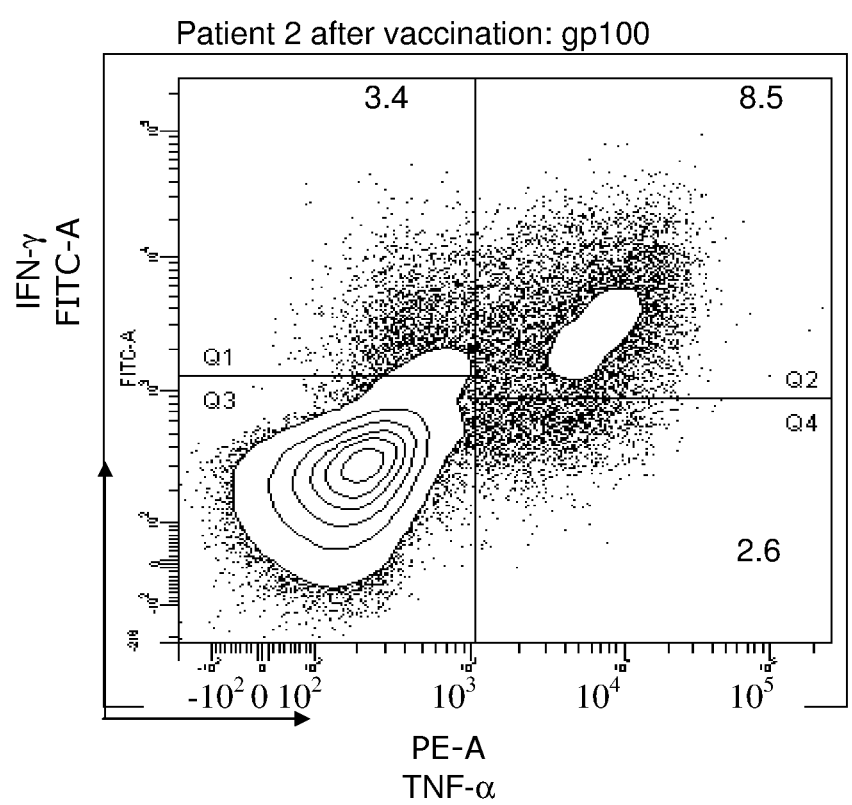
Figures 7, 8C:
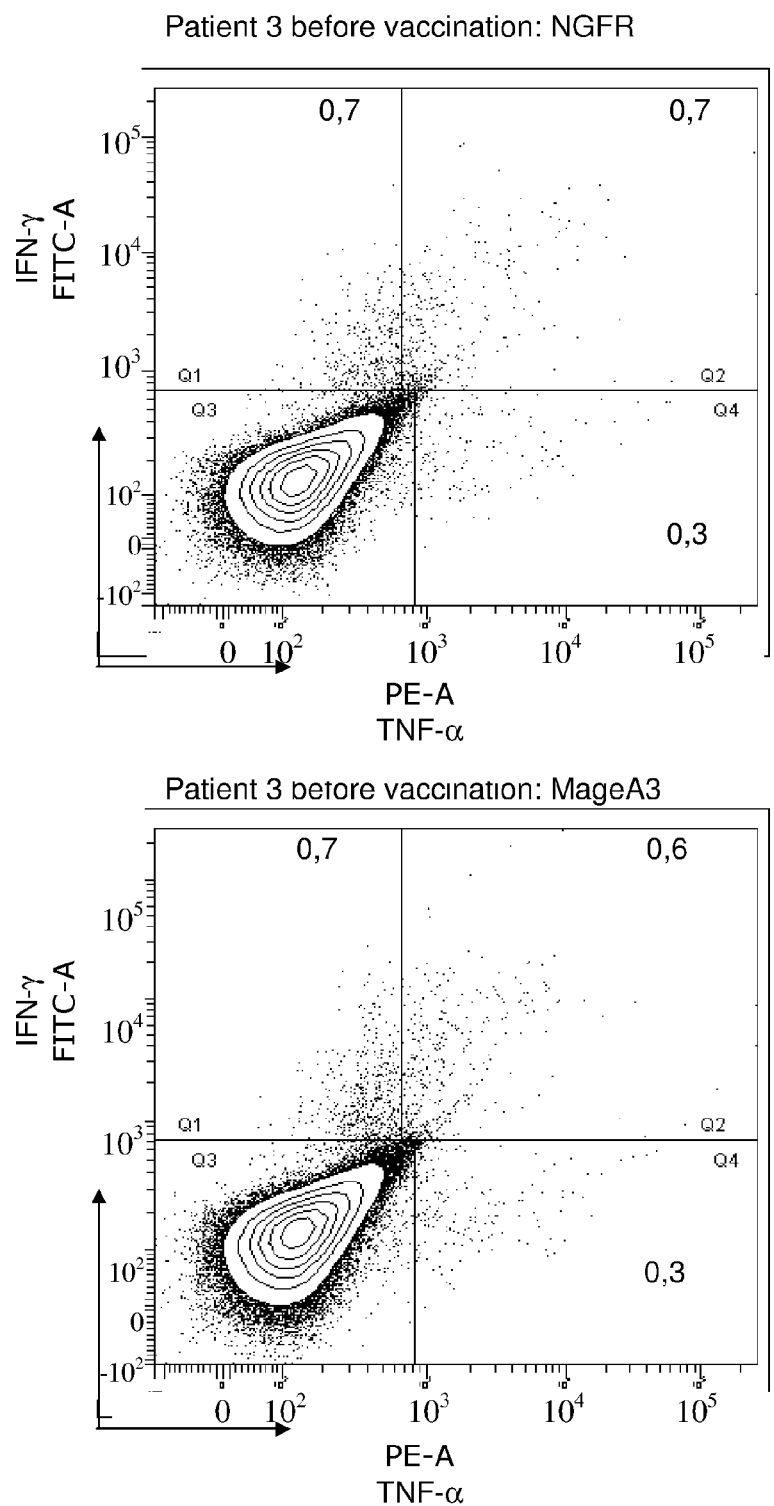
Figures 8, 8C:
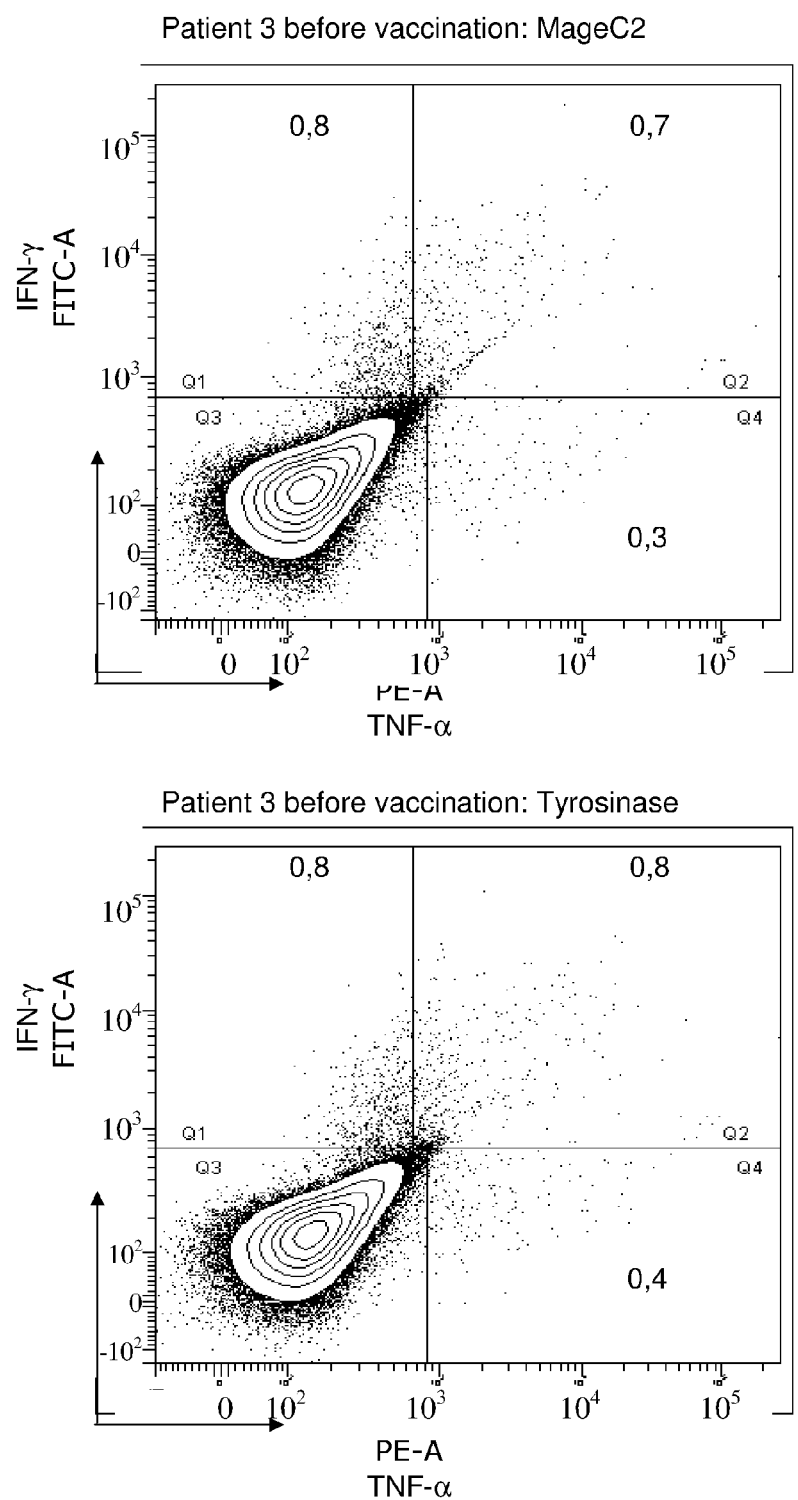
Figures 8, 8C, 9:
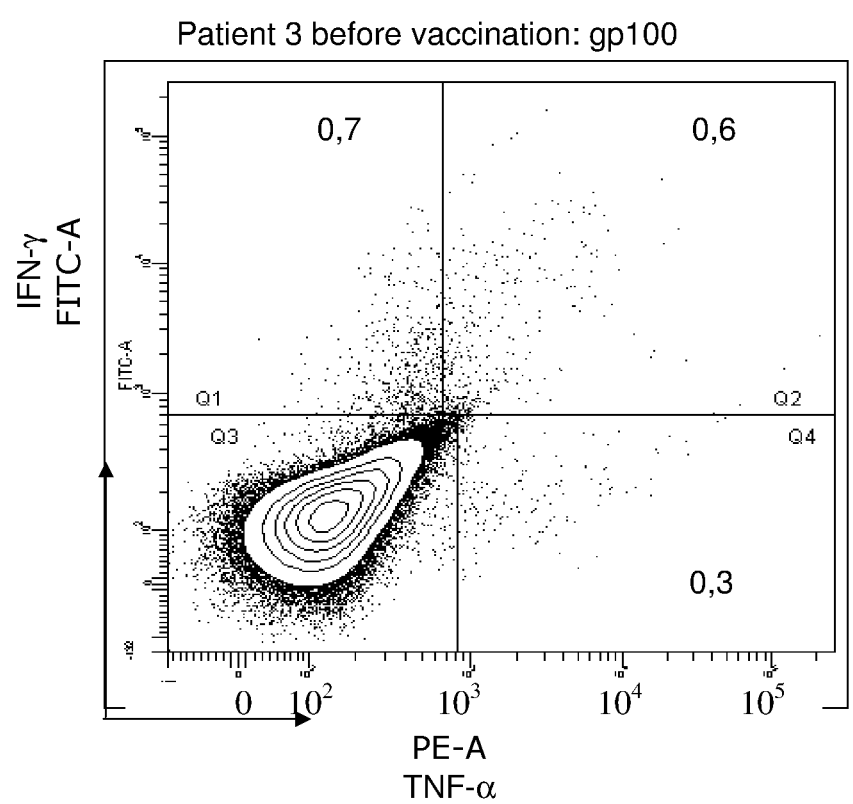
Figures 8, 8C, 9, 10:
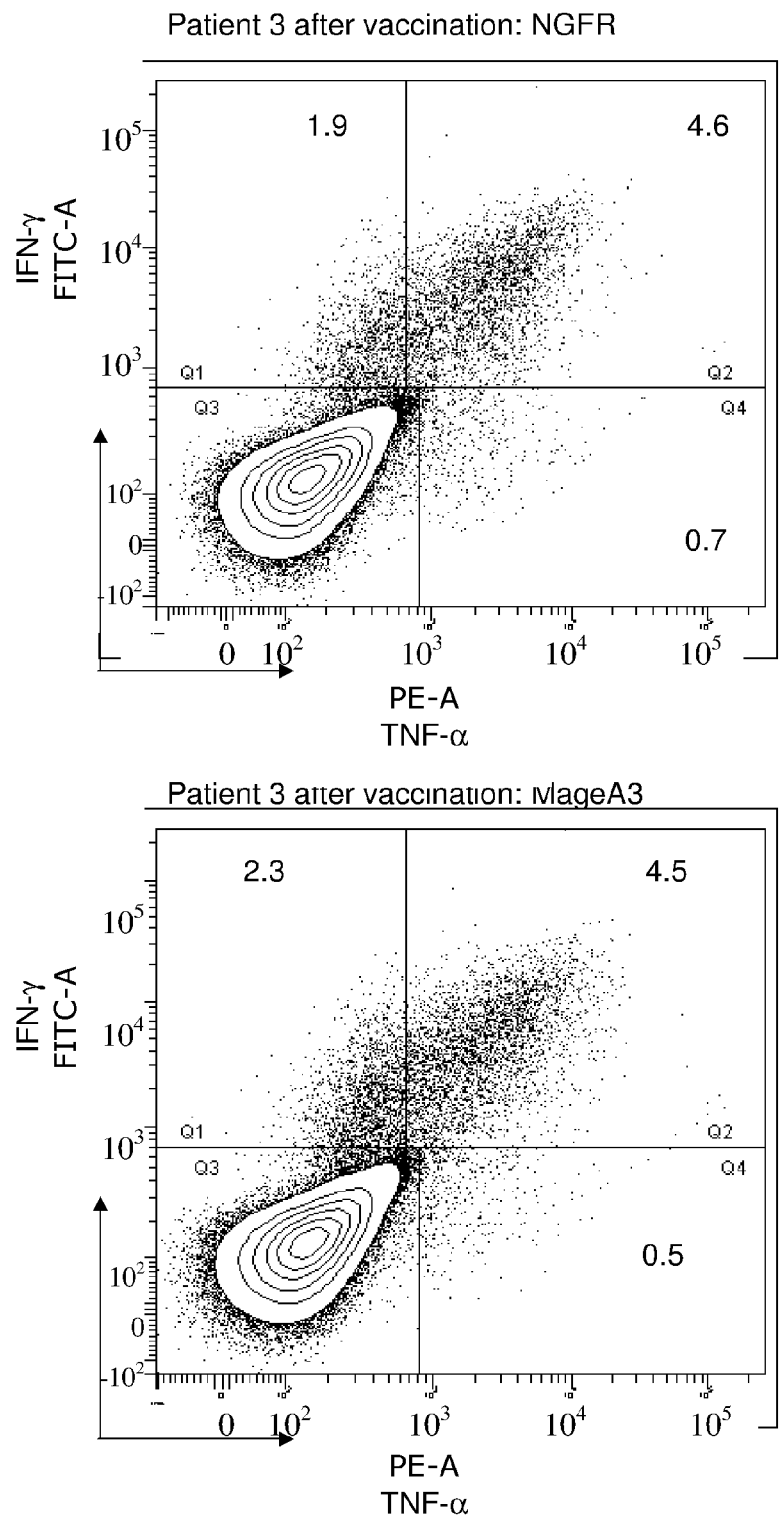
Figures 8, 8C, 9, 10, 11, 12:
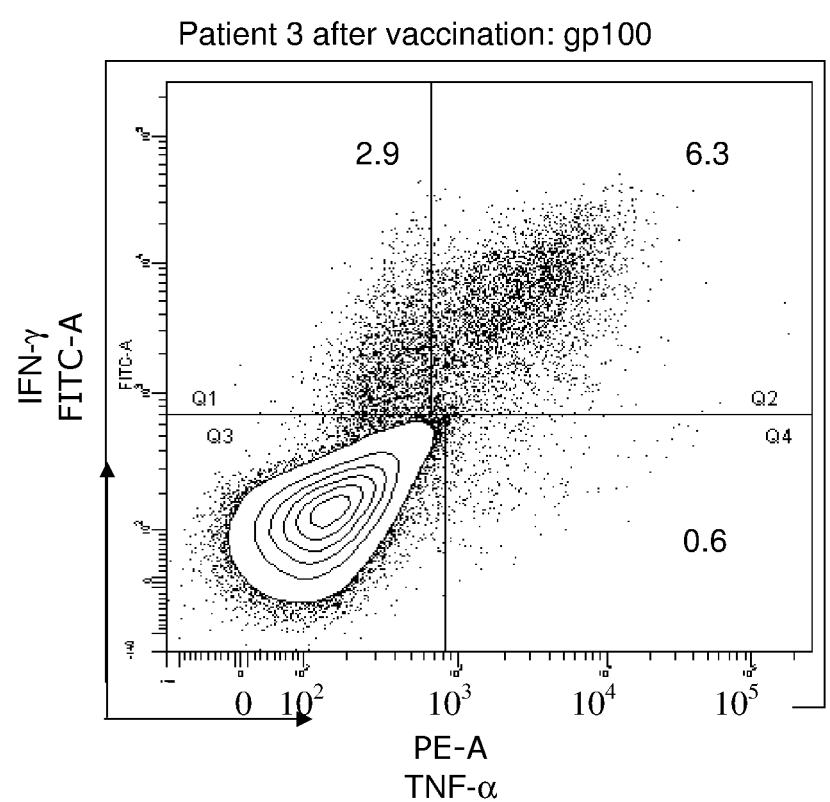
Figures 1, 9:
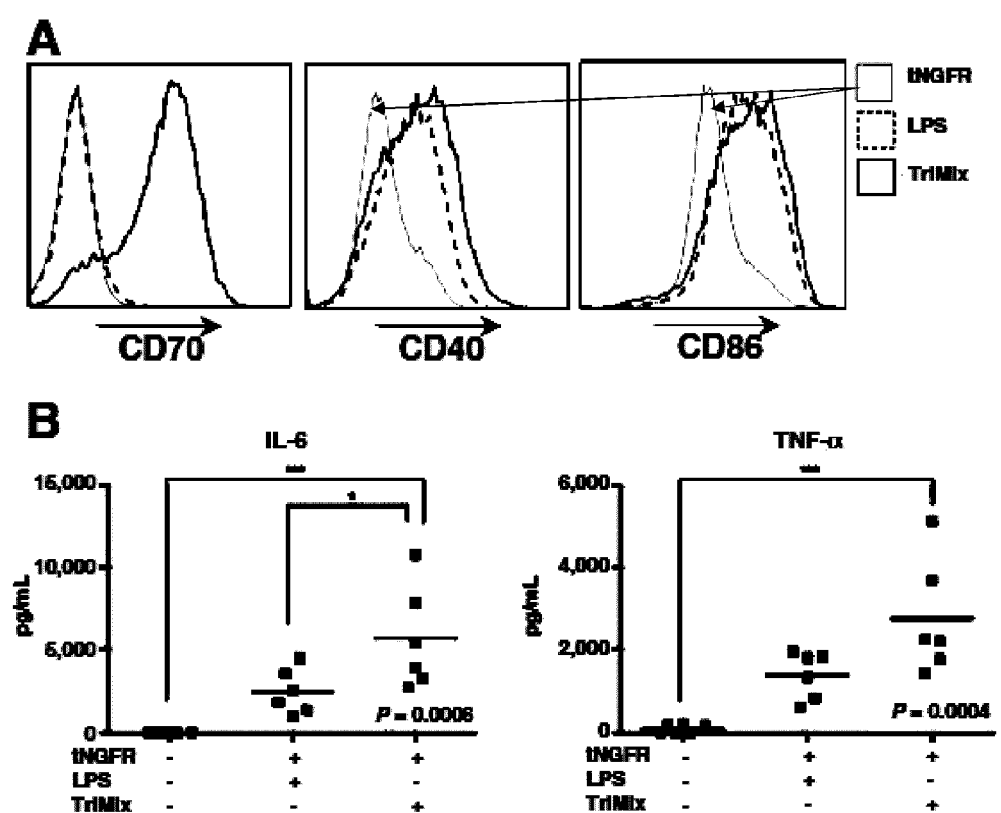
Figures 2, 9:
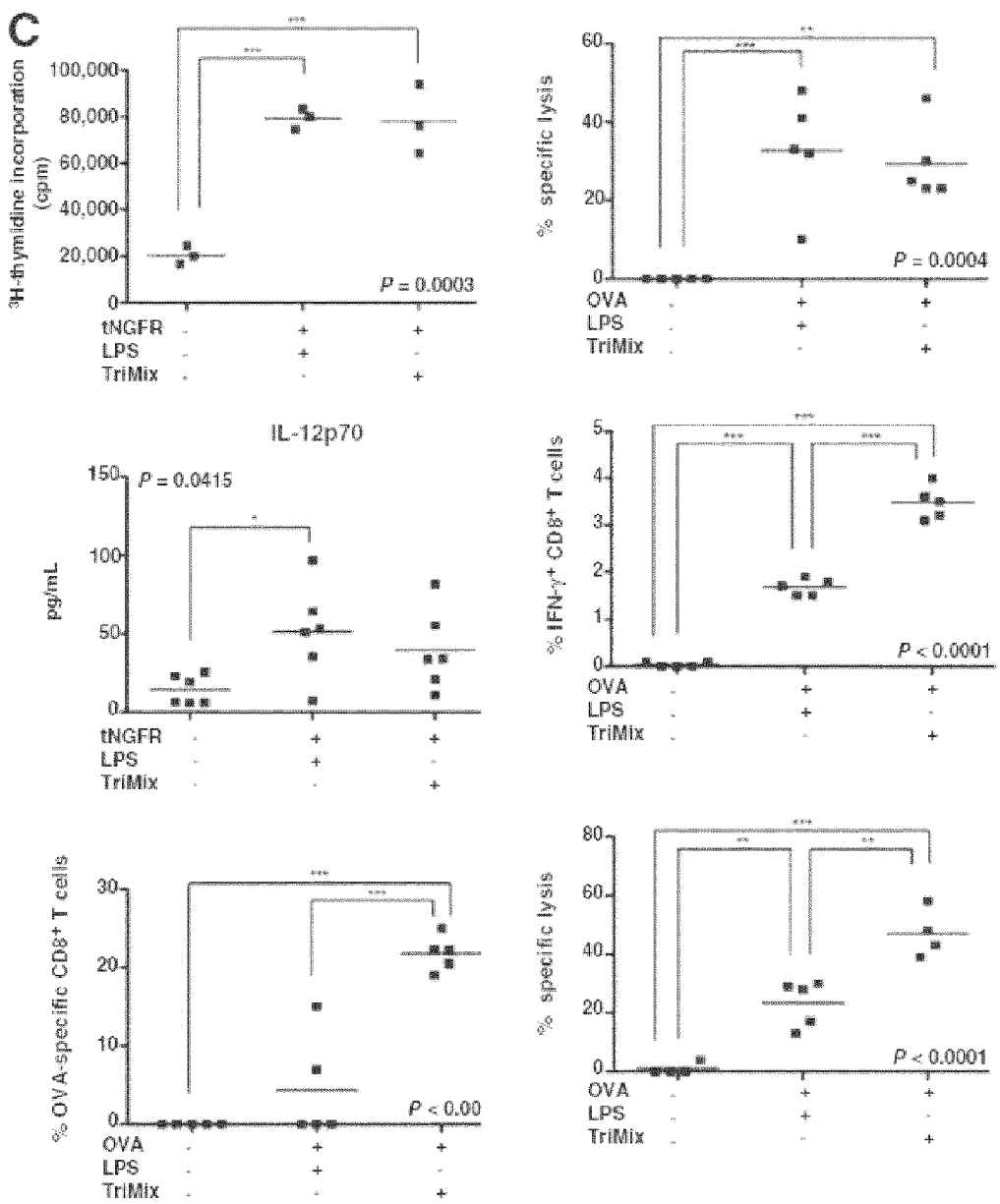
Figures 3, 9:
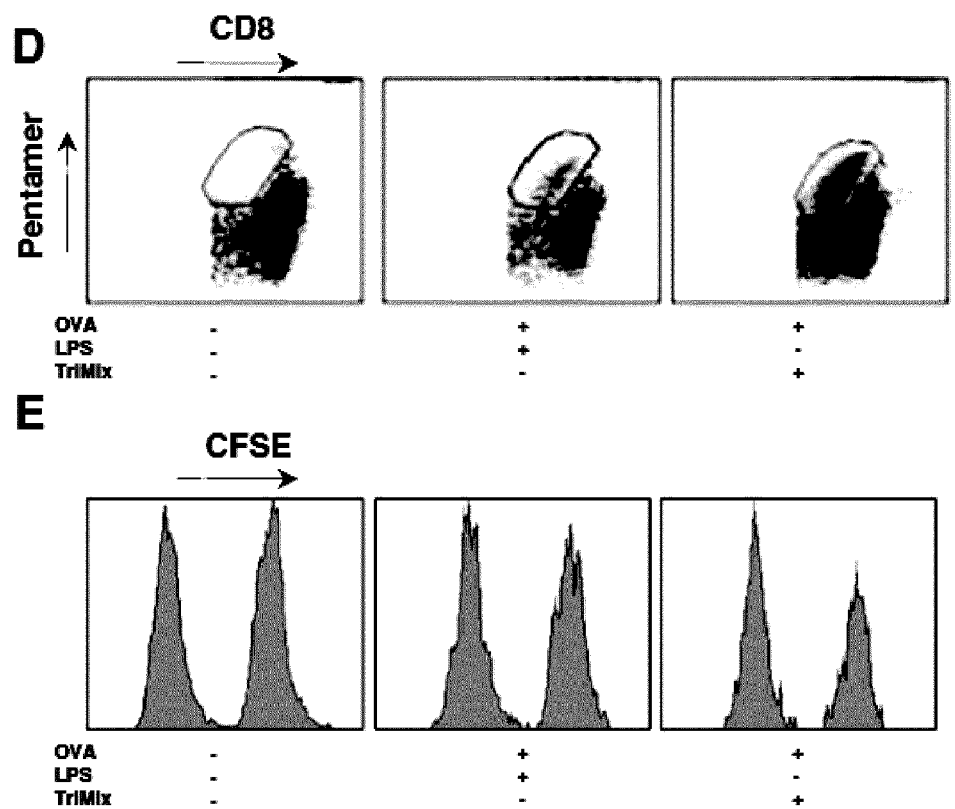
Figures 4, 9:
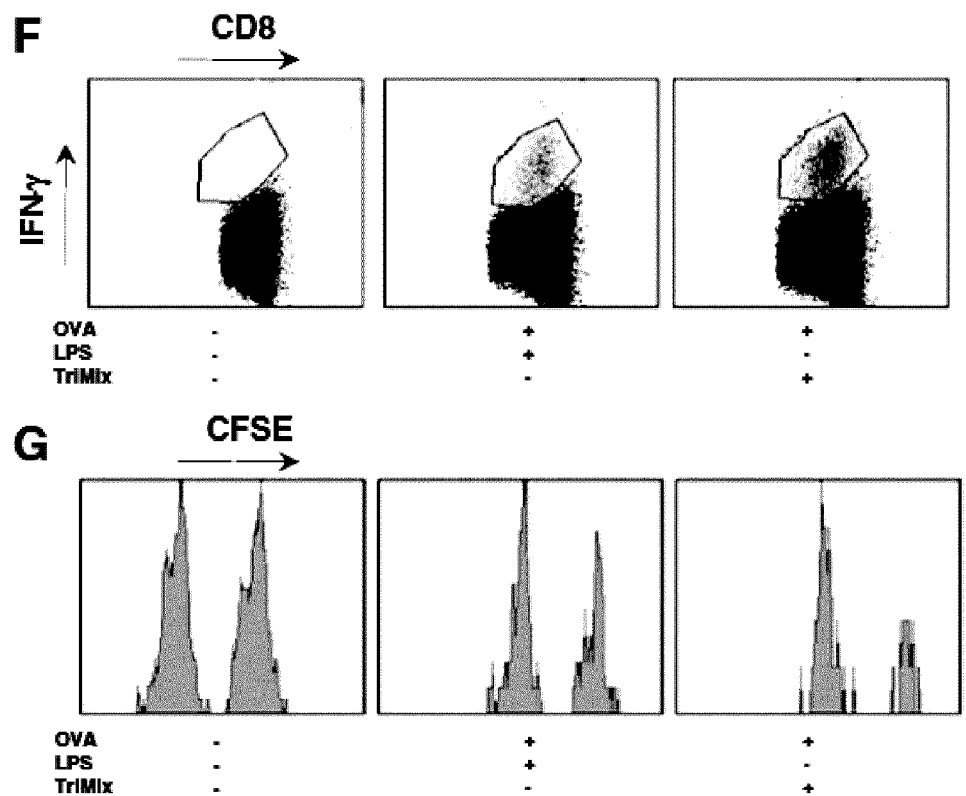
Figure 10:
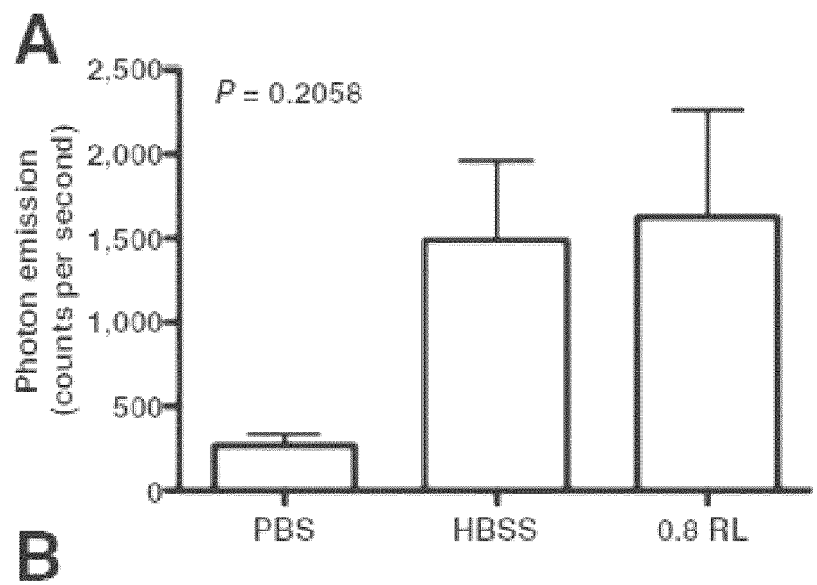
Figure 10:
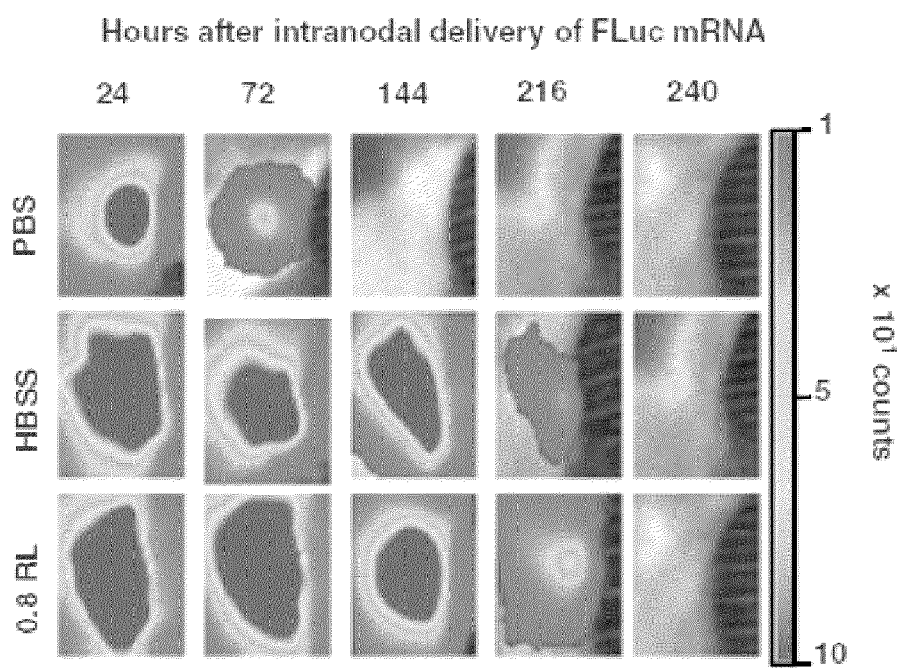
Figure 10:
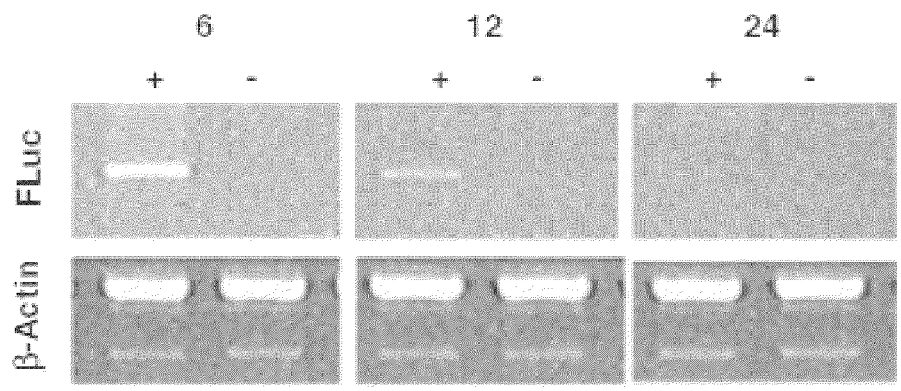
Figure 10:
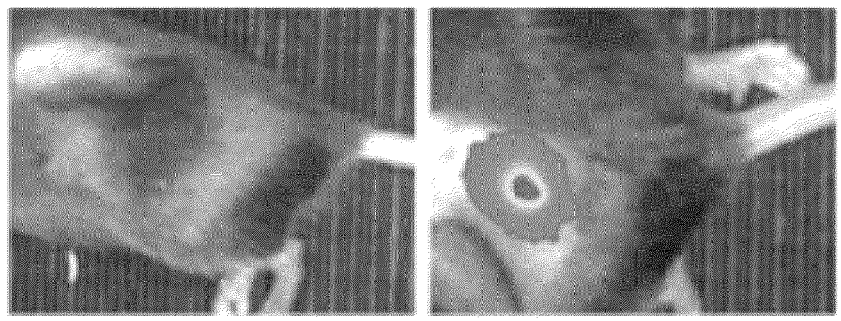
Figure 10:
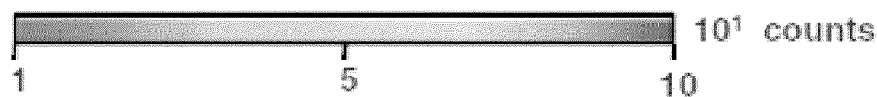
Figure 10:
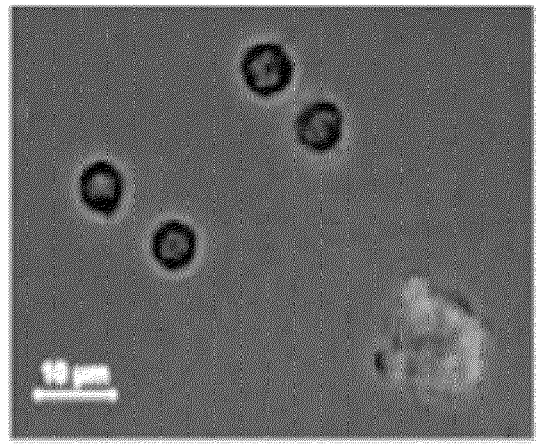
Figure 10:
Figure 10:
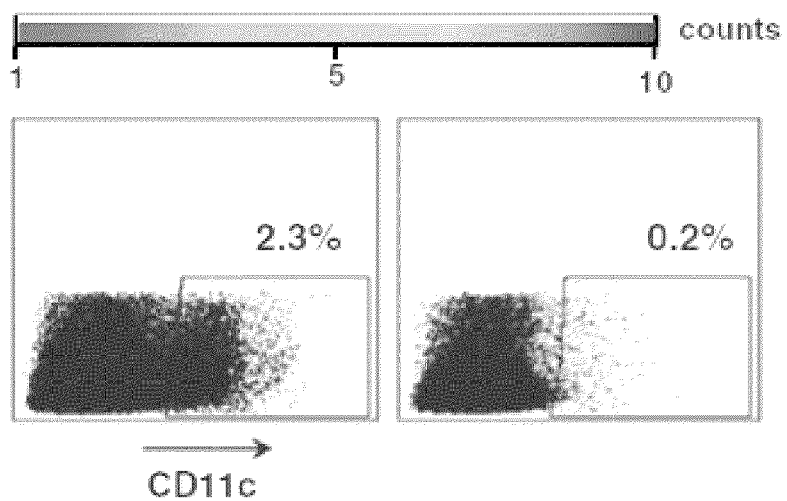
Figure 11:
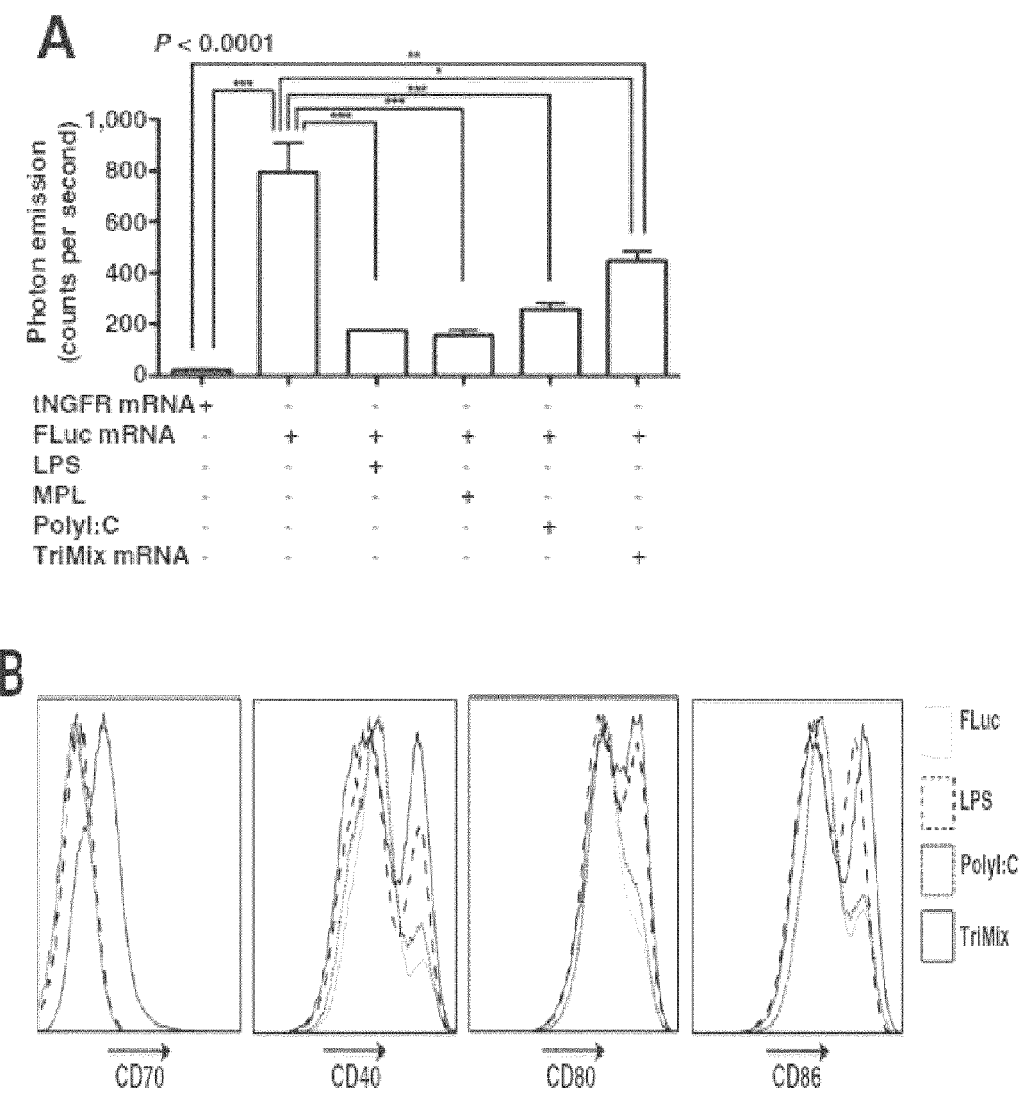
Figure 11:
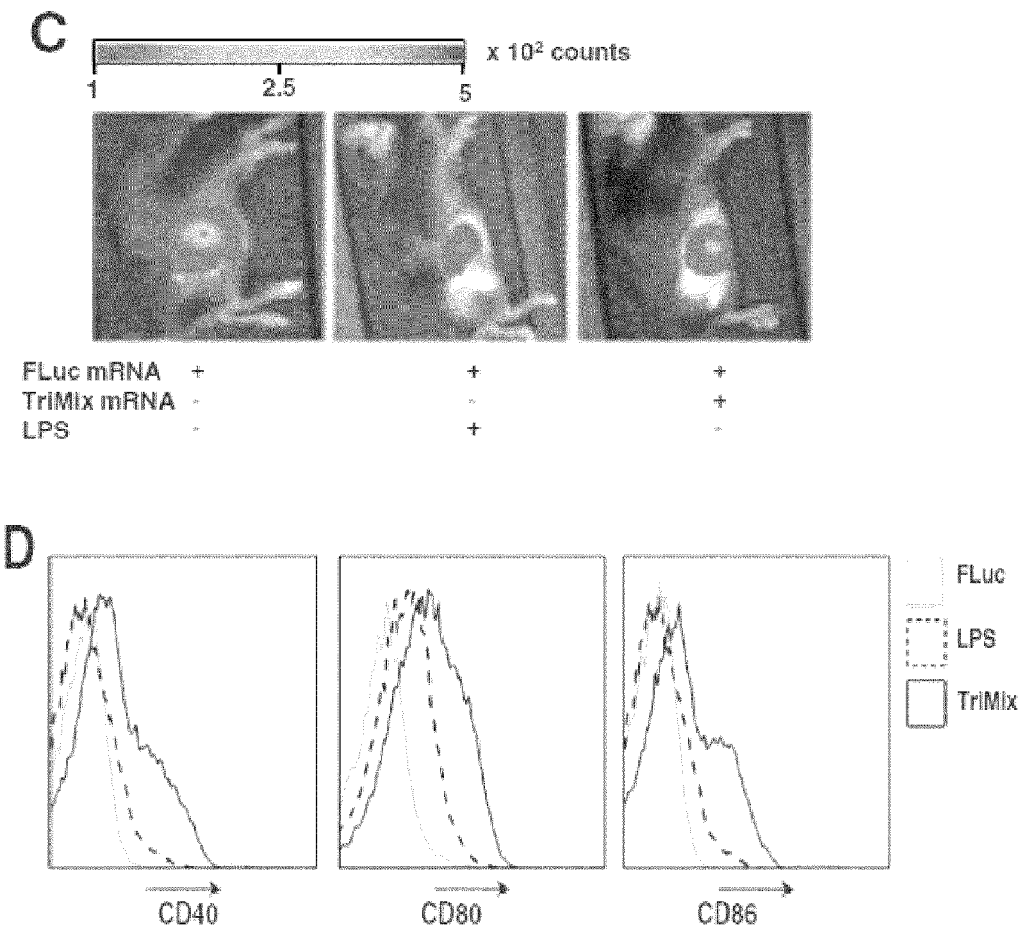
Figure 12:
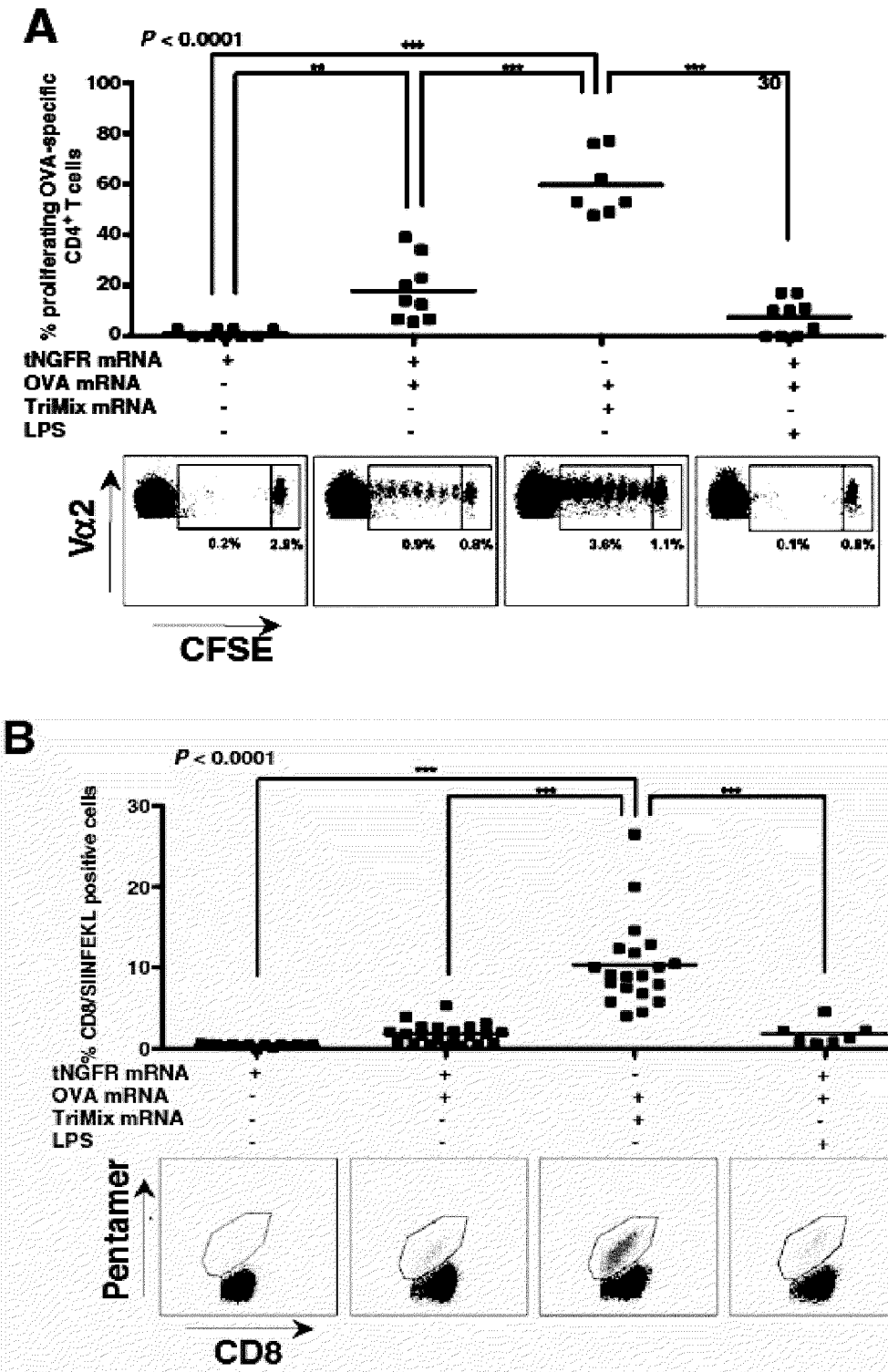
Figure 12:
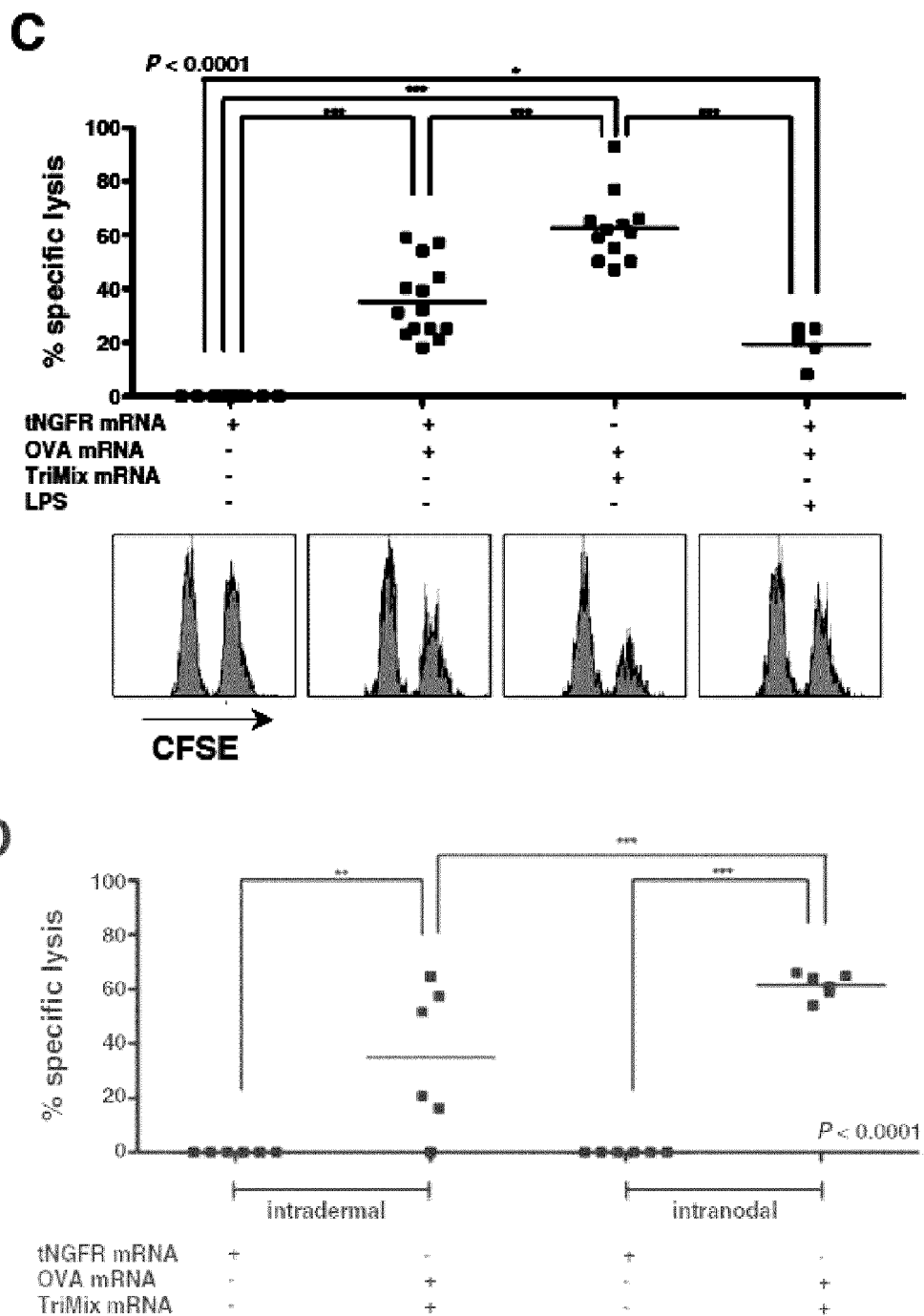

To evaluate the effect of TriMix and classical maturation stimuli on the engulfment of mRNA and the induction of an immune stimulatory environment, the inventors first passively pulsed DCs in vitro with FLuc mRNA and these maturation stimuli, showing a reduction in FLuc expression after pulsing of DCs with FLuc mRNA in the presence of LPS, MPL, or polyI:C. This reduction in protein expression was less pronounced when TriMix was codelivered (FIG. 11A). In addition, DCs pulsed with TriMix mRNA showed a higher expression of CD40, CD70, CD80, and CD86 than the DCs pulsed with MPL (data not shown), LPS, or polyI:C (FIG. 11B). Next, the uptake of FLuc mRNA was evaluated when delivered as such or together with LPS or TriMix in vivo. It was shown that codelivery of TriMix had a lesser impact on the uptake of mRNA than its codelivery with LPS (FIG. 11C). To increase the number of DCs that can be recovered from the injected lymph node for analysis, the mice were pretreated with a hydrodynamic injection of a plasmid encoding Flt3 ligand. In analogy with the data described by Kreiter and colleagues (Kreiter S. et al., 2011, Cancer Res. 71:6132-42), FLuc mRNA injected into these mice resulted in increased luminescence reflecting the specific uptake by the DCs (data not shown). Flow cytometry showed that DCs (CD11c$^\pm$) from lymph nodes coinjected with TriMix displayed the highest expression of CD40, CD80, and CD86 than DCs isolated from lymph nodes injected with FLuc mRNA alone or combined with LPS (FIG. 11D). These findings prompted the inventors to analyze, whether codelivery of TriMix promotes a T-cell-attracting and activating environment, by profiling the expression levels of maturation associated markers by quantitative RT-PCR. The inventors observed upregulation of several markers in lymph nodes injected with FLuc and tNGFR mRNA when compared with lymph nodes injected with 0.8 RL. Importantly, the upregulation of the following markers: MHC II, IL-6, IL-15, IFN-g, MCP-1, IP-10, granzyme B, SOCS1, and STAT1 was at least 2-fold higher when TriMix was codelivered (cf. Table 4).

TABLE 4

Intranodal delivery of TriMix mRNA generates an immunostimulatory environment.

| | Antigen mRNA | TriMix mRNA |
|---|---|---|
| Antigen-presenting molecules | | |
| MHC II | 6.2 ± 2.3 | 27.9 ± 6.5 |
| Proinflammatory cytokines | | |
| IL-6 | 3.7 ± 1.3 | 9.0 ± 3.0 |
| IL-15 | 5.9 ± 0.8 | 16.1 ± 1.5 |
| IFN-γ | 2.3 ± 0.1 | 5.1 ± 0.1 |
| T-cell-attracting molecules | | |
| MCP-1 | 1.9 ± 0.2 | 6.1 ± 1.1 |
| IP-10 | 10.3 ± 2.3 | 35.9 ± 5.1 |
| Signaling molecules | | |
| SOCS1 | 2.5 ± 0.6 | 7.1 ± 1.9 |
| STAT1 | 2.8 ± 0.7 | 4.3 ± 0.1 |
| Others | | |
| Granzyme B | 9.2 ± 1.7 | 24.4 ± 1.8 |

NOTE:
Mice received an intranodal injection of 0.8 RL, antigen mRNA combined with tNGFR mRNA, or with TriMix. Lymph nodes were removed 8 hours later, RNA extracted, cDNA synthesized, and quantitative RT-PCR carried out. It summarizes the molecules of which the upregulation was at least 2-fold higher when TriMix was coadministered when compared with antigen mRNA alone. The data show the relative upregulation compared with injection with 0.8 RL alone. The results are shown as mean SEM of 3 experiments.

11c. Intranodal delivery of TriMix but not LPS together with OVA mRNA results in expansion of OVA-specific CD4$^\pm$ and CD8$^\pm$ T cells with potent effector function Activation of CD4$^\pm$ T cells is critical for the induction of long-lasting antitumor immunity (Beva et al., 2004, Nat. Rev. Immunol. 4:595-602). Therefore, the inventors evaluated the expansion of OVA-specific CD4$^\pm$ T cells upon intranodal delivery of tNGFR mRNA, OVA mRNA, or combined with TriMix or LPS. Proliferation of CFSE-labeled CD4$^\pm$ OT-II cells was evaluated by flow cytometry, showing enhanced proliferation of OT-II cells in mice receiving OVA and TriMix mRNA. Of note, transferred T cells hardly proliferated when LPS was coinjected with OVA mRNA (FIG. 12A). Similar results were obtained with CD8$^\pm$ OT-I cells (data not shown). To further evaluate the expansion and function of OVA-specific CD8$^\pm$ T cells, mice were immunized 1 day after adoptive transfer of CD8$^\pm$ OT-I cells. Five days postimmunization, we carried out an H2-kb/SIINFEKL pentamer staining or an in vivo cytotoxicity assay. Both assays showed the enhanced stimulation of OVA-specific CD8$^\pm$ T cells when mice were immunized with OVA mRNA and TriMix when compared with mice immunized with OVAmRNA alone or combined with LPS (FIGS. 12B and 12C). Using the model antigen OVA, the inventors finally compared intradermal delivery of OVA and TriMix mRNA in mice pretreated with GM-CSF to its intranodal delivery. Using the in vivo cytotoxicity assay we showed that the lysis of target cells was the highest when the mRNA was delivered intranodally (FIG. 12D), although intradermal delivery also resulted in good lysis results.

Figure 13:
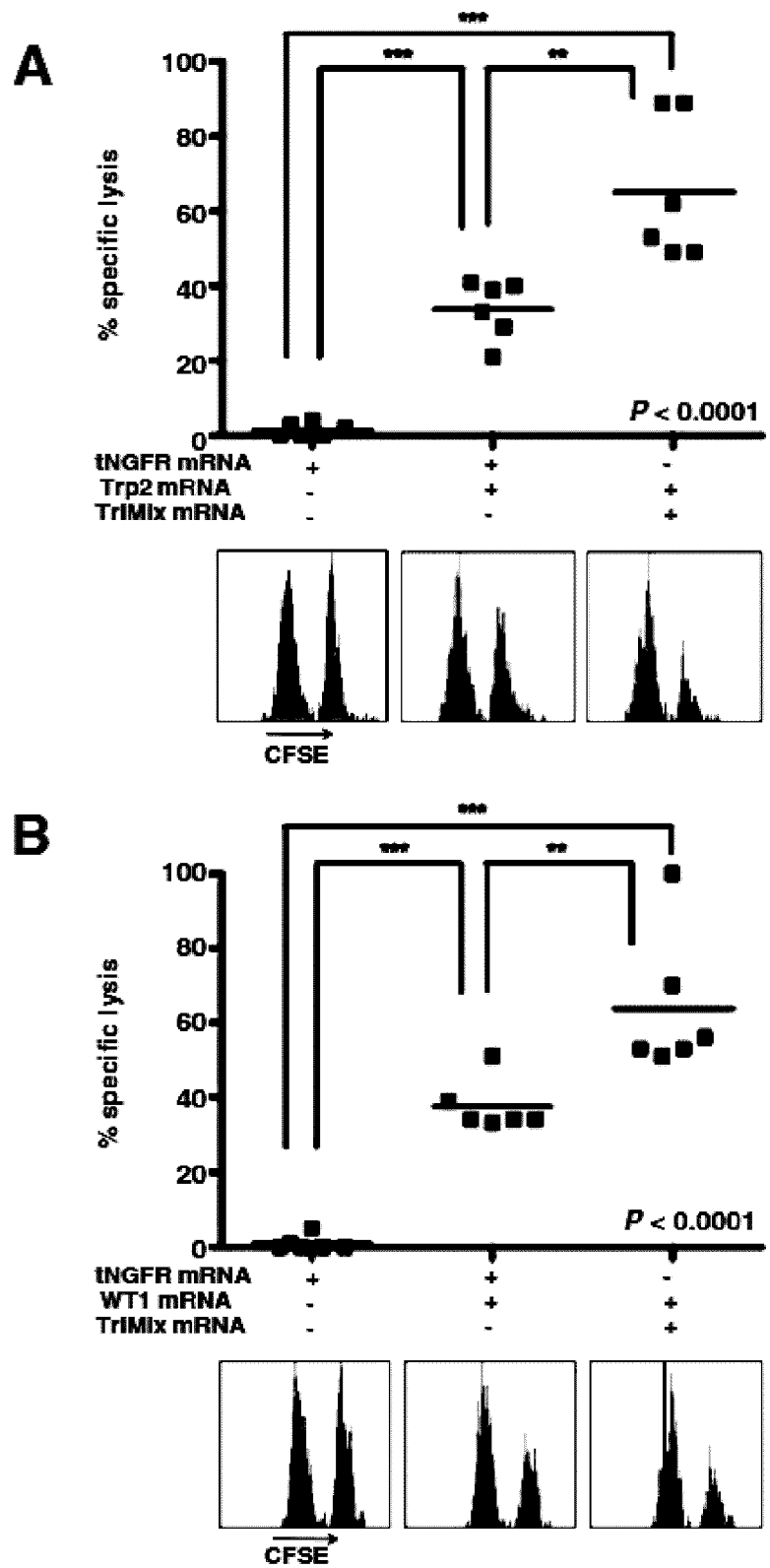
FIG. 13. Inclusion of TriMix in the mRNA vaccine enhances the induction of TAA-specific CTLs. An in vivo cytotoxicity assay was conducted to evaluate the induction of CTLs in mice immunized intranodally with TAA mRNA alone or combined with TriMix. The graphs depict the specific lysis of target cells upon immunization against (A) Trp2 (n=2), (B) WT1 (n=3), and (C) tyrosinase (n=2).
Figure 13:
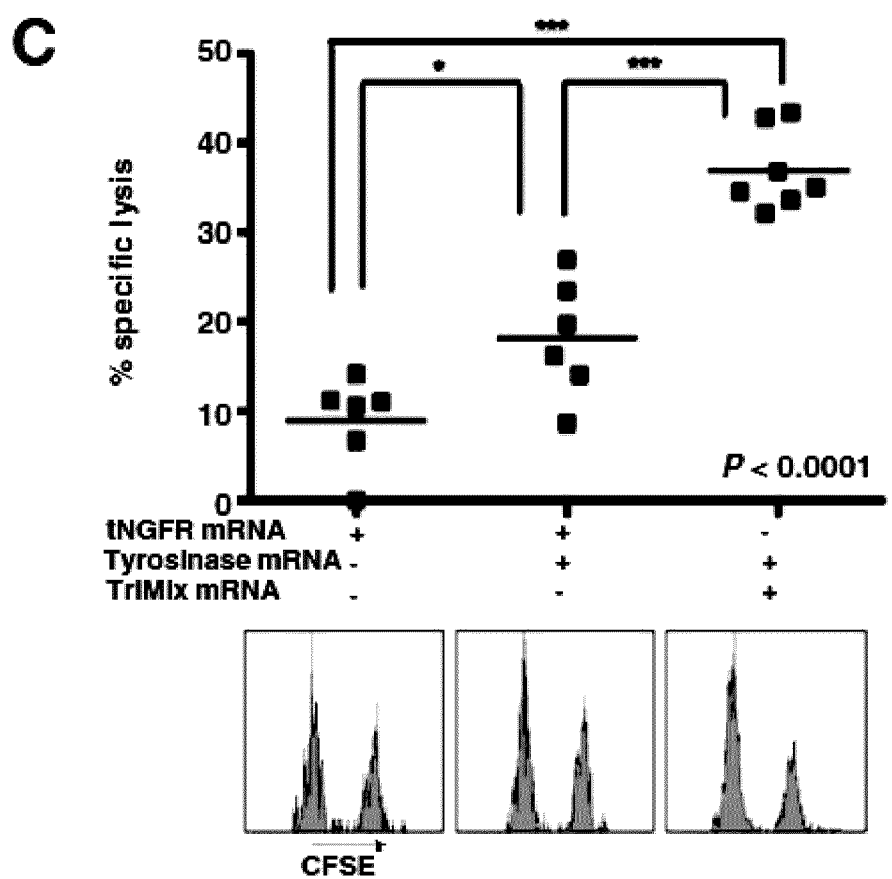

11d. Inclusion of TriMix in the mRNA-Based antitumor vaccine enhances the induction of TAA-Specific cytotoxic T cells Next, it was assessed whether the results obtained with the antigen OVA (ovalbumin) are representative for other TAAs. Mice were immunized with Trp2, WT1, or tyrosinase mRNA alone or combined with TriMix. The in vivo cytotoxicity assay showed enhanced lysis of target cells when TriMix was included in the immunization regimen (FIG. 13A-C).

Figure 14:
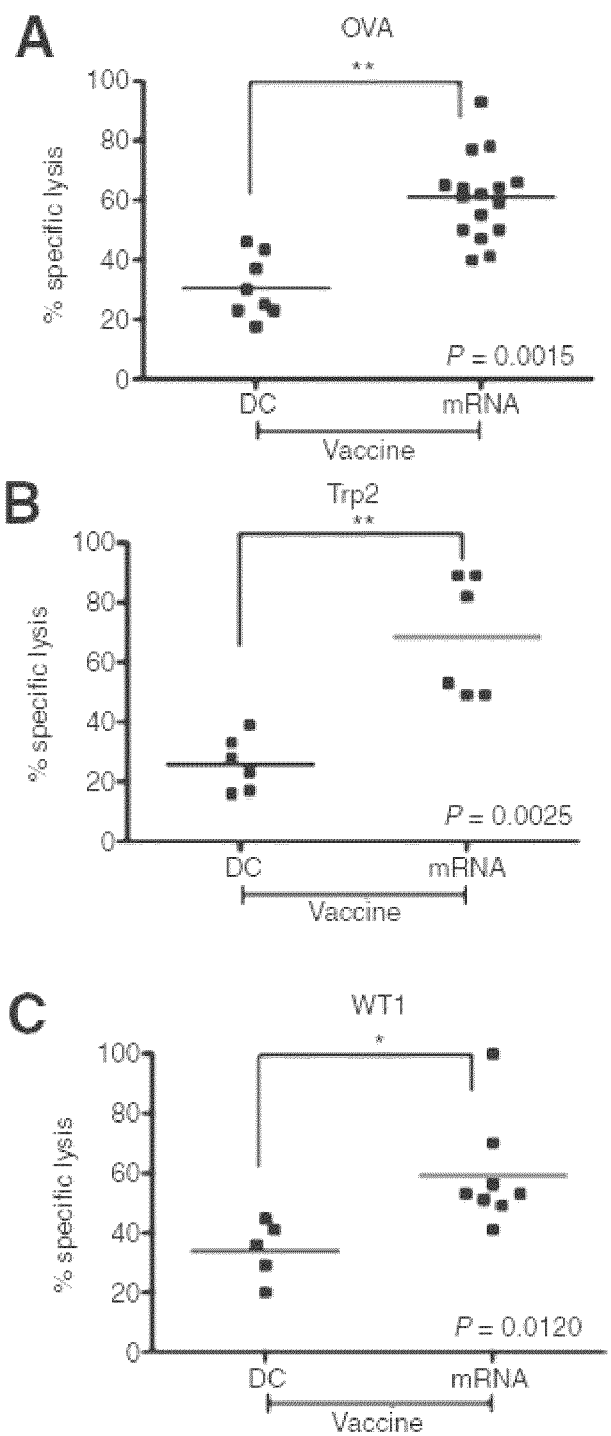
FIG. 14. In situ immunization with antigen mRNA and TriMix is as efficient in stimulation of CTLs and in therapy as immunization with ex vivo-modified DCs. A-C, C57BL/6 mice were immunized intravenously with antigen and TriMix mRNA-modified DCs or intranodally with antigen and Tri-Mix mRNA. The in vivo cytotoxicity assay was conducted 5 days later. The graphs show the specific lysis of target cells in peripheral blood upon immunization against (A) OVA (n=2), (B) Trp2 (n=2), or (C) WT1 (n=2). D-H, mice bearing palpable tumors (10 mice per group) were immunized by intravenous injection of antigen and TriMix mRNA—electroporated DCs or by intranodal injection with antigen and TriMix mRNA. The graphs show the tumor growth (left) and survival (right) in the MO4 model after immunization with the antigen OVA (D) or the TAA Trp2 (E), in the EG7-OVA model after immunization with OVA (F), in the C1498-WT1 model after immunization with the TAA WT1 (G) all in C57BL/6 mice, and in the P815 model after immunization with the TAA P1A (H) in DBA-2 mice.
Figure 14:
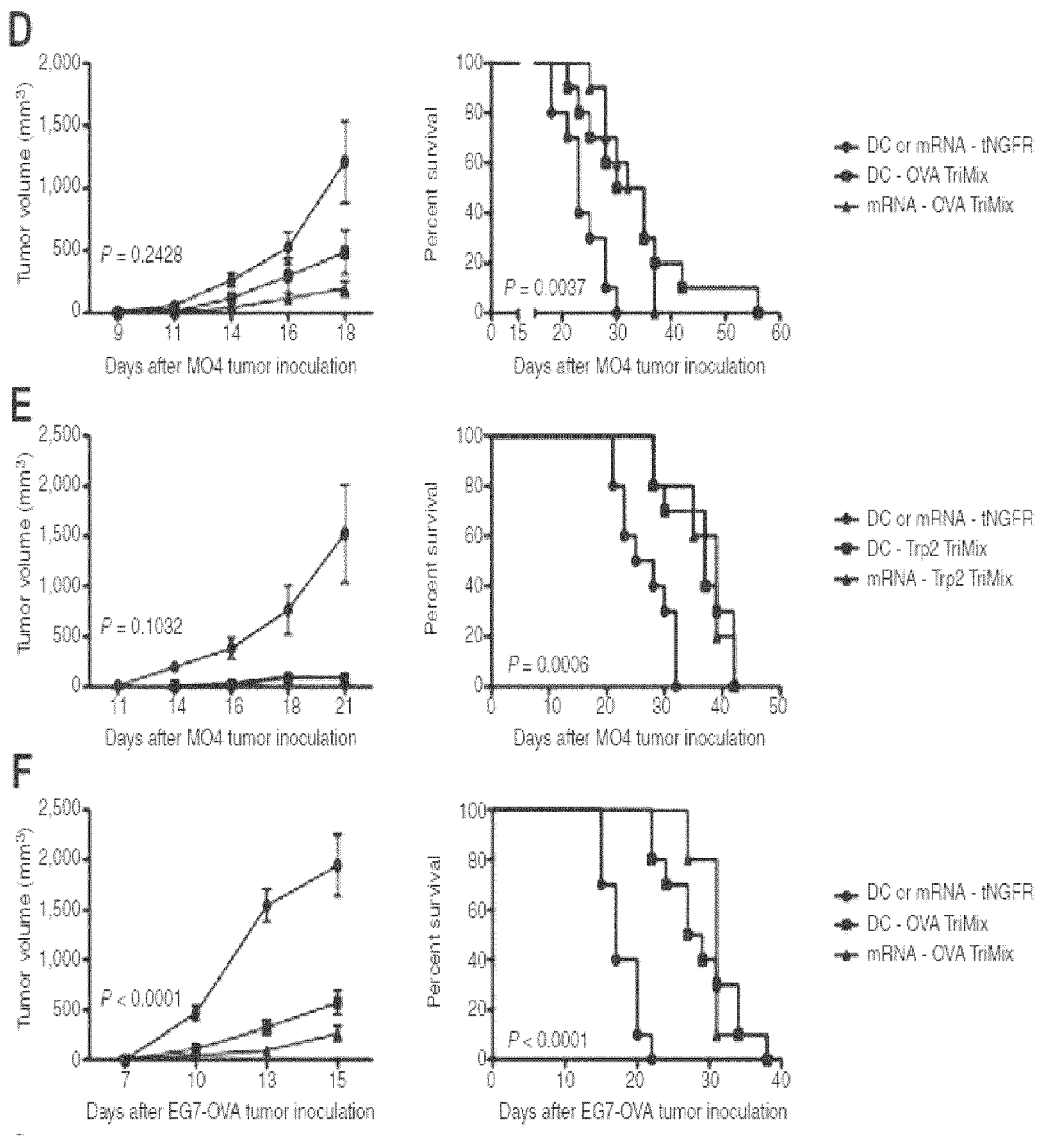
Figure 14:
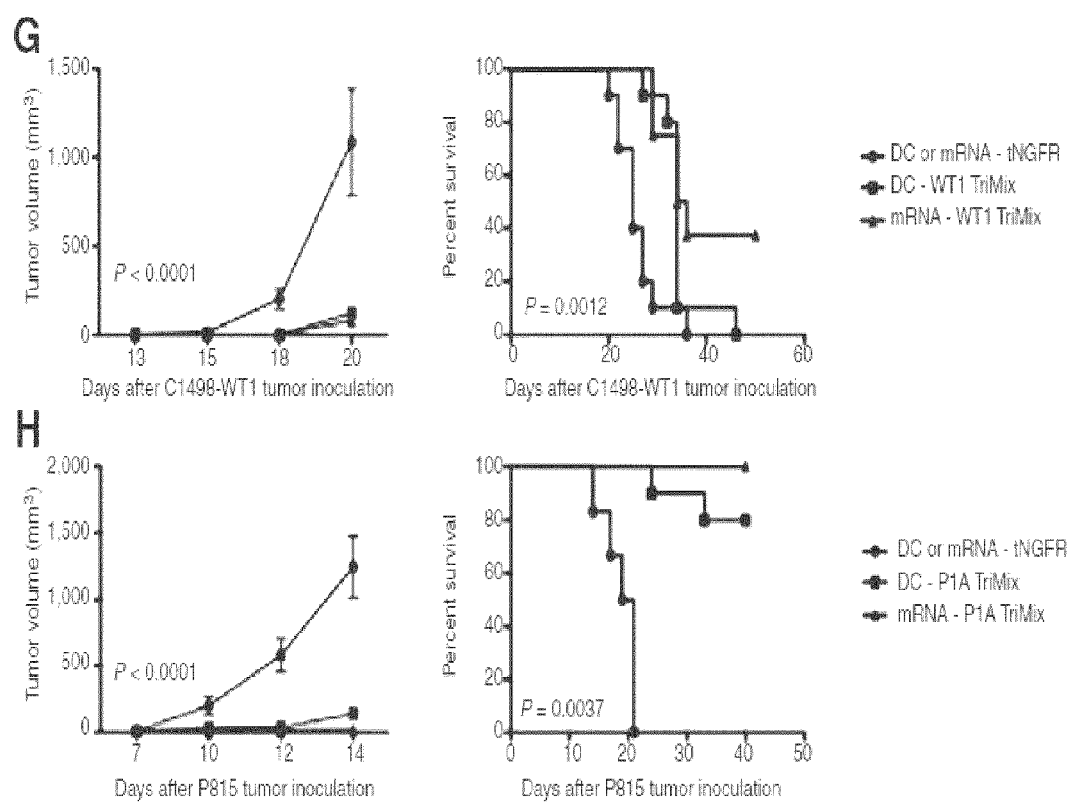

11e. Immunization with antigen mRNA and TriMix is as efficient in stimulating cytotoxic T cells and in therapy as immunization with ex vivo-modified DCs Next, the efficacy of DC- to mRNA-based immunization was compared, evaluating the induction of antigen-specific CTLs in vivo. Immunization with antigen and TriMix mRNA was proven to be as efficient as immunization with antigen and TriMix mRNA-electroporated DCs for the antigen OVA and the TAAs, Trp2, and WT1 (FIG. 14A-C).

In a next step, the therapeutic efficacy of such vaccines was evaluated. First, mice bearing MO4 tumors were treated with antigen and TriMix mRNA-modified DCs or antigen and TriMix mRNA as such. Similar results were obtained upon immunization with OVA (FIG. 6D) or Trp2 (FIG. 14E) as an antigen. Mice treated with tNGFR-electroporated DCs or tNGFR mRNA as such served as controls. Mice from control groups showed rapid tumor growth, whereas mice immunized with a single intravenous injection of DCs electroporated with antigen and TriMix mRNA or an intranodal injection of antigen and TriMix mRNA showed a reduced tumor growth, hence, prolonged survival. These data were extended to the mouse T-cell lymphoma EG7-OVA, the myeloid leukaemia C1498-WT1 in C57BL/6 mice, and the mastocytoma P815 in DBA-2 mice using OVA, WT1, and P1A as the antigen applied for immunization, respectively (FIG. 14F-H).

This showed that both using vaccines comprising in vitro stimulated DC's as well as using the in vivo DC stimulation strategy resulted in effective vaccination.

Example 12

Clinical Trials with DCs Manipulated In Vitro and Re-Introduced Intradermally and/or Intravenously Immature DCs were generated by culturing monocytes in the presence of 1% autologous plasma, 1000 U/mL GM-CSF and 500 U/mL interleukin (IL)-4. Following leukapheresis, monocytes were enriched by plastic adherence. On day 6, DCs were harvested and co-electroporated with TriMix-mRNA (CD40L, CD70, and caTLR4 encoding mRNA) and mRNA encoding 1 of 4 MAAs (MAGE-A3, MAGE-C2, tyrosinase, or gp100) linked to an HLA class II targeting signal. After electroporation, the four different TriMixDC-MEL cellular constituents (i.e., DCs expressing one of the four antigens) were mixed at equal ratios and cryopreserved. DCs were thawed 2-3 hours before injection. An in-process, as well as quality control (QC) of the final product, was performed.

Patients were allocated to four sequential cohorts receiving increasing doses of TriMixDC-MEL intravenously and/or intradermally. The first cohort received $20\times10^6$ DCs intradermally (id) and $4\times10^6$ DCs intravenously (iv); the second cohort $12\times10^6$ DCs id and $12\times10^6$ DCs iv, the third cohort $4\times10^6$ DCs id and $20\times10^6$ DCs iv and the fourth cohort received $24\times10^6$ DCs iv-only. The first four TriMixDC-MEL administrations were administered at a biweekly interval with a $5^{th}$ administration scheduled 8 weeks after the $4^{th}$ administration. DCs (suspended in 15 ml of physiologic saline solution) were administered iv during a 15 minutes infusion by constant flow rate in a peripheral vein, and/or DCs (suspended in 250 µl phosphate buffered saline containing 1% human serum albumin) were injected intradermally at 2 different anatomical sites (axilla and/or inguinal region). Each patient was closely monitored for at least 1 hour after the end of the iv-administration. Adverse events (AEs) were monitored continuously and graded using the National Cancer Institute Common Toxicity Criteria, version 4.0.

Secondary end points included immunogenicity of the TriMixDC-MEL therapy, tumor response (according to the Response Evaluation Criteria in Solid Tumors [RECIST] v1.1), time-to-progression, and overall survival (assessed by Kaplan-Meier survival probability estimates using IBM SPSS software v19.0).

Patient baseline characteristics and disposition

Between December 2009 and February 2011, 15 eligible patients with advanced pretreated melanoma were recruited. Median age was 51 years (range 41-78). Baseline serum lactate dehydrogenase (LDH), C-reactive protein and lymphocyte counts were normal in the majority of patients. Most (10/15) patients had a PS of 0-1 and AJCC stage 1V-M1c disease (8/15, including two patients with previously irradiated brain metastases). Thirteen patients had failed prior therapy with DTIC or TMZ chemotherapy, and 3 patients had failed treatment with a CTLA-4 blocking mAb. Only one patient was previously treated with a selective BRAF V600-inhibitor.

Patients were enrolled onto 4 cohorts, receiving increasing numbers of DCs by the iv-route and decreasing numbers id. Respectively, two and three patients were enrolled onto the first and second cohort. None of them experienced unexpected treatment-related side effects. Among the first three patients enrolled in the third cohort, one patient experienced an unexpected treatment-related adverse event (chills). Therefore this cohort was expanded with three additional patients. Recruitment to the fourth cohort ended when none of the first four patients experienced treatment-related limiting toxicity.

Eight patients received all five planned TriMixDC-MEL administrations. Five patients only received the first four biweekly administrations. Two patients could not receive more than three administrations because of clinical deterioration due to progressive disease. No relationship was observed between the number of administrations and the treatment cohort.

Treatment-related adverse events

TriMixDC-MEL was well tolerated and no severe toxicity (adverse events of grade ≥3 according to the Common Terminology Criteria for Adverse Events) was encountered. All patients experienced grade 2 local skin reactions (irritation, erythema and swelling) at the intradermal injection sites. Post-infusion grade 2 chills were observed in 3 out of the 15 patients. Chills typically started about 15 minutes after the end of the iv-infusion of TriMixDC-MEL, and resolved spontaneously within 30 minutes. In addition, grade 2 flu-like symptoms and fever (38-39° C.) that persisted for 2-3 days after the DC-injection were reported by respectively 8 and 3 patients.

Anti-tumor response and survival

The best objective response by RECIST consisted of a complete response in two patients, a partial response in two patients (for a best objective response rate of 26.6%), and a stable disease in six additional patients (for a disease control rate of 66.6%). Tumor regression was evident in all responding patients at the first evaluation 8 weeks after the first TriMixDC-MEL administration. Continued further regression of FDG-avid metastases was observed up to the last follow-up in both patients with a partial response. All four objective tumor responses were confirmed and are ongoing after a follow-up of respectively 13.2+, 17.8+, 22.6+ and 23.1+ months. Two patients with a stable disease had a clinically meaningful progression-free survival of more than six months (respectively 10 and 18.3+ months). After a median follow-up of 18.2 months (range 11.9-23.7), 8 patients have died. The median PFS and OS are respectively 5.1 months (95% Cl 0-10.4) and 14.4 months.

Assessment of T-cell responses

A DTH skin biopsy was obtained from 13 patients one week after the 4$^{th}$ DC administration. In 10 patients sufficient T-cells were obtained for assessment of the antigen specificity of the skin infiltrating T-cells (SKILs). In 4 (40%) patients CD8$^+$ T-cells were found with specificity for the melanoma associated antigens (MAA) presented by TriMixDC-MEL (MAA-DC). In 2 additional patients, with insufficient SKILs for direct monitoring, MAA specific CD8$^+$ SKILs could be detected after in vitro restimulation. Thus, in total 60% of the patients had treatment specific CD8$^+$ SKILs. A T-cell repertoire with specificity for more than one MAA was found in 4 patients and all four MAA's were recognized by the SKILs from 2 patients (Table 3). MAA-DC specific CD4+ T-cells could be detected in 5 out of 12 (42%) patients.

Example 13

Figure 15:
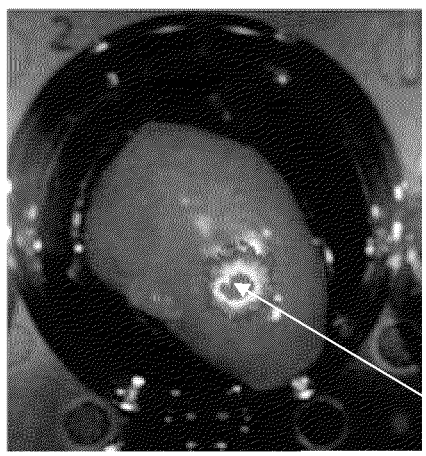
FIG. 15. Intranodal injection of the FLuc mRNA leads to FLuc protein expression. A) A cervical lymph node of a pig was transcutaneously injected with FLuc mRNA dissolved in Ringer lactate. Four hours after injection, the injected lymph node was resected and bioluminescence imaging was performed to obtain bioluminescent pseudo-color images, in which high luminescence [a measure for the amount of FLuc+ cells] is shown by the arrow.
Figure 15:
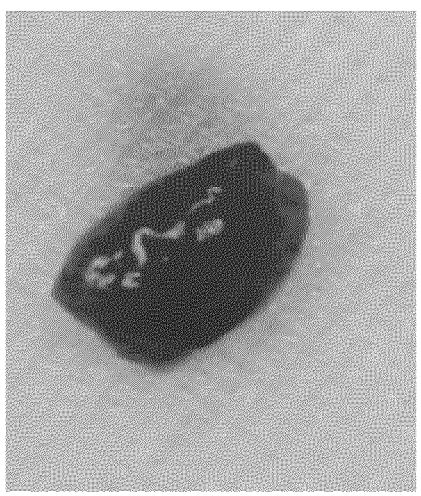
Figure 15:
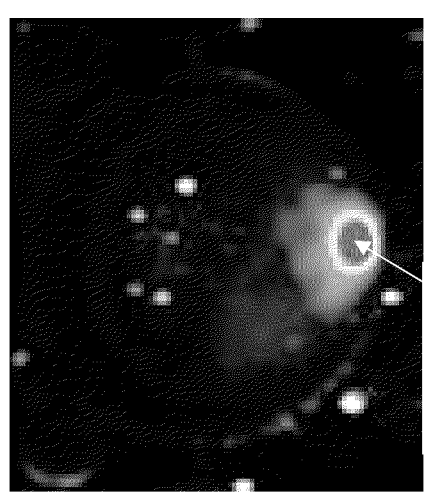

Intranodal Injection of FLuc mRNA Leads to Protein Expression; and Intranodal Injection of TriMix mRNA and Antigen-Encoding mRNA Stimulates a Specific Immune Response in Subjects A cervical lymph node of a pig was transcutaneously injected with FLuc mRNA dissolved in Ringer lactate. Four hours after injection, the injected lymph node was resected and bioluminescence imaging was performed to obtain bioluminescent pseudo-color images, in which high luminescence [a measure for the amount of FLuc+ cells] is shown by the arrow (FIG. 15A).

Subsequently, a human lymph node of a non-heartbeating organ donor was injected with 50 µg FLuc mRNA dissolved in Ringer Lactate. After 4 h of incubation in PBS, in vivo bioluminescence imaging was performed to obtain bioluminescent pseudo-color images, in which high luminescence [a measure for the amount of FLuc+ cells] is shown by the arrow (FIG. 15B). The LUT [Look up Table] displays the 'min' and 'max' to correlate the luminescence to an absolute amount of counts [relative light units].

Next, a healthy, CMV-protected volunteer was injected on the lower back with TriMix mRNA or TriMix mRNA together with the pp 65 antigen of CMV. 72 h later, a DTH reaction is visible on both injection places (redness and induration), but more pronounced where the CMV antigen is present. A skin biopsy was taken from the injection place, and cultured for 2.5 weeks in IL2 containing medium. Then, T cells were screened for CMV-specificity (FIG. 16). A CMV-specific CD4+ T cell response was observed in the cells derived from the biopsy after injection of TriMix+CMV mRNA, indicating that even through intradermal injection of the TriMix mRNA cocktail in combination with a target antigen, is capable of recruiting antigen-specific T-cells to the site of injection.

Example 14

Intratumoral Injection of TriMix mRNA (and Antigens) Elicits a Specific Immune Response in Subjects Transgenic CD11c-DTR mice (transgenic mouse model was generated in which the diphtheria toxin receptor is expressed under the CD11c promoter, cf. Hochweller et al., 2008, Eur J Immunol. October; 38(10):2776-83), which were pre-treated with PBS or DT, received an intratumoral injection with FLuc mRNA. In vivo bioluminescence imaging was performed 4 hours after administration of FLuc mRNA. Subsequently single cell suspensions were prepared from the tumors and analyzed by flow cytometry for the presence of CD11c+ cells. Kinetics of bioluminescence was performed until 11 days after intratumoral injection. The experiment shows that tumor-resident CD11c+ cells engulf intratumorally administered mRNA. The tumor environment of mice treated with TriMix mRNA also contains a higher number of CD11c+ cells, which have a similar maturation status as CD11c+ cells from tNGFR treated mice. In contrast, the number of CD11c+ cells in tumor draining lymph nodes does not differ between TriMix or tNGFR treated mice, whereas the maturation status of the former is increased. The tumor environment of mice treated with TriMix contains a lower number of CD11b+ cells, in particular CD11b+ Ly6G+ cells. These cells are immunosuppressive MDSC (myeloid derived suppressor cells).

These data prove two important things (cf. FIGS. 18-20). First the mRNA that has been injected intratumorally is indeed engulfed by resident APCs. When injected with TriMix mRNA, it is expected that—in analogy to lymph node resident DCs—these DCs would mature and start presenting tumor specific antigens. Here, the antigens would either originate from the tumor environment (cf. Example 16), or be co-injected. These DCs will then be able to elicit a specific immune response locally in the tumor, or in the tumor draining lymph node (as our data show that there are more mature DCs present in the tumor draining lymph node after intratumoral TriMix mRNA injection). Next, it shows that intratumoral TriMix mRNA injection leads to a change in the tumor environment. Indeed, less MDSC are present in the tumor environment. As a result, the immunosuppressive tumor-environment is altered by TriMix injection, and an environment is created that is more prone to the induction of tumor specific immune responses.

It was further shown that the intratumoral delivery of TriMix mRNA and antigen results in the induction of antigen-specific immune responses. CFSE-labeled CD8± OT-I cells (transgenic CD8+ cells specific for OVA (ovalbumin) antigen) were adoptively transferred 1 day before immunization of mice with tNGFR mRNA, OVA, TriMix mRNA alone, or a combination. Five days postimmunization, stimulation of T cells within the tumor was analyzed. Proliferation of CD8± OT-I cells was analyzed by flow cytometry. FIG. 17 clearly shows that the intratumoral injection of TriMix mRNA and OVA antigen resulted in a specific immuneresponse towards the OVA antigen. The table below shows that upon TriMix mRNA delivery in the tumor, a clear upregulation of DC maturation- and activation markers such as CCR5, CCR7, CD40, CD86 and increased secretion of cytokines such as IL-6, IL-12 and TNF-□ could be documented. Moreover, the expression of negative regulators such as IL-10 and STAT3 were reduced.

|  | % upregulated TriMix vs tNGFR mRNA | % downregulated TriMix vs tNGFR mRNA |
|---|---|---|
| Activation markers |  |  |
| CD80 | 12 |  |
| CD86 | 12 |  |
| Pro-inflammatory cytokines |  |  |
| IL-6 | 21 |  |
| IL-12 | 52 |  |
| TNF-a | 36 |  |
| Others |  |  |
| CCR5 | 31 |  |
| CCR7 | 12 |  |
| IL-10 |  | 51 |
| STAT3 |  | 9 |

Example 15

TriMix-DCs are Able to Counteract Treg Functions and to Reprogram Treg to Th1 Cells Under Certain Circumstances Regulatory T cells (Treg) counteract anticancer immune responses through a number of mechanisms, limiting DC-based anticancer immunotherapy. Here, the inventors investigated the influence of various DC activation stimuli on the Treg functionality. DCs activated by electroporation with mRNA encoding constitutively active TLR4 (caTLR4), CD40L and CD70 (TriMix-DCs) were compared with DCs matured in the presence of a cocktail of inflammatory cytokines (CC-DCs) for their ability to counteract Treg on different levels.

Immature DCs (iDCs) were thawed and electroporated with mRNA encoding a constitutively active form of TLR4 (caTLR4) and CD40L (further referred to as DiMix-DCs), or a combination of DiMix and CD70 encoding mRNA (further referred to as TriMix-DCs) The mock electroporated DCs were either kept immature or were matured for 24 hours using a cocktail of inflammatory cytokines (CC-DCs) containing 100 IU/ml IL-1β (home made), 1000 IU/ml IL-6 (Gentaur), 100 IU/ml TNF-α (Bachem) and 1 µg/ml PGE2 (Pfizer) as described by Jonuleit et al. 1997 (Eur J Immunol 27:3135-3142).

Lymphocytes were purified from fraction 2 and 3 of the elutriation product and were used as a source of T cells. After thawing, CD8+ Teff were sorted on LS columns using MACS CD8+ magnetic beads (Miltenyi Biotec). Treg were sorted as previously described (Ahmadzadeh and Rosenberg, 2006, Blood 107:2409-2414). For each experiment, Treg purity was verified by flow cytometry. For some experiments, Treg were pre-enriched by MACS separation as described above and further sorted by cell sorting on a FACS Aria III (BD Biosciences) to isolate CD4+CD25highCD127low T cells with high purity (>97%).

Flow cytometric analysis was performed using a FACS Canto flow cytometer or an LSR-Fortessa (both from BD Biosciences). FACS Diva (BD Biosciences) and FlowJo (Tree Star Inc.) software was used for acquisition and analysis of flow cytometry data, respectively. DC maturation was assessed using the following antibodies: allophycocyanin (APC)-conjugated anti-CD11c and anti-CD40 antibodies, fluorescein isothiocyanate (FITC)-conjugated anti-CD80 and anti-CD86 antibodies, and phycoerythrin (PE)-conjugated anti-CD83, and anti-CD70 antibodies (all from BD Pharmingen). The T-cell phenotype was assessed using APC-conjugated anti-CD3, PE-conjugated anti-CD8 (BD Pharmingen) and PE-cyanine 7 (Cy7)-conjugated anti-CD4 antibodies (eBioscience). Treg were specifically stained with a combination of PE-Cy7-conjugated anti-CD4 antibodies, PE-conjugated anti-CD25 antibodies (Miltenyi Biotec) and FITC-conjugated anti-CD127 antibodies (eBioscience). Intranuclear Foxp3 expression was assessed using an AFC-labeled anti-Foxp3 antibody (clone PCH101, eBioscience) in combination with a Foxp3 staining buffer set (eBioscience).

To assess Treg induction from naive CD4+ T cells, CD4+ CD25− T cells were sorted from the elutriated lymphocyte fraction using the CD4 Multisort Kit (Miltenyi Biotec). The CD4+ fraction was labeled with anti-CD25 microbeads and negative selection was performed using LD MACS columns (Miltenyi Biotec). CD4+CD25− T cells were cocultured with differentially matured autologous DCs at a DC:T cell ratio of 1:10, whereby $10^4$ DCs were cultured with $10^5$ T cells in IMDM (Gibco), supplemented with 100 U/ml penicillin, 100 µg/ml streptomycin, 2 mM L-glutamine, amino acids (Cambrex), 1% AB serum and 25 IU/ml IL-2 (Chiron), referred to as complete T-cell medium. Induction of Treg was assessed by flow cytometry after one week, with Treg being defined as CD4+CD25highCD127-Foxp3high T cells. These experiments were repeated in an allogeneic setting using a similar setup.

To assess the effect of Treg on the proliferation of naive CD8+ T cells, sorted CD8+ T cells were washed and resuspended in PBS (Lonza) at a cell density of 2×106 cells/ml, after which an equal volume of a 0.6 µM solution of carboxy-fluorescein succinimidyl ester (CFSE) (Molecular Probes) was added to achieve a final concentration of 0.3 µM CFSE. Activated DCs were treated as described above and subsequently cocultured with CFSE-labeled CD8+ T cells at a 1:10 ratio in complete T-cell medium. The CD8− fraction was used as a source of CD4+CD25high Treg. Treg were immediately added to the cultures at a CD8+ T cell:Treg ratio of 1:1. For T-cell stimulation, anti-CD3 beads were prepared using tosyl-activated Dynabeads (Invitrogen) and anti-CD3 antibody (clone OKT-3, prepared in house). Beads were used at a bead:CD8+ T cell ratio of 1:1. Cultures consisted of 105 CD8+ T cells in 200 µl complete T-cell medium, using round-bottom 96-well plates (Falcon). After 6 days of coculture, T cells were stained with CD3, CD4 and CD8, and inhibition of CD8+ T-cell proliferation by Treg was measured by flow cytometry.

To measure effector CD8+ T-cell suppression, DCs were cocultured with naive CD8+ T cells in complete T-cell medium for one week after which DCs were depleted using CD11c coated magnetic beads and an LD column. Purified CD8+ T cells were subsequently labeled with CFSE as described above. Treg were purified and cocultured with the preactivated CD8+ T cells at a 1:1 ratio in complete T-cell medium. For T-cell stimulation, anti-CD3/CD28 Dynabeads (Invitrogen) were added at a bead:T-cell ratio of 1:125. Six days later, the effect of Treg inhibition on CD8+ T cell proliferation was assessed by flow cytometry.

To study the interaction between DCs and Treg as well as their subsequent effect on CD8+ T-cell proliferation, differentially matured DCs were cocultured with Treg for 48-72 hours at a 1:1 ratio. Treg were isolated from these cocultures by cell sorting. Sorted Treg were then added to naive, CFSE-labeled CD8+ T cells for six days in complete T-cell medium in the presence of anti-CD3/CD28 Dynabeads at a bead:T-cell ratio of 1:20. After six days, Treg-mediated suppression of CD8+ T-cell proliferation was assessed by flow cytometry. In a second setup, DCs were cocultured with Treg for five days. As a control, DCs were cocultured with naive CD4+CD25− T cells. Intranuclear expression of Foxp3, T-bet and GATA3 was assessed using APC-conjugated anti-Foxp3 antibodies or AlexaFluor647-conjugated anti-T-bet antibodies respectively (both from eBioscience). Supernatants of these cocultures were assessed for TNF-α, IL-5, IL-13, IL-17, IL-2 and IL-10, on a Bio-Plex 200 System Luminex reader using a custom-made 7-plex bead array (BioRad) following the manufacturer's instructions. Secretion of IFN-γ was measured by ELISA (Thermo Scientific).

Results:

It was first demonstrated that there was no difference in the extent of Treg induction from CD4+CD25− T cells for the different DC maturation stimuli.

Secondly, it was shown that TriMix-DCs could partly alleviate Treg inhibition of CD8+ T cells (cf. FIG. 21). Note that the effect using the DiMix DCs, matured with CD40L and caTLR4 only, is far less pronounced.

Thirdly, it was observed that CD8+ T cells that had been precultured with TriMix-DCs, were partially protected against subsequent Treg suppression (cf. FIG. 22). Again, the effect is much more pronounced using the TriMix DCs.

Figure 24A:
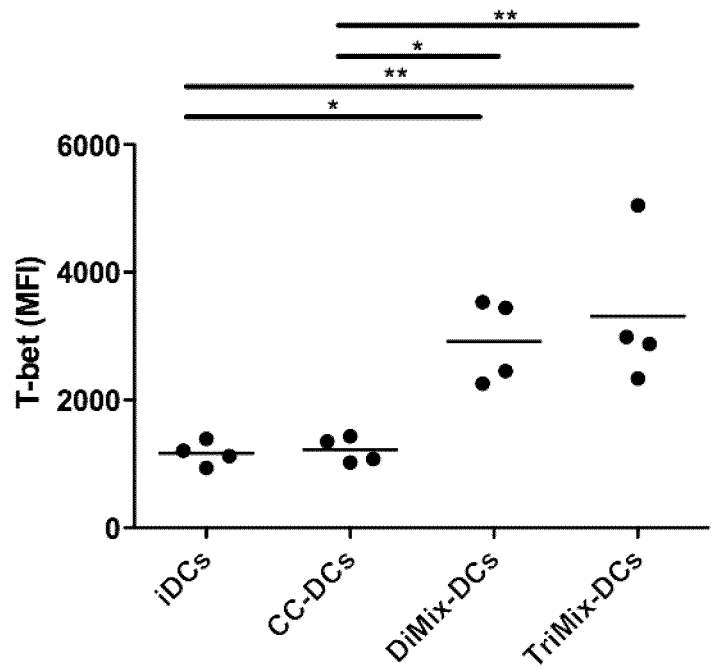
Figure 24B:
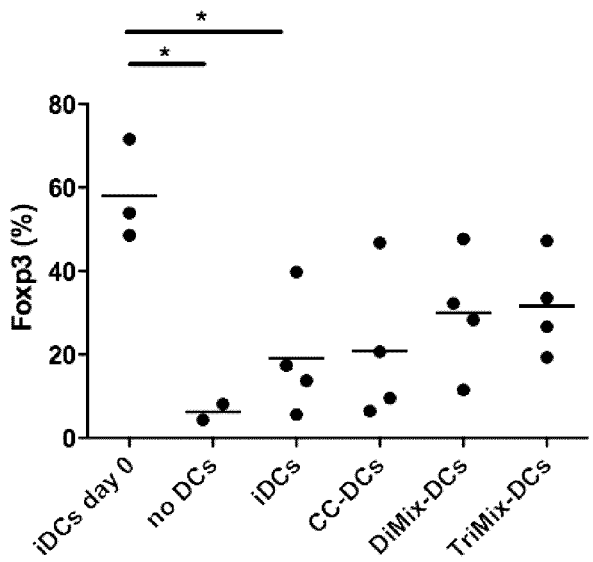
Figure 24C:
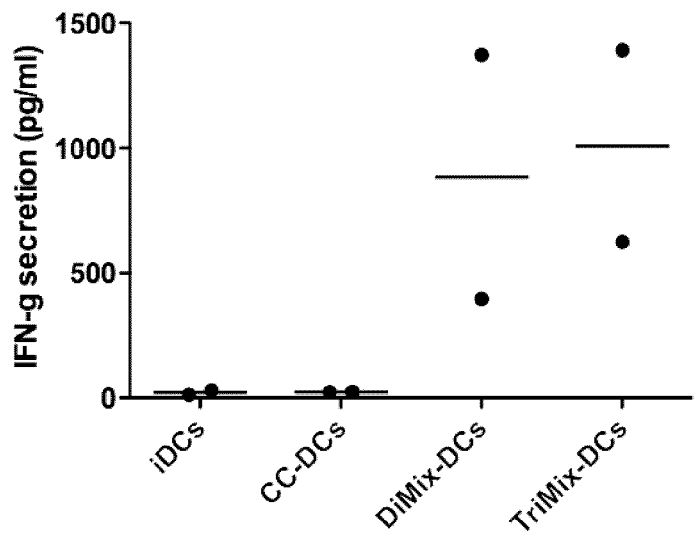
Figure 24D:
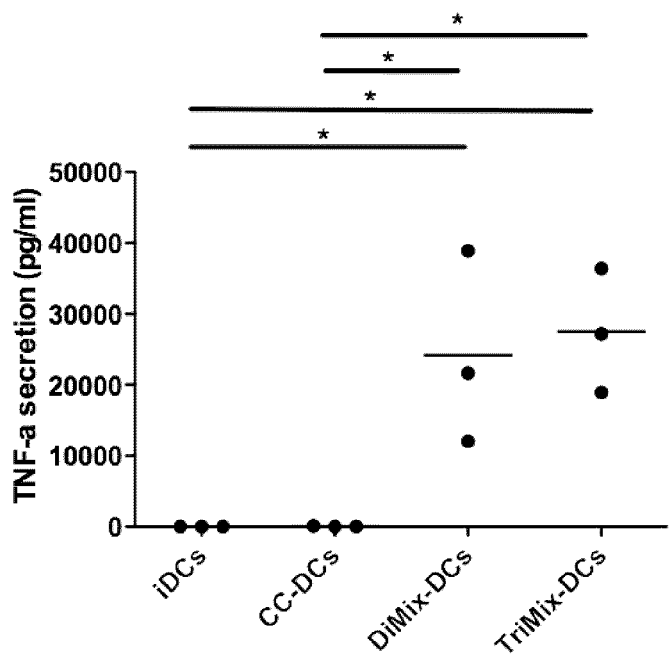

Finally, it was shown that Treg cocultured in the presence of TriMix-DCs partially lost their suppressive capacity. This finding was associated with a decrease in CD27 and CD25 expression on Treg, as well as an increase in expression of T-bet and secretion of IFN-γ, TNF-α and IL-10, suggesting a shift of the Treg phenotype towards a T helper 1 (Th1) phenotype (cf. FIG. 23 for CD27 expression). To confirm this, the differentially matured DCs were cocultured with Treg for five days, after which these Treg were analyzed for expression of Treg markers. Cells were stained for the Th1 transcription factor T-bet. An increase in T-bet expression was observed for Treg incubated with DiMix- and TriMix-DCs but not for the other conditions (FIG. 24A) We also observed a down-regulation of Foxp3 in DiMix and TriMix DCs (FIG. 24B). One of the characteristics of Treg is their low secretion of cytokines compared to Teff. A marked increased IFN-γ and TNF-α secretion by the Treg that were cocultured with either DiMix- or TriMix-DCs was observed (FIG. 24C), pointing towards a reprogramming of Treg towards a Th1 phenotype.

In conclusion, these data suggest that TriMix-DCs are not only able to counteract Treg functions but moreover are able to reprogram Treg to Th1 cells under certain circumstances.

Example 16

Intratumoral Injection of TriMix mRNA without Antigens Changes the Tumor Environment and Elicits a Specific and Systemic Anti-Tumor Immune Response in Subjects Dendritic cells (DC) are potent inducers of immune responses. Many tumors contain appreciable numbers of tumor-infiltrating DCs (TIDC), but the stimulatory capacity of these DCs is often compromised (Vicari, A. P. et al. Semin. Cancer Biol. 2002; 12: 33-42). These TIDC, which can cross-present the tumor antigens, are poorly activated because of a lack of danger signals and blockade of their maturation by tumor-derived cytokines such as vascular endothelial growth factor, leading to failed T-cell priming in tumor-draining lymph nodes (TDLN). TIDC have the potential to be manipulated and may therefore represent a promising target for cancer immunotherapy. Cancer cells harbor many immunogenic mutated peptides and continuously release antigens and apoptotic bodies. This spontaneous release can be enhanced by radiotherapy, immunogenic chemotherapy or different kinds of ablative treatments, like cryo or radiofrequency ablation. These released antigens are acquired by the TIDC. Tumor infiltrating lymphocytes (TIL) generally recognize mutated antigenic epitopes (Robbins, P. F. et al. Nat. Medicine 2013; 19: 747-752). Only a small portion of the T cells present in bulk TIL populations from 34 individuals with melanoma appeared in a recent study to recognize melanocyte differentiation antigens and cancer-germline antigens (Kvistborg, P. et al. OncoImmunology 2012; 1: 409-418). The TIL are however suppressed by many factors within the tumor environment. Chief among these is a subset of lymphocytes called Tregs that play a central role in maintaining immunologic tolerance to normal tissues.

We therefore performed the following experiment: C57Bl/6 mice were inoculated subcutaneously with tumor cells (ovalbumin expressing EL-4 thymoma cells (E.G7-OVA)).

In a first step (FIG. 25 A), control or TriMix mRNA was injected into the tumor nodules when the tumor reached a volume of about 150 mm3. Three days later, the tumor draining lymph nodes were resected and a single cell suspension was made. The CD11c+ cells present in this cell suspension were enriched by MACS and co-cultured with OT-I CD8+ T cells recognizing an ovalbumin derived epitope. The induction of T cell proliferation and the secretion of interferon-g by these T cells was analyzed. The induction of proliferation and the induction of IFN-g secretion by the OVA-specific T cells by the migrated tumor-resident DCs indicates that the tumor-resident DC have been loaded by tumor antigens present in the tumor microenvironment.

Next, again when the tumor reached a volume of about 150 mm3, the mice were injected intravenously with OT-I CD8+ T cells recognizing an ovalbumin derived epitope. The next day, control (tNGFR) or TriMix mRNA was injected into the tumor nodules. Five days later, the tumor draining lymph nodes were resected and a single cell suspension was made. The induction of the T cell proliferation was analyzed and indicates that the tumor-resident DC have been loaded by tumor antigens present in the tumor microenvironment and are activated to migrate to the draining lymph nodes.

Finally, (FIG. 25C) control or TriMix mRNA was injected into the tumor nodules when the tumor reached a volume of about 150 mm3. Five days later, the induction of an OVA-specific cytotoxic T cell response was analyzed. It is shown that Intratumoral administration of TriMix mRNA induces a tumor antigen specific immune response In these experiments, it is shown that the intratumoral delivery of Trimix mRNA can reprogram the TIDC. TIDC engulf and translate the administered mRNA in functionally competent proteins (FIG. 25 A). Intratumoral administration of TriMix mRNA activates the TIDC to migrate towards the TDLN (FIG. 25 B). These in-situ modified TIDC become potent activators of TIL and can cross-present tumor antigens to T cells present in the TDLN (FIG. 25 B).

To further analyse the effect of TriMix on tumor growth and survival, DBA/2 mice were inoculated subcutaneously with P815 mastocytoma cells in the left and right flank. Subsequently, control or TriMix mRNA was injected into left the tumor nodules when the tumor reached a volume of about 150 mm3. Tumor volumes were measured over time (FIG. 26).

In a parallel experiment, Balb/C mice were inoculated subcutaneously with A20 B lymphoma cells in the left and right flank. Control or TriMix mRNA was injected into the tumor nodules when the tumor reached a volume of about 150 mm3. Tumor volumes were again measured over time (FIG. 27).

As is shown in these syngeneic tumor models (cf. FIGS. 26 and 27) in situ immunomodulation via mRNA administration in a peripheral tumor site generates an antitumor immune response within the distant tumor sites, leading to their eradication and increased survival of subjects. Therefore, in situ immunomodulation with TriMix mRNA constitutes a powerful 'in situ DC-vaccine' for which no prior knowledge of tumor antigens is needed.

What is claimed is:

1. A method for the treatment of cancer, comprising the step of intratumoral administering to a subject in need thereof one or more isolated mRNA molecule(s) encoding for:
   a functional immunostimulatory protein CD40L, constitutively active TLR4 (caTLR4), and a functional immunostimulatory protein CD70; wherein said method does not include the administration of dendritic cells to said subject.

2. The method according to claim 1, additionally comprising the step of administering target-specific antigen(s) before, after, or simultaneously with the one or more isolated mRNA molecule(s).

3. The method of claim 2, wherein the target-specific antigen is a tumor antigen.

4. The method of claim 2, wherein said target-specific antigen(s) is selected from the group consisting of: total mRNA isolated from (a) target cell(s), one or more specific target mRNA molecules, protein lysates of (a) target cell(s), specific proteins from (a) target cell(s), a synthetic target-specific peptide or protein, and synthetic mRNA or DNA encoding a target-specific antigen or its derived peptide(s).

5. The method according to claim 1, wherein prior to said intratumoral administering, the tumor was treated by ablation, thereby freeing antigens.

6. The method of claim 1, additionally comprising the administration of mRNA or DNA encoding one or more of the following molecules: IL-12p70, EL-selectin, CCR7, and/or 4-1BBL.

7. The method according to claim 1, wherein said one or more isolated mRNA molecule(s) encoding the immunostimulatory proteins are part of a single mRNA molecule.

8. The method according to claim 7, wherein the single mRNA molecule is capable of expressing the two or more proteins simultaneously.

9. The method according to claim 1, wherein said mRNA is protected.

10. The method according to claim 1, wherein the cancer is chosen from leukemia, non-small cell lung cancer, small cell lung cancer, CNS cancer, melanoma, ovarian cancer, kidney cancer, prostate cancer, breast cancer, glioma, colon cancer, bladder cancer, sarcoma, pancreatic cancer, colorectal cancer, head and neck cancer, liver cancer, bone cancer, bone marrow cancer, stomach cancer, duodenum cancer, oesophageal cancer, thyroid cancer, hematological cancer, and lymphoma.

11. The method according to claim 1, wherein the method does not include the administration of a target specific antigen to said subject.

* * * * *

```
                              SEQUENCE LISTING

<160> NUMBER OF SEQ ID NOS: 16

<210> SEQ ID NO 1
   <211> LENGTH: 34
   <212> TYPE: DNA
   <213> ORGANISM: Artificial
   <220> FEATURE:
   <223> OTHER INFORMATION: primer

<400> SEQUENCE: 1
aaaaagcttc caccatggca cggccacatc cctg                                  34

<210> SEQ ID NO 2
   <211> LENGTH: 27
   <212> TYPE: DNA
   <213> ORGANISM: Artificial
   <220> FEATURE:
   <223> OTHER INFORMATION: primer

<400> SEQUENCE: 2
cccctcgagt caggggagc aggcagg                                           27

<210> SEQ ID NO 3
   <211> LENGTH: 30
   <212> TYPE: DNA
   <213> ORGANISM: Artificial
   <220> FEATURE:
   <223> OTHER INFORMATION: primer

<400> SEQUENCE: 3
gatggatccg tcatgatcga aacatacaac                                       30

<210> SEQ ID NO 4
   <211> LENGTH: 27
   <212> TYPE: DNA
   <213> ORGANISM: Artificial
   <220> FEATURE:
   <223> OTHER INFORMATION: primer

<400> SEQUENCE: 4
cggtacccat cagagtttga gtaagcc                                          27

<210> SEQ ID NO 5
   <211> LENGTH: 30
   <212> TYPE: DNA
   <213> ORGANISM: Artificial
   <220> FEATURE:
   <223> OTHER INFORMATION: primer

<400> SEQUENCE: 5 aaagcttcc accatgccgg aggagggttc                                        30

<210> SEQ ID NO 6
   <211> LENGTH: 27
   <212> TYPE: DNA
   <213> ORGANISM: Artificial
   <220> FEATURE:
   <223> OTHER INFORMATION: primer

<400> SEQUENCE: 6
```

```
gggggggaatt ctcaggggcg cacccac                                              27
```

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7

```
ggggatcctg tgctgagttt gaatatcacc                                            30
```

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8

```
gggaattctc agatagatgt tcttcctg                                              28
```

<210> SEQ ID NO 9
<211> LENGTH: 9
<212> TYPE: PRT
<213> ORGANISM: Artificial
<220> FEATURE:
<223> OTHER INFORMATION: synthetic

<400> SEQUENCE: 9

Phe Leu Trp Gly Pro Arg Ala Leu Val
1               5

<210> SEQ ID NO 10
<211> LENGTH: 9
<212> TYPE: PRT
<213> ORGANISM: Artificial
<220> FEATURE:
<223> OTHER INFORMATION: synthetic

<400> SEQUENCE: 10

Lys Val Ala Glu Leu Val His Phe Leu
1               5

<210> SEQ ID NO 11
<211> LENGTH: 9
<212> TYPE: PRT
<213> ORGANISM: Artificial
<220> FEATURE:
<223> OTHER INFORMATION: synthetic

<400> SEQUENCE: 11

Ala Leu Lys Asp Val Glu Glu Arg Val
1               5

<210> SEQ ID NO 12
<211> LENGTH: 9
<212> TYPE: PRT
<213> ORGANISM: Artificial
<220> FEATURE:
<223> OTHER INFORMATION: synthetic

<400> SEQUENCE: 12

Tyr Met Asp Gly Thr Met Ser Gln Val
1               5

```
<210> SEQ ID NO 13
<211> LENGTH: 9
<212> TYPE: PRT
<213> ORGANISM: Artificial
<220> FEATURE:
<223> OTHER INFORMATION: synthetic

<400> SEQUENCE: 13

Ile Thr Asp Gln Val Pro Phe Ser Val
1               5

<210> SEQ ID NO 14
<211> LENGTH: 9
<212> TYPE: PRT
<213> ORGANISM: Artificial
<220> FEATURE:
<223> OTHER INFORMATION: synthetic

<400> SEQUENCE: 14

Tyr Leu Glu Pro Gly Pro Val Thr Ala
1               5

<210> SEQ ID NO 15
<211> LENGTH: 9
<212> TYPE: PRT
<213> ORGANISM: Artificial
<220> FEATURE:
<223> OTHER INFORMATION: synthetic

<400> SEQUENCE: 15

Lys Thr Trp Gly Gln Tyr Trp Gln Val
1               5

<210> SEQ ID NO 16
<211> LENGTH: 9
<212> TYPE: PRT
<213> ORGANISM: Artificial
<220> FEATURE:
<223> OTHER INFORMATION: synthetic peptide

<400> SEQUENCE: 16

Ser Leu Leu Met Trp Ile Thr Gln Cys
1               5
```